US011414713B2

(12) United States Patent
Divakar et al.

(10) Patent No.: US 11,414,713 B2
(45) Date of Patent: Aug. 16, 2022

(54) METHODS OF SCREENING FOR ONYCHOMYCOTIC FUNGI

(71) Applicant: Bakotic Pathology Associates, LLC, Alpharetta, GA (US)

(72) Inventors: Kiran Madanahally Divakar, Shrewsbury, MA (US); Bradley Wayne Bakotic, Alpharetta, GA (US); Laurie Susan Page, Marietta, GA (US); Lori Ilene Bennett, Alpharetta, GA (US)

(73) Assignee: Bakotic Pathology Associates, LLC, Alpharetta, GA (US)

( * ) Notice: Subject to any disclaimer, the term of this patent is extended or adjusted under 35 U.S.C. 154(b) by 876 days.

(21) Appl. No.: 15/222,652

(22) Filed: Jul. 28, 2016

(65) Prior Publication Data

US 2017/0029906 A1 Feb. 2, 2017

Related U.S. Application Data

(60) Provisional application No. 62/198,598, filed on Jul. 29, 2015.

(51) Int. Cl.
*C12Q 1/6895* (2018.01)

(52) U.S. Cl.
CPC ..... *C12Q 1/6895* (2013.01); *C12Q 2600/158* (2013.01); *C12Q 2600/16* (2013.01)

(58) Field of Classification Search
None
See application file for complete search history.

(56) References Cited

PUBLICATIONS

Petinataud et al. Molecular diagnosis of onychomycosis. Journal de Mycologie Medicale 2014, 24, pp. 287-295 (Year: 2014).*
Gupta et al. Molecular Determination of Mixed Infections of Dermatophytes and Nondermatophyte Molds in Individuals with Onychomycosis. Journal of the American Podiatric Medical Association 2014, vol. 104, No. 4, pp. 330-336 (Year: 2014).*
Gupta et al. Fast and sensitive detection of Trichophyton rubrum DNA from the nail samples of patients with onychomycosis by a double-round polymerase chain reaction-based assay. British Journal of Dermatology, 2007, vol. 157, pp. 698-703 (Year: 2007).*
(Continued)

*Primary Examiner* — Olivia M. Wise
(74) *Attorney, Agent, or Firm* — Bozicevic, Field & Francis LLP; James S. Keddie

(57) ABSTRACT

Provided herein is a method of detecting an onychomycotic fungus in a sample, wherein the onychomycotic fungus belongs to a secondary clade member including one or more primary clade members. The method may include the steps of i) screening a sample using a first and second sets of secondary clade-specific primers to determine whether a secondary clade member among a plurality of secondary clade members is present or absent in the sample, where the plurality of secondary clade members includes (a) a dermatophyte, (b) a *candida*, and (c) a saprophyte, and ii) after determining the presence of the secondary clade member, screening the sample to determine whether an onychomycotic fungus is present or absent in the sample using primary clade-specific primers that are specific to a primary clade member that belongs to the secondary clade member. Also provided is a kit that finds use in implementing the present method.

10 Claims, 87 Drawing Sheets

Specification includes a Sequence Listing.

(56) References Cited

PUBLICATIONS

Skladny et al. Specific Detection of Aspergillus species in blood and bronchoalveolar lavage samples of immunocompromised patients by two-step PCR. Journal of Clinical Microbiology 1999, vol. 37, No. 12, pp. 3865-3871 (Year: 1999).*
Mackay et al. Real-time PCR in the microbiology laboratory. Clin Microbiol Infect 2004, vol. 10, pp. 190-212 (Year: 2004).*
Han et al. Rapid detection of dermatophytes and Candida albicans in onychomycosis specimens by an oligonucleotide array. BMC Infectious Diseases 2014, 14:581, pp. 1-7 (Year: 2014).*
Baskova, L., et al., (2007) "The PanAC assay: a singlereaction realtime PGR test for quantitative detection of a broad range of *Aspergillus* and *Candida* species" J Med Microbiol, 56(Pt9):1167-73.
Ebihara, M., et al., (2009) "Molecular detection of dermatophytes and nondermatophytes in onychomycosis by nested polymerase chain reaction based on 28S ribosomal RNA gene sequences" Br J. Dermatol, 161(5):1038-44.
Erali, Maria, et al., (2006) "Multiplex Single-Color PCR with Amplicon Melting Analysis for Identification of *Aspergillus* Species" Clin Chern. Jul. 2006;52(7):1443-5.
Li, HC, et al., (2008) "Identification of dermatophytes by sequence analysis of the rRNA gene internal transcribed spacer regions" J Med Microbiol, 57(Pt5):592-600.
Mandviwala, Tasneem, et al., (2010) "High-Throughput Identification and Quantification of *Candida* Species Using High Resolution Derivative Melt Analysis of Panfungal Amplicons" Journal of Molecular Diagnostics, 12(1):91-101.
Schabereiter-Gurtner, C., et al., (2007) "Development of novel real-time PCR assays for detection and differentiation of eleven medically important *Aspergillus* and *Candida* species in clinical specimens" Journal of Clinical Microbiology, 45(3):906-914.
Hanami T., et al., (2013) "Eprobe mediated real-time PCR monitoring and melting curve analysis" PLoS ONE 8(8):e70942. Doi: 10.1371 /journal.pone.0070942.
Luo T., et al., (2011) "Multiplex Real-Time PCR melting curve assay to detect drug-resistant mutations of *Mycobacterium tuberculosis*" Journal of Clinical Microbiology, 49(9):3132-3138.
Borman, A.M., et al., (2007) "Analysis of the dermatophyte species isolated in the British Isles between 1980 and 2005 and review of worldwide dermatophyte trends over the last three decades" Med Mycol., 45:131-141.
Elewski, B., (1998) "Onychomycosis: Pathogenesis, Diagnosis, and Management" Clinical Microbiology Reviews, 11:415-429.
Ghannoum, M.A., et al., (2000) "A large-scale North American study of fungal isolates from nails: the frequency of onychomycosis, fungal distribution, and antifungal susceptibility patterns" J Am Acad Dermatol, 43:641-648.
Gräser, Y., et al., (2012) "Diagnostic PCR of dermatophytes—an overview" J Dtsch Dermatol Ges, 10:721-725.
Horváth, Á., et al., (2013) "A novel, multiplex, real-time PCR-based approach for the detection of the commonly occurring pathogenic fungi and bacteria" BMC Microbiol, 13:300-307.
Kourkoumpetis, T.K., et al., (2012) "Polymerase chain reaction-based assays for the diagnosis of invasive fungal infections" Clin Infect Dis, 54:1322-1331.
Pontarelli, L.N., et al., (2005) "Onychomycosis by Scytalidium dimidiatum: Report of two cases in Santa Catarina, Brazil" Rev. Inst. Med. trop. S. Paulo, 47:351-353.
Bergmans, A.M.C., et al., (2010) "Evaluation of a single-tube real-time PCR for detection and identification of 11 Dermatophyte species in clinical material" Clin Microbiol Infect, 16:704-710.
Brillowska-Dabrowska, A., et al. (2007) "Five-Hour Diagnosis of Dermatophyte Nail Infections with Specific Detection of Trichophyton rubrum" J. Clin. Microbiol., 45:1200-1204.
Bristow, IR, et al., (2009 "Fungal foot infection, cellulitis and diabetes: a review" Diabet Med, 26:548-551.
Dhib, I., et al., (2014) Multiplex PCR assay for the detection of common Dermatophyte nail infections; Mycoses, 57:19-26.
Kim, J.Y., et al., "Identification of Dermatophytes using multiplex polymerase chain reaction" Ann Dermatol (2011), 23:304-312.
Luk, N. M., et al., (2012) "Evaluation of PCR for the diagnosis of dermatophytes in nail specimens from patients with suspected onychomycosis" Clin Exp Dermatol, 37:230-234.
Weitzman, I. and Summerbell, R.C., (1995) "The Dermatophytes" Clinical Microbiology Reviews, 8:240-259.
Wisselink, G.J., et al., (2011) "Trapped in keratin; a comparison of dermatophyte detection in nail, skin and hair samples directly from clinical samples using culture and real-time PCR" Journal of Microbiological Methods, 85:62-66.
Bartelli, T.F., et al., (2013) "Intraspecific comparative genomics of Candida albicans mitochondria reveals non-coding regions under neutral evolution" Infection, Genetics and Evolution, 14:302-312.
Bu, R., et al., (2005) "Monochrome LightCycler PCR assay for detection and quantification of five common species of *Candida* and *Aspergillus*" J Med Microbiol, 54:243-248.
Valach, M., et al., (2012) "Mitochondrial genome variability within the *Candida parapsilosis* species complex" Mitochondrion, 12:514-519.
Baudraz-Rosselet, F., et al., "Onychomycosis insensitive to systemic terbinafine and azole treatments reveals non-Dermatophyte moulds as infectious agents" Dermatology, (2010), 220:164 168.
Geiser, D.M., et al., (2004) "FUSARIUM-ID v. 1.0: A DNA sequence database for identifying Fusarium" European Journal of Plant Pathology, 110:473-479.
Gupta, A.K., et al., (2013) "Therapies for the treatment of onychomycosis" Clin Dermatol; 31:544-554.
Mayser, P., et al., "Toenail onychomycosis in diabetic patients: issues and management" Am J Clin Dermatol., (2009), 10:211-220.

* cited by examiner

FIG. 11A

Table 2.1

| Organism | Source | N | DNA (ng) Range Per reaction | Category | PCR Result | | |
|---|---|---|---|---|---|---|---|
| | | | | | Can | Derm | Sap |
| *C albicans* | In-House Culture | 3 | 20 - 0.01 | *Candida* | Pos | ND | ND |
| *C glabrata* | In-House Culture | 2 | 2.0 - 0.2 | *Candida* | Pos | ND | ND |
| *C guilliermondii* | In-House Culture | 2 | 2.0 - 0.2 | *Candida* | Pos | ND | ND |
| *C kruseii* | In-House Culture | 1 | 3.51 - 0.035 | *Candida* | Pos | ND | ND |
| *C lusitaniae* | In-House Culture | 2 | 2.0 - 0.2 | *Candida* | Pos | ND | ND |
| *C parapsilosis/ orthopsilosis* | In-House Culture | 6 | 20 - 0.04 | *Candida* | Pos | ND | ND |
| *C parapsilosis* | ATCC #22019D-5 | 1 | CLT = 0.02 | *Candida* | Pos | ND | ND |
| *M pachydermatis* | In-House Culture | 2 | | *Candida* | Pos | ND | ND |
| Cross reactivity of *Candida* organisms seen with neither dermatophyte nor saprophyte primers | | | | | | | |
| *T rubrum* | In-House Culture | 3 | 20 - 0.04 | Dermatophyte | ND | Pos | ND |
| *T interdigitale** | In-House Culture | 1 | 20 - 0.1 | Dermatophyte | ND | Pos | ND |
| *T mentagrophytes** | ATCC #9533D-2 | 1 | CTL = 0.004 | Dermatophyte | ND | Pos | ND |
| *T mentagrophytes** | In-House Culture | 1 | 6.8 - 0.068 | Dermatophyte | ND | Pos | ND |
| *Epidermophyton* | In-House Culture | 1 | 3.0 | Dermatophyte | ND | Pos | ND |
| *Microsporum* | In-House Culture | 1 | 4.5 | Dermatophyte | ND | Pos | ND |
| Cross reactivity of dermatophyte organisms seen with neither *Candida* nor saprophyte primers | | | | | | | |

| Organism | Source | N | DNA (ng) Range Per reaction | Category | PCR Result | | |
|---|---|---|---|---|---|---|---|
| | | | | | Can | Derm | Sap |
| *Acremonium* | In-House Culture | 2 | 20 - 0.04 | Saprophyte | ND | ND | Pos |
| *Alternaria* | In-House Culture | 3 | 20 - 0.1 | Saprophyte | ND | ND | Pos |
| *Aspergillus (sp?)* | In-House Culture | 4 | 20 - 0.1 | Saprophyte | ND | ND | Pos |
| *A flavus* | ATCC #204304D-2 | 1 | CTL = 0.035 | Saprophyte | ND | ND | Pos |
| *A terreus* | In-House Culture | 1 | 5.1 - 0.058 | Saprophyte | ND | ND | Pos |
| *Chaetomium* | In-House Culture | 3 | 20 - 4 | Saprophyte | ND | ND | Pos |
| *Curvularia* | In-House Culture | 4 | 20 - 0.1 | Saprophyte | ND | ND | Pos |
| *Fusarium (sp?)* | In-House Culture | 3 | 20 - 0.1 | Saprophyte | ND | ND | Pos |
| *F oxysporum* | In-House Culture | 1 | 3.1 - 0.031 | Saprophyte | ND | ND | Pos |
| *F solani* | In-House Culture | 1 | 2.5 - 0.025 | Saprophyte | ND | ND | Pos |
| *Mucor* | In-House Culture | 2 | 20 - 0.1 | Saprophyte | ND | ND | Pos |
| *Paecilomyces* | In-House Culture | 3 | 20 - 0.01 | Saprophyte | ND | ND | Pos |
| *Penicillium* | In-House Culture | 2 | 20 - 0.1 | Saprophyte | ND | ND | Pos |
| *Scopulariopsis* | In-House Culture | 2 | 20 - 0.1 | Saprophyte | ND | ND | Pos |
| Cross reactivity of *saprophyte* organisms seen with neither *Candida* nor dermatophyte primers | | | | | | | |

FIG. 11B

Table 2.2

| Organism | Source | DNA (ng) Range Per reaction | Category | PCR Result | | |
|---|---|---|---|---|---|---|
| | | | | Can | Derm | Sap |
| *C. albicans* | In-House Culture | 2.0 & 0.2 | *Candida* | Pos | ND | ND |
| *C. glabrata* | In-House Culture | 2.0 & 0.2 | *Candida* | Pos | ND | ND |
| *C. guilliermondii* | In-House Culture | 2.0 & 0.2 | *Candida* | Pos | ND | ND |
| *C. kruseii* | In-House Culture | 3.51 & 0.035 | *Candida* | Pos | ND | ND |
| *C. lusitaniae* | In-House Culture | 2.0 & 0.2 | *Candida* | Pos | ND | ND |
| *C. orthopsilosis* | In-House Culture | 2.0 & 0.2 | *Candida* | Pos | ND | ND |
| *C. parapsilosis* | In-House Culture | 2.0 & 0.2 | *Candida* | Pos | ND | ND |
| *C. parapsilosis* | ATCC #22019D-5 | 2.0 & 0.2 | *Candida* | Pos | ND | ND |
| *C. tropicalis* | In-House Culture | 2.0 & 0.2 | *Candida* | Pos | ND | ND |
| *M. pachydermatis* | In-House Culture | 2.0 & 0.2 | *Candida* | Pos | ND | ND |
| Cross reactivity of *Candida* organisms seen with neither dermatophyte nor Saprophyte assay | | | | | | |
| *Epidermophyton* | In-House Culture | 2.0 & 0.2 | Dermatophyte | ND | Pos | ND |
| *M. gypseum* | In-House Culture | 2.0 & 0.2 | Dermatophyte | ND | Pos | ND |
| *M. canis* | In-House Culture | 2.0 & 0.2 | Dermatophyte | ND | Pos | ND |
| *T. interdigitale** | In-House Culture | 2.0 & 0.2 | Dermatophyte | ND | Pos | ND |
| *T. mentagrophytes** | ATCC #9533D-2 | 2.0 & 0.2 | Dermatophyte | ND | Pos | ND |
| *T. rubrum* | In-House Culture | 2.0 & 0.2 | Dermatophyte | ND | Pos | ND |
| *T. tonsurans* | In-House Culture | 2.0 & 0.2 | Dermatophyte | ND | Pos | ND |
| *T. violaceum* | In-House Culture | 2.0 & 0.2 | Dermatophyte | ND | Pos | ND |
| Cross reactivity of Dermatophyte organisms seen with neither *Candida* nor Saprophyte assay | | | | | | |
| *Acremonium* | In-House Culture | 2.0 & 0.2 | Saprophyte | ND | ND | Pos |
| *Alternaria* | In-House Culture | 2.0 & 0.2 | Saprophyte | ND | ND | Pos |
| *Aspergillus* | In-House Culture | 2.0 & 0.2 | Saprophyte | ND | ND | Pos |
| *A flavus* | ATCC #204304D-2 | 2.0 & 0.2 | Saprophyte | ND | ND | Pos |
| *A terreus* | In-House Culture | 2.0 & 0.2 | Saprophyte | ND | ND | Pos |
| *Chaetomium* | In-House Culture | 2.0 & 0.2 | Saprophyte | ND | ND | Pos |
| *Curvularia* | In-House Culture | 2.0 & 0.2 | Saprophyte | ND | ND | Pos |
| *Fusarium* | In-House Culture | 2.0 & 0.2 | Saprophyte | ND | ND | Pos |
| *F oxysporum* | In-House Culture | 2.0 & 0.2 | Saprophyte | ND | ND | Pos |
| *F solani* | In-House Culture | 2.0 & 0.2 | Saprophyte | ND | ND | Pos |
| *Mucor* | In-House Culture | 2.0 & 0.2 | Saprophyte | ND | ND | Pos |
| *Paecilomyces* | In-House Culture | 2.0 & 0.2 | Saprophyte | ND | ND | Pos |
| *Penicillium* | In-House Culture | 2.0 & 0.2 | Saprophyte | ND | ND | Pos |
| *Scopulariopsis* | In-House Culture | 2.0 & 0.2 | Saprophyte | ND | ND | Pos |
| *Scytalidium* | In-House Culture | 2.0 & 0.2 | Saprophyte | ND | ND | Pos |
| Cross reactivity of Saprophyte organisms seen with neither *Candida* nor Dermatophyte assay | | | | | | |

**T. mentagrophytes* and *T. interdigitale* are anamorphs of the same organism

Pos: Positive; ND: not detected

FIG. 12

Table 3

| Organism | Source | DNA (ng) Range Per reaction | Category | PCR Result | | |
|---|---|---|---|---|---|---|
| | | | | Can | Derm | Sap |
| *Cladosporium* | In-House Culture | 2.0 & 0.2 | Saprophyte | ND | ND | ND |
| *Epicoccum* | In-House Culture | 2.0 & 0.2 | Saprophyte | ND | ND | ND |
| *Foncecea* | In-House Culture | 2.0 & 0.2 | Saprophyte | ND | ND | ND |

ND: not detected

FIG. 13

Table 4

| EC/IC Ct | EC/IC Tm | C/D Ct | Sap Ct | |
|---|---|---|---|---|
| 10 | 10 | 10 | 92 | N |
| 30.6 | 75.0 | 34.0 | 31.4 | Mean |
| 1.31 | 0.49 | 1.80 | 1.10 | SD |
| 4.27 | 0.65 | 5.28 | 3.50 | CV (%) |
| 28.2 | 74.2 | 30.2 | 28.8 | Min |
| 31.8 | 75.6 | 36.0 | 33.7 | Max |

FIG. 14

Table 5

| C/D Ct | Sap Ct | |
|---|---|---|
| 15 | 60 | N |
| 35.9 | 31.2 | Mean |
| 0.18 | 1.16 | SD |
| 0.50 | 3.72 | CV (%) |
| 35.3 | 28.1 | Min |
| 36.0 | 33.3 | Max |

FIG. 15A

Table 6.1

| | | PCR Results | | | | | | | | | | | |
|---|---|---|---|---|---|---|---|---|---|---|---|---|---|
| Bacteria ID | Genomic Equivalent | Bacterial only | | | *C parapsilosis* Pos + Bacteria | | | *T rubrum* Pos + Bacteria | | | *Aspergillus* Pos + Bacteria | | |
| | | Can | Derm | Sap | Can | Derm | Sap | Can | Derm | Sap | Can | Derm | Sap |
| *P aeruginosa* | $1.3 \times 10^4$ | ND | ND | ND | Pos | ND | ND | ND | Pos | ND | ND | ND | Pos |
| *P aeruginosa* | $1.3 \times 10^5$ | ND | ND | ND | Pos | ND | ND | ND | Pos | ND | ND | ND | Pos |
| *P mirabilus* | $2.3 \times 10^5$ | ND | ND | ND | Pos | ND | ND | ND | Pos | ND | ND | ND | Pos |
| *P mirabilus* | $2.3 \times 10^4$ | ND | ND | ND | Pos | ND | ND | ND | Pos | ND | ND | ND | Pos |
| *S aureus* | $1.1 \times 10^4$ | ND | ND | ND | Pos | ND | ND | ND | Pos | ND | ND | ND | Pos |
| *S aureus* | $1.1 \times 10^5$ | ND | ND | ND | Pos | ND | ND | ND | Pos | ND | ND | ND | Pos |
| *S marcescens* | $6.4 \times 10^5$ | ND | ND | ND | Pos | ND | ND | ND | Pos | ND | ND | ND | Pos |
| *S marcescens* | $6.4 \times 10^4$ | ND | ND | ND | Pos | ND | ND | ND | Pos | ND | ND | ND | Pos |
| *S pyogenes* | $4.9 \times 10^5$ | ND | ND | ND | Pos | ND | ND | ND | Pos | ND | ND | ND | Pos |
| *S pyogenes* | $4.9 \times 10^4$ | ND | ND | ND | Pos | ND | ND | ND | Pos | ND | ND | ND | Pos |

Pos: Positive; ND: not detected

Table 6.2

| | Bacteria | *P. aerug* | | *P. mirabil* | | *S. aureus* | | *S. marcen* | | *S. pyog* | |
|---|---|---|---|---|---|---|---|---|---|---|---|
| | DNA Quantity, ng | *2* | *0.2* | *2* | *0.2* | *2* | *0.2* | *2* | *0.2* | *2* | *0.2* |
| | DNA tested | | | | | | | | | | |
| *N/A* | Bacteria only | ND | ND | ND | ND | ND | ND | Scy^ | ND | ND | ND |
| *C. parapsilosis* | Bact. + Cp | Cp | Cp | Cp | Cp | Cp | Cp | Cp | Cp | Cp | Cp |
| *T. rubrum* | Bact. + Trub | Trub | Trub | Trub | Trub | Trub | Trub | Trub | Trub | Trub | Trub |
| *Aspergillus* | Bact. + Asp | Asp | Asp | Asp | Asp | Asp | Asp | Asp | Asp | Asp | Asp |
| *Fusarium* | Bact. + Fus | Fus | Fus | Fus | Fus | Fus# | Fus | Fus | Fus | Fus | Fus |
| *Scytalidium* | Bact. + Scy | Scy | Scy | Scy | Scy | Scy~ | Scy | Scy | Scy | Scy | Scy |

FIG. 15B

Table 7.1

| | | PCR Results | | | | | | | | | | | |
|---|---|---|---|---|---|---|---|---|---|---|---|---|---|
| Human DNA | Genomic Equivalent | Human DNA only | | | *C parapsilosis* Pos + Human DNA | | | *T rubrum* Pos + Human DNA | | | *Aspergillus* Pos + Human DNA | | |
| | | Can | Derm | Sap | Can | Derm | Sap | Can | Derm | Sap | Can | Derm | Sap |
| 0.5 ng | ~80 | ND | ND | ND | Pos | ND | ND | ND | Pos | ND | ND | ND | Pos |
| 1.0 ng | ~160 | ND | ND | ND | Pos | ND | ND | ND | Pos | ND | ND | ND | Pos |
| 2.0 ng | ~320 | ND | ND | ND | Pos | ND | ND | ND | Pos | ND | ND | ND | Pos |

Pos: Positive; ND: not detected

Table 7.2

| | | hgDNA | | | |
|---|---|---|---|---|---|
| DNA Quantity, ng | | *2* | *1* | *0.5* | *0.2* |
| | DNA tested | | | | |
| *N/A* | hgDNA only | ND | ND | ND | ND |
| *C. parapsilosis* | hgDNA + Cp | Cp | Cp | Cp | |
| *T. rubrum* | hgDNA + Asp | Trub | Trub | Trub | |
| *Aspergillus* | hgDNA + Asp | Asp | | | Asp |
| *Fusarium* | hgDNA + Fus | Fus | | | Fus |
| *Scytalidium* | hgDNA + Scy | Scy | | | Scy |

ND: Not Detected Cp: *C. parapsilosis* Trub: *T. rubrum* Asp: *Aspergillus* Fus: *Fusarium* Scy: *Scytalidim*

FIG. 16A

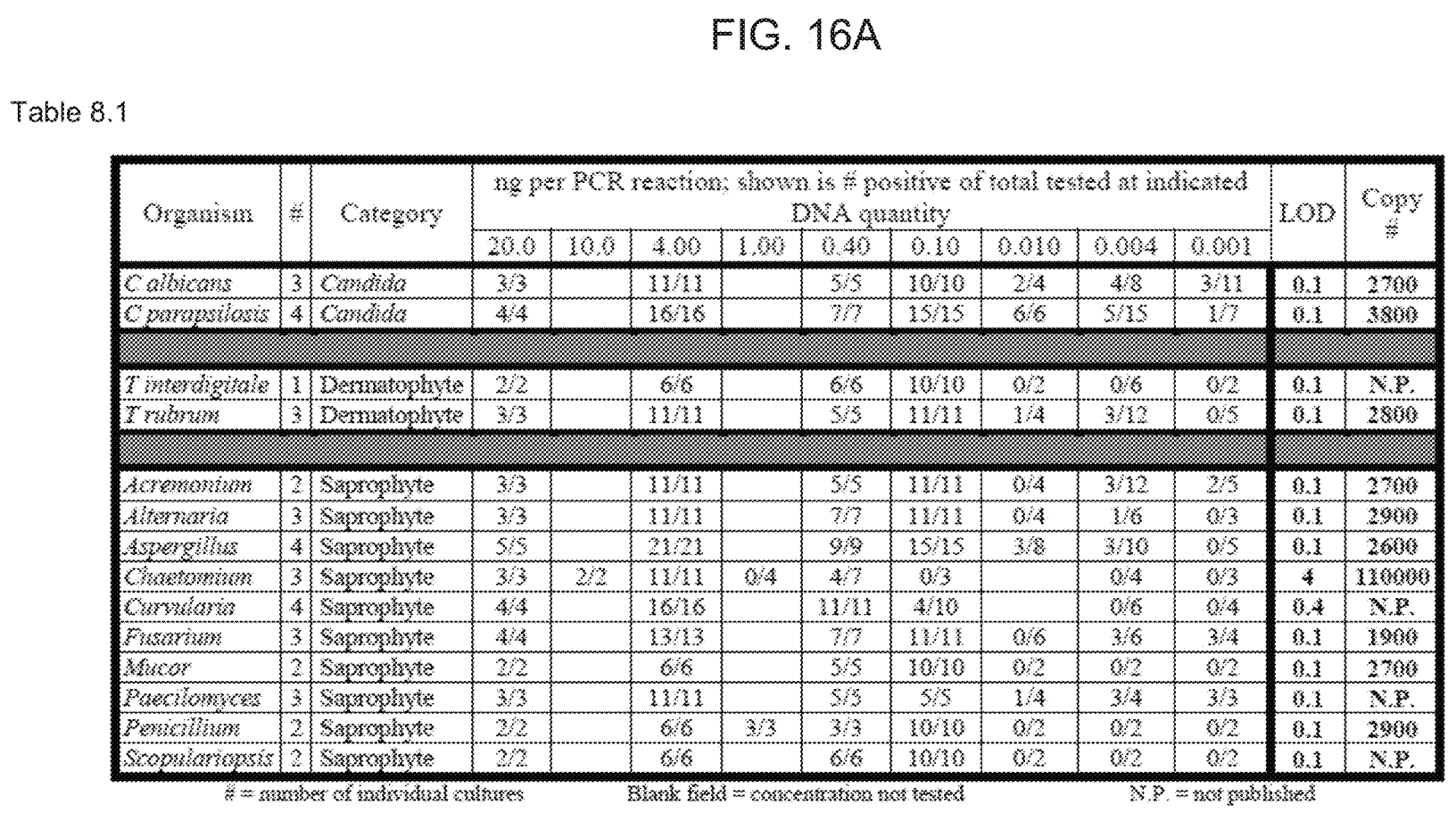

Table 8.1

| Organism | # | Category | ng per PCR reaction; shown is # positive of total tested at indicated DNA quantity | | | | | | | | | LOD | Copy # |
|---|---|---|---|---|---|---|---|---|---|---|---|---|---|
| | | | 20.0 | 10.0 | 4.00 | 1.00 | 0.40 | 0.10 | 0.010 | 0.004 | 0.001 | | |
| *C albicans* | 3 | *Candida* | 3/3 | | 11/11 | | 5/5 | 10/10 | 2/4 | 4/8 | 3/11 | **0.1** | **2700** |
| *C parapsilosis* | 4 | *Candida* | 4/4 | | 16/16 | | 7/7 | 15/15 | 6/6 | 5/15 | 1/7 | **0.1** | **3800** |
| *T interdigitale* | 1 | Dermatophyte | 2/2 | | 6/6 | | 6/6 | 10/10 | 0/2 | 0/6 | 0/2 | **0.1** | **N.P.** |
| *T rubrum* | 3 | Dermatophyte | 3/3 | | 11/11 | | 5/5 | 11/11 | 1/4 | 3/12 | 0/5 | **0.1** | **2800** |
| *Acremonium* | 2 | Saprophyte | 3/3 | | 11/11 | | 5/5 | 11/11 | 0/4 | 3/12 | 2/5 | **0.1** | **2700** |
| *Alternaria* | 3 | Saprophyte | 3/3 | | 11/11 | | 7/7 | 11/11 | 0/4 | 1/6 | 0/3 | **0.1** | **2900** |
| *Aspergillus* | 4 | Saprophyte | 5/5 | | 21/21 | | 9/9 | 15/15 | 3/8 | 3/10 | 0/5 | **0.1** | **2600** |
| *Chaetomium* | 3 | Saprophyte | 3/3 | 2/2 | 11/11 | 0/4 | 4/7 | 0/3 | | 0/4 | 0/3 | **4** | **110000** |
| *Curvularia* | 4 | Saprophyte | 4/4 | | 16/16 | | 11/11 | 4/10 | | 0/6 | 0/4 | **0.4** | **N.P.** |
| *Fusarium* | 3 | Saprophyte | 4/4 | | 13/13 | | 7/7 | 11/11 | 0/6 | 3/6 | 3/4 | **0.1** | **1900** |
| *Mucor* | 2 | Saprophyte | 2/2 | | 6/6 | | 5/5 | 10/10 | 0/2 | 0/2 | 0/2 | **0.1** | **2700** |
| *Paecilomyces* | 3 | Saprophyte | 3/3 | | 11/11 | | 5/5 | 5/5 | 1/4 | 3/4 | 3/3 | **0.1** | **N.P.** |
| *Penicillium* | 2 | Saprophyte | 2/2 | | 6/6 | 3/3 | 3/3 | 10/10 | 0/2 | 0/2 | 0/2 | **0.1** | **2900** |
| *Scopulariopsis* | 2 | Saprophyte | 2/2 | | 6/6 | | 6/6 | 10/10 | 0/2 | 0/2 | 0/2 | **0.1** | **N.P.** |

# = number of individual cultures Blank field = concentration not tested N.P. = not published

FIG. 16B

Table 8.2

| | ng per PCR reaction; shown is # positive of total tested at indicated DNA quantity | | | | | | | | | | | | | LOD | |
|---|---|---|---|---|---|---|---|---|---|---|---|---|---|---|---|
| | 20 | 4 | 1 | 0.40 | 0.10 | 0.04 | 0.01 | 0.004 | 0.001 | 0.0004 | 0.0001 | 0.00004 | 0.00001 | ng | Copy # |
| *Dermatophyte* | | | | | | | | | | | | | | | |
| *T. interdigitale* | 2/2 14.5 - 14.7 | 6/6 16.9 - 17.8 | x | 6/6 19.8 - 21.8 | 10/10 22.0 - 25.8 | x | 0/2 30.2 - 30.7 | 0/6 30.4 - 34.7 | 0/2 31.5 - 32.1 | x | x | x | x | 0.1 | 1667* |
| *T. rubrum* | 3/3 12.0 - 18.1 | 11/11 14.6 - 16.8 | x | 5/5 18.2 - 21.9 | 11/11 19.5 - 27.5 | x | 1/4 29.8 - 31.6 | 3/12 29.5 - 34.5 | 0/5 30.2 - 34.3 | x | x | x | x | 0.1 | 1667 |
| *Saprophyte* | | | | | | | | | | | | | | | |
| *Acremonium* | x | x | 3/3 17.4 - 17.8 | 3/3 19.0 - 19.2 | 5/5 20.4 - 21.1 | 5/5 22.1- 22.7 | 10/10 24.0 - 24.6 | 10/10 24.4 - 25.9 | 10/10 26.0 - 27.7 | 10/10 25.8 - 28.1 | 4/10 26.5 - 29.1 | 4/10 25.8 - 30.7 | 0/10^ 28.4 - 31.0 | 0.0004 | 4 |
| *Alternaria* | x | x | 3/3 20.2 | 5/5 21.2 - 22.1 | 5/5 23.6 - 23.9 | 10/10 25.0 - 25.4 | 10/10 25.7 - 27.5 | 10/10 26.3 - 28.4 | 1/10 28.1 - 29.6 | 0/10 29.5 - 30.2 | x | x | x | 0.004 | 63 |
| *Aspergillus* | x | x | 3/3 17.2 - 18.0 | 5/5 20.6 - 21.0 | 5/5 21.0 - 21.9 | 10/10 23.8 - 24.4 | 10/10 24.1 - 24.9 | 4/10 25.7 - 27.3 | 6/10 26.9 - 27.8 | 0/10 26.7 - 29.6 | x | x | x | 0.01 | 143 |
| *A. terreus* | x | x | x | 5/5 22.2 - 23.1 | 5/5 22.7 - 24.8 | 10/10 24.2 - 25.7 | 10/10 25.6 - 27.4 | 9/10 27.0 - 28.6 | 3/10 28.3 - 30.0 | 0/10 29.0 - 30.5 | 5/10 27.6 - 29.7 | 0/10 26.7- 31.0 | 0/10 26.7- 31.0 | 0.01 | 152 |
| *Chaetomium* | x | 8/8 26.0 - 26.8 | 6/8 26.4 - 28.8 | 4/10 27.7 - 29.8 | 0/10 29.4 - 30.4 | 0/6 27.2 - 31.0 | 0/6 27.7 - 31.1 | 0/6 30.7 - 31.4 | 0/6 27.8 - 31.2 | x | x | x | x | 4 | 54054 |
| *Curvularia* | x | x | 3/3 23.2 - 23.9 | 5/5 24.8 - 28.2 | 5/5 25.8 - 26.9 | 15/20 27.3 - 31.8 | 3/10 26.1 - 29.5 | 3/10 27.6 - 30.2 | 3/10 26.6 - 30.3 | 0/10 28.1 - 30.7 | x | 0/10 25.5 - 29.3 | 0/10 25.5 - 29.3 | 0.1 | 1220* |
| *Fusarium* | x | x | 3/3 17.8 - 18.5 | 3/3 20.3 - 20.5 | 5/5 20.7 - 22.0 | 5/5 23.5 - 24.2 | 10/10 23.2 - 25.3 | 10/10 26.3 - 27.2 | 9/10 24.5 - 28.3 | 7/10 27.5 - 29.7 | 3/20 27.0 - 30.7 | 0/10 28.7 - 30.9 | 0/10 29.2 - 31.1 | 0.004 | 37 |
| *F. oxysporum* | x | x | x | x | 5/5 21.2 - 21.4 | 5/5 23.2 - 23.4 | 10/10 24.7 - 24.8 | 10/10 26.4 - 26.7 | 10/10 27.1 - 28.1 | 1/10 27.7 - 31.3 | 0/10 27.8 - 30.5 | 0/10 27.1 - 30.7 | 0/10 27.1 - 30.7 | 0.001 | 9 |
| *F. solani* | x | x | x | x | 5/5 23.7 - 23.8 | 5/5 25.0- 25.5 | 10/10 26.7 - 27.4 | 4/10 27.7 - 28.8 | 2/10 28.1 - 30.2 | 0/10 29.0 - 31.0 | 0/10 28.5 - 31.4 | 0/10 25.8 - 30.9 | 0/10 25.8 - 30.9 | 0.01 | 93# |
| *Mucor* | x | x | 3/3 23.6 - 23.7 | 5/5 25.0- 25.5 | 5/5 26.1- 27.6 | 5/10 27.8 - 28.6 | 0/10 27.6 - 29.4 | 0/10 27.2 - 30.4 | 0/10 28.4 - 31.8 | 0/10 27.2- 31.1 | x | x | x | 0.1 | 1316 |
| *Paecilomyces* | x | x | 3/3 17.0 - 17.1 | 3/3 19.3- 19.5 | 5/5 19.3- 20.5 | 5/5 23.1- 23.3 | 10/10 22.7- 23.8 | 10/10 26.1 - 27.0 | 10/10 26.1 - 27.0 | 0/10 28.5- 29.5 | 0/10 28.7- 32.1 | 0/10 25.1- 28.9 | 0/10 25.1- 28.9 | 0.001 | 12* |
| *Penicillium* | x | x | 3/3 22.5- 22.6 | 5/5 24.3- 24.8 | 5/5 25.8- 26.2 | 10/10 27.3- 27.9 | 1/10 28.0- 29.0 | 0/10 28.3- 30.7 | 0/10 29.1 - 30.9 | 0/10 27.9 - 31.0 | x | x | x | 0.04 | 625 |
| *Rhizopus* | x | x | 3/3 19.3- 19.5 | 5/5 21.0- 21.2 | 5/5 22.7- 23.0 | 10/10 24.0- 24.9 | 10/10 25.1- 27.8 | 2/10 26.9- 29.0 | 0/10 28.2- 29.9 | 0/10 28.7- 30.7 | x | x | x | 0.01 | 125 |
| *Scopulariopsis* | x | x | 3/3 18.4- 18.7 | 5/5 19.4- 20.8 | 5/5 22.0- 23.0 | 10/10 22.9- 23.9 | 10/10 25.0- 27.1 | 10/10 26.1 - 27.0 | 9/20 26.1 - 30.1 | 1/10 28.0 - 28.9 | 0/10 26.3 - 30.8 | x | 0/10 25.6- 30.7 | 0.004 | 49* |
| *Scytalidium* | x | 5/5 22.8 - 23.1 | 5/5 23.9 - 25.4 | 10/10 25.4 - 26.9 | 10/10 27.0 - 28.0 | 3/10 27.7 - 28.9 | 0/10 28.2 - 30.2 | 0/10 29.7 - 30.7 | 0/3 29.8 - 31.3 | x | x | x | x | 0.1 | 1220* |

X = concentration not tested

* = C values not published. Value used was the mean of C values of 64 different saprophytes, 0.04.

# = C values not published. Value used was the mean of C values of 16 different Fusarium, 0.054.

Ct range shown under # positive

FIG. 16C

Table 8.3

| Organism | CFU (ng DNA) / Extraction shown is # positive of total tested at indicated DNA quantity | | | | | | | | | CFU | ng DNA |
|---|---|---|---|---|---|---|---|---|---|---|---|
| | 357143 | 142857 | 35714 | 14286 | 3574 | 714 | 357 | 179 | 71 (0.002) | | |
| *Candida* | | | | | | | | | | | |
| *C. albicans* | 10/10<br>14.6 - 15.3 | 10/10<br>16.3 - 21.6 | 10/10<br>18.9 - 19.8 | 10/10<br>20.8 - 21.6 | 10/10<br>23.4 - 24.1 | 9/15<br>25.2 - 33.9 | 0/10<br>32.3 - 34.9 | 0/10<br>31.7 - > 36 | 0/10<br>33.4 - > 36 | 3571 | 0.10 |
| *C. parapsilosis* | 5/5<br>15.0 - 16.7 | 5/5<br>17.3 - 19.3 | 10/10<br>20.5 - 26.9 | 10/10<br>24.8 - 28.0 | 10/10<br>24.8 - 29.8 | 3/10<br>28.6 - > 36 | 1/10<br>29.6 - > 36 | 0/10<br>31.1 - > 36 | 0/10<br>32.9 - > 36 | 3571 | 0.10 |

Ct range shown under # positive

FIG. 17

Table 9

| EC/IC Ct | EC/IC Tm | N = 12 |
|---|---|---|
| 27.3 | 75.7 | Mean |
| 1.36 | 0.355 | SD |
| 4.99 | 0.468 | CV (%) |
| 25.2 | 75.1 | Min |
| 29.7 | 76.2 | Max |

FIG. 18

Table 10

| C/D Ct | C/D Tm | N = 15 |
|---|---|---|
| 23.2 | 77.8 | Mean |
| 0.695 | 0.561 | SD |
| 3.00% | 0.72% | CV (%) |
| 22.0 | 76.4 | Min |
| 25.1 | 78.7 | Max |

FIG. 19

Table 11

| C/D Ct | C/D Tm1 | C/D Tm2 | N = 15 |
|---|---|---|---|
| 24.5 | 83.6 | 80.3 | Mean |
| 0.878 | 0.504 | 0.544 | SD |
| 3.58% | 0.60% | 0.68% | CV (%) |
| 22.3 | 82.4 | 78.9 | Min |
| 25.7 | 84.3 | 81.1 | Max |

FIG. 20

Table 12.1

| Sap Ct | Sap Tm | N = 60 |
|---|---|---|
| 20.84 | 80.43 | Mean |
| 0.92 | 0.38 | SD |
| 4.41 | 0.48 | CV (%) |
| 18.67 | 79.40 | Min |
| 22.87 | 81.10 | Max |

Table 12.2

| Sap Ct | Sap Tm | N = 41 |
|---|---|---|
| 21.6 | 84.7 | Mean |
| 0.924 | 0.53 | SD |
| 4.27 | 0.62 | CV (%) |
| 19.8 | 83.3 | Min |
| 23.5 | 85.70 | Max |

FIG. 21A

Table 13.1

| Sample | Organism | *Candida* + | Dermatophyte + | Saprophyte + |
|---|---|---|---|---|
| 391 | *Aspergillus* | 0/3 | 0/3 | 3/3 |
| 424 | *Paecilomyces* | 0/3 | 0/3 | 3/3 |
| 390 | *Aspergillus* | 0/3 | 0/3 | 3/3 |
| 355 | *T rubrum* | 0/3 | 3/3 | 0/3 |
| 398 | *T rubrum* | 0/3 | 3/3 | 0/3 |
| 480 | *T rubrum* | 0/3 | 3/3 | 0/3 |
| CaA | *C albicans* | 4/4 | 0/4 | 0/4 |
| CaB | *C albicans* | 4/4 | 0/4 | 0/4 |
| CpA | *C parapsilosis* | 4/4 | 0/4 | 0/4 |
| CpB | *C parapsilosis* | 4/4 | 0/4 | 0/4 |

FIG. 21B

Table 13.2

| Sample | Reference | *PCR result* | Ct Range | # of Replicates |
|---|---|---|---|---|
| | | *Candida* | | |
| CaA | *C. albicans* | *Candida* | 25.5 - 28.8 | 4/4 |
| CaB | *C. albicans* | *Candida* | 23.9 - 25.2 | 4/4 |
| CpA | *C. parapsilosis* | *Candida* | 26.2 - 26.5 | 4/4 |
| CpB | *C. parapsilosis* | *Candida* | 24.5 - 25.7 | 4/4 |
| | | | Total | 16/16 |
| | | | Repeatability | 100% |
| | | Dermatophytes | | |
| 355 | *T. rubrum* | *Dermatophyte* | 16.5 - 21.3 | 3/3 |
| 398 | *T. rubrum* | *Dermatophyte* | 18.1 - 19.6 | 3/3 |
| 480 | *T. rubrum* | *Dermatophyte* | 19.6 - 21.5 | 3/3 |
| | | | Total | 9/9 |
| | | | Repeatability | 100% |
| | | Saprophytes | | |
| AcrL1 | *Acremonium* | *Saprophyte* | 23.7 -26.0 | 6/6 |
| AcrL2 | *Acremonium* | *Saprophyte* | 22.0 - 23.5 | 6/6 |
| AcrL3 | *Acremonium* | *Saprophyte* | 21.3 - 22.2 | 6/6 |
| AltL1 | *Alternaria* | *Saprophyte* | 23.4 - 25.3 | 6/6 |
| AltL2 | *Alternaria* | *Saprophyte* | 23.0 - 24.7 | 6/6 |
| AltL3 | *Alternaria* | *Saprophyte* | 22.1 - 23.0 | 6/6 |
| AspL1 | *Aspergillus* | *Saprophyte* | 24.1 - 24.8 | 6/6 |
| AspL2 | *Aspergillus* | *Saprophyte* | 23.3 - 23.9 | 6/6 |
| AspL3 | *Aspergillus* | *Saprophyte* | 21.9 - 24.1 | 6/6 |
| CurvL1 | *Curvularia* | *Saprophyte* | 25.3 - 26.9 | 6/6 |
| CurvL2 | *Curvularia* | *Saprophyte* | 24.7 - 25.7 | 6/6 |
| CurvL3 | *Curvularia* | *Saprophyte* | 23.9 - 25.1 | 6/6 |
| FusL1 | *Fusarium* | *Saprophyte* | 22.7 - 22.9 | 6/6 |
| FusL2 | *Fusarium* | *Saprophyte* | 21.2 - 22.0 | 6/6 |
| FusL3 | *Fusarium* | *Saprophyte* | 20.2 - 21.3 | 5/6 |
| MucL1 | *Mucor* | *Saprophyte* | 24.8 - 25.6 | 6/6 |
| MucL2 | *Mucor* | *Saprophyte* | 24.0 - 25.2 | 6/6 |
| MucL3 | *Mucor* | *Saprophyte* | 22.6 - 23.9 | 6/6 |
| PaecL1 | *Paecilomyces* | *Saprophyte* | 22.3 - 23.1 | 6/6 |
| PaecL2 | *Paecilomyces* | *Saprophyte* | 21.2 - 21.8 | 6/6 |
| PaecL3 | *Paecilomyces* | *Saprophyte* | 20.1 - 21.3 | 6/6 |
| PenL1 | *Penicillium* | *Saprophyte* | 24.1 - 25.1 | 6/6 |
| PenL2 | *Penicillium* | *Saprophyte* | 23.5 - 26.0 | 6/6 |
| PenL3 | *Penicillium* | *Saprophyte* | 22.0 - 22.9 | 6/6 |
| RhizL1 | *Rhizopus* | *Saprophyte* | 22.4 - 22.8 | 6/6 |

FIG. 21C

| **Sample** | **Reference** | ***PCR result*** | **Ct Range** | **# of Replicates** |
|---|---|---|---|---|
| RhizL2 | *Rhizopus* | *Saprophyte* | 21.3 - 22.1 | 6/6 |
| RhizL3 | *Rhizopus* | *Saprophyte* | 20.3 - 20.8 | 6/6 |
| ScopL1 | *Scopulariopsis* | *Saprophyte* | 22.8 - 23.6 | 6/6 |
| ScopL2 | *Scopulariopsis* | *Saprophyte* | 22.0 - 22.6 | 6/6 |
| ScopL3 | *Scopulariopsis* | *Saprophyte* | 20.5 - 21.2 | 6/6 |
| ScyL1 | *Scytalidium* | *Saprophyte* | 28.7 - 28.3 | 6/6 |
| ScyL2 | *Scytalidium* | *Saprophyte* | 24.3 - 28.1 | 6/6 |
| ScyL3 | *Scytalidium* | *Saprophyte* | 24.1 - 26.6 | 6/6 |
| 391 | *Aspergillus* | *Saprophyte* | 15.9 - 23.7 | 3/3 |
| 424 | *Paecilomyuces* | *Saprophyte* | 19.9 - 20.9 | 3/3 |
| 390 | *Aspergillus* | *Saprophyte* | 16.1 - 18.0 | 3/3 |
| | | | Total | 206/207 |
| | | | Repeatability | 99.5% |

FIG. 22

Table 14.1

| Task | DNA Extraction | Screen PCR |
|---|---|---|
| # Performed | 13 | 15 |
| # of Operators | 4 | 2 |
| Over # of days | 48 | 22 |
| # of Reagent Lots | 2 | 2 |
| # of Primer Lots | N/A | 1 |
| CTL Status | N/A | 100% pass |
| # of Platforms | N/A | 2 |

Table 14.2

| Task | DNA Extraction | Sap Screen PCR |
|---|---|---|
| # Performed | 51 | 63 |
| # of Operators | 5 | 2 |
| Over # of days | 120 | 68 |
| # of Reagent Lots | 1 | 4 |
| # of Primer Lots | N/A | 2 |
| CTL Status | N/A | 100% pass |
| # of Platforms | 2 | 8 (6 PCR, 2 Set-Up) |

FIG. 23A

Table 15.1

| Culture + | Histology + | Histology - | Total |
|---|---|---|---|
| *Candida* | 17 (5.56%) | 5 (4.85%) | 22 |
| Dermatophyte | 67 (21.9%) | 1 (0.97%) | 68 |
| Saprophyte | 70 (22.9%) | 6 (5.83%) | 76 |
| Sap X2 | 16 (5.23%) | 5 (4.85%) | 21 |
| Negative | 136 (44.4%) | 86 (83.5%) | 222 |
| Total | 306 | 103 | 409 |

| PCR+ | Histology + | Histology - | Total |
|---|---|---|---|
| *Candida* | 14 (4.58%) | 7 (6.80%) | 21 |
| Dermatophyte | 185 (60.5%) | 13 (12.6%) | 198 |
| Saprophyte | 35 (11.4%) | 8 (7.77%) | 43 |
| Sap X2 | 5 (1.63%) | 2 (1.94%) | 7 |
| Negative | 67 (21.9%) | 73 (70.9%) | 140 |
| Total | 306 | 103 | 409 |

FIG. 23B

Table 15.2

| Culture + | Histology + | Histology - | Total |
|---|---|---|---|
| *Candida* | 17 (5.56%) | 5 (4.85%) | 22 |
| Dermatophyte | 67 (21.9%) | 1 (0.97%) | 68 |
| Saprophyte | 70 (22.9%) | 6 (5.83%) | 76 |
| Sap X2 | 16 (5.23%) | 5 (4.85%) | 21 |
| Negative | 136 (44.4%) | 86 (83.5%) | 222 |
| Total | 306 | 103 | 409 |

Table 15.3

| Histopathology | PCR + | PCR - | Total |
|---|---|---|---|
| Florid + | 513 (33.4 %) | 33 (2.7 %) | 546 (19.9%) |
| Moderate + | 520 (33.8 %) | 78 (6.3 %) | 598 (21.8%) |
| Minimal + | 208 (13.5 %) | 116 (9.4 %) | 324 (11.8%) |
| Rare + | 225 (14.6 %) | 288 (23.4 %) | 513 (17.9%) |
| Negative | 72 (4.7 %) | 715 (58.1 %) | 787 (28.6%) |
| Total | 1538 | 1230 | 2768 |

FIG. 24

Table 16

| PCR | Culture | | | | Total |
|---|---|---|---|---|---|
| | *Candida* | Dermatophyte | Saprophyte | Negative | |
| *Candida* | 26* | 1 | 3 | 7 | 37 |
| Dermatophyte | 7 | 59 | 43 | 89 | 198 |
| Saprophyte | 0 | 1 | 28 | 21 | 50 |
| Negative | 5 | 7 | 23 | 105 | 140 |
| Total | 38 | 68 | 97 | 222 | 425 |

*Includes 16 samples prepared by spiking *Candida* DNA into negative normal nails; these samples are not included in Histology Concordance results.

FIG. 25

Table 17

| | Culture + | Culture - | Total |
|---|---|---|---|
| PCR + | 26* | 11 | 37 |
| PCR - | 12 | 376 | 388 |
| Total | 38 | 387 | 425 |

| N = 425* | |
|---|---|
| Concordance | 94.6% |
| Sensitivity | 68.4% |
| Specificity | 97.2% |

Table 18:

| | Culture + | Culture - | Total |
|---|---|---|---|
| PCR + | 59 | 139 | 198 |
| PCR - | 9 | 218 | 227 |
| Total | 68 | 357 | 425 |

| N = 425* | |
|---|---|
| Concordance | 65.2% |
| Sensitivity | 86.8% |
| Specificity | 61.1% |

Table 19:

| | Culture + | Culture - | Total |
|---|---|---|---|
| PCR + | 28 | 22 | 50 |
| PCR - | 69 | 306 | 375 |
| Total | 97 | 328 | 425 |

| N = 425* | |
|---|---|
| Concordance | 78.6% |
| Sensitivity | 28.9% |
| Specificity | 93.3% |

*Includes 16 samples prepared by spiking *Candida* DNA into negative normal nails

FIG.26

Table 20

| PCR | Sequencing-Concordant *Candida* | Dermatophyte | Saprophyte | Negative | Total |
|---|---|---|---|---|---|
| *Candida* | 1 | 0 | 0 | 0 | 1 |
| Dermatophyte | 0 | 11 | 0 | 0 | 11 |
| Saprophyte | 0 | 0 | 1 | 0 | 1 |
| Negative | 0 | 1 | 0 | 16 | 17 |
| Total | 1 | 12 | 1 | 16 | 30 |

Table 21

| PCR | Sequencing-Discordant *Candida* | Dermatophyte | Saprophyte | Negative | Total |
|---|---|---|---|---|---|
| *Candida* | 4 | 0 | 1* | 0 | 5 |
| Dermatophyte | 1 | 127 | 1* | 0 | 129 |
| Saprophyte | 0 | 0 | 13 | 0 | 13 |
| Negative | 0 | 5 | 1 | 10 | 16 |
| Total | 5 | 132 | 16 | 10 | 163 |

*Sequence result = Fusarium

FIG. 27

Table 22

| | Seq. + | Seq. - | Total |
|---|---|---|---|
| PCR + | 5 | 1 | 6 |
| PCR - | 1 | 186 | 187 |
| Total | 6 | 187 | 193 |

| N = 193 | |
|---|---|
| Concordance | 99.0% |
| Sensitivity | 83.3% |
| Specificity | 99.5% |

Table 23

| | Seq. + | Seq. - | Total |
|---|---|---|---|
| PCR + | 138 | 2 | 140 |
| PCR - | 6 | 47 | 53 |
| Total | 144 | 49 | 193 |

| N = 193 | |
|---|---|
| Concordance | 95.9% |
| Sensitivity | 95.8% |
| Specificity | 95.9% |

Table 24

| | Seq. + | Seq. - | Total |
|---|---|---|---|
| PCR + | 14 | 0 | 14 |
| PCR - | 3 | 176 | 179 |
| Total | 17 | 176 | 193 |

| N = 193 | |
|---|---|
| Concordance | 98.5% |
| Sensitivity | 82.4% |
| Specificity | 100% |

SEQ ID NO:68

FIG. 30

Table 26

| Organism | Source | N | DNA (ng) Range Per reaction | Category | C alb | C parap |
|---|---|---|---|---|---|---|
| *C. albicans* | In-House Culture | 2 | 4.0 - 0.4 | *Candida* | Pos | ND |
| *C. parapsilosis* | In-House Culture | 2 | 4.0 - 0.4 | *Candida* | ND | Pos |
| *C. parapsilosis* | ATCC #22019D-5 | 1 | CLT = 0.02 | *Candida* | ND | Pos |
| *C. dubliniensis* | In-House Culture | 1 | 1.0 - 0.1 | *Candida* | ND | ND |
| *C. kruseii* | In-House Culture | 2 | 3.51 - 0.035 | *Candida* | ND | ND |
| *C. glabrata* | In-House Culture | 2 | 20 | *Candida* | ND | ND |
| *C. guilliermondii* | In-House Culture | 2 | 20 | *Candida* | ND | ND |
| *C. haemulonii* | In-House Culture | 2 | 17 - 20 | *Candida* | ND | ND |
| *C. lusitaniae* | In-House Culture | 2 | 20 | *Candida* | ND | ND |
| *C. troplicalis* | In-House culture | 1 | 1.0 - 0.1 | *Candida* | ND | ND |
| *M. pachydermatis* | In-House Culture | 2 | 14 - 20 | *Yeast* | ND | ND |
| *Acremonium* | In-House Culture | 2 | 4.0 - 0.4 | Saprophyte | ND | ND |
| *Alternaria* | In-House Culture | 2 | 4.0 - 0.4 | Saprophyte | ND | ND |
| *Aspergillus* | In-House Culture | 2 | 4.0 - 0.4 | Saprophyte | ND | ND |
| *A flavus* | ATCC #204304D-2 | 1 | CTL = 0.035 | Saprophyte | ND | ND |
| *Curvularia* | In-House Culture | 2 | 4.0 - 0.4 | Saprophyte | ND | ND |
| *Fusarium* | In-House Culture | 2 | 4.0 - 0.4 | Saprophyte | ND | ND |
| *Mucor* | In-House Culture | 1 | 4.0 - 0.4 | Saprophyte | ND | ND |
| *Paecilomyces* | In-House Culture | 1 | 4.0 - 0.4 | Saprophyte | ND | ND |
| *Penicillium* | In-House Culture | 1 | 4.0 - 0.4 | Saprophyte | ND | ND |
| *Epidermophyton* | In-House Culture | 1 | 0.75 | Dermatophyte | ND | ND |
| *Microsporum* | In-House Culture | 1 | 1.1 | Dermatophyte | ND | ND |
| *T. mentagrophytes** | ATCC #9533D-2 | 1 | CTL = 0.004 | Dermatophyte | ND | ND |
| *T. interdigitale** | In-House Culture | 1 | 10.0 - 0.004 | Dermatophyte | ND | ND |
| *T. rubrum* | In-House Culture | 2 | 4.0 - 0.4 | Dermatophyte | ND | ND |

C alb: *C. albicans* C parap: *C. parapsilosis*
N: # of individual cultures per organism
Pos: Positive; ND: not detected

FIG. 31

Table 27

| Run ID | Sample ID | PCR Raw Data | PCR Result | |
|---|---|---|---|---|
| | | Ct | C alb | C parap |
| 2015-01-06-MD01-VAL01CAN | RB | Und | Neg | Neg |
| 2015-01-06-MD01-VAL01CAN | RB | Und | Neg | Neg |
| 2015-02-12-AH-01-VAL07CAN | RB | Und | Neg | Neg |
| 2015-02-12-AH-01-VAL07CAN | RB-C09 | Und | Neg | Neg |
| 2015-02-12-AH-01-VAL07CAN | RB-C10 | Und | Neg | Neg |
| 2015-02-12-AH-01-VAL07CAN | RB-C11 | Und | Neg | Neg |
| 2015-02-12-AH-01-VAL07CAN | RB-C12 | Und | Neg | Neg |
| 2015-02-12-AH-01-VAL07CAN | RB-C12 | Und | Neg | Neg |

C alb: *C. albicans* C parap: *C. parapsilosis*
Und: Undetermined (No amplification before Cycle 36)

Table 28

| Run ID | Sample ID | PCR Raw Data | | PCR Result | |
|---|---|---|---|---|---|
| | | Ct | Tm1 | C alb | C parap |
| 2015-01-06-MD01-VAL01CAN | NTC | Und | 71.2 | Neg | Neg |
| 2015-01-06-MD02-VAL02CAN | NTC | Und | 71.2 | Neg | Neg |
| 2015-01-22-MD02-VAL02CAN | NTC | Und | 71.3 | Neg | Neg |
| 2015-02-03-MD02-VAL03CAN | NTC | Und | 71.5 | Neg | Neg |
| 2015-02-03-MD-VAL04CAN | NTC | Und | 71.4 | Neg | Neg |
| 2015-02-05-MD02-VAL05CAN | NTC | Und | 71.7 | Neg | Neg |
| 2015-02-05-MD02-VAL06CAN | NTC | Und | 71.9 | Neg | Neg |
| 2015-02-12-AH-01-VAL07CAN | NTC | 35.7 | 71.5 | Neg | Neg |
| 2015-02-12-AH-02-VAL08CAN | NTC | Und | 71.6 | Neg | Neg |
| 2015-02-25-LB-01-VAL10CAN | NTC | Und | 71.1 | Neg | Neg |
| 2015-02-25-LB-02 VAL09CAN | NTC | Und | 71.5 | Neg | Neg |
| 2015-03-03-MD01-VAL12CAN | NTC | Und | 71.5 | Neg | Neg |
| 2015-03-03-MD02-VAL11CAN | NTC | Und | 71.5 | Neg | Neg |
| 2015-03-04-MD01-VAL13CAN | NTC | Und | 71.9 | Neg | Neg |
| 2015-03-04-MD02-VAL14CAN | NTC | Und | 71.5 | Neg | Neg |

FIG. 32

Table 29

| Bacteria ID | Copy Number | Bacterial DNA only | | Bacterial DNA + *C. albicans* | | Bacterial DNA + *C. parapsilosis* | |
|---|---|---|---|---|---|---|---|
| | | C alb | C parap | C alb | C parap | C alb | C parap |
| *P aeruiginosa* | 1.3 x $10^4$ | ND | ND | Pos | ND | ND | Pos |
| *P aeruiginosa* | 1.3 x $10^5$ | ND | ND | Pos | ND | ND | Pos |
| *P mirabilus* | 2.3 x $10^3$ | ND | ND | Pos | ND | ND | Pos |
| *P mirabilus* | 2.3 x $10^4$ | ND | ND | Pos | ND | ND | Pos |
| *S aureus* | 1.1 x $10^4$ | ND | ND | *Pos | ND | ND | Pos |
| *S aureus* | 1.1 x $10^5$ | ND | ND | *Pos | ND | ND | Pos |
| *S marcescens* | 6.4 x $10^3$ | ND | ND | *Pos | ND | ND | Pos |
| *S marcescens* | 6.4 x $10^4$ | ND | ND | *Pos | ND | ND | Pos |
| *S pyogenes* | 4.9 x $10^3$ | ND | ND | Pos | ND | ND | Pos |
| *S pyogenes* | 4.9 x $10^4$ | ND | ND | Pos | ND | ND | Pos |

C alb: *C. albicans* C parap: *C. parapsilosis*
Pos: Positive; ND: not detected
*Tested in triplicate Table 30

| hgDNA Quantity | Copy Number | hgDNA only | | hgDNA + *C. albicans* DNA | | hgDNA + *C. parapsilosis* DNA | |
|---|---|---|---|---|---|---|---|
| | | C alb | C parap | C alb | C parap | C alb | C parap |
| 0.5 ng | ~80 | ND | ND | Pos | ND | ND | Pos |
| 1.0 ng | ~160 | ND | ND | Pos | ND | ND | Pos |
| 2.0 ng | ~320 | ND | ND | Pos | ND | ND | Pos |

C alb: *C. albicans* C parap: *C. parapsilosis*
Pos: Positive; ND: not detected

FIG. 33

Table 31.1

| Organism | ng per PCR reaction: shown is # positive of total tested at indicated DNA quantity | | | | | | | LOD | Copy # |
|---|---|---|---|---|---|---|---|---|---|
| | 10.0 | 4.00 | 0.40 | 0.10 | 0.02 | 0.01 | 0.004 | | |
| *C. albicans* | 6/6 | 6/6 | 6/6 | 6/6 | 10/10 | 9/11 | 2/6 | **0.02** | **540** |
| *C. parapsilosis* | 5/5 | 11/11 | 9/9 | 11/11 | 12/12 | 9/9 | 7/7 | **0.004** | **150** |

Table 31.2

| Organism | CFU (ng DNA) / Extraction | | | | | | | | | LOD |
|---|---|---|---|---|---|---|---|---|---|---|
| | 357143 (10.00) | 142857 (4.00) | 35714 (1.00) | 14286 (0.40) | 3571 (0.10) | 714 (0.02) | 357 (0.01) | 179 (0.005) | 71 (0.002) | CFU (ng)/ ext'n |
| *C. albicans* | 10/10<br>20.5 - 24.6 | 10/10<br>22.3 - 28.9 | 10/10<br>25.0 - 25.8 | 10/10<br>26.0 - 27.7 | **10/10**<br>28.7- 30.3 | 9/15<br>31.1 - <36 | 0/10<br>35.1 - >36 | 0/10<br>35.4 - >36 | 0/10<br>35.6 - >36 | **3571 (0.10)** |
| *C. parapsilosis* | 5/5<br>15.6 - 17.1 | 5/5<br>18.5 - 19.7 | 10/10<br>21.2 - 26.6 | 10/10<br>24.7 - 27.3 | **10/10**<br>25.9- 29.7 | 9/10<br>30.7 - >36 | 5/10<br>30.7 - >36 | 5/10<br>30.7 - >36 | 0/10<br>33.3 - >36 | **3571 (0.10)** |

positive of total tested at indicated DNA quantity is shown. Ct range is shown below # positive.

FIG. 34

Table 32

| Run ID | Sample ID | PCR Raw Data | | PCR Result | |
|---|---|---|---|---|---|
| | | Ct | Tm1 | C alb | C parap |
| 2015-01-06-MD01-VAL01CAN | CAN2 CTL | 26.9* | 73.0 | Pos | Neg |
| 2015-01-06-MD02-VAL02CAN | CAN2 CTL | 26.9* | 73.0 | Pos | Neg |
| 2015-02-05-MD02-VAL05CAN | CAN2 CTL | 22.8 | 73.3 | Pos | Neg |
| 2015-02-05-MD02-VAL06CAN | CAN2 CTL | 22.9 | 73.3 | Pos | Neg |
| 2015-02-12-AH-01-VAL07CAN | CAN2 CTL | 23.0 | 73.1 | Pos | Neg |
| 2015-02-12-AH-02-VAL08CAN | CAN2 CTL | 23.4 | 73.0 | Pos | Neg |
| 2015-02-25-LB-01-VAL09CAN | CAN2 CTL | 22.8 | 73.4 | Pos | Neg |
| 2015-02-25-LB-02 VAL10CAN | CAN2 CTL | 23.3 | 73.0 | Pos | Neg |
| 2015-03-03-MD01-VAL11CAN | CAN2 CTL | 23.2 | 73.1 | Pos | Neg |
| 2015-03-03-MD01-VAL11CAN | CAN2 CTL | 23.3 | 73.1 | Pos | Neg |
| 2015-03-03-MD02-VAL12CAN | CAN2 CTL | 24.0 | 73.1 | Pos | Neg |
| 2015-03-04-MD01-VAL13CAN | CAN2 CTL | 23.5 | 73.0 | Pos | Neg |
| 2015-03-04-MD02-VAL14CAN | CAN2 CTL | 23.0 | 73.1 | Pos | Neg |
| | Average | 23.8 | 73.1 | | |
| | StdDev | 1.44 | 0.15 | | |
| | CV (%) | 6.03%* | 0.20% | | |
| | Min | 22.8 | 73.0 | | |
| | Max | 26.9* | 73.4 | | |

C alb: *C. albicans* C parap: *C. parapsilosis*

Und: Undetermined (No amplification before Cycle 36)

*Ct values were higher for VAL01 and VAL02. The working stock prepared and used after on subsequent runs was a higher concentration of DNA. Statistics without VAL01 & VAL02: Mean: 23.2; StdDev: 0.35; CV%: 1.5%; Min: 22.8; Max: 24.0

FIG. 35

Table 33

| Run ID | Sample ID | PCR Raw Data | | PCR Result | |
|---|---|---|---|---|---|
| | | Ct | Tm1 | C alb | C parap |
| 2015-01-06-MD01-VAL01CAN | CAN1 CTL | 25.5 | 69.9 | Neg | Pos |
| 2015-01-06-MD02-VAL02CAN | CAN1 CTL | 24.8 | 70.1 | Neg | Pos |
| 2015-01-22-MD02-VAL02aCAN | CAN1 CTL | 24.9 | 70.6 | Neg | Pos |
| 2015-02-03-MD02-VAL03CAN | CAN1 CTL | 22.5 | 70.4 | Neg | Pos |
| 2015-02-03-MD01-VAL04CAN | CAN1 CTL | 22.7 | 70.5 | Neg | Pos |
| 2015-02-05-MD02-VAL05CAN | CAN1 CTL | 22.9 | 70.5 | Neg | Pos |
| 2015-02-05-MD02-VAL06CAN | CAN1 CTL | 22.8 | 70.5 | Neg | Pos |
| 2015-02-12-AH-01-VAL07CAN | CAN1 CTL | 23.3 | 70.2 | Neg | Pos |
| 2015-02-12-AH-02-VAL08CAN | CAN1 CTL | 23.3 | 70.1 | Neg | Pos |
| 2015-02-25-LB-01-VAL09CAN | CAN1 CTL | 24.0 | 70.8 | Neg | Pos |
| 2015-02-25-LB-02 VAL10CAN | CAN1 CTL | 24.5 | 70.5 | Neg | Pos |
| 2015-03-03-MD01-VAL11CAN | CAN1 CTL | 23.7 | 70.6 | Neg | Pos |
| 2015-03-03-MD02-VAL12CAN | CAN1 CTL | 24.5 | 70.1 | Neg | Pos |
| 2015-03-04-MD01-VAL13CAN | CAN1 CTL | 24.1 | 70.3 | Neg | Pos |
| 2015-03-04-MD02-VAL14CAN | CAN1 CTL | 23.7 | 70.5 | Neg | Pos |
| | Average | 23.8 | 70.4 | | |
| | StdDev | 0.91 | 0.23 | | |
| | CV (%) | 3.83% | 0.32% | | |
| | Min | 22.5 | 69.9 | | |
| | Max | 25.5 | 70.8 | | |

C alb: *C. albicans* C parap: *C. parapsilosis*
Und: Undetermined (No amplification before Cycle 36)

FIG. 36

Table 34

| Sample | Reference | *PCR result* | Replicates |
|---|---|---|---|
| C alb5.0 | *C. albicans* | *C. albicans* | 4 |
| C alb2.0 | *C. albicans* | *C. albicans* | 4 |
| C alb1 | *C. albicans* | *C. albicans* | 3 |
| C alb2 | *C. albicans* | *C. albicans* | 3 |
| C para5.0 | *C. parapsilosis* | *C. parapsilosis* | 4 |
| C para2.0 | *C. parapsilosis* | *C. parapsilosis* | 4 |
| C parap1 | *C. parapsilosis* | *C. parapsilosis* | 3 |
| C para2p | *C. parapsilosis* | *C. parapsilosis* | 3 |

FIG. 37

Table 35

| Extraction | | Date | Instrument # | Run ID | By* | CTL Results | |
|---|---|---|---|---|---|---|---|
| Date | By* | | | | | C alb | C parap |
| 12-NOV-2014<br>17-NOV-2014<br>18-NOV-2014 | AH<br>MD<br>MD | 06-Jan-2015 | 01 | VAL01CAN | MD | PASS | PASS |
| 12-NOV-2014<br>13-NOV-2014 | AH<br>MD | 06-Jan-2015 | 02 | VAL02CAN | MD | PASS | PASS |
| 22-JAN-2015 | AH | 22-Jan-2015 | 02 | VAL02aCAN | MD | N/A | PASS |
| N/A | N/A | 03-Feb-2015 | 02 | VAL03CAN | MD | N/A | PASS |
| N/A | N/A | 03-Feb-2015 | 02 | VAL04CAN | MD | N/A | PASS |
| N/A | N/A | 05-Feb-2015 | 02 | VAL05CAN | MD | PASS | PASS |
| 06-FEB-2016 | AH | 09-Feb-2015 | 02 | VAL06CAN | MD | PASS | PASS |
| 20-OCT-2014<br>31-OCT-2014<br>03-NOV-2014<br>12-NOV-2014<br>10-FEB-2015 | LP<br>AH<br>MD<br>AH<br>MD | 12-Feb-2015 | 01 | VAL07CAN | AH | PASS | PASS |
| 07-OCT-2014<br>09-OCT-2014<br>20-OCT-2014<br>21-OCT-2014<br>12-NOV-2014<br>13-NOV-2014<br>18-NOV-2014<br>11-FEB-2015 | LB<br>LB<br>LP<br>LB<br>AH<br>MD<br>MD<br>MD | 12-Feb-2015 | 02 | VAL08CAN | AH | PASS | PASS |
| N/A | N/A | 25-Feb-2015 | 02 | VAL09CAN | LB | PASS | PASS |
| N/A | N/A | 25-Feb-2015 | 01 | VAL10CAN | LB | PASS | PASS |
| N/A | N/A | 03-Mar-2015 | 02 | VAL11CAN | MD | PASS | PASS |
| N/A | N/A | 03-Mar-2015 | 01 | VAL12CAN | MD | PASS | PASS |
| N/A | N/A | 04-Mar-2015 | 01 | VAL13CAN | MD | PASS | PASS |
| N/A | N/A | 04-Mar-2015 | 02 | VAL14CAN | MD | PASS | PASS |

*Initials of analyst performing either Extraction or PCR for the indicated run
N/A: no nail specimens were included in the run (DNA from culture only)

FIG. 38

Table 36

| | *Candida* Screen + | *Candida* Screen - | Total |
|---|---|---|---|
| *Candida* PCR + | 67 | 3 | 70 |
| *Candida* PCR - | 2 | 172 | 174 |
| Total | 69 | 175 | 244 |

| N = 244 | |
|---|---|
| Concordance | 98.0% |
| Sensitivity | 97.1% |
| Specificity | 98.3% |

Table 37

| | *C. albicans* Sequencing + | *C. albicans* Sequencing - | Total |
|---|---|---|---|
| *C. albicans* ID by PCR + | 30 | 0 | 30 |
| *C. albicans* ID by PCR - | 0 | 38 | 38 |
| Total | 30 | 38 | 68 |

| N = 68 | |
|---|---|
| Concordance | 100% |
| Sensitivity | 100% |
| Specificity | 100% |

Table 38

| | *C. parapsilosis* Sequencing + | *C. parapsilosis* Sequencing - | Total |
|---|---|---|---|
| *C. parapsilosis* ID by PCR + | 37 | 0 | 37 |
| *C. parapsilosis* ID by PCR - | 1 | 30 | 31 |
| Total | 38 | 30 | 68 |

| N = 68 | |
|---|---|
| Concordance | 98.5% |
| Sensitivity | 97.4% |
| Specificity | 100% |

FIG. 39

Example report A

| | | |
|---|---|---|
| *Candida* genus: | Not Identified | |
| Dermatophytic fungi: | Not Identified | |
| Saprophytic fungi: | Not Identified | |

Example report B

| | | |
|---|---|---|
| *Candida* genus: | DETECTED | |
| *C. albicans* | | DETECTED |
| *C. parapsilosis* | | Not Identified |
| Dermatophytic fungi: | Not Identified | |
| Saprophytic fungi: | Not Identified | |

Example report C

| | | |
|---|---|---|
| *Candida* genus: | DETECTED | |
| *C. albicans* | | Not Identified |
| *C. parapsilosis* | | DETECTED |
| Dermatophytic fungi: | Not Identified | |
| Saprophytic fungi: | Not Identified | |

FIG. 43

Table 40

| **Organism** | **Source** | **N** | **DNA (ng) Range Per reaction** | **Category** | **Tr m** | **Tr r** | **Epi** | **Mic** |
|---|---|---|---|---|---|---|---|---|
| *C albicans* | In-House Culture | 2 | 4.0 - 0.4 | *Candida* | ND | ND | ND | ND |
| *C parapsilosis* | In-House Culture | 2 | 4.0 - 0.4 | *Candida* | ND | ND | ND | ND |
| *C parapsilosis* | ATCC #22019D-5 | 1 | CLT = 0.02 | *Candida* | ND | ND | ND | ND |
| Cross reactivity of *Candida* organisms not seen with Dermatophyte Identification primers | | | | | | | | |
| *Acremonium* | In-House Culture | 2 | 4.0 - 0.1 | Saprophyte | ND | ND | ND | ND |
| *Alternaria* | In-House Culture | 2 | 4.0 - 0.1 | Saprophyte | ND | ND | ND | ND |
| *Aspergillus* | In-House Culture | 2 | 4.0 - 0.1 | Saprophyte | ND | ND | ND | ND |
| *A flavus* | ATCC #204304D-2 | 1 | CTL = 0.035 | Saprophyte | ND | ND | ND | ND |
| *Curvularia* | In-House Culture | 2 | 4.0 - 0.4 | Saprophyte | ND | ND | ND | ND |
| *Fusarium* | In-House Culture | 2 | 4.0 - 0.4 | Saprophyte | ND | ND | ND | ND |
| *Mucor* | In-House Culture | 1 | 4.0 - 0.4 | Saprophyte | ND | ND | ND | ND |
| *Paecilomyces* | In-House Culture | 2 | 4.0 - 0.4 | Saprophyte | ND | ND | ND | ND |
| *Penicillium* | In-House Culture | 1 | 4.0 - 0.4 | Saprophyte | ND | ND | ND | ND |
| Cross reactivity of *saprophyte* organisms not seen with Dermatophyte Identification primers | | | | | | | | |
| *Epidermophyton* | gBlock DNA | 1 | $10^{-4}$ - $10^{-7}$ | Dermatophyte | ND | ND | Pos | ND |
| *Microsporum* | In-House Culture | 1 | 1.1 | Dermatophyte | ND | ND | ND | Pos |
| *Microsporum* | In-House Amplicon | 2 | 0.1 | Dermatophyte | ND | ND | ND | Pos |
| *T. mentagrophytes** | ATCC #9533D-2 | 1 | CTL = 0.004 | Dermatophyte | Pos | ND | ND | ND |
| *T interdigitale** | In-House Culture | 1 | 10.0 - 0.004 | Dermatophyte | Pos | ND | ND | ND |
| *T. rubrum* | In-House Culture | 1 | 10.0 - 0.01 | Dermatophyte | ND | Pos | ND | ND |
| *T. verrucosum* | gBlock DNA | 1 | 1:$10^3$ - 1:$10^7$ | Dermatophyte | Pos* | ND | ND | ND |
| *T. tonsurans* | ATCC #56186 | 1 | 2.0 – 0.02 | Dermatophyte | Pos* | ND | ND | ND |
| *T. violaceum* | gBlock DNA | 1 | 1:$10^3$ - 1:$10^7$ | Dermatophyte | ND | Pos* | ND | ND |
| Seven dermatophytes detected with the Dermatophyte Identification primers. *Cross reactive at high concentrations. | | | | | | | | |

FIG. 44

Table 41

| Run ID | Sample ID | PCR Raw Data | PCR Result | | | |
|---|---|---|---|---|---|---|
| | | Ct | Tr m | Tr r | Epi | Mic |
| 2014-12-04-MD01-VAL01DERM | RB | Und | Neg | Neg | Neg | Neg |
| 2014-12-04-MD01-VAL01DERM | RB | Und | Neg | Neg | Neg | Neg |
| 2015-02-09-MD01-Val09DERM | RB | 35.5 | Neg | Neg | Neg | Neg |
| 2015-02-09-MD01-Val09DERM | RB | 35.5 | Neg | Neg | Neg | Neg |
| 2015-02-09-MD01-Val09DERM | RB | Und | Neg | Neg | Neg | Neg |
| 2015-02-09-MD01-Val09DERM | RB2 | 34.1 | Neg | Neg | Neg | Neg |
| 2015-02-09-MD01-Val10DERM | RB1 | 35.9 | Neg | Neg | Neg | Neg |
| 2015-02-10-MD02-Val11DERM | RB | Und | Neg | Neg | Neg | Neg |
| 2015-02-12-AH-02-Val14Derm | RB1 | Und | Neg | Neg | Neg | Neg |
| 2015-02-12-AH-02-Val14Derm | RB2 | Und | Neg | Neg | Neg | Neg |
| 2015-02-13-MD02-Val15DERM | RB1 | Und | Neg | Neg | Neg | Neg |
| 2015-02-13-MD02-Val15DERM | RB2 | Und | Neg | Neg | Neg | Neg |
| 2015-03-11-AH02-VAL20DERM | RB1 | Und | Neg | Neg | Neg | Neg |
| 2015-03-11-AH02-VAL20DERM | RB2 | Und | Neg | Neg | Neg | Neg |

Tr m: *T. mentagrophytes* Tr r: *T. rubrum* Epi: *Epidermophyton* Mic: *Microsporum*
Und: Undetermined (No amplification before Cycle 36)

FIG. 45

Table 42

| Run ID | Sample ID | PCR Raw Data | | PCR Result | | | |
|---|---|---|---|---|---|---|---|
| | | Ct | Tm1 | Tr m | Tr r | Epi | Mic |
| 2014-12-04-MD01-VAL01DERM | NTC | Und | 71.2 | Neg | Neg | Neg | Neg |
| 014-12-04-MD02-VAL02DERM | NTC | Und | 71.3 | Neg | Neg | Neg | Neg |
| -MD02 DERM gBlock Tests | NTC | Und | 69.1 | Neg | Neg | Neg | Neg |
| 2015-02-03-MD02-VAL03DERM | NTC | Und | 71.3 | Neg | Neg | Neg | Neg |
| 2015-01-23-MD01-VAL04DERM | NTC | Und | 71.3 | Neg | Neg | Neg | Neg |
| 2015-02-04-MD01-VAL05DERM | NTC | Und | 71.1 | Neg | Neg | Neg | Neg |
| 2015-02-04-MD02-VAL06DERM | NTC | Und | 71.1 | Neg | Neg | Neg | Neg |
| 2015-02-05-MD01-VAL07DERM | NTC | Und | 72.0 | Neg | Neg | Neg | Neg |
| 2015-02-05-MD01-VAL08DERM | NTC | Und | 71.9 | Neg | Neg | Neg | Neg |
| 2015-02-09-MD01-VAL09DERM | NTC | Und | 71.2 | Neg | Neg | Neg | Neg |
| 2015-02-09-MD01-VAL10DERM | NTC | Und | 71.2 | Neg | Neg | Neg | Neg |
| 2015-02-10-MD02-VAL11DERM | NTC | Und | 71.0 | Neg | Neg | Neg | Neg |
| 2015-02-11-AH-02-VAL12DERM | NTC | Und | 71.2 | Neg | Neg | Neg | Neg |
| 2015-02-11-AH-01-VAL13DERM | NTC | Und | 67.8 | Neg | Neg | Neg | Neg |
| 2015-02-12-AH-02-VAL14DERM | NTC | 35.5 | 71.4 | Neg | Neg | Neg | Neg |
| 2015-02-13-MD02-VAL15DERM | NTC | Und | 71.5 | Neg | Neg | Neg | Neg |
| 2015-03-09-MD01-VAL16DERM | NTC | Und | 71.5 | Neg | Neg | Neg | Neg |
| 2015-03-10-LB01-VAL17DERM | NTC | 35.7 | 71.1 | Neg | Neg | Neg | Neg |
| 2015-03-11-MD02-VAL18DERM | NTC | Und | 72.5 | Neg | Neg | Neg | Neg |
| 2015-03-11-MD02-VAL19DERM | NTC | Und | 71.6 | Neg | Neg | Neg | Neg |
| 2015-03-11-AH02-VAL20DERM | NTC | Und | 71.3 | Neg | Neg | Neg | Neg |

Tr m: *T. mentagrophytes* Tr r: *T. rubrum* Epi: *Epidermophyton* Mic: *Microsporum*
Und: Undetermined (No amplification before Cycle 36)

FIG. 46

Table 43

| Bacteria | Copy Number | Bacterial DNA only | | | | Bacterial DNA + *T. mentagrophytes* DNA | | | | Bacterial DNA + *T. rubrum* DNA | | | | Bacterial DNA + *Epidermophyton* DNA | | | | Bacterial DNA + *Microsporum* DNA | | | |
|---|---|---|---|---|---|---|---|---|---|---|---|---|---|---|---|---|---|---|---|---|---|
| | | Tr m | Tr r | Epi | Mic | Tr m | Tr r | Epi | Mic | Tr m | Tr r | Epi | Mic | Tr m | Tr r | Epi | Mic | Tr m | Tr r | Epi | Mic |
| *P. aerug* | 1.3 x $10^4$ | ND | ND | ND | ND | Pos | ND | ND | ND | ND | Pos | ND | ND | ND | ND | Pos | ND | ND | ND | ND | Pos |
| *P. aerug* | 1.3 x $10^5$ | ND | ND | ND | ND | Pos | ND | ND | ND | ND | Pos | ND | ND | ND | ND | Pos | ND | ND | ND | ND | Pos |
| *P. mirabil* | 2.3 x $10^3$ | ND | ND | ND | ND | Pos | ND | ND | ND | ND | Pos | ND | ND | ND | ND | Pos | ND | ND | ND | ND | Pos |
| *P. mirabil* | 2.3 x $10^4$ | ND | ND | ND | ND | Pos | ND | ND | ND | ND | Pos | ND | ND | ND | ND | Pos | ND | ND | ND | ND | Pos |
| *S. aureus* | 1.1 x $10^4$ | ND | ND | ND | ND | Pos | ND | ND | ND | ND | Pos | ND | ND | ND | ND | Pos | ND | ND | ND | ND | Pos |
| *S. aureus* | 1.1 x $10^5$ | ND | ND | ND | ND | Pos | ND | ND | ND | ND | Pos | ND | ND | ND | ND | Pos | ND | ND | ND | ND | Pos |
| *S. marcen* | 6.4 x $10^3$ | ND | ND | ND | ND | Pos | ND | ND | ND | ND | Pos | ND | ND | ND | ND | Pos | ND | ND | ND | ND | Pos |
| *S. marcen* | 6.4 x $10^4$ | ND | ND | ND | ND | Pos | ND | ND | ND | ND | Pos | ND | ND | ND | ND | Pos | ND | ND | ND | ND | Pos |
| *S. pyog* | 4.9 x $10^3$ | ND | ND | ND | ND | Pos | ND | ND | ND | ND | Pos | ND | ND | ND | ND | Pos | ND | ND | ND | ND | Pos |
| *S. pyog* | 4.9 x $10^4$ | ND | ND | ND | ND | Pos | ND | ND | ND | ND | Pos | ND | ND | ND | ND | Pos | ND | ND | ND | ND | Pos |

Tr m: *T. mentagrophytes* Tr r: *T. rubrum* Epi: *Epidermophyton* Mic: *Microsporum*

Pos: Positive; ND: not detected

FIG. 47

Table 44

| hgDNA | Copy Number | hgDNA only | | | | hgDNA + *T. mentagrophytes* DNA | | | | hgDNA + *T. rubrum* DNA | | | | hgDNA + *Epidermophyton* DNA | | | | hgDNA + *Microsporum* DNA | | | |
|---|---|---|---|---|---|---|---|---|---|---|---|---|---|---|---|---|---|---|---|---|---|
| | | Tr m | Tr r | Epi | Mic | Tr m | Tr r | Epi | Mic | Tr m | Tr r | Epi | Mic | Tr m | Tr r | Epi | Mic | Tr m | Tr r | Epi | Mic |
| 0.5 ng | ~80 | ND | ND | ND | ND | Pos | ND | ND | ND | ND | Pos | ND | ND | ND | ND | Pos | ND | ND | ND | ND | Pos |
| 1.0 ng | ~160 | ND | ND | ND | ND | Pos | ND | ND | ND | ND | Pos | ND | ND | ND | ND | Pos | ND | ND | ND | ND | Pos |
| 2.0 ng | ~320 | ND | ND | ND | ND | Pos | ND | ND | ND | ND | Pos | ND | ND | ND | ND | Pos | ND | ND | ND | ND | Pos |

Tr m: *T. mentagrophytes* Tr r: *T. rubrum* Epi: *Epidermophyton* Mic: *Microsporum*

FIG. 48

Table 45.1

| Organism | ng per PCR reaction; shown is # positive of total tested at indicated DNA quantity | | | | | | | LOD | Copy # |
|---|---|---|---|---|---|---|---|---|---|
| | 10.0 | 4.00 | 0.40 | 0.10 | 0.02 | 0.01 | 0.004 | | |
| *T. mentagrophytes* | 6/6 | 5/5 | 7/7 | 5/5 | 5/5 | 11/11 | 9/11 | **0.01** | **280*** |
| *T. rubrum* | 6/6 | 6/6 | 8/8 | 6/6 | 10/10 | 10/10 | 4/6 | **0.01** | **280** |

| Organism | fg per PCR reaction; shown is # positive of total tested at indicated DNA quantity | | | | | | LOD | Copy # |
|---|---|---|---|---|---|---|---|---|
| | 40 | 4.0 | 1.6 | 0.4 | 0.16 | 0.04 | | |
| *Epidermophyton* | 6/6 | 6/6 | 6/6 | 10/10 | 7/14 | 0/14 | **0.4** | **1900** |

| Organism | fg per PCR reaction; shown is # positive of total tested at indicated DNA quantity | | | | | | LOD | Copy # |
|---|---|---|---|---|---|---|---|---|
| | 800 | 200 | 80 | 20 | 8 | 2 | | |
| *Microsporum* | 6/6 | 6/6 | 6/6 | 6/6 | 10/10 | 0/10 | **8** | **6500** |

* = genome size of *T. mentagrophytes* not published; presumed to be similar to sizes of 2 published species sizes: *T. rubrum* and *T verrucosum*

FIG. 49

Table 45.2

| Organism | ng per PCR reaction; shown is # positive of total tested , Ct range shown under # positive | | | | | | | | | | LOD (ng) | Copy # |
|---|---|---|---|---|---|---|---|---|---|---|---|---|
| | 4.0 | 0.4 | 0.1 | 0.02 | 0.01 | 0.004 | 0.001 | 0.0004 | 0.0001 | 0.00004 | | |
| *T. rubrum* Cutoff is 33.6 | | | 5/5 26.5 - 27.5 | 5/5 28.4 - 30.3 | 10/10 29.2 - 31.6 | 10/10 31.2 - 32.2 | 9/10 32.3 - 33.9 | 0/10 34.2 - >36 | 0/10 35.8 - >36 | | 0.004 | 67 |
| *T. mentagrophytes* Cutoff is 33.6 | 5/5 23.1 - 24.4 | 5/5 27.2 - 28.6 | 10/10 29.1 - 30.43 | 10/10 31.0 - 32.0 | 10/10 30.7 - 32.1 | 0/10 34.4 - >36 | 0/10 35.2 - >36 | 0/10 35.2 - >36 | | | 0.01 | 167* |
| *Epidermophyton* Cutoff is 31.5 | | | 5/5 26.0 - 26.3 | 5/5 27.1 - 27.9 | 5/5 28.2- 29.0 | 10/10 30.3 - 30.8 | 9/10 31.3 - 32.3 | 0/10 32.1 - 33.7 | | | 0.004 | 67* |
| *Microsporum* Cutoff is 33.6 | | | | 5/5 26.3 - 26.9 | 5/5 27.9 - 28.1 | 10/10 29.3 - 29.9 | 10/10 30.7 - 31.4 | 9/10 29.5 - 32.1 | 0/10 33.5 - 35.3 | 0/10 34.2 - 35.0 | 0.001 | 21 |

*used the avg value for 6 *Trichophyton* sp. C value determinations.

FIG. 50

Table 46

| Run ID | Sample ID | PCR Raw Data | | | PCR Result | | | |
|---|---|---|---|---|---|---|---|---|
| | | Ct | Tm1 | Tm2 | Tr m | Tr r | Epi | Mic |
| 2014-12-04-MD01-VAL01DERM | Derm1 CTL | 30.1* | 84.2 | 77.2 | Pos | Neg | Neg | Neg |
| 2014-12-04-MD02-VAL02DERM | Derm1 CTL | 28.7* | 84.6 | 77.4 | Pos | Neg | Neg | Neg |
| 2014-12-24-MD02 Derm gBlock Tests | Derm1 CTL | 26.8 | 84.7 | 77.8 | Pos | Neg | Neg | Neg |
| 2015-02-03-MD02-VAL03DERM | Derm1 CTL | 26.2 | 84.2 | 77.2 | Pos | Neg | Neg | Neg |
| 2015-01-23-MD01-VAL04DERM | Derm1 CTL | 28.7 | 84.0 | 77.2 | Pos | Neg | Neg | Neg |
| 2015-02-04-MD01-VAL05DERM | Derm1 CTL | 27.0 | 83.8 | 76.8 | Pos | Neg | Neg | Neg |
| 2015-02-04-MD02-VAL06DERM | Derm1 CTL | 26.5 | 84.2 | 77.2 | Pos | Neg | Neg | Neg |
| 2015-02-05-MD01-VAL07DERM | Derm1 CTL | 27.8 | 84.0 | 77.2 | Pos | Neg | Neg | Neg |
| 2015-02-05-MD01-VAL08DERM | Derm1 CTL | 27.0 | 84.1 | 77.1 | Pos | Neg | Neg | Neg |
| 2015-02-09-MD01-VAL09DERM | Derm1 CTL | 27.2 | 83.7 | 76.9 | Pos | Neg | Neg | Neg |
| 2015-02-09-MD01-VAL10DERM | Derm1 CTL | 27.1 | 83.8 | 77.0 | Pos | Neg | Neg | Neg |
| 2015-02-10-MD02-VAL11DERM | Derm1 CTL | 27.0 | 83.8 | 76.9 | Pos | Neg | Neg | Neg |
| 2015-02-11-AH-02-VAL12DERM | Derm1 CTL | 26.5 | 83.8 | 76.9 | Pos | Neg | Neg | Neg |
| 2015-02-11-AH-01-VAL13DERM | Derm1 CTL | 27.6 | 83.8 | 76.9 | Pos | Neg | Neg | Neg |
| 2015-02-12-AH-02-VAL14DERM | Derm1 CTL | 27.0 | 83.9 | 77.0 | Pos | Neg | Neg | Neg |
| 2015-02-13-MD02-VAL15DERM | Derm1 CTL | 27.8 | 84.0 | 77.1 | Pos | Neg | Neg | Neg |
| 2015-03-09-MD01-VAL16DERM | Derm1 CTL | 29.1 | 83.9 | 76.9 | Pos | Neg | Neg | Neg |
| 2015-03-10-LB01-VAL17DERM | Derm1 CTL | 28.7 | 83.7 | 76.7 | Pos | Neg | Neg | Neg |
| 2015-03-11-MD02-VAL18DERM | Derm1 CTL | 26.7 | 84.6 | 77.6 | Pos | Neg | Neg | Neg |
| 2015-03-11-MD02-VAL19DERM | Derm1 CTL | 27.5 | 84.3 | 77.2 | Pos | Neg | Neg | Neg |
| 2015-03-11-AH02-VAL20DERM | Derm1 CTL | 27.5 | 84.1 | 77.1 | Pos | Neg | Neg | Neg |
| | Average | 27.5 | 84.0 | 77.1 | | | | |
| | SD | 1.01 | 0.30 | 0.26 | | | | |
| | CV (%) | 3.65% | 0.35% | 0.34% | | | | |
| | Min | 26.2 | 83.7 | 76.7 | | | | |
| | Max | 30.1 | 84.7 | 77.8 | | | | |

Tr m: *T. mentagrophytes* Tr r: *T. rubrum* Epi: *Epidermophyton* Mic: *Microsporum*

*Ct values were higher for VAL01 and VAL02. The working stock prepared and for VAL03 (2014-12-24) and used on subsequent runs was a higher concentration of DNA.

FIG. 51

Table 47

| Run ID | Sample ID | PCR Raw Data | | | PCR Result | | | |
|---|---|---|---|---|---|---|---|---|
| | | Ct | Tm1 | Tm2 | Tr m | Tr r | Epi | Mic |
| 2014-12-04-MD01-VAL01DERM | Derm2 CTL | 22.3 | 87.5 | 77.8 | Neg | Pos | Neg | Neg |
| 2014-12-04-MD02-VAL02DERM | Derm2 CTL | 21.7 | 87.6 | 78.0 | Neg | Pos | Neg | Neg |
| 2014-12-24-MD02 Derm gBlock Tests | Derm2 CTL | 21.0 | 87.6 | 78.0 | Neg | Pos | Neg | Neg |
| 2015-02-03-MD02-VAL03DERM | Derm2 CTL | 21.1 | 87.2 | 77.6 | Neg | Pos | Neg | Neg |
| 2015-02-04-MD01-VAL05DERM | Derm2 CTL | 21.7 | 87.0 | 77.6 | Neg | Pos | Neg | Neg |
| 2015-02-04-MD02-VAL06DERM | Derm2 CTL | 21.6 | 87.0 | 77.6 | Neg | Pos | Neg | Neg |
| 2015-02-05-MD01-VAL07DERM | Derm2 CTL | 22.3 | 86.8 | 77.6 | Neg | Pos | Neg | Neg |
| 2015-02-05-MD01-VAL08DERM | Derm2 CTL | 22.0 | 86.9 | 77.4 | Neg | Pos | Neg | Neg |
| 2015-02-09-MD01-VAL09DERM | Derm2 CTL | 22.3 | 86.7 | 77.2 | Neg | Pos | Neg | Neg |
| 2015-02-09-MD01-VAL10DERM | Derm2 CTL | 22.2 | 86.9 | 77.3 | Neg | Pos | Neg | Neg |
| 2015-02-10-MD02-VAL11DERM | Derm2 CTL | 21.8 | 87.0 | 77.5 | Neg | Pos | Neg | Neg |
| 2015-02-11-AH-02-VAL12DERM | Derm2 CTL | 22.6 | 86.8 | 77.5 | Neg | Pos | Neg | Neg |
| 2015-02-11-AH-01-VAL13DERM | Derm2 CTL | 22.5 | 86.9 | 77.4 | Neg | Pos | Neg | Neg |
| 2015-02-12-AH-02-VAL14DERM | Derm2 CTL | 22.1 | 86.8 | 77.4 | Neg | Pos | Neg | Neg |
| 2015-02-13-MD02-VAL15DERM | Derm2 CTL | 21.9 | 86.9 | 77.4 | Neg | Pos | Neg | Neg |
| 2015-03-10-LB01-VAL17DERM | Derm2 CTL | 19.8 | 86.8 | 77.3 | Neg | Pos | Neg | Neg |
| 2015-03-11-MD02-VAL18DERM | Derm2 CTL | 18.6 | 87.6 | 77.8 | Neg | Pos | Neg | Neg |
| 2015-03-11-MD02-VAL19DERM | Derm2 CTL | 19.5 | 87.1 | 77.7 | Neg | Pos | Neg | Neg |
| 2015-03-11-AH02-VAL20DERM | Derm2 CTL | 19.5 | 87.1 | 77.5 | Neg | Pos | Neg | Neg |
| | Average | 21.6 | 87.1 | 77.6 | | | | |
| | SD | 0.82 | 0.30 | 0.21 | | | | |
| | CV (%) | 3.79% | 0.34% | 0.28% | | | | |
| | Min | 19.6 | 86.7 | 77.2 | | | | |
| | Max | 22.6 | 87.6 | 78.0 | | | | |

Tr m: *T. mentagrophytes* Tr r: *T. rubrum* Epi: *Epidermophyton* Mic: *Microsporum*

FIG. 52

Table 48

| Run ID | Sample ID | PCR Raw Data | | PCR Result | | | |
|---|---|---|---|---|---|---|---|
| | | Ct | Tm1 | Tr m | Tr r | Epi | Mic |
| 2014-12-04-MD01-VAL01DERM | Derm3 CTL | 28.9 | 82.3 | Neg | Neg | Pos | Neg |
| 2014-12-04-MD02-VAL02DERM | Derm3 CTL | 28.3 | 82.4 | Neg | Neg | Pos | Neg |
| 2014-12-24-MD02 Derm gBlock Tests | Derm3 CTL | 27.6 | 82.2 | Neg | Neg | Pos | Neg |
| 2015-01-23-MD01-VAL04DERM | Derm3 CTL | 26.4 | 81.7 | Neg | Neg | Pos | Neg |
| 2015-02-05-MD01-VAL07DERM | Derm3 CTL | 28.1 | 81.7 | Neg | Neg | Pos | Neg |
| 2015-02-05-MD01-VAL08DERM | Derm3 CTL | 27.8 | 81.7 | Neg | Neg | Pos | Neg |
| 2015-02-09-MD01-VAL09DERM | Derm3 CTL | 27.5 | 81.7 | Neg | Neg | Pos | Neg |
| 2015-02-09-MD01-VAL10DERM | Derm3 CTL | 27.3 | 81.8 | Neg | Neg | Pos | Neg |
| 2015-02-10-MD02-VAL11DERM | Derm3 CTL | 29.8 | 81.8 | Neg | Neg | Pos | Neg |
| 2015-02-11-AH-02-VAL12DERM | Derm3 CTL | 29.2 | 81.8 | Neg | Neg | Pos | Neg |
| 2015-02-11-AH-01-VAL13DERM | Derm3 CTL | 29.9 | 81.9 | Neg | Neg | Pos | Neg |
| 2015-02-12-AH-02-VAL14DERM | Derm3 CTL | 30.0 | 81.7 | Neg | Neg | Pos | Neg |
| 2015-02-13-MD02-VAL15DERM | Derm3 CTL | 29.9 | 81.7 | Neg | Neg | Pos | Neg |
| 2015-03-09-MD01-VAL16DERM | Derm3 CTL | 27.0 | 81.8 | Neg | Neg | Pos | Neg |
| 2015-03-10-LB01-VAL17DERM | Derm3 CTL | 26.9 | 81.6 | Neg | Neg | Pos | Neg |
| 2015-03-11-MD02-VAL18DERM | Derm3 CTL | 25.1 | 82.4 | Neg | Neg | Pos | Neg |
| 2015-03-11-MD02-VAL19DERM | Derm3 CTL | 26.5 | 81.8 | Neg | Neg | Pos | Neg |
| 2015-03-11-AH02-VAL20DERM | Derm3 CTL | 25.9 | 81.9 | Neg | Neg | Pos | Neg |
| | Average | 28.1 | 81.9 | | | | |
| | SD | 1.23 | 0.25 | | | | |
| | CV (%) | 4.38% | 0.32% | | | | |
| | Min | 26.1 | 81.6 | | | | |
| | Max | 30.0 | 82.4 | | | | |

Tr m: *T. mentagrophytes* Tr r: *T. rubrum* Epi: *Epidermophyton* Mic: *Microsporum*

FIG. 53

Table 49

| Run ID | Sample ID | PCR Raw Data | | | PCR Result | | | |
|---|---|---|---|---|---|---|---|---|
| | | Ct | Tm1 | Tm2 | Tr m | Tr r | Epi | Mic |
| 2014-12-04-MD01-VAL01DERM | Derm4 CTL | 25.0 | 85.1 | - | Neg | Neg | Neg | Pos |
| 2014-12-04-MD02-VAL02DERM | Derm4 CTL | 24.5 | 85.1 | - | Neg | Neg | Neg | Pos |
| 2014-12-24-MD02 Derm gBlock Test | Derm4 CTL | 24.1 | 84.7 | 69.5 | Neg | Neg | Neg | Pos |
| 2015-01-23-MD01-VAL04DERM | Derm4 CTL | 23.2 | 84.2 | 69.0 | Neg | Neg | Neg | Pos |
| 2015-02-05-MD01-VAL08DERM | Derm4 CTL | 23.4 | 84.4 | 69.0 | Neg | Neg | Neg | Pos |
| 2015-02-09-MD01-VAL09DERM | Derm4 CTL | 23.4 | 84.4 | 69.0 | Neg | Neg | Neg | Pos |
| 2015-02-09-MD01-VAL10DERM | Derm4 CTL | 23.3 | 84.5 | 68.9 | Neg | Neg | Neg | Pos |
| 2015-02-10-MD02-VAL11DERM | Derm4 CTL | 23.1 | 84.5 | 69.2 | Neg | Neg | Neg | Pos |
| 2015-02-11-AH-02-VAL12DERM | Derm4 CTL | 22.6 | 84.5 | - | Neg | Neg | Neg | Pos |
| 2015-02-11-AH-01-VAL13DERM | Derm4 CTL | 23.2 | 84.6 | 69.0 | Neg | Neg | Neg | Pos |
| 2015-02-12-AH-02-VAL14DERM | Derm4 CTL | 23.0 | 84.5 | - | Neg | Neg | Neg | Pos |
| 2015-03-09-MD01-VAL16DERM | Derm4 CTL | 24.6 | 84.1 | - | Neg | Neg | Neg | Pos |
| 2015-03-10-LB01-VAL17DERM | Derm4 CTL | 25.5 | 84.1 | 69.2 | Neg | Neg | Neg | Pos |
| 2015-03-11-MD02-VAL18DERM | Derm4 CTL | 25.2 | 84.6 | 69.3 | Neg | Neg | Neg | Pos |
| 2015-03-11-MD02-VAL19DERM | Derm4 CTL | 25.9 | 84.1 | 70.4 | Neg | Neg | Neg | Pos |
| 2015-03-11-AH02-VAL20DERM | Derm4 CTL | 23.8 | 84.8 | 69.3 | Neg | Neg | Neg | Pos |
| | Average | 24.0 | 84.5 | | | | | |
| | SD | 1.00 | 0.30 | | | | | |
| | CV (%) | 4.19% | 0.36% | | | | | |
| | Min | 22.6 | 84.1 | | | | | |
| | Max | 25.9 | 85.1 | | | | | |

Tr m: *T. mentagrophytes* Tr r: *T. rubrum* Epi: *Epidermophyton* Mic: *Microsporum*

*Tm1 for *Microsporum* overlaps with that of *T. mentagrophytes*. The absence of a Tm2 peak greater than 76.0 differentiates *T. mentagrophytes* from *Microsporum*.

FIG. 54

Table 50

| Sample | Reference | *PCR result* | # of Replicates |
|---|---|---|---|
| 2043 | *Not Detected* | *Not Detected* | 3 |
| 2226 | *T. mentagrophytes* | *T. mentagrophytes* | 3 |
| 327 | *T. rubrum* | *T. rubrum* | 3 |
| 355 | *T. rubrum* | *T. rubrum* | 3 |
| 376 | *T. rubrum* | *T. rubrum* | 3 |
| Tr m1 | *T. mentagrophytes* | *T. mentagrophytes* | 3 |
| Tr m2 | *T. mentagrophytes* | *T. mentagrophytes* | 3 |
| Tr m3 | *T. mentagrophytes* | *T. mentagrophytes* | 3 |
| Epi1 | *Epidermophyton* | *Epidermophyton* | 3 |
| Epi2 | *Epidermophyton* | *Epidermophyton* | 3 |
| Epi3 | *Epidermophyton* | *Epidermophyton* | 3 |
| Micr0.1 | *Microsporum* | *Microsporum* | 3 |
| Micr0.01 | *Microsporum* | *Microsporum* | 3 |
| Micr0.004 | *Microsporum* | *Microsporum* | 3 |

FIG. 55

Table 51

| Extraction Date | Extraction By* | Date | Instrument # | Run ID | By* | CTL Results Tr m | CTL Results Tr r | CTL Results Epi | CTL Results Mic |
|---|---|---|---|---|---|---|---|---|---|
| 07-OCT-2014<br>09-OCT-2014<br>15-OCT-2014 | LB<br>LB<br>LB | 12-DEC-2014 | 01 | VAL01 | MD | PASS | PASS | PASS | PASS |
| 20-OCT-2014<br>21-OCT-2014 | LP<br>LB | 12-DEC-2014 | 02 | VAL02 | MD | PASS | PASS | PASS | PASS |
| N/A | N/A | 24-DEC-2014 | 02 | Derm gBlock Tess | MD | PASS | PASS | PASS | PASS |
| 30-OCT-2014<br>31-OCT-2014<br>03-NOV-2014 | MD<br>AH<br>MD | 03-FEB-2015 | 02 | VAL03 | MD | PASS | PASS | N/A | N/A |
| N/A | N/A | 23-JAN-2015 | 01 | VAL04 | MD | PASS | N/A | PASS | PASS |
| N/A | N/A | 04-FEB-2015 | 01 | VAL05 | MD | PASS | PASS | N/A | N/A |
| N/A | N/A | 04-FEB-2015 | 02 | VAL06 | MD | PASS | PASS | N/A | N/A |
| N/A | N/A | 05-FEB-2015 | 01 | VAL07 | MD | PASS | PASS | PASS | N/A |
| N/A | N/A | 05-FEB-2015 | 01 | VAL08 | MD | PASS | PASS | PASS | PASS |
| 06-FEB-2015<br>30-OCT-2014<br>31-OCT-2014 | AH<br>MD<br>AH | 09-FEB-2015 | 01 | VAL09 | MD | PASS | PASS | PASS | PASS |
| 20-OCT-2014<br>21-OCT-2014<br>03-NOV-2014<br>11-NOV-2014<br>13-NOV-2014<br>17-NOV-2014 | LP<br>LB<br>MD<br>MD<br>MD<br>MD | 09-FEB-2015 | 01 | VAL10 | MD | PASS | PASS | PASS | PASS |
| 11-NOV-2014<br>13-NOV-2014<br>10-FEB-2015 | MD<br>MD<br>MD | 10-FEB-2015 | 02 | VAL11 | MD | PASS | PASS | PASS | PASS |
| 13-NOV-2014<br>17-NOV-2014<br>18-NOV-2014<br>07-OCT-2014 | MD<br>MD<br>MD<br>LB | 11-FEB-2015 | 02 | VAL12 | AH | PASS | PASS | PASS | PASS |
| 11-NOV-2014<br>12-NOV-2014 | MD<br>AH | 11-FEB-2015 | 01 | VAL13 | AH | PASS | PASS | PASS | PASS |
| 10-FEB-2015 | MD | 12-FEB-2015 | 02 | VAL14 | AH | PASS | PASS | PASS | PASS |
| 12-FEB-2015 | MD | 13-FEB-2015 | 02 | VAL15 | MD | PASS | PASS | PASS | N/A |
| N/A | N/A | 09-MAR-2015 | 01 | VAL16 | LB | PASS | PASS | PASS | PASS |
| N/A | N/A | 10-MAR-2015 | 01 | VAL17 | LB | PASS | PASS | PASS | PASS |
| N/A | N/A | 11-MAR-2015 | 02 | VAL18 | MD | PASS | PASS | PASS | PASS |
| N/A | N/A | 11-MAR-2015 | 02 | VAL19 | MD | PASS | PASS | PASS | PASS |
| 11-MAR-2015 | AH | 11-MAR-2015 | 02 | VAL20 | AH | PASS | PASS | PASS | PASS |

Tr m: *T. mentagrophytes* Tr r: *T. rubrum* Epi: *Epidermophyton* Mic: *Microsporum*

*Initials of analyst N/A:no nail specimens were included in the run (DNA from culture only)

FIG. 56

Table 52

| | Fungal Detection by PCR: Dermatophyte + | Fungal Detection by PCR: Dermatophyte - | Total |
|---|---|---|---|
| Dermatophyte PCR +* | 102 | 2 | 104 |
| Dermatophyte PCR -* | 1 | 95 | 96 |
| Total | 103 | 97 | 200 |

| N = 200 | |
|---|---|
| Concordance | 98.5% |
| Sensitivity | 99.0% |
| Specificity | 97.9% |

*Positive or negative for any of the four organisms by the Dermatophyte Identification by PCR Specimens prepared by spiking normal nails with Epidermophyton gBlock DNA are not included. The gBlock was designed to interact with the Epidermophyton-specific primers, but does not include the Epidermophyton genome region detected with the dermatophyte primers used in the "Fungal Detection by PCR" (Screening Assay).

FIG. 57

Table 53

| | *T. mentagrophytes* Sequencing + | *T mentagrophytes* Sequencing - | Total |
|---|---|---|---|
| *T. mentagrophytes* ID by PCR + | 32 | 0 | 32 |
| *T. mentagrophytes* ID by PCR - | 1 | 133 | 134 |
| Total | 33 | 135 | 166 |

| N = 166 | |
|---|---|
| Concordance | 99.4% |
| Sensitivity | 97.0% |
| Specificity | 100% |

Table 54

| | *T. rubrum* Sequencing + | *T rubrum* Sequencing - | Total |
|---|---|---|---|
| *T. rubrum* *ID* by PCR + | 72 | 0 | 72 |
| *T. rubrum* ID by PCR - | 1 | 93 | 94 |
| Total | 73 | 93 | 166 |

| N = 166 | |
|---|---|
| Concordance | 99.4% |
| Sensitivity | 98.6% |
| Specificity | 100% |

Table 55

| | *Epidermophyton* Sequencing + | *Epidermophyton* Sequencing - | Total |
|---|---|---|---|
| *Epidermophyton* ID by PCR + | 30 | 0 | 30 |
| *Epidermophyton* ID by PCR - | 0 | 136 | 136 |
| Total | 30 | 136 | 166 |

| N = 166 | |
|---|---|
| Concordance | 100% |
| Sensitivity | 100% |
| Specificity | 100% |

Table 56

| | Microsporum Sequencing + | Microsporum Sequencing - | Total |
|---|---|---|---|
| *Microsporum* ID by PCR + | 29 | 0 | 29 |
| *Microsporum* ID by PCR - | 1 | 136 | 137 |
| Total | 30 | 136 | 166 |

| N = 166 | |
|---|---|
| Concordance | 99.4% |
| Sensitivity | 96.7% |
| Specificity | 100% |

FIG. 58

Example report A

| | | |
|---|---|---|
| *Candida* genus: | Not Identified | |
| Dermatophytes: | Not Identified | |
| Saprophytes: | Not Identified | |

Example report B

| | | |
|---|---|---|
| *Candida* genus: | Not Identified | |
| Dermatophytic fungi: | DETECTED | |
| *T. mentagrophytes* | | DETECTED |
| *T. rubrum* | | Not Identified |
| *Epidermophyton* | | Not Identified |
| *Microsporum* | | Not Identified |
| Saprophytic fungi: | Not Identified | |

Example report C

| | | |
|---|---|---|
| *Candida* genus: | Not Identified | |
| Dermatophytic fungi: | DETECTED | |
| *T. mentagrophytes* | | Not Identified |
| *T. rubrum* | | DETECTED |
| *Epidermophyton* | | Not Identified |
| *Microsporum* | | Not Identified |
| Saprophytic fungi: | Not Identified | |

Example report D

| | | |
|---|---|---|
| *Candida* genus: | Not Identified | |
| Dermatophytic fungi: | DETECTED | |
| *T. mentagrophytes* | | Not Identified |
| *T. rubrum* | | Not Identified |
| *Epidermophyton* | | DETECTED |
| *Microsporum* | | Not Identified |
| Saprophytic fungi: | Not Identified | |

Example report E

| | | |
|---|---|---|
| *Candida* genus: | Not Identified | |
| Dermatophytic fungi: | DETECTED | |
| *T. mentagrophytes* | | Not Identified |
| *T. rubrum* | | Not Identified |
| *Epidermophyton* | | Not Identified |
| *Microsporum* | | DETECTED |
| Saprophytic fungi: | Not Identified | |

FIG. 59

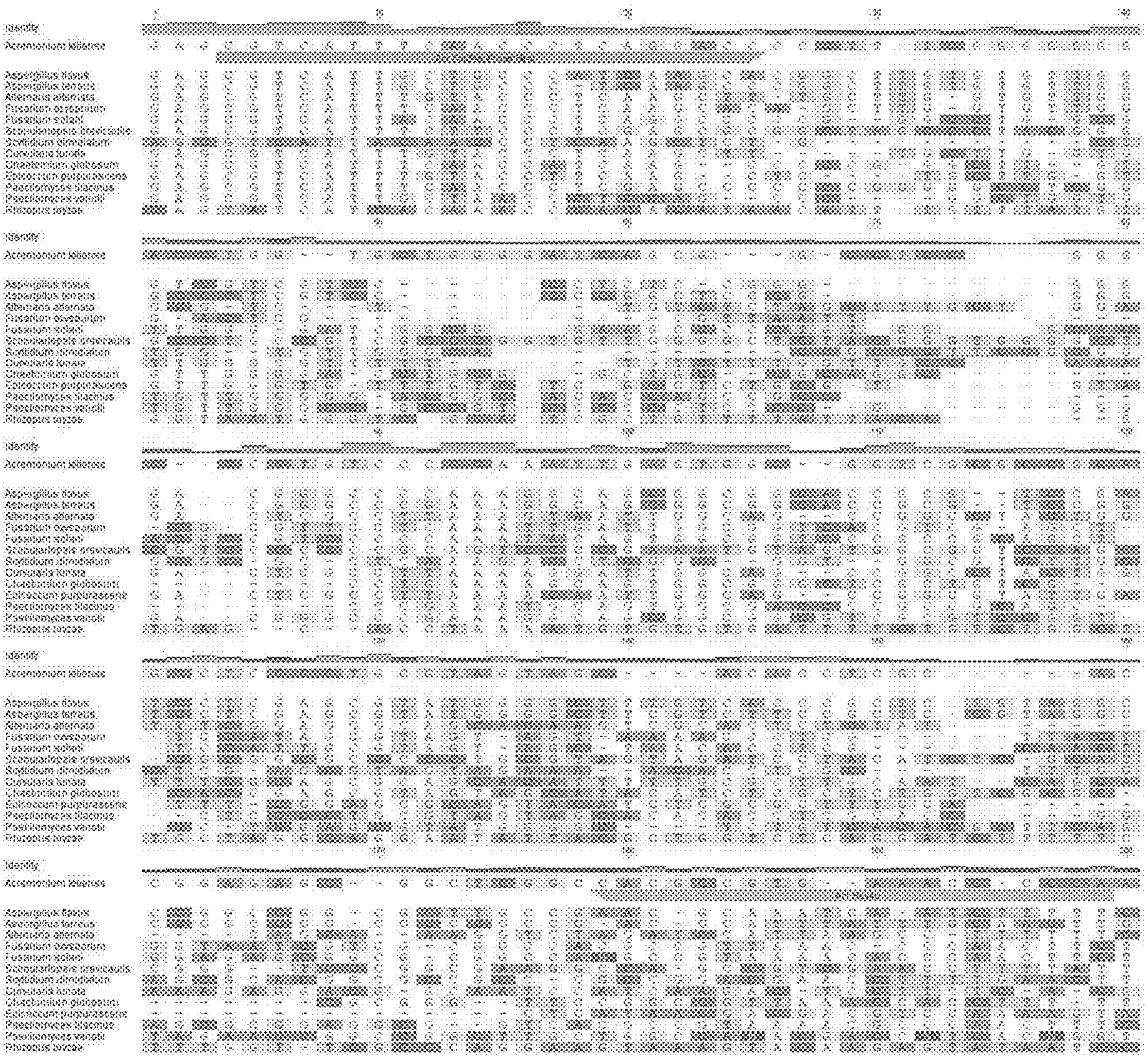

*Acremonium kiliense* SEQ ID NO:124

*Aspergillus flavus* SEQ ID NO:125
*Aspergillus terreus* SEQ ID NO:126
*Alternaria alternata* SEQ ID NO:127
*Fusarium oxysporum* SEQ ID NO:128
*Fusarium solani* SEQ ID NO:129
*Scopulariopsis brevicaulis* SEQ ID NO:130
*Scytalidium dimidiatum* SEQ ID NO:131
*Curvularia lunata* SEQ ID NO:132
*Chaetomium globosum* SEQ ID NO:133
*Epicoccum purpurascens* SEQ ID NO:134
*Paecilomyces lilacinus* SEQ ID NO:135
*Paecilomyces variotii* SEQ ID NO:136
*Rhizopus oryzae* SEQ ID NO:137

FIG. 60

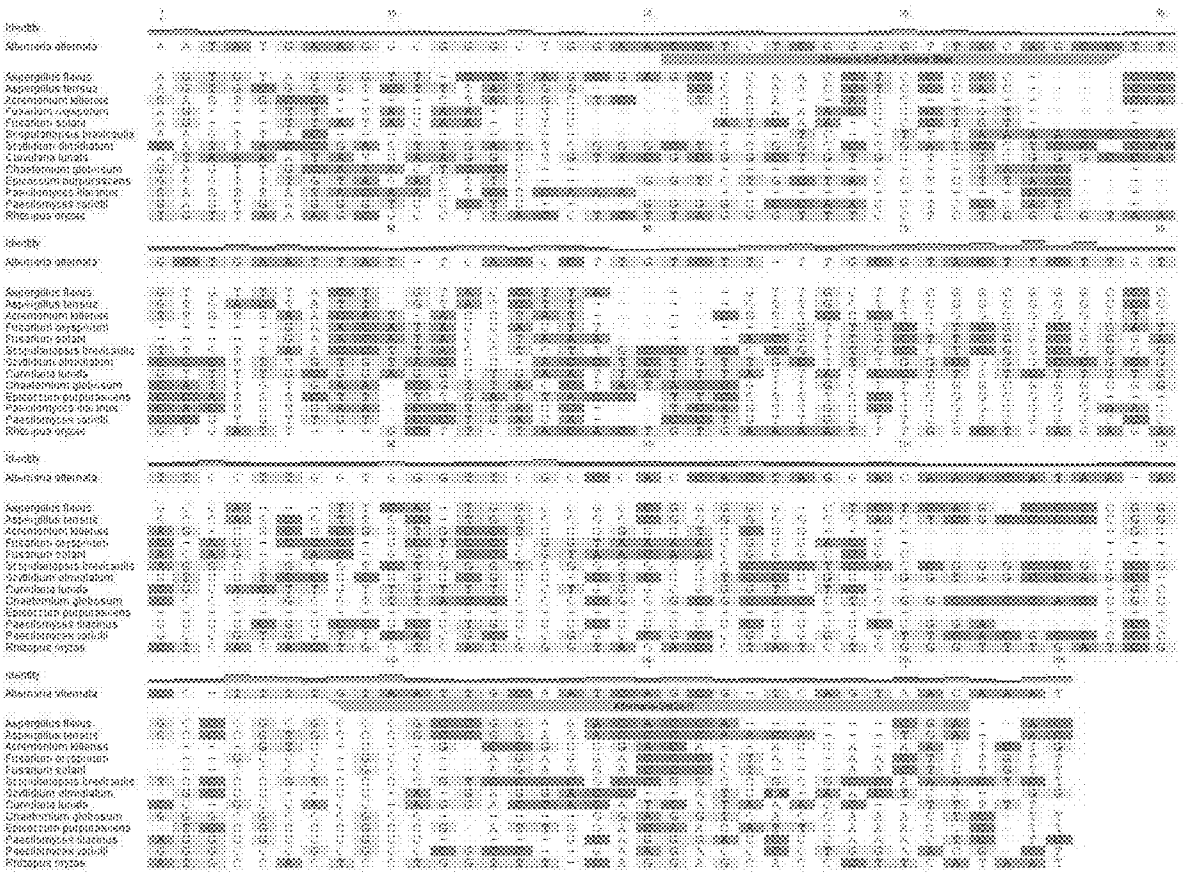

| | |
|---|---|
| *Alternaria alternata* | SEQ ID NO:138 |
| *Aspergillus flavus* | SEQ ID NO:139 |
| *Aspergillus terreus* | SEQ ID NO:140 |
| *Acremonium kiliense* | SEQ ID NO:141 |
| *Fusarium oxysporum* | SEQ ID NO:142 |
| *Fusarium solani* | SEQ ID NO:143 |
| *Scopulariopsis brevicaulis* | SEQ ID NO:144 |
| *Scytalidium dimidiatum* | SEQ ID NO:145 |
| *Curvularia lunata* | SEQ ID NO:146 |
| *Chaetomium globosum* | SEQ ID NO:147 |
| *Epicoccum purpurascens* | SEQ ID NO:148 |
| *Paecilomyces lilacinus* | SEQ ID NO:149 |
| *Paecilomyces variotii* | SEQ ID NO:150 |
| *Rhizopus oryzae* | SEQ ID NO:151 |

FIG. 61B

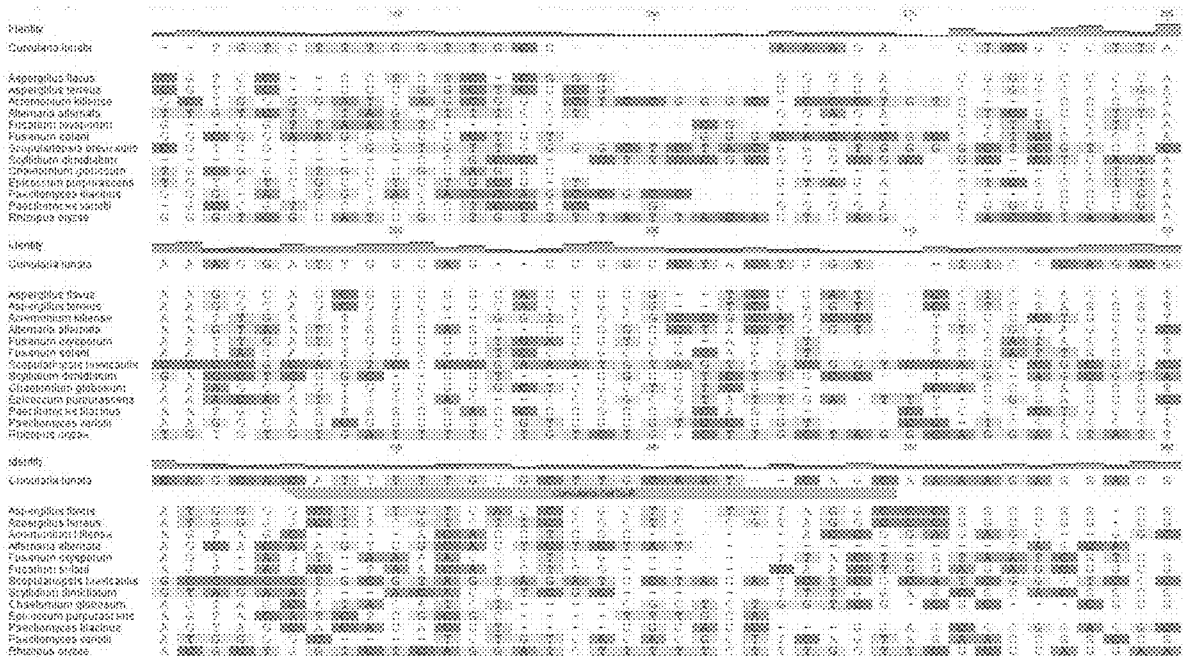

| | |
|---|---|
| *Curvularia lunata* | SEQ ID NO:152 |
| *Aspergillus flavus* | SEQ ID NO:153 |
| *Aspergillus terreus* | SEQ ID NO:154 |
| *Acremonium kiliense* | SEQ ID NO:155 |
| *Alternaria alternata* | SEQ ID NO:156 |
| *Fusarium oxysporum* | SEQ ID NO:157 |
| *Fusarium solani* | SEQ ID NO:158 |
| *Scopulariopsis brevicaulis* | SEQ ID NO:159 |
| *Scytalidium dimidiatum* | SEQ ID NO:160 |
| *Chaetomium globosum* | SEQ ID NO:161 |
| *Epicoccum purpurascens* | SEQ ID NO:162 |
| *Paecilomyces lilacinus* | SEQ ID NO:163 |
| *Paecilomyces variotii* | SEQ ID NO:164 |
| *Rhizopus oryzae* | SEQ ID NO:165 |

FIG. 62

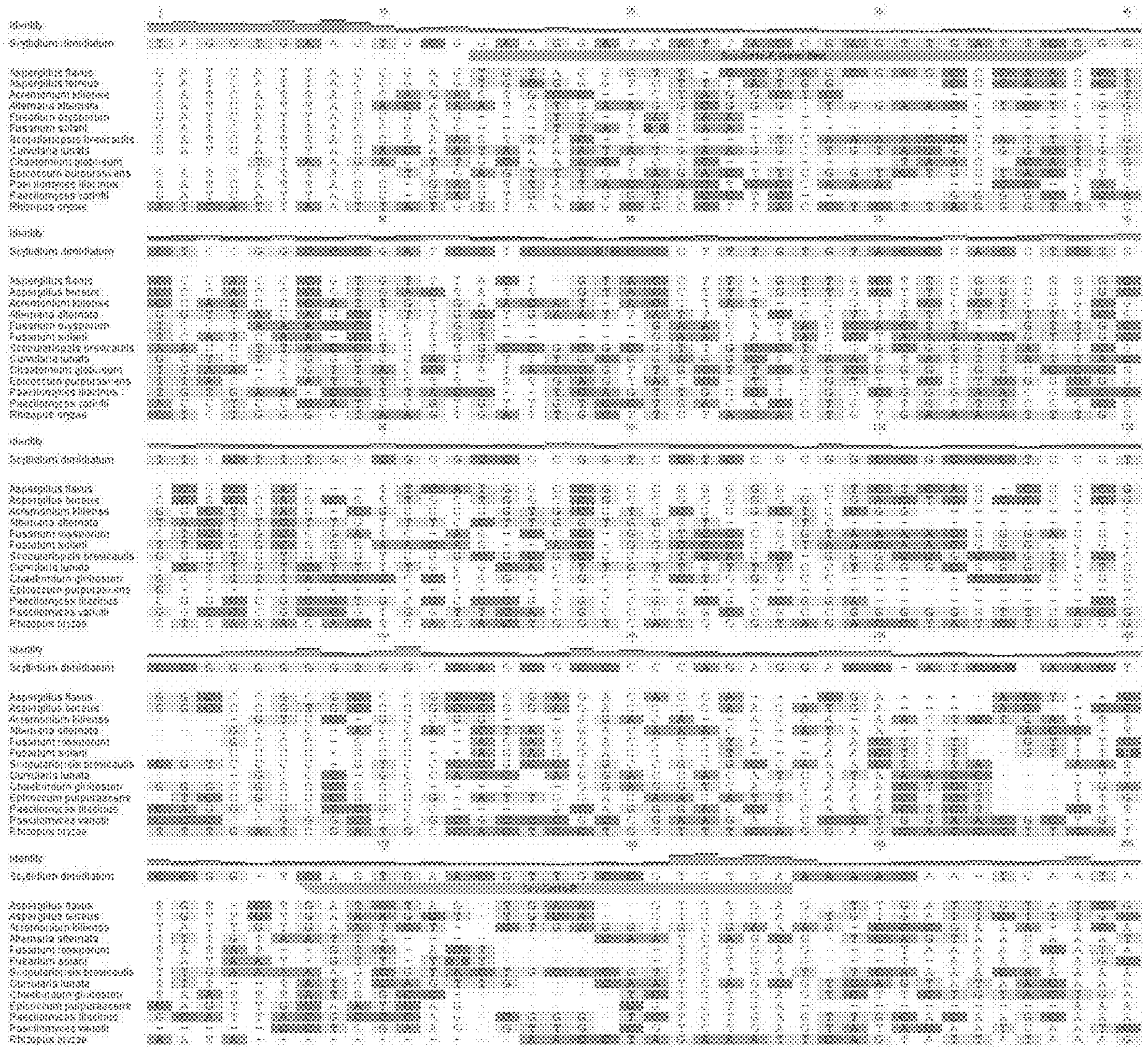

*Scytalidium dimidiatum* SEQ ID NO:166

*Aspergillus flavus* SEQ ID NO:167
*Aspergillus terreus* SEQ ID NO:168
*Acremonium kiliense* SEQ ID NO:169
*Alternaria alternata* SEQ ID NO:170
*Fusarium oxysporum* SEQ ID NO:171
*Fusarium solani* SEQ ID NO:172
*Scopulariopsis brevicaulis* SEQ ID NO:173
*Curvularia lunata* SEQ ID NO:174
*Chaetomium globosum* SEQ ID NO:175
*Epicoccum purpurascens* SEQ ID NO:176
*Paecilomyces lilacinus* SEQ ID NO:177
*Paecilomyces variotii* SEQ ID NO:178
*Rhizopus oryzae* SEQ ID NO:179

FIG. 63

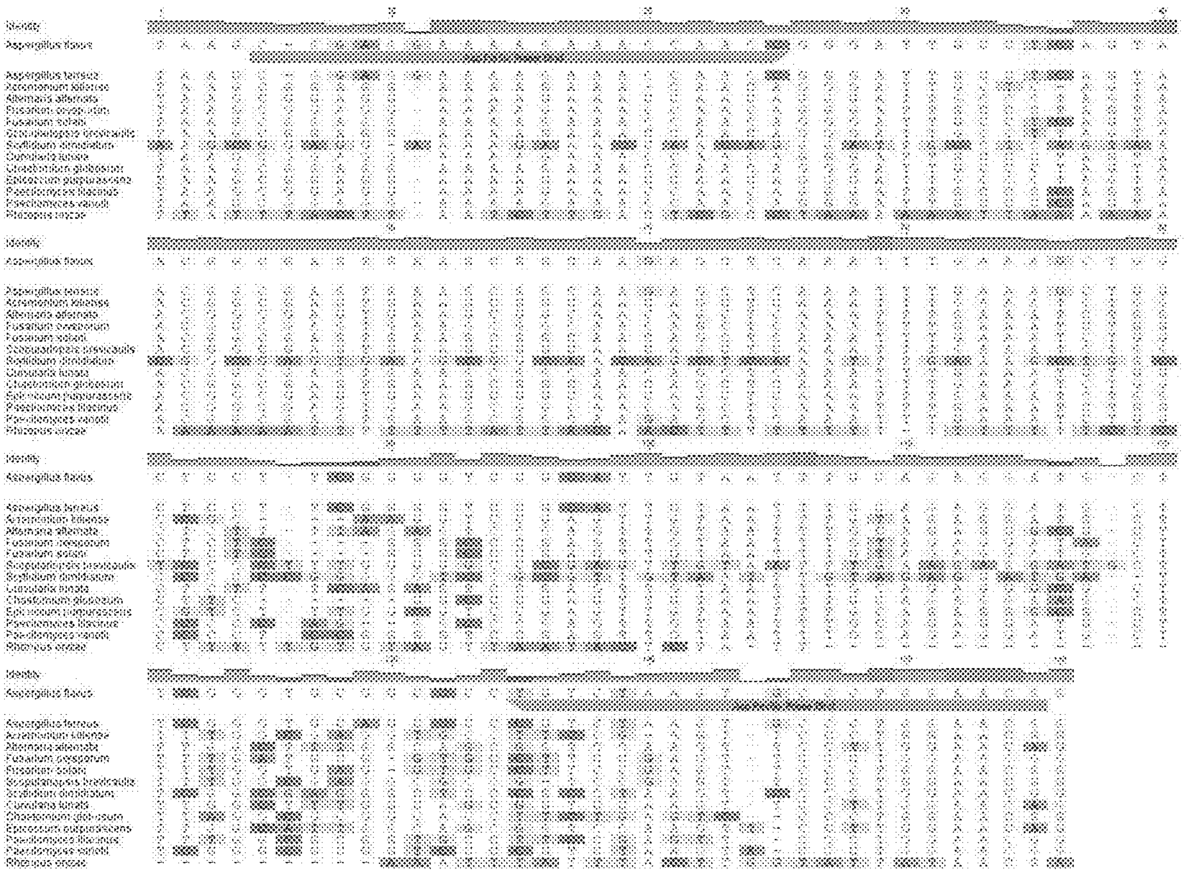

*Aspergillus flavus* SEQ ID NO:180

*Aspergillus terreus* SEQ ID NO:181
*Acremonium kiliense* SEQ ID NO:182
*Alternaria alternata* SEQ ID NO:183
*Fusarium oxysporum* SEQ ID NO:184
*Fusarium solani* SEQ ID NO:185
*Scopulariopsis brevicaulis* SEQ ID NO:186
*Scytalidium dimidiatum* SEQ ID NO:187
*Curvularia lunata* SEQ ID NO:188
*Chaetomium globosum* SEQ ID NO:189
*Epicoccum purpurascens* SEQ ID NO:190
*Paecilomyces lilacinus* SEQ ID NO:191
*Paecilomyces variotii* SEQ ID NO:192
*Rhizopus oryzae* SEQ ID NO:193

FIG. 64

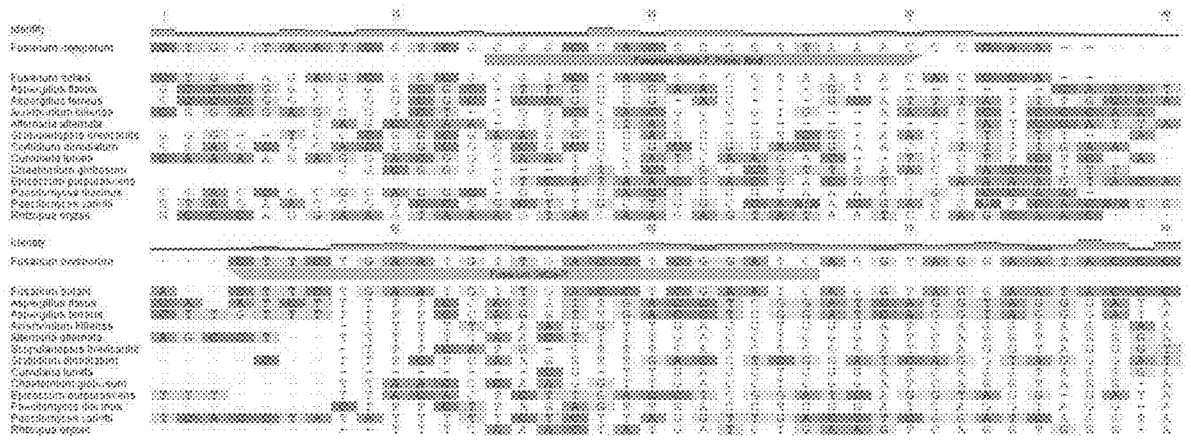

| | |
|---|---|
| *Fusarium oxysporum* | SEQ ID NO:194 |
| | |
| *Fusarium solani* | SEQ ID NO:195 |
| *Aspergillus flavus* | SEQ ID NO:196 |
| *Aspergillus terreus* | SEQ ID NO:197 |
| *Acremonium kiliense* | SEQ ID NO:198 |
| *Alternaria alternata* | SEQ ID NO:199 |
| *Scopulariopsis brevicaulis* | SEQ ID NO:200 |
| *Scytalidium dimidiatum* | SEQ ID NO:201 |
| *Curvularia lunata* | SEQ ID NO:202 |
| *Chaetomium globosum* | SEQ ID NO:203 |
| *Epicoccum purpurascens* | SEQ ID NO:204 |
| *Paecilomyces lilacinus* | SEQ ID NO:205 |
| *Paecilomyces variotii* | SEQ ID NO:206 |
| *Rhizopus oryzae* | SEQ ID NO:207 |

FIG. 65

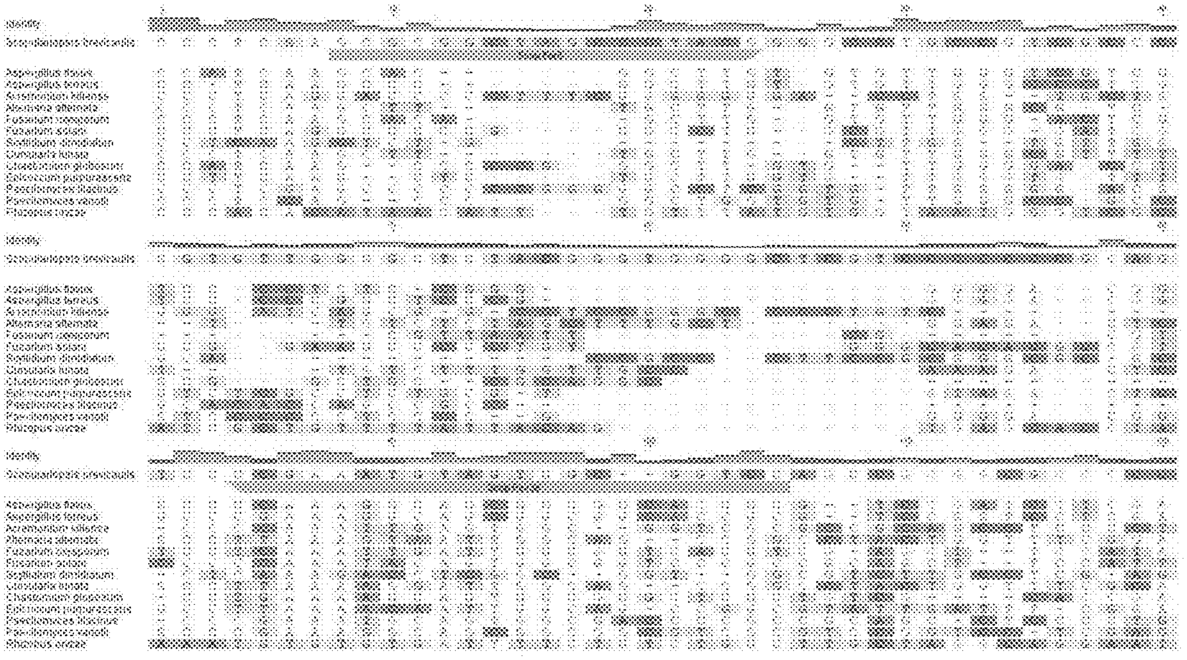

Scopulariopsis brevicaulis SEQ ID NO:208

Aspergillus flavus SEQ ID NO:209
Aspergillus terreus SEQ ID NO:210
Acremonium kiliense SEQ ID NO:211
Alternaria alternata SEQ ID NO:212
Fusarium oxysporum SEQ ID NO:213
Fusarium solani SEQ ID NO:214
Scytalidium dimidiatum SEQ ID NO:215
Curvularia lunata SEQ ID NO:216
Chaetomium globosum SEQ ID NO:217
Epicoccum purpurascens SEQ ID NO:218
Paecilomyces lilacinus SEQ ID NO:219
Paecilomyces variotii SEQ ID NO:220
Rhizopus oryzae SEQ ID NO:221

FIG. 66

Table 58

| Organism | Source | DNA (ng) Range Per reaction | Category | Acr | Alt | Asp | Curv | Fus | Scy | Scop |
|---|---|---|---|---|---|---|---|---|---|---|
| *C. albicans* | In-House Culture | 2.0 & 0.2 | *Candida* | ND | ND | ND | ND | ND | ND | ND |
| *C. glabrata* | In-House Culture | 2.0 & 0.2 | *Candida* | ND | ND | ND | ND | ND | ND | ND |
| *C. guilliermondii* | In-House Culture | 2.0 & 0.2 | *Candida* | ND | ND | ND | ND | ND | ND | ND |
| *C. lusitaniae* | In-House Culture | 2.0 & 0.2 | *Candida* | ND | ND | ND | ND | ND | ND | ND |
| *C. orthopsilosis* | In-House Culture | 2.0 & 0.2 | *Candida* | ND | ND | ND | ND | ND | ND | ND |
| C. parapsilosis | In-House Culture | 2.0 & 0.2 | *Candida* | ND | ND | ND | ND | ND | ND | ND |
| *C. parapsilosis* | ATCC #22019D-5 | 2.0 & 0.2 | *Candida* | ND | ND | ND | ND | ND | ND | ND |
| *C. tropicalis* | In-House Culture | 2.0 & 0.2 | *Candida* | ND | ND | ND | ND | ND | ND | ND |
| *M. pachydermatitis* | In-House Culture | 2.0 & 0.2 | *Candida* | ND | ND | ND | ND | ND | ND | ND |
| Cross reactivity of *Candida* organisms (yeast) not seen with Saprophyte Reflex Assay | | | | | | | | | | |
| *Epidermophyton* | In-House Cutlure | 2.0 & 0.2 | Dermatophyte | ND | ND | ND | ND | ND | ND | ND |
| *M. gypseum* | In-House Culture | 2.0 & 0.2 | Dermatophyte | ND | ND | ND | ND | ND | ND | ND |
| *M. canis* | In-House Culture | 2.0 & 0.2 | Dermatophyte | ND | ND | ND | ND | ND | ND | ND |
| *T. interdigitale* | In-House Culture | 2.0 & 0.2 | Dermatophyte | ND | ND | ND | ND | ND | ND | ND |
| *T. mentagrophytes* | ATCC #9533D-2 | 2.0 & 0.2 | Dermatophyte | ND | ND | ND | ND | ND | ND | ND |
| *T. rubrum* | In-House Culture | 2.0 & 0.2 | Dermatophyte | ND | ND | ND | ND | ND | ND | ND |
| *T. tonsurans* | ATCC#56186 | 2.0 & 0.2 | Dermatophyte | ND | ND | ND | ND | ND | ND | ND |
| *T. violaceum* | ATCC #28944 | 2.0 & 0.2 | Dermatophyte | ND | ND | ND | ND | ND | ND | ND |
| Cross reactivity of Dermatophyte organisms not seen with Saprophyte Reflex Assay | | | | | | | | | | |
| *Chaetomium* | In-House Culture | 2.0 & 0.2 | Saprophyte | ND | ND | ND | ND | ND | ND | ND |
| *Cladosporium* | In-House Culture | 2.0 & 0.2 | Saprophyte | ND | ND | ND | ND | ND | ND | ND |
| *Epicoccum* | In-House Culture | 2.0 & 0.2 | Saprophyte | ND | ND | ND | ND | ND | ND | ND |
| *Foncecea* | In-House Culture | 2.0 & 0.2 | Saprophyte | ND | ND | ND | ND | ND | ND | ND |
| *Mucor* | In-House Culture | 2.0 & 0.2 | Saprophyte | ND | ND | ND | ND | ND | ND | ND |
| *Paecilomyces* | In-House Culture | 2.0 & 0.2 | Saprophyte | ND | ND | ND | ND | ND | ND | ND |
| *Penicillium* | In-House Culture | 2.0 & 0.2 | Saprophyte | ND | ND | ND | ND | ND | ND | ND |
| *Rhizopus* | In-House Culture | 2.0 & 0.2 | Saprophyte | ND | ND | ND | ND | ND | ND | ND |
| Cross reactivity of non-targeted Saprophyte organisms not seen with Saprophyte Reflex Assay | | | | | | | | | | |

Acr: *Acremonium*, Alt: *Alternaria*, Asp: *Aspergillus*, Cur: *Curvularia*, Fus: *Fusarium*, Scy: *Scytalidium*, Scop: *Scopulariopsis*, ND: not detected

| Organism | Source | DNA (ng) Range Per reaction | Category | Acr | Alt | Asp | Curv | Fus | Scy | Scop |
|---|---|---|---|---|---|---|---|---|---|---|
| *Acremonium* | In-House Culture | 2.0 & 0.2 | Saprophyte | Pos | ND | ND | ND | ND | ND | ND |
| *Alternaria* | In-House Culture | 2.0 & 0.2 | Saprophyte | ND | Pos | ND | ND | ND | ND | ND |
| *Aspergillus* | In-House Culture | 2.0 & 0.2 | Saprophyte | ND | ND | Pos | ND | ND | ND | ND |
| *A. flavus* | ATCC #204304D-2 | 2.0 & 0.2 | Saprophyte | ND | ND | Pos | ND | ND | ND | ND |
| *A. terreus* | In-House Culture | 2.0 & 0.2 | Saprophyte | ND | ND | Pos | ND | ND | ND | ND |
| *Curvularia* | In-House Culture | 2.0 & 0.2 | Saprophyte | ND | ND | ND | Pos | ND | ND | ND |
| *Fusarium* | In-House Culture | 2.0 & 0.2 | Saprophyte | ND | ND | ND | ND | Pos | ND | ND |
| *F. oxysporum* | In-House Culture | 2.0 & 0.2 | Saprophyte | ND | ND | ND | ND | Pos | ND | ND |
| *F. solani* | In-House Culture | 2.0 & 0.2 | Saprophyte | ND | ND | ND | ND | Pos | ND | ND |
| *Scopulariopsis* | In-House Culture | 2.0 & 0.2 | Saprophyte | ND | ND | ND | ND | ND | Pos | ND |
| *Scytalidium* | In-House Culture | 2.0 & 0.2 | Saprophyte | ND | ND | ND | ND | ND | ND | Pos |
| Seven targeted saprophytes were detected with the Saprophyte Identification Assay | | | | | | | | | | |

Acr: *Acremonium*, Alt: *Alternaria*, Asp: *Aspergillus*, Cur: *Curvularia*, Fus: *Fusarium*, Scy: *Scytalidium*, Scop: *Scopulariopsis*

Pos: Positive; ND: not detected

FIG. 67

Table 59

| SapA_Ct | SapB_Ct | N = 12 |
|---|---|---|
| 33.4 | 35.2 | **Mean** |
| 33.2 | 36.0 | **Median** |
| 1.47 | 0.970 | **SD** |
| 4.42 | 2.70 | **CV (%)** |
| 31.4 | 33.8 | **Min** |
| 36.0 | 36.0 | **Max** |

FIG. 68

Table 60

| SapA_Ct | SapB_Ct | N = 75 |
|---|---|---|
| 34.7 | 35.9 | **Mean** |
| 34.9 | 36.0 | **Median** |
| 1.26 | 0.254 | **SD** |
| 3.61 | 0.704 | **CV (%)** |
| 29.9 | 34.9 | **Min** |
| 36.0 | 36.0 | **Max** |

FIG. 69

Table 61

| | **Bacteria** | *P. aerug* | | *P. mirabil* | | *S. aureus* | | *S. marcen* | | *S. pyog* | |
|---|---|---|---|---|---|---|---|---|---|---|---|
| | **DNA Quantity, ng** | *2* | *0.2* | *2* | *0.2* | *2* | *0.2* | *2* | *0.2* | *2* | *0.2* |
| **Saprophyte** | **DNA tested** | | | | | | | | | | |
| ***N/A*** | **Bacteria only** | ND | ND | ND | ND | ND | ND | Scy^ | ND | ND | ND |
| ***Acremonium*** | **Bact. + Acr** | Acr | Acr | Acr | Acr | Acr | Acr | Acr | Acr | Acr | Acr |
| ***Alternaria*** | **Bact. + Alt** | Alt | Alt | Alt | Alt | Alt | Alt | Alt | Alt | Alt | Alt |
| ***Aspergillus*** | **Bact. + Asp** | Asp | Asp | Asp | Asp | Asp* | Asp | Asp | Asp | Asp | Asp |
| ***Curvularia*** | **Bact. + Curv** | Curv | Curv | Curv | Curv | ND | ND | Curv | Curv | Curv | Curv |
| ***Fusarium*** | **Bact. + Fus** | Fus | Fus | Fus | Fus | Fus | Fus | Fus | Fus | Fus | Fus |
| ***Scopulariopsis*** | **Bact. + Scop** | Scop | Scop | Scop /Scy | Scop /Scy | ND | Scop /Scy | Scop /Scy | Scop /Scy | Scop /Scy | Scop /Scy |
| ***Scytalidium*** | **Bact. + Scy** | Scy | Scy | Scy | Scy | Scy* | Scy | Scy | Scy | Scy | Scy |

Acr: *Acremonium*, Alt: *Alternaria*, Asp: *Aspergillus*, Cur: *Curvularia*, Fus: *Fusarium*, Scy: *Scytalidium*, Scop: *Scopulariopsis*
ND: Not Detected, ^ 6 of 8 detected as weak *Scytalidium*, *Ct increased by 1-2 cycles; *Scytalidium* detected

FIG. 70

Table 62

| | | hgDNA | |
|---|---|---|---|
| | DNA Quantity, ng | *2* | *0.2* |
| **Saprophyte** | **DNA tested** | | |
| ***N/A*** | **hgDNA only** | ND | ND |
| ***Acremonium*** | **hgDNA + Acr** | Acr | Acr |
| ***Alternaria*** | **hgDNA + Alt** | Alt | Alt |
| ***Aspergillus*** | **hgDNA + Asp** | Aso | Asp |
| ***Curvularia*** | **hgDNA + Curv** | Curv | Curv |
| ***Fusarium*** | **hgDNA + Fus** | Fus | Fus |
| ***Scopulariopsis*** | **hgDNA + Scop** | Scop | Scop |
| ***Scytalidium*** | **hgDNA + Scy** | Scy | Scy* |

Acr: *Acremonium* Alt: *Alternaria* Asp: *Aspergillus* Cur: *Curvularia*
Fus: *Fusarium* Scy: *Scytalidium* Scop: *Scopulariopsis*
ND: Not Detected,
*Diminished peak shape, but detectable

FIG. 71

Table 63

| Organism | ng per PCR reaction; shown is # positive of total tested at indicated DNA quantity | | | | | | | | | | | LOD | Copy # |
|---|---|---|---|---|---|---|---|---|---|---|---|---|---|
| | 4 | 1 | .4 | .1 | 0.04 | 0.01 | 0.004 | .001 | .0004 | .0001 | .00004 | | |
| *Acremonium* | x | x | x | x | 5/5 22.6 - 23.1 | 5/5 24.6 - 24.7 | 8/8^ 25.9 - 26.3 | 10/10 26.8 - 28.4 | 3/10 28.8 - 29.4 | 0/10 30.1 - 30.7 | 0/10 31.0 - 31.6 | **0.001** | **11** |
| *Alternaria* | x | x | 5/5 22.2 - 22.4 | 5/5 24.5 - 24.9 | 10/10 25.7 - 26.0 | 9/9^ 27.7 - 28.0 | 0/10 28.9 - 29.3 | 0/10 30.6 - 31.1 | 0/10 31.4 - 32.2 | x | x | **0.01** | **156** |
| *Aspergillus* | x | x | 5/5 22.0 - 23.4 | 5/5 22.0 - 23.2 | 10/10 24.6 - 26.1 | 10/10 24.6 - 25.7 | 10/10 27.7 - 28.6 | 9/10 31.0 - 32.2 | 0/10 32.9 - 34.4 | x | x | **0.004** | **57** |
| *Curvularia* | x | x | 5/5 22.2 - 23.5 | 5/5 21.8 - 24.1 | 10/10 25.5 - 26.2 | 10/10 24.8 - 27.2 | 10/10 28.6 - 29.4 | 10/10 24.8 - 29.2 | 1/10 28.9 - 30.7 | 0/10 32.9 - 34.1 | 0/10 32.3 - 34.5 | **0.001** | **12*** |
| *Fusarium* | x | x | x | 15/15 23.7 - 27.0 | 10/10 25.9 - 26.5 | 5/5 28.1 - 28.6 | 9/9^ 28.7 - 29.1 | 10/10 30.9 - 31.8 | 0/10 34.0 - 35.0 | 2/10 32.5 - 33.5 | x | **0.001** | **9** |
| *Scopulariopsis* | x | x | x | x | 5/5 26.6 - 27.2 | 5/5 29.2 - 29.7 | 10/10 30.6 - 31.7 | 1/10 31.5 - 34.1 | 0/10 34.0 - 35.0 | 0/10 35.5 - > 36 | 0/10 34.9 - > 36 | **0.004** | **49*** |
| *Scytalidium* | 5/5 19.9 - 20.1 | 5/5 21.9 - 22.1 | 10/10 23.5 - 23.9 | 10/10 25.1 - 25.6 | 10/10 26.5 - 27.0 | 10/10 28.0 - 29.3 | 10/10 29.0 - 30.0 | 0/10 35.4 - > 36 | 0/10 35.6 - > 36 | x | x | **0.004** | **12*** |

x = concentration not tested ^ = Outlier replicates dropped
* = C values not published. Value used (0.4) was the mean of 64 different saprophytes

FIG. 72

Table 64

| SapA_Ct | SapA_Tm1 | SapB_Ct | N = 75 |
|---|---|---|---|
| 17.5 | 83.17 | 32.0 | Mean |
| 17.5 | 83.16 | 31.8 | Median |
| 0.517 | 0.268 | 1.12 | SD |
| 2.96 | 0.323 | 3.51 | CV (%) |
| 16.3 | 82.54 | 30.0 | Min |
| 18.9 | 83.79 | 34.7 | Max |

FIG. 73

Table 65

| SapA_Ct | SapA_Tm1 | SapB_Ct | N = 75 |
|---|---|---|---|
| 18.8 | 76.18 | 33.4 | Mean |
| 18.8 | 76.17 | 33.4 | Median |
| 0.291 | 0.230 | 1.27 | SD |
| 1.55 | 0.302 | 3.81 | CV (%) |
| 17.6 | 75.46 | 31.0 | Min |
| 19.6 | 76.61 | 36.0 | Max |

FIG. 74

Table 66

| SapA_Ct | SapA_Tm1 | SapB_Ct | N = 75 |
|---|---|---|---|
| 20.2 | 85.29 | 33.8 | Mean |
| 20.1 | 85.26 | 33.6 | Median |
| 0.690 | 0.229 | 1.31 | SD |
| 3.43 | 0.268 | 4.01 | CV (%) |
| 19.0 | 84.70 | 30.9 | Min |
| 23.8 | 85.75 | 36.0 | Max |

FIG. 75

Table 67

| SapA_Ct | SapA_Tm1 | SapB_Ct | N = 75 |
|---|---|---|---|
| 19.1 | 79.69 | 33.4 | Mean |
| 19.1 | 79.64 | 33.1 | Median |
| 0.635 | 0.300 | 1.18 | SD |
| 3.32 | 0.377 | 3.56 | CV (%) |
| 17.4 | 78.99 | 31.4 | Min |
| 20.2 | 80.46 | 36.0 | Max |

FIG. 76

Table 68

| SapA_Ct | SapB_Ct | SapB_Tm1 | N = 75 |
|---|---|---|---|
| 31.4 | [illegible] | [illegible] | Mean |
| 31.5 | [illegible] | [illegible] | Median |
| 1.56 | [illegible] | [illegible] | StdDev |
| 4.94 | [illegible] | [illegible] | CV (%) |
| 24.0 | [illegible] | [illegible] | Min |
| 35.0 | [illegible] | [illegible] | Max |

FIG. 77

Table 69

| SapA_Ct | SapB_Ct | SapB_Tm | N = 74 |
|---|---|---|---|
| 28.5 | 23.2 | 73.33 | Mean |
| 28.3 | 23.0 | 73.44 | Median |
| 1.17 | 1.16 | 0.389 | SD |
| 4.15 | 4.99 | 0.530 | CV (%) |
| 26.5 | 20.8 | 72.33 | Min |
| 31.9 | 25.2 | 74.08 | Max |

FIG. 78

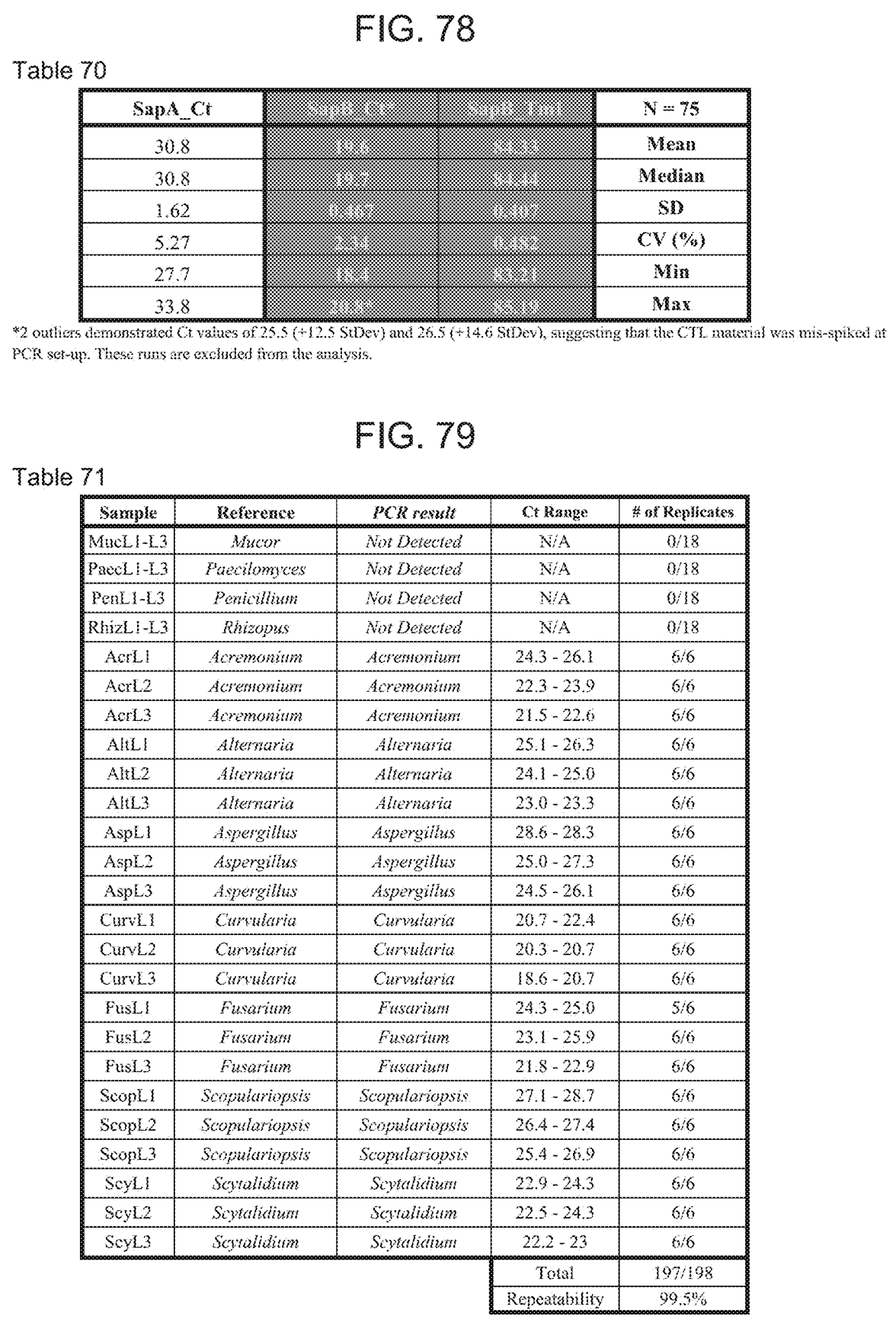

Table 70

| SapA_Ct | [illegible] | [illegible] | N = 75 |
|---|---|---|---|
| 30.8 | 19.6 | 84.33 | **Mean** |
| 30.8 | 19.7 | 84.43 | **Median** |
| 1.62 | 0.457 | 0.407 | **SD** |
| 5.27 | 2.34 | 0.482 | **CV (%)** |
| 27.7 | 18.4 | 83.21 | **Min** |
| 33.8 | 20.8* | 85.19 | **Max** |

*2 outliers demonstrated Ct values of 25.5 (+12.5 StDev) and 26.5 (+14.6 StDev), suggesting that the CTL material was mis-spiked at PCR set-up. These runs are excluded from the analysis.

FIG. 79

Table 71

| Sample | Reference | *PCR result* | Ct Range | # of Replicates |
|---|---|---|---|---|
| MucL1-L3 | *Mucor* | *Not Detected* | N/A | 0/18 |
| PaecL1-L3 | *Paecilomyces* | *Not Detected* | N/A | 0/18 |
| PenL1-L3 | *Penicillium* | *Not Detected* | N/A | 0/18 |
| RhizL1-L3 | *Rhizopus* | *Not Detected* | N/A | 0/18 |
| AcrL1 | *Acremonium* | *Acremonium* | 24.3 - 26.1 | 6/6 |
| AcrL2 | *Acremonium* | *Acremonium* | 22.3 - 23.9 | 6/6 |
| AcrL3 | *Acremonium* | *Acremonium* | 21.5 - 22.6 | 6/6 |
| AltL1 | *Alternaria* | *Alternaria* | 25.1 - 26.3 | 6/6 |
| AltL2 | *Alternaria* | *Alternaria* | 24.1 - 25.0 | 6/6 |
| AltL3 | *Alternaria* | *Alternaria* | 23.0 - 23.3 | 6/6 |
| AspL1 | *Aspergillus* | *Aspergillus* | 28.6 - 28.3 | 6/6 |
| AspL2 | *Aspergillus* | *Aspergillus* | 25.0 - 27.3 | 6/6 |
| AspL3 | *Aspergillus* | *Aspergillus* | 24.5 - 26.1 | 6/6 |
| CurvL1 | *Curvularia* | *Curvularia* | 20.7 - 22.4 | 6/6 |
| CurvL2 | *Curvularia* | *Curvularia* | 20.3 - 20.7 | 6/6 |
| CurvL3 | *Curvularia* | *Curvularia* | 18.6 - 20.7 | 6/6 |
| FusL1 | *Fusarium* | *Fusarium* | 24.3 - 25.0 | 5/6 |
| FusL2 | *Fusarium* | *Fusarium* | 23.1 - 25.9 | 6/6 |
| FusL3 | *Fusarium* | *Fusarium* | 21.8 - 22.9 | 6/6 |
| ScopL1 | *Scopulariopsis* | *Scopulariopsis* | 27.1 - 28.7 | 6/6 |
| ScopL2 | *Scopulariopsis* | *Scopulariopsis* | 26.4 - 27.4 | 6/6 |
| ScopL3 | *Scopulariopsis* | *Scopulariopsis* | 25.4 - 26.9 | 6/6 |
| ScyL1 | *Scytalidium* | *Scytalidium* | 22.9 - 24.3 | 6/6 |
| ScyL2 | *Scytalidium* | *Scytalidium* | 22.5 - 24.3 | 6/6 |
| ScyL3 | *Scytalidium* | *Scytalidium* | 22.2 - 23 | 6/6 |
| | | | Total | 197/198 |
| | | | Repeatability | 99.5% |

FIG. 80

Table 72

| Task | DNA Extraction | SapA PCR | SapB PCR |
|---|---|---|---|
| # Performed | 51 | 103 | 88 |
| # of Operators | 5 | 3 | 3 |
| Over # of days | 120 | 103 | 47 |
| # of Reagent Lots | 1 | 4 | 3 |
| # of Primer Lots | N/A | 4 | 2 |
| # of Platforms | 2 | 7 (6 PCR, 1 Set-Up) | 7 (6 PCR, 1 Set-Up) |

FIG. 81

Table 73

| | Fungal Screen Saprophyte + | Fungal Screen Saprophyte - | Total |
|---|---|---|---|
| Saprophyte Reflex + | 317 (22.4%) | 38 (2.69%) | 356 |
| Saprophyte Reflex - | 106 (7.50%) | 953 (67.4%) | 1062 |
| Total | 426 | 992 | |

| N = 1414 | |
|---|---|
| Concordance | 89.8 % |
| Sensitivity | 74.9 % |
| Specificity | 96.2 % |

FIG. 82A

Table 74

| | *Acremonium* Reflex + | *Acremonium* Reflex - | Total |
|---|---|---|---|
| *Acremonium* Sequencing + | 57 | 2 | 59 |
| *Acremonium* Sequencing - | 0 | 145 | 150 |
| Total | 57 | 152 | |

| N = 204 | |
|---|---|
| Concordance | 99.0 % |
| Sensitivity | 96.6 % |
| Specificity | 100 % |

Table 75

| | *Alternaria* Reflex + | *Alternaria* Reflex - | Total |
|---|---|---|---|
| *Alternaria* Sequencing + | 51 | 1 | 52 |
| *Alternaria* Sequencing - | 0 | 152 | 152 |
| Total | 51 | 153 | |

| N = 204 | |
|---|---|
| Concordance | 99.5 % |
| Sensitivity | 98.1 % |
| Specificity | 100 % |

FIG. 82B

Table 76

| | *Scytalidium* Reflex + | *Scytalidium* Reflex - | Total |
|---|---|---|---|
| *Scytalidium* Sequencing + | 44 | 0 | 44 |
| *Scytalidium* Sequencing - | 0 | 160 | 160 |
| Total | 44 | 160 | |

| N = 204 | |
|---|---|
| Concordance | 100 % |
| Sensitivity | 100 % |
| Specificity | 100 % |

Table 77

| | *Curvularia* Reflex + | *Curvularia* Reflex - | Total |
|---|---|---|---|
| *Curvularia* Sequencing + | 49 | 0 | 49 |
| *Curvularia* Sequencing - | 0 | 155 | 155 |
| Total | 49 | 155 | |

| N = 204 | |
|---|---|
| Concordance | 100 % |
| Sensitivity | 100 % |
| Specificity | 100 % |

Table 78

| | *Aspergillus* Reflex + | *Aspergillus* Reflex - | Total |
|---|---|---|---|
| *Aspergillus* Sequencing + | 170 | 5 | 175 |
| *Aspergillus* Sequencing - | 0 | 190 | 190 |
| Total | 170 | 195 | |

| N = 365 | |
|---|---|
| Concordance | 98.6 % |
| Sensitivity | 97.1 % |
| Specificity | 100 % |

Table 79

| | *Fusarium* Reflex + | *Fusarium* Reflex - | Total |
|---|---|---|---|
| *Fusarium* Sequencing + | 123 | 13 | 135 |
| *Fusarium* Sequencing - | 0 | 229 | 229 |
| Total | 123 | 242 | |

| N = 365 | |
|---|---|
| Concordance | 96.4 % |
| Sensitivity | 90.4 % |
| Specificity | 100 % |

Table 80

| | *Scopulariopsis* Reflex + | *Scopulariopsis* Reflex - | Total |
|---|---|---|---|
| *Scopulariopsis* Sequencing + | 50 | 4 | 54 |
| *Scopulariopsis* Sequencing - | 0 | 311 | 311 |
| Total | 50 | 315 | |

| N = 365 | |
|---|---|
| Concordance | 98.9 % |
| Sensitivity | 92.6 % |
| Specificity | 100 % |

FIG. 83

Table 81

| | Saprophyte Reflex + | Saprophyte Reflex - | Total |
|---|---|---|---|
| Seq (7 Saps) + | 553 (76.7%) | 25 (3.47%) | 578 |
| Seq (7 Saps) - | 1 (0.14%) | 144 (19.7%) | 145 |
| Total | 554 | 169 | |

| N = 723 | |
|---|---|
| Concordance | 96.4 % |
| Sensitivity | 95.7 % |
| Specificity | 99.3 % |

FIG. 84A

Example report A

*Candida* genus: Not Identified
Dermatophytes: Not Identified
Saprophytes: Not Identified

Example report B

Saprophytes: DETECTED
*Acremonium* DETECTED
*Alternaria* Not Detected
*Scytalidium* Not Detected
*Curvularia* Not Detected
*Aspergillus* Not Detected
*Fusarium* Not Detected
*Scopulariopsis* Not Detected
*Candida* genus: Not Identified
Dermatophytes: Not Identified

Example report C

Saprophytes: DETECTED
*Acremonium* Not Detected
*Alternaria* DETECTED
*Scytalidium* Not Detected
*Curvularia* Not Detected
*Aspergillus* Not Detected
*Fusarium* Not Detected
*Scopulariopsis* Not Detected
*Candida* genus: Not Identified
Dermatophytes: Not Identified

FIG. 84B

Example report D

| | | |
|---|---|---|
| Saprophytes: | DETECTED | |
| *Acremonium* | | Not Detected |
| *Alternaria* | | Not Detected |
| *Scytalidium* | | DETECTED |
| *Curvularia* | | Not Detected |
| *Aspergillus* | | Not Detected |
| *Fusarium* | | Not Detected |
| *Scopulariopsis* | | Not Detected |
| *Candida* genus: | Not Identified | |
| Dermatophytes: | Not Identified | |

Example report E

| | | |
|---|---|---|
| Saprophytes: | DETECTED | |
| *Acremonium* | | Not Detected |
| *Alternaria* | | Not Detected |
| *Scytalidium* | | Not Detected |
| *Curvularia* | | DETECTED |
| *Aspergillus* | | Not Detected |
| *Fusarium* | | Not Detected |
| *Scopulariopsis* | | Not Detected |
| *Candida* genus: | Not Identified | |
| Dermatophytes: | Not Identified | |

Example report F

| | | |
|---|---|---|
| Saprophytes: | DETECTED | |
| *Acremonium* | | Not Detected |
| *Alternaria* | | Not Detected |
| *Scytalidium* | | Not Detected |
| *Curvularia* | | Not Detected |
| *Aspergillus* | | DETECTED |
| *Fusarium* | | Not Detected |
| *Scopulariopsis* | | Not Detected |
| *Candida* genus: | Not Identified | |
| Dermatophytes: | Not Identified | |

FIG. 84C

Example report G

| | | |
|---|---|---|
| Saprophytes: | DETECTED | |
| *Acremonium* | | Not Detected |
| *Alternaria* | | Not Detected |
| *Scytalidium* | | Not Detected |
| *Curvularia* | | Not Detected |
| *Aspergillus* | | Not Detected |
| *Fusarium* | | DETECTED |
| *Scopulariopsis* | | Not Detected |
| *Candida* genus: | Not Identified | |
| Dermatophytes: | Not Identified | |

Example report H

| | | |
|---|---|---|
| Saprophytes: | DETECTED | |
| *Acremonium* | | Not Detected |
| *Alternaria* | | Not Detected |
| *Scytalidium* | | Not Detected |
| *Curvularia* | | Not Detected |
| *Aspergillus* | | Not Detected |
| *Fusarium* | | Not Detected |
| *Scopulariopsis* | | DETECTED |
| *Candida* genus: | Not Identified | |
| Dermatophytes: | Not Identified | |

| % Freq | Ct < 28 | Organism |
|---|---|---|
| 32.8 | 150 | Aspergillus |
| 2.0 | 9 | Penicilium |
| 0.7 | 3 | Paecilomyces |
| 0.2 | 1 | Mucor |
| 3.7 | 17 | Scopulariopsis |
| 3.7 | 17 | Scytalidium |
| 2.4 | 11 | Acremonium |
| 2.2 | 10 | Alternaria |
| 0.2 | 1 | Chaetomium |
| 23.4 | 107 | Fusarium |
| 0.2 | 1 | Curvularia |
| 1.5 | 7 | Candida |
| 0.4 | 2 | Cladosporium |
| 0.4 | 2 | Dermatophyte |
| 2.4 | 11 | Epicoccum |
| 3.7 | 17 | Malassezia |
| 12.2 | 56 | No reliable seq |
| 4.6 | 21 | Other |
| 0.2 | 1 | Phoma |
| 0.2 | 1 | Pithomyces |
| 0.2 | 1 | Rhodotorula |
| 0.4 | 2 | T mentag |
| 2.2 | 10 | T rubrum |

| Organism | Number | % |
|---|---|---|
| Sap panel | 327 | 71.4 |
| Non panel | 75 | 16.4 |
| No seq | 56 | 12.2 |

| % Freq | Ct > 28 | Organism |
|---|---|---|
| 1.7 | 20 | Fusarium |
| 0.1 | 1 | Paecilomyces |
| 0.1 | 1 | Rhizopus |
| 1.6 | 19 | Aspergillus |
| 24.6 | 295 | No reliable seq |
| 0.8 | 10 | Curvularia |
| 0.6 | 7 | Penicilium |
| 6.7 | 81 | Epicoccum |
| 0.5 | 6 | Scytalidium |
| 0.2 | 3 | Alternaria |
| 0.2 | 2 | Scopulariopsis |
| 0.1 | 1 | Acremonium |
| 0.1 | 1 | Mucor |
| 5.5 | 66 | Candida |
| 2.1 | 25 | Cladosporium |
| 1.7 | 21 | Dermatophyte |
| 0.2 | 2 | Epidermophyton |
| 8.9 | 107 | Malassezia |
| 10.7 | 129 | Other |
| 0.4 | 5 | Phoma |
| 0.1 | 1 | Pithomyces |
| 0.4 | 5 | Rhodotorul |
| 0.2 | 2 | S cerevisia |
| 3.6 | 43 | T mentag |
| 29.0 | 348 | T rubrum |

| Organism | Number | % |
|---|---|---|
| Sap panel | 71 | 5.9 |
| Non panel | 835 | 69.5 |
| No seq | 295 | 24.6 |

FIG. 87A gtctgggaaatcttgtgaaactccgtcgtgctggggatagagcattgtaattrttgctcttcaa
cgaggaattcctagtaagcgcaagtcatcagcttgcgttgattacgtccctgccctttgtacac
accgcccgtcgctactaccgattgaatggc (SEQ ID NO:108)

FIG. 87B gaggttggaaacgaccgcccagggccggaaagttggtcaaactcggtcatttagaggaagtaaa
agtcgtaacaaggtttccgtaggtgaacctgcggaaggatcattaacgcgcaggccggangytg
gccccccacgnnatcmggkcnccsacgkgccwtcaggggtgagcagaggtgcgccggccgyacg
ncccattcttgtctacntsacccggttgcctcggcgggc (SEQ ID NO:109)

FIG. 87C ggggctcttttgggtctcgtaattggaatgagtacaatctaaatcccttaacgaggaacaattg
gagggcaagtctggtgccagcagccgcggtaattccagctccaatagcgtatattaaagttgtt
gcagttaaaaagctcgtagttgaaccttgggtctggctggccggtccgcctcaccgcgagtact
ggtccggctggac (SEQ ID NO:110)

FIG. 87D agaggtgggcaactaccactcagggccggaaagctctccaaactcggtcatttagaggaagtaa
aagtcgtaacaaggtctccgttggtgaaccagcg (SEQ ID NO:111)

FIG. 87E tggcaacgaccaccycaagccggaaagttcgtcaaactcggtcatttagaggaagtaaaagtcg
taacaaggtctccgtaggtgaacctgcggagggatcattacacaantawgaakrcgnnggctgk
(SEQ ID NO:112)

FIG. 87F actcaccaggtccagacatagtaaggattgacagattgaaagctctttctagattctatgggtg
gtggtgc (SEQ ID NO:113)

FIG. 87G gaaggatcattaccgagttgattcgggctccggcccgatcctcccnccctttgtgtacccacct
ctgttgctttggcgggccgcggtcctccgcggccgccctccgtccgggggtggccagcgcccg
ccagaggaccatcraactccggtcagtgaacgttgccgtctga (SEQ ID NO:246)

FIG. 88A gtagctgagcgtaagacattaggttatatgcaacggagagttggtcctaatgctgtaggttatt
atggtattttaatggctattgctgatgcagctaaattattacttaaagagattgttgttcctac
acatgcagataaacttatcttatttgtaagtcctatgatttcattgatatctgcattactatgt
tgatctgttatacctttcgcacccggagttactat(SEQ ID NO:114)

FIG. 88B tctgaaggttgtacgaaatggggaaaaatacaaactctcagtgaagtatttagtactctagata
tagctttagtggtaatattaagtttaatgagaatgaatccttattataaaattggttcagcgat
actagggtcttctg (SEQ ID NO:115)

FIG. 88C gtcaggggtgagcagatgtgcgccggccgtaccgccccattcttgtctacattactcggttgcc
tcggcgggccgcgctctcccaggagagccgttcggcgagcctctctttagtggctaaacgctgg
accgcgcccgccggaggacagacgcaaaaaaattctttcagaagagctgtcagtctgagcg
(SEQ ID NO:116)

FIG. 88D atcaggggtgagcagacgtgcgccggccgtacgcccccattcttgtctacctcacccggttgcc
tcggcgggccgcgctccccctgccagggagagccgtccggcgggccccttctgggagcctcgag
ccggaccgcgcccgccggaggacagacaccaagaaaaaattctctgaagagctgtcagtctgag
cg (SEQ ID NO:117)

FIG. 88E cattgcgccctctggtattccgggggcatgcctgttcgagcgtcatttcaacccctcaagccc
ggcttgtgtgatggacgaccgtccgaccgcctttgcatcccccgttccaccgggagaggagaaa
ggtggag(SEQ ID NO:118)

FIG. 88F ttgtctactgacccggttgcctcggcggggccgcgcctgctgtgctacagcggccgttcggggg
ggacgcctgaggggactcttgtttc (SEQ ID NO:119)

FIG. 88G cgtcatttcaaccctcaggacccccttttcgggggggacctggtgctggggatcagcggcctccg
ggcccctgtccccaaattgagtggcggtcgcgccgcagcctcccctgcgtagtagcacacctc
gcaccggagagcggctcggccacgccgtgaaaccccca (SEQ ID NO:236)

FIG. 88H cctctcggggttacagccttgctgaattattcacccttgtcttttgcgtacttcttgtttcctt
ggtgggttcgcccaccactaggacaaacataaacctttttgtaattgcaatcagcgtcagtaac
(SEQ ID NO:237)

FIG. 88I gcaatcagcgtcagtataacaaatgtaaatcatttacaactttcaacaacggatctcttggttc
tggcatcgatgaagaacgcagcgaaatgcgatacgtagtgtgaattgcagaattcagtgaatca
tcgaatctttgaacgcacattgcgccctttggtattccaaagggcatgcctgttcgagcgtcat
ttgtaccctcaagctttgcttggtgttgggcgtttttttgtctttggttgccaaagactcgcctt
aaaaggattggcagccggcctactggtttcgcagcgcagcacatttttgcgcttgcaatcagc
(SEQ ID NO:238)

FIG. 88J gaaggatcattaccgagttgattcgggctccggcccgatcctcccnccctttgtgtacccacct
ctgttgctttggcgggccgcggtcctccgcggccgccctccgtccgggggggtggccagcgcccg
ccagaggaccatcraactccggtcagtgaacgttgccgtctga (SEQ ID NO:239)

FIG. 88K cggaggaaaagaaaccaaccgggattgcctcagtaacggcgagtgaagcggcaagagctcaaat
ttgaaagctggctccttcggggtccgcattgtaatttgcagaggatgcttcgggtgcggcccct
gtctaagtgccctggaacgg (SEQ ID NO:240)

FIG. 88L cggccacgccgttaaaccccaacttctgaatgttgacctcggatc (SEQ ID NO:241)

FIG. 88M cggccahgccgtaaaacacccaacttctgaatgttgacctcgaatc (SEQ ID NO:242)

FIG. 88N gcgcggctagccctacggggcctgccgtcgcccggtgttggggctctacgggtggggctcgtcc
ccccgcagtccccgaaatgtagtggcggtcc (SEQ ID NO:243)

PCR Detection Logic Workflow

* Only re-run PCR Experiment where the control failed

If Candida or Dermatophyte control failed, re-run Candid-Dermatophyte PCR experiment.
If Saprophyte control failed, re-run Saprophyte PCR experiment.

METHODS OF SCREENING FOR ONYCHOMYCOTIC FUNGI

CROSS-REFERENCE TO RELATED APPLICATIONS

This application claims priority benefit of U.S. provisional application Ser. No. 62/198,598, filed Jul. 29, 2015, which application is incorporated by reference herein in its entirety.

INTRODUCTION

Onychomycosis, i.e., a fungal infection of the nail, is an important public health problem due to its high incidence, increasing prevalence (10% and rising in the U.S. population), and associated complications. Individuals with onychomycosis have shown to be at increased risk to develop cellulitis, skin ulcerations, both of which may lead to loss of digits or limb. Complications related to onychomycosis is prevalent among individuals, such as elderly individuals, type 1 and type 2 diabetics, and other immunocompromised individuals, who are most susceptible to serious infections. In addition to advanced age and immunological deficiencies, additional predisposing factors are chronic microtrauma to the nail apparatus, onycholysis, onychoschezia, and genetic predisposing factors.

The most common pathogens implicated in onychomycosis are a class of keratin metabolizing organisms designated as the dermatophytes, the most common of which are *Trichophyton* rubrum, *Trichophyton interdigitale/mentagrophytes, Epidermophyton* and *Microsporum*. Other pathogens which have been implicated in the development of onychomycosis include *Candida* species and various saprophytes such as *Aspergillus, Acremonium* and *Alternaria.*

SUMMARY

Provided herein is a method of detecting an onychomycotic fungus in a sample, wherein the onychomycotic fungus belongs to a secondary clade member including one or more primary clade members. The method may include the steps of i) screening a sample using a first and second sets of secondary clade-specific primers to determine the presence or absence of a secondary clade member among a plurality of secondary clade members that include (a) a dermatophyte, (b) a *candida*, and (c) a saprophyte, and ii) after determining the presence of the secondary clade member, screening the sample to determine the presence or absence of an onychomycotic fungus using primary clade-specific primers that are specific to a primary clade member that belongs to the secondary clade member. In some embodiments, the screening step i) includes performing a first polymerase chain reaction (PCR) using the first set of secondary clade-specific primers in a first reaction mixture, and performing a second PCR using the second set of secondary clade-specific primers in a second reaction mixture.

In any embodiment, the first and second sets of secondary clade-specific primers may each include a primer pair that amplifies a secondary clade-specific nucleotide sequence encoding an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S or 5.8S ribosomal RNA.

In any embodiment, the first and second sets of one or more secondary clade-specific primers may each include one or more primer pairs that amplify a nucleotide sequence containing a sequence 80% or more identical to a sequence selected from either of SEQ ID NOs:108 and 109, or SEQ ID NOs: 110, 111, 112, 113 and 246.

In any embodiment, the screening step i) may include i-1) performing a first real-time PCR using the first set of secondary clade-specific primers to obtain a first cycle threshold (Ct) value ($Ct_1$), i-2) performing a second real-time PCR using the second set of secondary clade-specific primers to obtain a second Ct value ($Ct_2$), and i-3) analyzing the obtained first and second Ct values to determine the presence or absence of a secondary clade member. In some embodiments, the first set of secondary clade-specific primers is specific for a first set of one or more secondary clade members, and the second set of one or more secondary clade-specific primers is specific for a second set of one or more secondary clade members, wherein the first and second sets of one or more secondary clade members are different sets, and wherein the analyzing step i-3) includes determining the presence or absence in the sample a set among the first and second sets of one or more secondary clade members to which a secondary clade member present in the sample belongs, based on a comparison between $Ct_1$ and a first cutoff Ct value ($Ct_{cutoff1}$), a comparison between $Ct_2$ and a second cutoff Ct value ($Ct_{cutoff2}$), and/or a difference between $Ct_1$ and $Ct_2$. In some embodiments, the determining step includes, when $Ct_1$ is below $Ct_{cutoff1}$ and $Ct_2$ is below $Ct_{cutoff2}$, calculating $\Delta Ct_{2\text{-}1}=Ct_2-Ct_1$, comparing $\Delta Ct_{2\text{-}1}$ with a reference Ct range ($\Delta Ct_{range}$) defining an upper limit and a lower limit, and determining that the first but not the second set of one or more secondary clade members is present, when $\Delta Ct_{2\text{-}1}$ is greater than the upper limit of $\Delta Ct_{range}$, that the second but not the first set of one or more secondary clade members is present, when $\Delta Ct_{2\text{-}1}$ is lower than the lower limit of $\Delta Ct_{range}$, and that the first and the second sets of one or more secondary clade members are present, when $\Delta Ct_{2\text{-}1}$ is within $\Delta Ct_{range}$. In some embodiments, the determining step includes determining that the first but not the second set of one or more secondary clade members is present, when $Ct_1$ is below $Ct_{cutoff1}$ and $Ct_2$ is above $Ct_{cutoff2}$, that the second but not the first set of one or more secondary clade members is present, when $Ct_1$ is above $Ct_{cutoff1}$ and $Ct_2$ is below $Ct_{cutoff2}$, and that the first and the second sets of one or more secondary clade members are absent, when $Ct_1$ is above $Ct_{cutoff1}$ and $Ct_2$ is above $Ct_{cutoff2}$.

In any embodiment, the analyzing step i-3) may include obtaining one or more melting temperature (Tm) values for reaction products of the real-time PCR performed using the set of secondary clade-specific primers specific for the identified set of one or more secondary clade members, and after determining the presence of the set of one or more secondary clade members to which the secondary clade member present in the sample belongs, determining the presence or absence of a secondary clade member based on a comparison of the obtained one or more first Tm values and one or more reference Tm ranges specific for secondary clade members belonging to the identified set of one or more secondary clade members, wherein the secondary clade member is determined to be present in the sample when the one of more Tm values is within the one or more reference Tm ranges specific for the secondary clade member. In some embodiments, the obtaining one or more Tm values comprises using high resolution melt analysis.

In any embodiment, the first set of one or more secondary clade members may include a dermatophyte and a *candida*, and the second set of one or more secondary clade members may include a saprophyte.

In any embodiment, the screening step ii) may include performing one or more real-time PCR using the primary clade-specific primers. In some cases, the screening step ii) further includes obtaining one or more third Ct values, and one or more second Tm values, and analyzing the obtained third Ct and second Tm values to detect the presence or absence of an onychomycotic fungus in the sample. In some instances, the onychomycotic fungus is determined to be present when the obtained one or more Ct and Tm values fall within one or more reference Ct and Tm ranges specific for the onychomycotic fungus.

In any embodiment, the sample may be obtained from a human subject.

In any embodiment, the method may further include preparing the sample before the screening step i). In some embodiments, the preparing step includes releasing nucleic acids from a cellular compartment in the sample by subjecting the sample to mechanical, chemical, thermal and/or enzymatic treatments.

Also provided herein is a method including the steps of i) obtaining, in a sample, a first Ct value ($Ct_1$) from a first real-time PCR performed in a first reaction mixture using a first set of primers designed to amplify nucleic acid products that include a first set of one or more nucleotide sequences, and a second Ct value ($Ct_2$) from a second real-time PCR performed in a second reaction mixture using a second set of primers designed to amplify nucleic acid products that include a second set of one or more nucleotide sequences, ii) determining the presence or absence of a set of one or more nucleotide sequences to which a nucleic acid in the sample belongs, based on a comparison between $Ct_1$ and a first cutoff Ct value ($Ct_{cutoff1}$), a comparison between $Ct_2$ and a second cutoff Ct value ($Ct_{cutoff2}$), and/or a difference between $Ct_1$ and $Ct_2$, iii) obtaining one or more Tm values for the reaction products of, or Tm values with specific hybridization probes to the reaction products of, the real-time PCR performed using the set of primers designed to amplify nucleic acid products that contains the identified set of one or more nucleotide sequences, and iv) after determining the presence of the set of one or more nucleotide sequences to which the nucleic acid in the sample belongs, determining the presence or absence of the nucleic acid in the sample based on the obtained one or more Tm values and one or more reference Tm ranges specific for nucleic acid products amplified by the set of primers designed to amplify nucleic acid products containing the identified set of one or more nucleotide sequences, wherein the nucleic acid is determined to be present in the sample when the obtained one or more Tm values are within the one or more reference Tm ranges. In some instances, the determining step includes, when $Ct_1$ is below $Ct_{cutoff1}$ and $Ct_2$ is below $Ct_{cutoff2}$, calculating $\Delta Ct_{2-1}=Ct_2-Ct_1$, comparing $\Delta Ct_{2-1}$ with a reference Ct range ($\Delta Ct_{range}$) defining an upper limit and a lower limit, and determining that the first but not the second set of one or more nucleotide sequences is present, when $\Delta Ct_{2-1}$ is greater than the upper limit of $\Delta Ct_{range}$, that the second but not the first set of one or more nucleotide sequences is present, when $\Delta Ct_{2-1}$ is lower than the lower limit of $\Delta Ct_{range}$, and that the first and the second sets of one or more nucleotide sequences are present, when $\Delta Ct_{2-1}$ is within $\Delta Ct_{range}$. In some embodiments, the determining step ii) includes determining that the first but not the second set of one or more nucleotide sequences is present, when $Ct_1$ is below $Ct_{cutoff1}$ and $Ct_2$ is above $Ct_{cutoff2}$, that the second but not the first set of one or more nucleotide sequences is present, when $Ct_1$ is above $Ct_{cutoff1}$ and $Ct_2$ is below $Ct_{cutoff2}$, and that the first and second sets of one or more nucleotide sequences are absent, when $Ct_1$ is above $Ct_{cutoff1}$ and $Ct_2$ is above $Ct_{cutoff2}$.

A computer-implemented method of analyzing Ct and Tm values to determine the presence or absence of a secondary clade member of an onychomycotic fungus in a sample is also provided. In general terms, the computer-implemented method may include inputting, into a computer system configured to perform any method of analyzing Ct and Tm values as described above, a first Ct value ($Ct_1$) and one or more first Tm values from a first real-time PCR performed on a sample in a first reaction mixture using a first set of secondary-clade specific primers for a first secondary clade member, a second Ct value ($Ct_2$) and one or more first Tm values from a second real-time PCR performed on the sample in a second reaction mixture using a second set of secondary-clade primers for a second secondary clade member, wherein the first and second secondary clade members are chosen from dermatophytes, *candida*, and saprophytes, and combinations thereof, to generate a report, wherein the report indicates the presence or absence of a secondary clade member of an onychomycotic fungus in the sample.

Also provided herein is a computer system that includes a) a processor, and b) a memory operably coupled to the processor, wherein the memory includes instructions stored therein for analyzing Ct and Tm values to determine the presence or absence of an onychomycotic fungus in a sample, wherein the instructions, when executed by the processor, cause the processor to perform the method of analyzing Ct and Tm values, as described above.

A kit that finds use in implementing the present method of identifying an onychomycotic fungus in a sample is also provided.

A method of making real-time PCR primers for screening a sample is also provided. The method may include i) identifying a target nucleotide sequence specific to a clade containing a plurality of species and that includes a nucleotide sequence conserved within the clade, ii) generating a primer pair designed to amplify nucleic acid products containing the target nucleotide sequence, and iii) performing a plurality of real-time PCRs using the generated primer pair in (a) a positive control sample that includes the target nucleotide sequence to obtain one or more ranges of one or more Tm values, thereby generating one or more reference Tm ranges, and (b) a negative control sample that does not include the target nucleotide sequence to obtain a range of Ct values, thereby generating a cutoff Ct value, wherein the one or more reference Tm ranges and the cutoff Ct value provide for a determination of the presence or absence in a sample of a species belonging to the clade when the generated primer pair is used to perform a real-time PCR in the sample. In some embodiments, the method includes adding a nucleotide sequence tag to one or more primers of the primer pair to generate a tagged primer pair when the target nucleotide sequence amplified by the primer pair without the sequence tag does not provide for a determination of the presence of a species belonging to the clade in the sample.

BRIEF DESCRIPTION OF THE DRAWINGS

FIGS. 11A-11B show Tables 2.1 and 2.2, showing results of specificity testing for *candida*-, dermatophyte- and saprophyte-specific primers using DNA from culture, according to embodiments of the present disclosure.

FIG. 12 shows Table 3, showing results of specificity testing for *candida*-specific primers using DNA from culture, according to embodiments of the present disclosure.

FIG. 13 shows Table 4, showing test results of reagent blank (RB) using Extraction Control/Inhibition Control (EC/IC) control (CTL) for EC/IC, *candida*-, dermatophyte- and saprophyte-specific primers, according to embodiments of the present disclosure.

FIG. 14 shows Table 5, showing test results for no template control (NTC) using *candida*-, dermatophyte- and saprophyte-specific primers, according to embodiments of the present disclosure.

FIGS. 15A-15B Tables 6.1 and 6.2, showing the effect of bacterial interference on detection of *candida*, Dermatophytes or Saprophytes; and Tables 7.1 and 7.2, showing the effect of human genomic DNA interference on detection of *candida*, dermatophytes or saprophytes, according to embodiments of the present disclosure.

FIGS. 16A-16C show Tables 8.1, 8.2, and 8.3, showing the sensitivity of detecting *candida*, dermatophytes or saprophytes, according to embodiments of the present disclosure.

FIG. 17 shows Table 9, showing inter-assay reproducibility for Extraction Control/Inhibition Control (EC/IC) control (CTL) for EC/IC primers, according to embodiments of the present disclosure.

FIG. 18 shows Table 10, showing inter-assay reproducibility for *candida* CTL with *candida* primers, according to embodiments of the present disclosure.

FIG. 19 shows Table 11, showing inter-assay reproducibility for dermatophyte CTL with dermatophyte primers, according to embodiments of the present disclosure.

FIG. 20 shows Tables 12.1 and 12.2, showing inter-assay reproducibility for saprophyte CTL for two different saprophyte genera using saprophyte primers, according to embodiments of the present disclosure.

FIGS. 21A-21C show Tables 13.1, showing intra-assay repeatability for detection of *candida* and dermatophytes; and Table 13.2, showing intra-assay repeatability for detection of saprophytes, according to embodiments of the present disclosure.

FIG. 22 shows Tables 14.1 and 14.2, showing a summary of assay runs for detection of *candida*, dermatophytes or saprophytes, according to embodiments of the present disclosure.

FIGS. 23A-23B show Table 15.1, showing a summary comparison of histology results vs. Culture or PCR; Table 15.2, showing a summary comparison of histology results vs. Culture; and Table 15.3, showing a summary comparison of PCR results vs. Histology, according to embodiments of the present disclosure.

FIG. 24 shows Table 16, showing a summary comparison of fungal culture vs. fungal PCR, according to embodiments of the present disclosure.

FIG. 25 shows Table 17, showing the degree of concordance between *candida* detection by culture vs. PCR assay; Table 18, showing the degree of concordance between dermatophyte detection by culture vs. PCR; and Table 19, showing the degree of concordance between saprophyte detection by culture vs. PCR, according to embodiments of the present disclosure.

FIG. 26 shows Table 20, showing a summary of the concordance of detection by sequencing vs. PCR assay when culture vs. PCR assay is concordant; and Table 21, showing a summary of the concordance of detection by sequencing vs. PCR assay when culture vs. PCR assay is discordant, according to embodiments of the present disclosure.

FIG. 27 shows Table 22, showing concordance of *candida* detection by sequencing vs. PCR assay; Table 23, showing concordance of dermatophyte detection by sequencing vs. PCR assay; and Table 24, showing concordance of saprophyte detection by sequencing vs. PCR assay, according to embodiments of the present disclosure.

FIG. 30 shows Table 26, showing results of specificity testing for *C. albicans*- and *C. parapsilosis*-specific primers using DNA from culture, according to embodiments of the present disclosure.

FIG. 31 shows Table 27, showing test results of reagent blank (RB) using *C. albicans*- and *C. parapsilosis*-specific primers; and Table 28, showing test results for no template control (NTC) using *C. albicans*- and *C. parapsilosis*-specific primers, according to embodiments of the present disclosure.

FIG. 32 shows Table 29, showing the effect of bacterial interference on detection of *C. albicans* and *C. parapsilosis*; and Table 30, showing the effect of human genomic DNA interference on detection of *C. albicans* and *C. parapsilosis*, according to embodiments of the present disclosure.

FIG. 33 shows Table 31.1 and Table 31.2, showing the sensitivity of detecting *C. albicans* and *C. parapsilosis*, according to embodiments of the present disclosure.

FIG. 34 shows Table 32, showing inter-assay reproducibility for *C. albicans* CTL, according to embodiments of the present disclosure.

FIG. 35 shows Table 33, showing inter-assay reproducibility for *C. parapsilosis* CTL, according to embodiments of the present disclosure.

FIG. 36 shows Table 34, showing intra-assay repeatability for detection of *C. albicans* and *C. parapsilosis*, according to embodiments of the present disclosure.

FIG. 37 shows Table 35, showing a summary of assay runs for detection of *C. albicans* and *C. parapsilosis*, according to embodiments of the present disclosure.

FIG. 38 shows Table 36, showing a summary of the concordance of "Fungal detection by PCR" (Example 1) vs. *Candida* identification by PCR assays; Table 37, showing concordance of *C. albicans* detection by sequencing vs. PCR assay; and Table 38, showing concordance of *C. parapsilosis* detection by sequencing vs. PCR assay, according to embodiments of the present disclosure.

FIG. 39 shows examples of reports indicating the presence or absence of *candida*, dermatophyte and saprophyte, and/or the presence or absence of *C. albicans* and *C. parapsilosis* in a sample, according to embodiments of the present disclosure.

FIG. 43 shows Table 40, showing results of specificity testing for *Trichophyton*-, *Epidermophyton*- and *Microsporum*-specific primers, according to embodiments of the present disclosure.

FIG. 44 shows Table 41, showing test results of reagent blank (RB) using *Trichophyton*-, *Epidermophyton*- and *Microsporum*-specific primers, according to embodiments of the present disclosure.

FIG. 45 shows Table 42, showing test results for no template control (NTC) using *Trichophyton*-, *Epidermophyton*- and *Microsporum*-specific primers, according to embodiments of the present disclosure.

FIG. 46 shows Table 43, showing the effect of bacterial interference on detection of *T. mentagrophytes, T. rubrum, Epidermophyton* and *Microsporum*, according to embodiments of the present disclosure.

FIG. 47 shows Table 44, showing the effect of human genomic DNA interference on detection of *T. mentagrophytes, T. rubrum, Epidermophyton* and *Microsporum*, according to embodiments of the present disclosure.

FIG. 48 shows Table 45.1, showing the sensitivity of detecting *T. mentagrophytes, T. rubrum, Epidermophyton* and *Microsporum*, according to embodiments of the present disclosure.

FIG. 49 shows Table 45.2, showing the sensitivity of detecting *T. mentagrophytes, T. rubrum, Epidermophyton* and *Microsporum*, according to embodiments of the present disclosure.

FIG. 50 shows Table 46, showing inter-assay reproducibility for *T. mentagrophytes* control, according to embodiments of the present disclosure.

FIG. 51 shows Table 47, showing inter-assay reproducibility for *T. rubrum* control, according to embodiments of the present disclosure.

FIG. 52 shows Table 48, showing inter-assay reproducibility for *Epidermophyton* CTL, according to embodiments of the present disclosure.

FIG. 53 shows Table 49, showing inter-assay reproducibility for *Microsporum* CTL, according to embodiments of the present disclosure.

FIG. 54 shows Table 50, showing intra-assay repeatability for detection of *T. mentagrophytes, T. rubrum, Epidermophyton* and *Microsporum*, according to embodiments of the present disclosure.

FIG. 55 shows Table 51, showing a summary of assay runs for detection of *T. mentagrophytes, T. rubrum, Epidermophyton* and *Microsporum*, according to embodiments of the present disclosure.

FIG. 56 shows Table 52, showing a summary of the concordance of "Fungal detection by PCR" (Example 1) vs. "Dermatophyte Identification by PCR" assays, according to embodiments of the present disclosure.

FIG. 57 shows Table 53, showing degree of concordance of *T. mentagrophytes* detection by sequencing vs. PCR assay; Table 54, showing degree of concordance of *T. rubrum* detection by sequencing vs. PCR assay; Table 55, showing degree of concordance of *Epidermophyton* detection by sequencing vs. PCR assay; and Table 56, showing degree of concordance of *Microsporum* detection by sequencing vs. PCR assay, according to embodiments of the present disclosure.

FIG. 58 shows examples of reports indicating the presence or absence of *candida*, dermatophyte and saprophyte, and/or the presence or absence of *T. mentagrophytes, T. rubrum, Epidermophyton* and *Microsporum* in a sample, according to embodiments of the present disclosure.

FIG. 59 shows alignments to genomic regions of primers designed to amplify *Acremonium kiliense*-specific target sequences, according to embodiments of the present disclosure.

FIG. 60 shows alignments to genomic regions of primers designed to amplify *Alternaria alternata*-specific target sequences, according to embodiments of the present disclosure.

FIGS. 61A-61B show alignments to genomic regions of primers designed to amplify *Curvularia lunata*-specific target sequences, according to embodiments of the present disclosure.

FIG. 62 shows alignments to genomic regions of primers designed to amplify *Scytalidium dimidiatum*-specific target sequences, according to embodiments of the present disclosure.

FIG. 63 shows alignments to genomic regions of primers designed to amplify *Aspergillus flavus*-specific target sequences, according to embodiments of the present disclosure.

FIG. 64 shows alignments to genomic regions of primers designed to amplify *Fusarium oxysporum*-specific target sequences, according to embodiments of the present disclosure.

FIG. 65 shows alignments to genomic regions of primers designed to amplify *Scopulariopsis brevicaulis*-specific target sequences, according to embodiments of the present disclosure.

FIG. 66 shows Table 58, showing results of specificity testing for saprophyte primary clade-specific primers, according to embodiments of the present disclosure.

FIG. 67 shows Table 59, showing test results of reagent blank (RB) controls using saprophyte primary clade-specific primers, according to embodiments of the present disclosure.

FIG. 68 shows Table 60, showing test results for no template control (ntc) using saprophyte primary clade-specific primers, according to embodiments of the present disclosure.

FIG. 69 shows Table 61, showing the effect of bacterial interference on detection of saprophytes, according to embodiments of the present disclosure.

FIG. 70 shows Table 62, showing the effect of human genomic DNA interference on detection of saprophytes, according to embodiments of the present disclosure.

FIG. 71 shows Table 63, showing the sensitivity of detecting a saprophyte, according to embodiments of the present disclosure.

FIG. 72 shows Table 64, showing inter-assay reproducibility for *Acremonium* control, according to embodiments of the present disclosure.

FIG. 73 shows Table 65, showing inter-assay reproducibility for *Alternaria* control, according to embodiments of the present disclosure.

FIG. 74 shows Table 66 showing inter-assay reproducibility for *Scytalidium* control, according to embodiments of the present disclosure.

FIG. 75 shows Table 67, showing inter-assay reproducibility for *Curvularia* control, according to embodiments of the present disclosure.

FIG. 76 shows Table 68, showing inter-assay reproducibility for *Aspergillus* control, according to embodiments of the present disclosure.

FIG. 77 shows Table 69, showing inter-assay reproducibility for *Fusarium* control, according to embodiments of the present disclosure.

FIG. 78 shows Table 70, showing inter-assay reproducibility for *Scopulariopsis* control, according to embodiments of the present disclosure.

FIG. 79 shows Table 71, showing intra-assay repeatability for detection of a saprophyte, according to embodiments of the present disclosure.

FIG. 80 shows Table 72, showing a summary of assay runs for detection of a saprophyte, according to embodiments of the present disclosure.

FIG. 81 shows Table 73, showing a summary of the concordance of "Fungal detection by PCR" ("Fungal Screen") vs. "Saprophyte identification by PCR" ("Saprophyte Reflex") assays, according to embodiments of the present disclosure.

FIGS. 82A-82B show Table 74, showing degree of concordance of *Acremonium* detection by sequencing vs. PCR assay ("Reflex"); Table 75, showing degree of concordance of *Alternaria* detection by sequencing vs. PCR assay ("Reflex"); Table 76, showing degree of concordance of *Scytalidium* detection by sequencing vs. PCR assay ("Reflex"); Table 77, showing degree of concordance of *Curvularia* detection by sequencing vs. PCR assay ("Reflex"); Table 78, showing degree of concordance of *Aspergillus* detection by sequencing vs. PCR assay ("Reflex"); Table 79, showing degree of concordance of *Fusarium* detection by sequencing vs. PCR assay ("Reflex"); Table 80, showing degree of concordance of *Scopulariopsis* detection by sequencing vs. PCR assay ("Reflex").

FIG. 83 shows Table 81, showing a summary of the concordance of saprophyte detection by sequencing ("Seq") vs. "Saprophyte identification by PCR" ("Saprophyte Reflex") assays, according to embodiments of the present disclosure.

FIGS. 84A-84C show examples of reports indicating the presence or absence of a saprophyte in a sample, according to embodiments of the present disclosure.

FIGS. 87A-87G show consensus sequences of target nucleotide sequences amplified by secondary clade-specific primers, according to embodiments of the present disclosure.

FIGS. 88A-88N show target nucleotide sequences amplified by primary clade-specific primers, according to embodiments of the present disclosure.

DEFINITIONS

Figure 1:
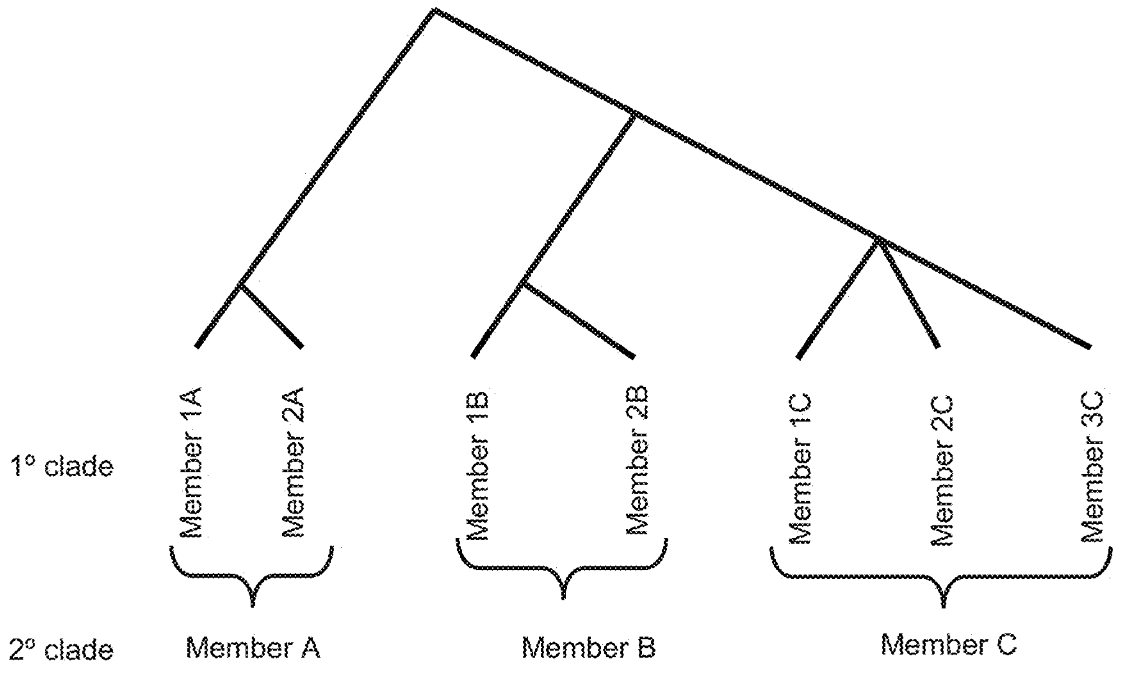
FIG. 1 schematically depicts an example of a relationship between primary and secondary clade members, according to embodiments of the present disclosure.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

Nucleotides, may be referred to by their commonly accepted single-letter codes, as defined in conformity with the IUPAC-IUBMB standards described in *Nucleic Acids Res.* 13:3021-3030 (1985) and in the *Biochemical J.* 219(2): 345-373 (1984) which are herein incorporated by reference. Nucleotide or nucleic acid sequences defined herein are represented by one-letter symbols for the bases as follows:

A (adenine);
C (cytosine);
G (guanine);
T (thymine);
U (uracil);
M (A or C);
R (A or G);
W (A or T/U);

S (C or G);

Y (C or T/U);

K (G or T/U);

V (A or C or G; not T/U);

H (A or C or T/U; not G);

D (A or G or T/U; not C);

B (C or G or T/U; not A);

N (A or C or G or T/U) or (unknown).

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection.

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Preferred, non-limiting examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, JMB, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karhn and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST®, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST® programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST® analyses is publicly available through the National Center for Biotechnology Information (NCBI; www(dot)ncbi(dot)nlm(dot)nih(dot)gov).

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product," depending on the context.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

As used herein, the term "portion," when used in reference to a nucleotide sequence, refers to fragments of that sequence. The fragments may range in size from ten nucleotides to the entire nucleotide sequence minus one nucleotide (e.g., 10 nucleotides or more, 20 nucleotides or more, 50 nucleotides or more, 100 nucleotides or more, 1000 nucleotides or more, etc., up to the entire nucleotide sequence minus one nucleotide).

A "nuclear-encoded ribosomal RNA gene" as used herein, may refer to a nucleotide sequence of a nuclear genome of a cell, where the nucleotide sequence corresponds to a transcriptional unit of one or more ribosomal RNA (rRNA) coding regions. Where the transcriptional unit includes multiple rRNAs, the nucleotide sequence may include a nucleotide sequence of the internal transcribed spacer (ITS) region that is interposed between consecutive rRNA coding regions. In some embodiments, the nuclear-encoded rRNA gene includes an 18S rRNA, 5.8S rRNA, 28S rRNA and two ITS regions (ITS1 and ITS2). The nuclear-encoded rRNA gene may have a structure represented by the formula: 5'-(18S)-(ITS1)-(5.8S)-(ITS2)-(28S)-3', where 18S is the 18S rRNA, 5.8S is the 5.8S rRNA, 28S is the 28S rRNA, ITS1 is the first ITS region, and ITS2 is the second ITS region.

As used herein, a "subject" refers to any animal, such as a mammal like a dog, cat, bird, livestock, and including a human.

A "set" may contain one or more elements that constitute the set.

"Within," as used in reference to a number being within a range of numbers, is meant to be inclusive of the values defining the upper and lower limits of the range.

"Onychomycosis" refers to a superficial fungal infection involving keratin of the nail unit of an animal, e.g., a human subject. An "Onychomycotic fungus" is the etiological agent for onychomycosis, and may include dermatophytes, *Candida* spp., and saprophytic molds.

A "dermatophyte" refers to a group of onychomycotic etiological agents that includes the genera *Trichophyton, Epidermophyton*, and *Microsporum*. Species within *Trichophyton* include, but are not limited to, *T. interdigitale/mentagrophytes* (which are allomorphs of the same species) and *T. rubrum.*

"*Candida*" and "*candida* fungus" are used interchangeably in reference to a group of onychomycotic etiological agents that includes the *Candida* genus, which includes *Candida* species, such as, but not limited to *C. albicans, C. parapsilosis, C. tropicalius*, and *C. guiliermondii*. In some cases, *candida* includes *Malassezia pachydermatis.*

"Saprophyte," and "saprophytic mold" are used interchangeably to refer to a group of onychomycotic etiological agents that is not a dermatophyte or a *candida*. A saprophyte may include, but is not limited to, the genera *Aspergillus, Acremonium, Alternaria, Penicillium, Paecilomyces, Fusarium, Scopulariopsis, Chaetomium, Curvularia, Mucor, Scytalidium* and *Rhizopus*.

A "clade," as used herein, refers to a group of organisms which share one or more feature(s) of a nucleic acid molecule(s) associated with an organism of the group. The nucleic acid molecule may be a DNA molecule, e.g., genomic DNA, mitochondrial DNA, etc., or a portion thereof, of the organism, or may be a RNA molecule, e.g., a transcribed RNA molecule, in the organism. The feature of the nucleic acid molecule shared by organisms in a clade may include structural features, such as sequence identity of a homologous nucleotide sequence contained in the nucleic acid molecule, or functional features, such as the melting temperature of an amplification product containing a homologous nucleotide sequence amplified from the nucleic acid molecule, or the melting temperature of a hybridization between an amplification product containing a homologous nucleotide sequence amplified from the nucleic acid molecule and a clade-specific hybridization probe. An organism that belongs to a specific clade will in general share all the features of the nucleic acid containing the nucleotide sequence that defines the clade with all other organisms in the same clade. Clades may be categorized by a level, where a clade of higher-numbered level (e.g., secondary clade) requires fewer shared nucleic acid features than a clade of lower-numbered level (e.g., primary clade). For example, a "primary" clade requires an organism share more nucleic acid features than required by a "secondary" clade. Thus a primary clade will encompass fewer organisms than a secondary clade. In some cases, the clade of lowest-numbered level corresponds to a phylogenetic species. The features of the nucleic acids containing a nucleotide sequence defining a clade may include, but are not limited to, sequence identity, annealing/melting temperature with a selected nucleic acid, rate of PCR amplification by primers that amplify the nucleotide sequence, and/or combinations thereof.

A "clade member," as used herein, refers to a clade defined by a predetermined set of feature(s) (e.g., the sequence identity of a homologous nucleotide sequence, the melting temperature of an amplification product containing a homologous nucleotide sequence, etc., as described above) of a nucleic acid molecule associated with organisms belonging to the clade. A first clade member "contains" or "comprises" a second clade member, and conversely, the second clade member "belongs to" or "is within" the first clade member, when all the defining features of the first clade member is shared with the second clade member, but when defining features of the second clade member that are different from the defining features of the first clade member are not all shared by other clade members having all the defining features of the first clade member.

"Clade-specific," as used in reference to a clade-specific reagent, refers to a reagent (e.g., primer or probe) having the necessary structural properties to provide an empirical measurement, obtained by using the reagent, of one or more feature(s) of the nucleic acid defining the clade member, by which measurement the clade member can be differentiated from another clade members defined by different feature(s) of a nucleic acid defining the second clade member. In certain cases, a reagent specific to a first clade member does not provide information about the presence or absence of a second clade member that belongs to the first clade member and is at a level lower than the level of the first clade member. Thus, a secondary clade-specific detection reagent used to determine the presence of a secondary clade member may not allow determination of the presence or absence of a primary clade member that belongs to the secondary clade member.

Before embodiments of the present disclosure are further described, it is to be understood that this embodiments of the present disclosure are not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges, and are also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of embodiments of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an onychomycotic fungus" includes a plurality of such onychomycotic fungi and reference to "the primer pair" includes reference to one or more primer pairs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the present disclosure, which are, for clarity, described in the context of separate embodiments, may also be provided in combination in a single embodiment. Conversely, various features of the present disclosure, which are, for brevity, described in the context of a single embodiment, may also be provided separately or in any suitable sub-combination. All combinations of the embodiments pertaining to the present disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

DETAILED DESCRIPTION

As summarized above, a method of detecting an onychomycotic fungus in a sample, wherein the onychomycotic fungus belongs to a primary clade nested within a secondary clade, is provided. The method may include the steps of i) screening a sample using a first and second sets of secondary clade-specific primers to determine the presence or absence of a secondary clade member among a plurality of secondary clade members that include (a) a dermatophyte, (b) a *candida*, and (c) a saprophyte, and ii) after determining the presence of the secondary clade member, screening the sample to determine the presence or absence of an onychomycotic fungus that belongs to a primary clade member belonging to the secondary clade member using primary clade-specific primers. Further aspects of the present disclosure are described now, with reference to the figures.

FIG. 1 shows a schematic diagram, showing an example of a relationship between individual members of a primary (1°) clade, which may correspond to, e.g., individual species or genera of fungi. The primary clade members may in turn be grouped into members of different secondary (2°) clades. Secondary clades are defined such that a primary clade member belongs to only one secondary clade. In some embodiments, where the primary clade member corresponds to a species, the secondary clade to which the primary clade member belongs may correspond to a genus, family, order, etc., or a subset thereof, e.g., of fungi. According to embodiments of the present disclosure, the relationship between members of the primary and secondary clades may be defined by features of nucleic acid molecules containing nucleotide sequences associated with organisms that belong to the respective clades, where the features are detectable by clade-specific detection reagents, such as clade-specific primers designed to amplify clade-specific nucleic acid products.

Figure 2:
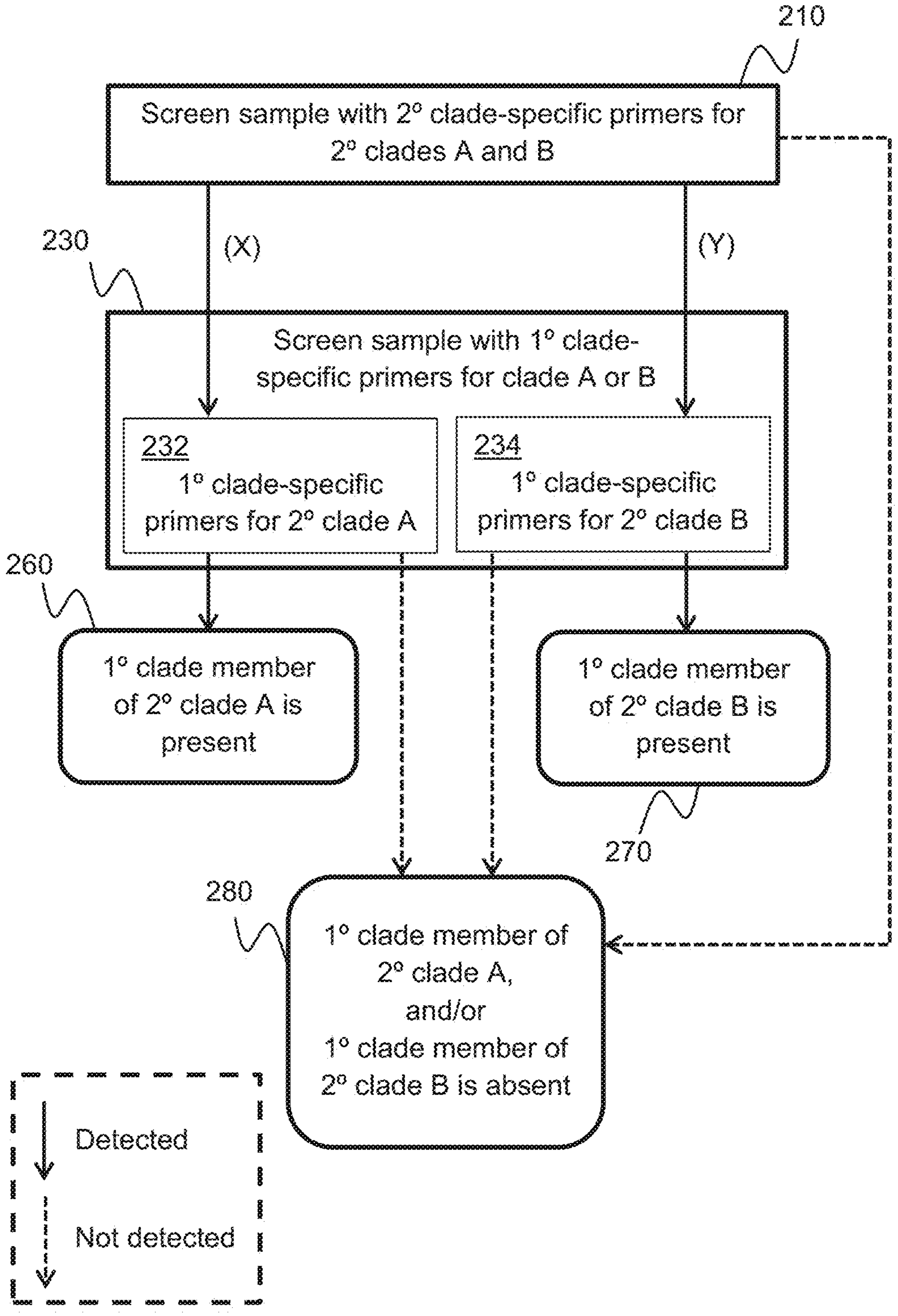
FIG. 2 shows a flow chart representing embodiments of the present disclosure.

With reference to FIG. 2, aspects of the present disclosure include a method including i) screening 210 a sample for a target organism that belongs to a primary clade member by using secondary clade-specific detection reagents, e.g., secondary clade-specific primers, to determine the presence or absence of a secondary clade member to which the primary clade member belongs, and ii) screening 230 the sample to determine the presence or absence of the target organism by using detection reagents specific to primary clades that belong to the secondary clade member, e.g., primary clade-specific primers 232/234, in samples for which the presence of the secondary clade member has been determined. Detection of a primary clade member by the primary clade-specific detection reagents allows for the determination 260/270 that the organism that belongs to the primary clade member is present in the sample. The determination 280 that the organism that belongs to the primary clade member is not present in the sample is made when the secondary clade member to which the organism belongs is not detected in the sample using secondary clade-specific detection reagents, or when the primary clade member to which the organism belongs is not detected in the sample using primary clade-specific detection reagents.

Figure 3:
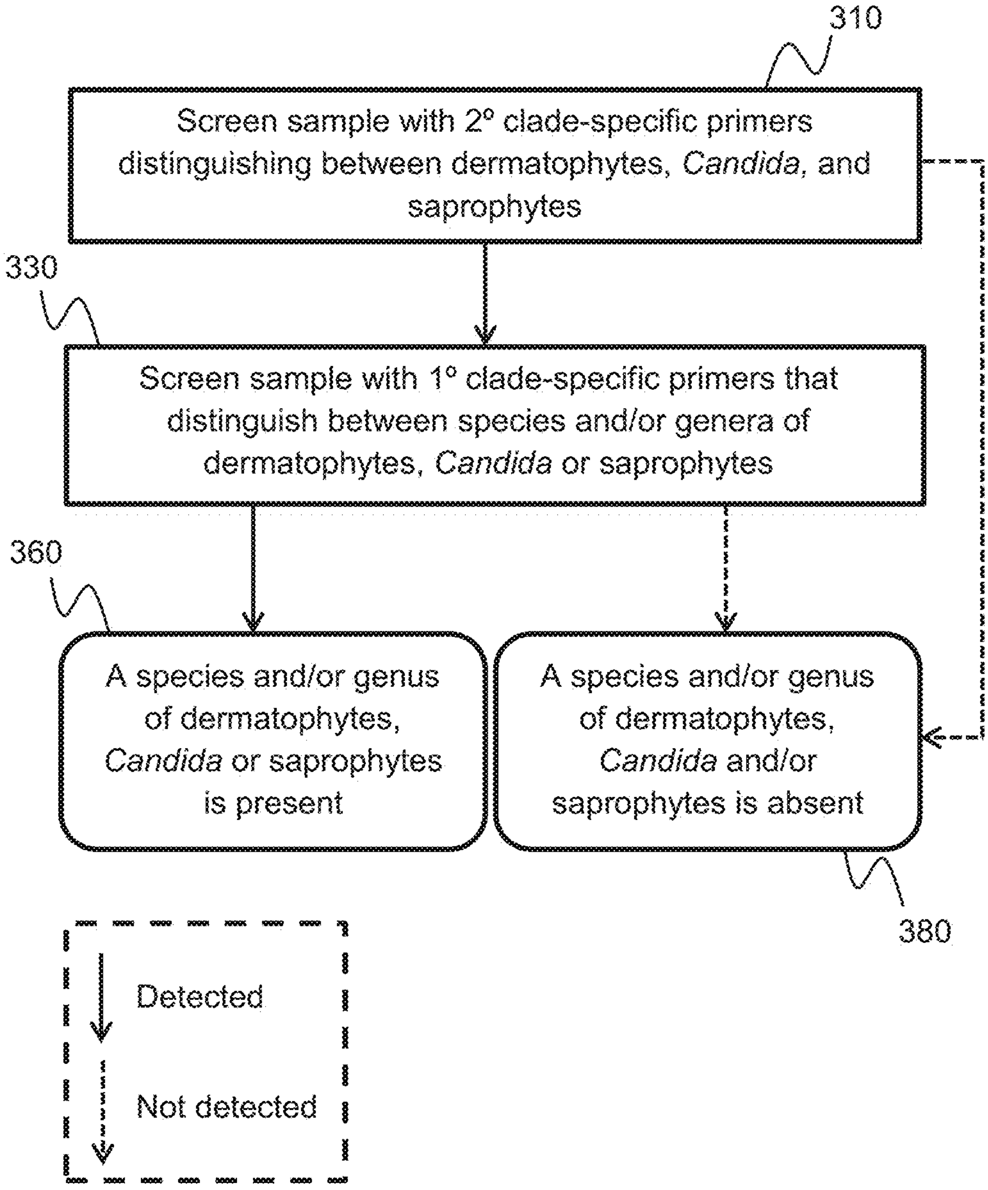
FIG. 3 shows a flow chart representing embodiments of the present disclosure.

FIG. 3 shows an embodiment of the present method for detecting an onychomycotic fungus in a sample. The first round of screening 310 may be performed using the secondary clade-specific primers that distinguish between different secondary clades of onychomycotic fungi. The secondary clade-specific primers may be used to run a polymerase chain reaction (PCR), e.g., real-time PCR, using the nucleic acids present in the sample as template, to obtain a cycle threshold (Ct) value for the reaction and/or melting temperature (Tm) value(s) for the nucleic acid product amplified by the secondary clade-specific primers, or the Tm values of a secondary clade-specific hybridization probe to the nucleic acid product amplified by the secondary clade-specific primers. The obtained Ct value and Tm value(s) may be analyzed to determine the presence or absence of a secondary clade member in the sample, as described in detail below. In certain embodiments, the onychomycotic fungi are divided into the secondary clade members: dermatophytes, *candida*, and saprophytes (i.e., non-dermatophyte, non-*candida* fungi).

Upon determining the presence of one or more secondary clade members, in the sample, the sample may be screened 330 using primary clade-specific primers that distinguish between different primary clade members of dermatophytes, *candida*, or saprophytes to determine the presence or absence of a primary clade member, e.g., a particular species of *Candida*, a particular species or genus of dermatophytes, or a particular species or genus of saprophytes. The primary clade-specific primers may be used to run a PCR, e.g., real-time PCR, using the nucleic acids present in the sample as template, to obtain a cycle threshold (Ct) value for the reaction and/or melting temperature (Tm) value(s) for the nucleic acid product amplified by the primary clade-specific primers, or the Tm values of a primary clade-specific hybridization probe to the nucleic acid product amplified by the primary clade-specific primers. The obtained Ct value and Tm value(s) may be analyzed to determine the presence or absence of a primary clade member in the sample, as described in detail below. Detection of a primary clade member by the primary clade-specific primers allows for the determination 360 that an onychomycotic fungus species or genus that belongs to the detected primary clade member is present in the sample. The determination 380 that the onychomycotic fungus species or genus that belongs to the primary clade member is not present in the sample is made when the secondary clade member to which the onychomycotic fungus species or genus belongs is not detected in the sample using the secondary clade-specific primers, or when the primary clade member to which the onychomycotic fungus species or genus belongs is not detected in the sample using the primary clade-specific primers.

Figure 4:
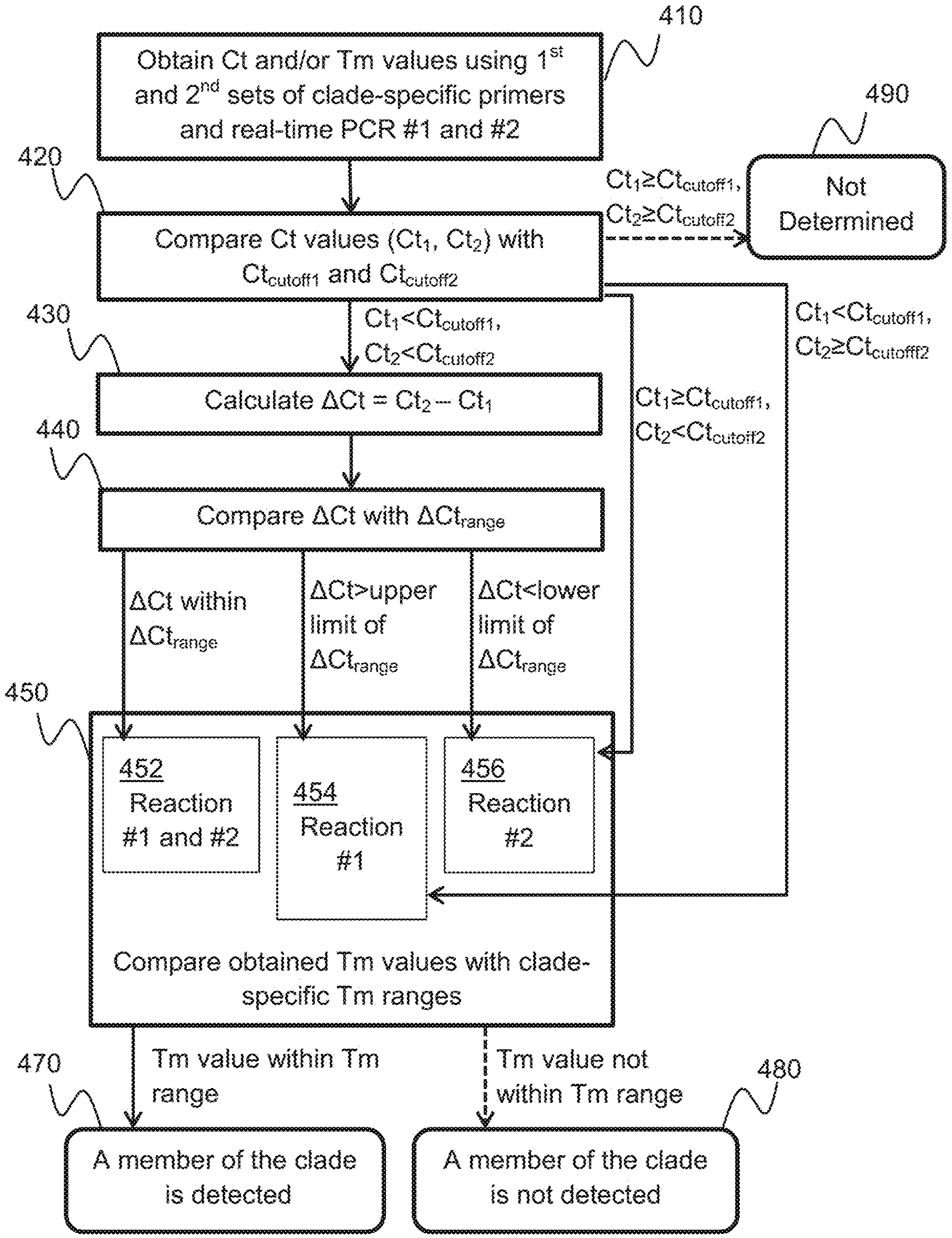
FIG. 4 shows a flow chart representing embodiments of the present disclosure.

FIG. 4 shows an embodiment of a method for analyzing Ct values and Tm values obtained by using secondary clade-specific primers, as described for FIG. 3 above, in a real-time PCR. In general terms, the method may include obtaining 410 a Ct value for a first real-time PCR using a first set of secondary clade-specific primers ($Ct_1$), and a Ct value for a second real-time PCR using a second set of secondary clade-specific primers ($Ct_2$), where the first set and second set of secondary clade-specific primers are specific to a first set and second set, respectively, of secondary clade members. Each pair of secondary clade-specific primers in a set of secondary clade-specific primers may be associated with a predetermined reference Ct range.

The Ct values are compared 420 to a predetermined cutoff Ct value for the first real-time PCR ($Ct_{cutoff1}$) and a predetermined cutoff Ct value for the second real-time PCR ($Ct_{cutoff2}$). A Ct value equal to or higher than the corresponding cutoff Ct value indicates that a secondary clade member for which the secondary clade-specific primers were targeted is absent from the sample. Thus, both $Ct_1$ and $Ct_2$ being greater than or equal to $Ct_{cutoff1}$ and $Ct_{cutoff2}$, respectively, provides for a determination 490 that a secondary clade member belonging to either the first or second sets of secondary clade members is not detected in the sample.

If upon comparison 420, both $Ct_1$ and $Ct_2$ are less than $Ct_{cutoff1}$ and $Ct_{cutoff2}$, respectively, the difference between $Ct_1$ and $Ct_2$ may be calculated 430 to obtain ΔCt (e.g., $\Delta Ct_{2-1}=Ct_2-Ct_1$). Comparing 440 ΔCt with a predetermined reference ΔCt range ($\Delta Ct_{range}$) may provide for the determination of the presence of a secondary clade member belonging to the first or second set of secondary clade members. Once a secondary clade member belonging to the first or second set of secondary clade members is identified, Tm value(s) for the nucleic acids amplified in the real-time PCR for which the secondary clade member was identified are analyzed 450.

Determination of the presence of a secondary clade member belonging to the first or second set of secondary clade members may be achieved in the following way. If the ΔCt is within $\Delta Ct_{range}$ (inclusive of the upper and lower limits of $\Delta Ct_{range}$), it may be determined that a secondary clade member belonging to the first set of secondary clade members and another secondary clade member belonging to the second set of secondary clade members are present in the sample. Then, Tm value(s) for nucleic acids amplified in both reactions are analyzed 452. On the other hand, if ΔCt is greater than the upper range limit of $\Delta Ct_{range}$, it may be determined that a secondary clade member belonging to the first set of secondary clade members, but not the second set of secondary clade members, is present in the sample. Then, Tm value(s) for nucleic acids amplified in reaction #1 are analyzed 454. If ΔCt is less than the lower range limit of $\Delta Ct_{range}$, it may be determined that a secondary clade member belonging to the second set of secondary clade members, but not the first set of secondary clade members, is present in the sample. Then, Tm value(s) for nucleic acids amplified in reaction #2 are analyzed 456.

If upon comparison 420, $Ct_2$ is greater than or equal to $Ct_{cutoff2}$ and $Ct_1$ is less than $Ct_{cutoff1}$, it may be determined that a secondary clade member belonging to the first set of secondary clade members, but not the second set of secondary clade members, is present in the sample. Then, Tm value(s) for nucleic acids amplified in reaction #1 are analyzed 454. If upon comparison 420, $Ct_1$ is greater than or equal to $Ct_{cutoff1}$ and $Ct_2$ is less than $Ct_{cutoff2}$, it may be determined that a secondary clade member belonging to the second set of secondary clade members, but not the first set of secondary clade members, is present in the sample. Then, Tm value(s) for nucleic acids amplified in reaction #2 are analyzed 456.

The Tm value(s) for one or more of the real-time PCR nucleic acid products, or a secondary clade-specific hybridization probe against the real-time PCR nucleic acid products are analyzed by comparing 450 the Tm value(s) with reference Tm range(s) that are specific to the secondary clade member targeted by the secondary clade-specific primers used to amplify the nucleic acid products. If the Tm value(s) are within the secondary clade-specific reference Tm range(s), it may be determined 470 that a secondary clade member targeted by the secondary clade-specific primers is present in the sample. If the Tm value(s) are not within the secondary clade-specific reference Tm range(s), it may be determined 480 that a secondary clade member targeted by the secondary clade-specific primers is absent from the sample.

In some embodiments, where two or more Tm values are derived from the real-time PCR, analyzing the Tm values may include calculating a difference between two Tm values (ΔTm), and comparing the difference against a reference Tm difference range. Thus, in some embodiments, the real-time PCR performed using secondary clade-specific primers on a sample may generate a first Tm value ($Tm_1$) and a second Tm value ($Tm_2$) for the amplification product. Then, the Tm difference (ΔTm) may be calculated as $\Delta Tm=|Tm_2-Tm_1|$, where || represents the absolute value. If the Tm difference (ΔTm) is within the secondary clade-specific reference Tm difference range, it may be determined that a secondary clade member targeted by the secondary clade-specific primers is present in the sample.

After determining the presence or absence of a secondary clade member in a sample, as described above, the method may include screening 230, 330 the sample for which the presence of the secondary clade member was detected to determine the presence or absence of a primary clade member that belongs to the secondary clade member. The screening step for the primary clade member may include performing a PCR (e.g., a real-time PCR) using primary clade-specific primers and nucleic acids in the sample as template, to obtain a Ct value for the reaction and one or more Tm values for any nucleic acid products amplified by the primary clade-specific primers, or Tm values for any primary clade-specific hybridization probe against any nucleic acid products amplified by the primary clade-specific primers. The obtained Ct value may be compared to a predetermined cutoff Ct value for the primary clade member. If the obtained Ct value is equal to or above the cutoff Ct value, then it may be determined that the primary clade member targeted by the primary clade-specific primers used in the PCR is absent from the sample. If the obtained Ct value is less than the cutoff Ct value, the analysis may proceed to analyzing one or more Tm value(s) for the real-time PCR reaction performed using the primary clade-specific primers, and comparing the obtained Ct value and Tm value(s) with a predetermined reference Ct range and predetermined reference Tm range(s), respectively, that are characteristic for the real-time PCR reaction performed using the primary clade-specific primers. An onychomycotic fungus belonging to the primary clade member may be determined to be present in the sample if the obtained Ct value is within the reference Ct range, and the obtained Tm value(s) are within the respective Tm range(s). For example, if the amplification product generates two Tm values defining a lower and higher Tm values, and there are two reference Tm ranges defining a lower and higher reference Tm ranges, then to satisfy the condition for determining the presence of an onychomycotic fungus belonging to the primary clade member in the sample, both the obtained lower Tm value is within the lower reference Tm range, and the obtained higher Tm value is within the higher reference Tm range, in addition to the obtained Ct value being within the reference Ct range. If the obtained Ct value or any one of the obtained Tm value(s) does not fall within the respective reference ranges, an onychomycotic fungus belonging to the primary clade member may be determined to be absent from the sample.

Clade-Specific Primers

Aspects of the present disclosure include clade-specific primers, e.g., secondary and primary clade-specific primers, that are designed to amplify (e.g., when combined with a polymerase, a template and a source of nucleotides under suitable conditions, such as a PCR condition) target sequences within the genomes of clade members to produce nucleic acid products that distinguish one clade member from another clade member. The genomic locus targeted by clade-specific primers specific for a first clade member may be the same or a different genomic locus targeted by clade-specific primers specific for a second, different clade member.

In certain embodiments, clade-specific primers are designed to amplify a nucleic acid product when the primers are used to perform PCR with template nucleic acids obtained from an organism that belongs to a clade member present in a sample, and are designed not to amplify a nucleic acid product when the clade member is not present in the sample assayed. In certain embodiments, clade-specific primers are designed to amplify a nucleic acid product when the primers are used to perform PCR with template nucleic acids in a sample containing a target clade member, and are designed not to amplify a nucleic acid product in a sample containing a non-target clade member but not the target clade member. Thus, clade-specific primers that specifically amplify a nucleic acid product in target clade members may be designed to amplify homologous nucleotide sequences that have a high percentage of sequence identity among organisms each of which belong to a target clade member, but do not amplify a homologous nucleotide sequence that have a low percentage of sequence identity in organisms which belong to a non-target clade member. In certain embodiments, the clade-specific primers may be designed to amplify in a sample containing a target clade member a target nucleotide sequence that is 70% or more, e.g., 80% or more, 85% or more, 90% or more, including 95% or more, and that is 100% or less, e.g., 95% or less, 90% or less, 85% or less, including 80% or less identical to a homologous nucleotide sequence in one or more other organisms, each of which belongs to a target clade member. In some cases, the clade-specific primers may be designed to amplify in a sample containing a target clade member a target nucleotide sequence that is 70% to 100%, e.g., 80% to 100%, including 85% to 100% identical to a homologous nucleotide sequence in one or more other organisms, each of which belongs to a target clade member.

In some embodiments, clade-specific primers are configured to amplify a nucleic acid product when nucleic acids containing the target nucleotide sequence from the target clade member as well as non-fungal nucleic acids are present in the sample, and not to amplify a nucleic acid product when the non-fungal nucleic acids are present but the nucleic acids from the target clade member is absent from the sample. In certain embodiments, the non-fungal nucleic acids include human genomic DNA and/or bacterial DNA. In certain embodiments, the clade-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences. Bacteria from which bacterial genomic sequences may be derived include, but are not limited to, *Pseudomonas aeruginosa, Proteus mirabilus, Staphylococcus aureus, Serratia marcescens*, and *Streptococcus pyogenes*.

Clade-specific primers, e.g., a pair of clade-specific primers, may be associated with a reference, or expected, Ct range for real-time PCR reactions in which a clade-specific nucleic acid product is amplified by the clade-specific primers. The clade-specific reference Ct range may provide one indication that a clade member is present in a sample when a Ct value obtained for the real-time PCR reaction using the clade-specific primers in the sample is within the clade-specific reference Ct range. In some embodiments, the clade-specific reference Ct range for a first clade member covers a distinct range of Ct values than the clade-specific reference Ct range for a second clade member.

Clade-specific primers, e.g., a pair of clade-specific primers, may be associated with one or more reference, or expected, Tm ranges of a clade-specific nucleic acid product amplified by the clade-specific primers. The clade-specific reference Tm ranges may provide one indication that a clade member is present in a sample when one or more Tm values obtained for an amplification product of the real-time PCR reaction, or from a hybridization between the amplification product of the real-time PCR reaction and a clade-specific hybridization, using the clade-specific primers in the sample is within the reference Tm ranges. In some embodiments, one or more Tm ranges of the clade-specific reference Tm ranges for a first clade member covers distinct ranges of Tm values than the clade-specific reference Tm ranges for a second, different clade member.

In some cases, clade-specific primers are designed to amplify a first nucleic acid product when the primers are used to perform PCR with template nucleic acids in a sample containing a first clade member, and are designed to amplify a second nucleic acid product when the primers are used to perform PCR with template nucleic acids in a sample containing a second clade member that is different from the first clade member, where the first and second nucleic acid products are distinguishable. In some cases, a pair of clade-specific primers is designed to amplify a first nucleic acid product when the pair is used to perform PCR with template nucleic acids obtained from a first clade member present in a sample, and the same pair of primers are designed to amplify a second nucleic acid product when the pair is used to perform PCR with template nucleic acids obtained from a second clade member present in a sample, where the first and second nucleic acid products are distinguishable. In some cases, a first set of clade-specific primers are designed to amplify a first nucleic acid product when the primers are used to perform PCR with template nucleic acids in a sample containing a first clade member, and a second set of clade-specific primers are designed to amplify a second nucleic acid product when the primers are used to perform PCR with template nucleic acids in a sample containing a second clade member, where the first and second nucleic acid products are distinguishable.

In some cases, the first and second nucleic acid products are distinguishable by having different rates of amplification, as measured by a Ct value. In some embodiments, the first clade-specific primers may be configured to amplify a first nucleic acid product in a reaction with a different Ct value than a reaction carried out using the second clade-specific primers configured to amplify a second nucleic acid product that contains a different target nucleotide sequence from the first nucleic acid product. The range of Ct values expected from the first reaction and the range of Ct values expected from the second reaction may be different by 1 cycle or more, e.g., 2 cycles or more, 2.5 cycles or more, 3 cycles or more, 4 cycles or more, 5 cycles or more, 6 cycles or more, 8 cycles or more, including 10 cycles or more, and may be different by 12 cycles or less, 11 cycles or less, 10 cycles or less, 9 cycles or less, 8 cycles or less, 7 cycles or less, 6 cycles or less, including 5 cycles or less, as measured between the medians of the respective ranges. In some cases, the Ct values expected from the first reaction and the Ct values expected from the second reaction may be different by 1 to 12 cycles, e.g., 2 to 10 cycles, 2 to 9 cycles, including 3 to 8 cycles, as measured between the medians of the respective ranges In some cases, the first and second nucleic acid products are distinguishable by having distinct melting temperature (Tm) value(s) that fall within corresponding reference Tm range(s), as determined by performing a melt analysis. The Tm may be the temperature about which on average 50% of a population of a specific double-stranded DNA molecule are dissociated into the two complementary strands that form the double-stranded DNA. Equivalently, at the about the Tm, on average 50% of two populations of complementary strands of DNA are annealed to each other. The Tm may be estimated empirically, e.g., through an analysis of a melt curve for the population of double-stranded DNA, as the temperature(s) that corresponds to one or more main peaks of the derivative of the melt curve. The temperature may be estimated from the melt curve using a suitable commercial software.

Thus in some cases, clade-specific primers may be configured to amplify a nucleic acid product having 1 or more, e.g., 2 or more, including 3 or more reference Tm ranges, and may be configured to amplify a nucleic acid product having 4 or less, e.g. 3 or less, including 2 or less reference Tm ranges. In some embodiments, clade-specific primers may be configured to amplify a nucleic acid product having one, two, or three reference Tm ranges. In some embodiments, the first clade-specific primers are configured to amplify a first nucleic acid product that has a different number of reference Tm ranges than a nucleic acid product amplified by the second clade-specific primers configured to amplify a second nucleic acid product.

In some embodiments, the first clade-specific primers may be configured to amplify a first nucleic acid product that has, or is characterized by, a different reference Tm range than the reference Tm range characteristic of a nucleic acid product amplified by the second clade-specific primers configured to amplify a second nucleic acid product. The reference Tm range of the first nucleic acid product and the reference Tm range of the second nucleic acid product may be different by 0.5° C. or more, e.g., 1° C. or more, 2° C. or more, 3° C. or more, 4° C. or more, 5° C. or more, 6° C. or more, 8° C. or more, 10° C. or more including 15° C. or more, and may be different by 20° C. or less, e.g., 15° C. or less, 12° C. or less, 10° C. or less, 9° C. or less, 8° C. or less, 7° C. or less, 6° C. or less, including 5° C. or less, as measured between the medians of the respective ranges. In some cases, the Tm range of the first nucleic acid product and the Tm range of the second nucleic acid product may be different by 0.5 to 20° C., e.g., 1 to 15° C., 1 to 10° C., including 2 to 10° C., as measured between the medians of the respective ranges.

In some embodiments, the clade-specific primers are configured to amplify a nucleic acid product that anneals with a clade-specific hybridization probe, which hybridization product may be characterized a reference Tm range(s), as determined by performing a melt analysis. Thus in some cases, clade-specific primers may be configured to amplify a nucleic acid product that, when annealed to the clade-specific hybridization probe, is characterized by 1 or more, e.g., 2 or more, including 3 or more Tm ranges, and in some cases is characterized by 4 or less, e.g. 3 or less, including 2 or less reference Tm ranges. In some embodiments, clade-specific primers may be configured to amplify a nucleic acid product that, when annealed to clade-specific hybridization probe, is characterized by one, two, or three reference Tm ranges. In some embodiments, the first clade-specific primers are configured to amplify a first nucleic acid product that, when annealed to clade-specific hybridization probe, is characterized by a different number of reference Tm ranges than a nucleic acid product amplified by the second clade-specific primers configured to amplify a second nucleic acid product and annealed to the clade-specific hybridization probe.

In some embodiments, the first clade-specific primers may be configured to amplify a first nucleic acid product that, when annealed to a clade-specific hybridization probe, is characterized by a different reference Tm range than the reference Tm range characteristic of a nucleic acid product amplified by the second clade-specific primers configured to amplify a second nucleic acid product and annealed to the clade-specific hybridization probe. The reference Tm range of the first nucleic acid product, when annealed to the clade-specific hybridization probe, and the reference Tm range of the second nucleic acid product, when annealed to the clade-specific hybridization probe, may be different by 0.5° C. or more, e.g., 1° C. or more, 2° C. or more, 3° C. or more, 4° C. or more, 5° C. or more, 6° C. or more, 8° C. or more, 10° C. or more including 15° C. or more, and may be different by 20° C. or less, e.g., 15° C. or less, 12° C. or less, 10° C. or less, 9° C. or less, 8° C. or less, 7° C. or less, 6° C. or less, including 5° C. or less, as measured between the medians of the respective ranges. In some cases, the Tm range of the first nucleic acid product, when annealed to the clade-specific hybridization probe, and the Tm range of the second nucleic acid product, when annealed to the clade-specific hybridization probe, may be different by 0.5 to 20° C., e.g., 1 to 15° C., 1 to 10° C., including 2 to 10° C., as measured between the medians of the respective ranges.

In certain embodiments, the first clade-specific primers and second clade-specific primers are configured such that a combination of the Ct values and the Tm values provides for distinguishing between the presence of a first clade member and a second clade member present in a sample. In certain embodiments, the first clade-specific primers and second clade-specific primers are configured such that a combination of the number of Tm ranges and the value of the Tm ranges provides for distinguishing between the presence of a first clade member and a second clade member present in a sample. In certain embodiments, the first clade-specific primers and second clade-specific primers are configured such that a combination of the Ct values, the number of Tm ranges and the value of the Tm ranges provides for distinguishing between the presence of a first clade member and a second clade member present in a sample.

In some embodiments, one or more primers of clade-specific primers contain one or more nucleotide sequence tags. Thus, in some cases, a primer of a clade-specific primer pair may contain a first region that is complementary to a first nucleotide sequence found in the clade member, and a second region adjacent the first region, where the second region is a nucleotide sequence tag that is not complementary to a second nucleotide sequence adjacent to the first nucleotide sequence found in the clade member. The tag may be any suitable nucleotide sequence. In some embodiments, clade-specific primers contain one or more nucleotide sequence tags to alter the melting temperature of the nucleic acid product amplified by the clade-specific primers when used to perform PCR in a sample containing a clade member. The length of the tag sequence may vary depending on the desired change in melting temperature to be achieved, and may in some cases be 1 nt or more, e.g., 2 nt or more, 3 nt or more, 4 nt or more, 5 nt or more, 7 nt or more, including 10 nt or more, and may be 15 nt or less, e.g., 13 nt or less, 11 nt or less, 10 nt or less, 9 nt or less, including 8 nt or less. In certain embodiments, the tag sequence has a length in the range of 1 to 15 nt, e.g., 1 to 13 nt, including 1 to 10 nt. In some embodiments, the tag sequence is ATC.

The clade-specific primers may be designed to target any suitable nucleotide sequence that has sufficient sequence identity among sequences associated with organisms that belong to a clade member and that is divergent in organisms that do not belong to the clade member.

Clade-specific primers may be designed to be used in the present method in a single reaction mixture that includes any convenient number of clade-specific primers. In certain embodiments, a pair (e.g., forward and reverse primer pair) of clade-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of clade-specific primers, each pair in the reaction mixture being configured to amplify a different clade-specific nucleotide sequence. In certain embodiments, a pair (e.g., forward and reverse primer pair) of clade-specific primers is designed to be used in a single reaction mixture that includes 1 to 10 pairs, e.g. 1 to 8 pairs, 1 to 6 pairs, 1 to 5 pairs, including 1 to 4 pairs of clade-specific primers, each pair in the reaction mixture being configured to amplify a different clade-specific nucleotide sequence.

Secondary Clade-Specific Primers

Aspects of the present disclosure include secondary clade-specific primers that are designed to amplify target sequences within the genomes of organisms that belong to a secondary clade member to produce nucleic acid products that distinguish one secondary clade member from another secondary clade member. In some instances, a secondary clade member contains a plurality of (e.g., 2 or more, 3 or more, 4 or more, or 5 or more) primary clade members. As the secondary clade-specific primers are designed to be specific to a secondary clade member, the secondary clade-specific primers, when used to perform PCR on a sample, may not provide information that distinguishes between the presence or absence of a first primary clade member that belongs to the secondary clade member from the presence or absence of a second primary clade member that belongs to the same secondary clade member as the first primary clade member, when the primers are used to determine that the secondary clade member is present in the sample.

In certain embodiments, secondary clade-specific primers are designed to amplify a nucleic acid product when the primers are used to perform PCR with template nucleic acids obtained from an organism that belongs to a secondary clade member present in a sample, and designed not to amplify a nucleic acid product when the secondary clade member is not present in the sample assayed. In certain embodiments, secondary clade-specific primers are designed to amplify a nucleic acid product when the primers are used to perform PCR with template nucleic acids in a sample containing a target secondary clade member, and designed not to amplify a nucleic acid product in a sample containing a non-target secondary clade member but not the target secondary clade member. Thus, secondary clade-specific primers that specifically amplify a nucleic acid product in a target secondary clade member may be designed to amplify homologous nucleotide sequences that have a high percentage of sequence identity among organisms each of which belong to a target secondary clade member, but do not amplify a homologous nucleotide sequence that have a low percentage of sequence identity in organisms which belong to a non-target secondary clade member. In certain embodiments, the secondary clade-specific primers may be designed to amplify in a sample containing a target secondary clade member a target nucleotide sequence that is 70% or more, e.g., 80% or more, 85% or more, 90% or more, including 95% or more, and that is 100% or less, e.g., 95% or less, 90% or less, 85% or less, including 80% or less identical to a homologous nucleotide sequence in one or more other organisms, each of which belongs to a target secondary clade member. In some cases, the secondary clade-specific primers may be designed to amplify in a sample containing a target secondary clade member a target nucleotide sequence that is 70% to 100%, e.g., 80% to 100%, including 85% to 100% identical to a homologous nucleotide sequence in one or more other organisms, each of which belongs to a target secondary clade member.

In some cases, secondary-clade specific primers are configured such that when the primers are used to perform a real-time PCR on a sample containing template nucleic acid from a secondary clade member targeted by the primers, a Ct value and/or one or more Tm values may be obtained, where the Ct value and/or Tm values may provide for detecting the presence of the secondary clade member in the sample and distinguishing the secondary clade member from other secondary clade members that are not targeted by the primers. In certain embodiments, secondary clade-specific primers are configured such that a combination of the Ct values and the Tm values provides for detecting the presence of a secondary clade member among other secondary clade members. In certain embodiments, secondary clade-specific primers are configured such that a combination of the number of Tm ranges and the value of the Tm ranges provides for determining the presence of a secondary clade member among other secondary clade members. In certain embodiments, secondary clade-specific primers are configured such that a combination of the Ct values, the number of Tm ranges and the value of the Tm ranges provides for detecting the presence of a secondary clade member among other secondary clade members.

Secondary clade-specific primers may be designed to be used in the present method in a single reaction mixture that includes any convenient number of secondary clade-specific primers. In certain embodiments, a pair (e.g., forward and reverse primer pair) of secondary clade-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair in the reaction mixture being configured to amplify a different secondary clade-specific nucleotide sequence. In certain embodiments, a pair of secondary clade-specific primers is designed to be used in a single reaction mixture that includes 1 to 10 pairs, e.g. 1 to 8 pairs, 1 to 6 pairs, 1 to 5 pairs, including 1 to 4 pairs of secondary clade-specific primers, each pair in the reaction mixture being configured to amplify a different secondary clade-specific nucleotide sequence.

The secondary clade-specific primers may be designed to target any suitable nucleotide sequence that has a high percentage of sequence identity among organisms that belong to a secondary clade member and that is divergent in organisms that do not belong to the secondary clade member. In certain embodiments, the secondary clade-specific primers are configured to amplify a secondary clade-specific nucleotide sequence within a nuclear-encoded ribosomal RNA gene. In certain embodiments, the secondary clade-specific primers are configured to amplify a secondary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the secondary clade-specific primers are configured to amplify a secondary clade-specific nucleotide sequence encoding an 18S ribosomal RNA, or a portion thereof, and/or an internal transcribed spacer, or a portion thereof, adjacent the nucleotide sequence encoding the 18S ribosomal RNA.

The secondary clade member may be any suitable group of organisms that can be defined by one or more feature(s) of a nucleic acid containing nucleotide sequence(s) associated with organisms that belong to the group. The group of organisms may include a group of fungi, bacteria, archaea, protists, plants, animals, etc.

*Candida*

In some instances, the secondary clade member is *candida*. The *candida* secondary clade member may include a plurality of species of the *Candida* genus and *Malassezia pachydermatis*. In some instances, the plurality of primary clade members that belong to *candida* include, without limitation, the species *C. albicans, C. parapsilosis, C. glabrata, C. tropicalis, C. guilliermondii, C. krusei*, and *Malassezia pachydermatis*. Thus, in certain embodiments, *candida*-specific primers include primers that are designed to amplify target sequences within the genome of a *candida* fungus to produce nucleic acid products that distinguish a *candida* from a non-*candida* (e.g., dermatophyte, or other non-*candida* saprophyte). As the *candida*-specific primers are designed to be specific to *candida*, the *candida*-specific primers, when used to perform PCR on a sample, may not provide information that is sufficient to identify individual species of *candida*, when the primers are used to determine that a *candida* fungus is present in the sample.

In certain embodiments, *candida*-specific primers are designed to amplify a nucleic acid product when the primers are used to perform PCR with template nucleic acids obtained from a *candida* fungus present in a sample, and designed not to amplify a nucleic acid product when a *candida* fungus is not present in the sample assayed. In certain embodiments, *candida*-specific primers are designed to amplify a nucleic acid product when the primers are used to perform PCR with template nucleic acids in a sample containing a *candida* fungus, and designed not to amplify a nucleic acid product in a sample containing a non-*candida* but not containing a *candida* fungus. Thus, *candida*-specific primers that specifically amplify a nucleic acid product in *candida* may be designed to amplify homologous nucleotide sequences that have a high percentage of sequence identity among *candida* fungi, but have lower percentage of sequence identity in non-*candida* organisms (e.g., dermatophytes and saprophytes). In certain embodiments, the *candida*-specific primers are designed to amplify in a sample containing a first *candida* fungus a target nucleotide sequence that is 70% or more, e.g., 80% or more, 85% or more, 90% or more, including 95% or more, and that is 100% or less, e.g., 95% or less, 90% or less, 85% or less, including 80% or less identical to a homologous nucleotide sequence in one or more other *candida* fungi. In some cases, the *candida*-specific primers may be designed to amplify in a sample containing a first *candida* fungus a target nucleotide sequence that is 70% to 100%, e.g., 80% to 100%, including 85% to 100% identical to a homologous nucleotide sequence in one or more other *candida* fungi.

In some embodiments, *candida*-specific primers are configured to amplify a nucleic acid product when nucleic acids containing the target nucleotide sequence from the *candida* fungus as well as non-fungal nucleic acids are present in the sample, and not to amplify a nucleic acid product when the nucleic acids from the *candida* fungus is absent from the sample and non-fungal nucleic acids are present in the sample. The non-fungal nucleic acids may include human genomic DNA and/or bacterial DNA. In certain embodiments, the *candida*-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In some cases, *candida*-specific primers are designed to amplify a first nucleic acid product when the *candida*-specific primers are used to perform PCR with template nucleic acids in a sample containing a *candida* fungus, and non-*candida*-specific primers are designed to amplify a second nucleic acid product when the non-*candida*-specific primers are used to perform PCR with template nucleic acids in a sample containing the non-*candida* organism targeted by the non-*candida*-specific primers, where the first and second nucleic acid products are distinguishable.

*Candida* secondary clade-specific primers may be designed to be used in the present method in a single reaction mixture that includes any convenient number of secondary clade-specific primers. In certain embodiments, a pair of *candida*-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair being configured to amplify a different secondary clade-specific nucleotide sequence. In certain embodiments, a pair of *candida*-specific primers is designed to be used in a single reaction mixture that includes 1 to 10 pairs, e.g. 1 to 5 pairs, including 1 to 4 pairs of secondary clade-specific primers, each pair being configured to amplify a different secondary clade-specific nucleotide sequence. In certain embodiments, the pair of *candida*-specific primers is designed to be used in a single reaction mixture that includes a pair of dermatophyte- and/or one or more pairs of saprophyte secondary clade-specific primers.

The *candida*-specific primers may be designed to target any suitable nucleotide sequence that has a high percentage of sequence identity among *candida* fungi and is divergent in non-*candida*. In certain embodiments, the *candida*-specific primers are configured to amplify a *candida*-specific nucleotide sequence within a nuclear-encoded ribosomal RNA gene. In certain embodiments, the *candida*-specific primers are configured to amplify a *candida*-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the *candida*-specific primers are configured to amplify a *candida*-specific nucleotide sequence encoding an 18S ribosomal RNA, or a portion thereof, and/or an internal transcribed spacer, or a portion thereof, adjacent the nucleotide sequence encoding the 18S ribosomal RNA.

In certain embodiments, the *candida*-specific primers are configured to amplify a nucleotide sequence that includes a sequence 70% or more, e.g., 80% or more, 90% or more, 95% or more, 97% or more, and up to 100% identical to the sequence set forth in SEQ ID NO:108. In certain embodiments, the *candida*-specific primers are configured to amplify a nucleotide sequence 70% or more, e.g., 80% or more, 90% or more, 95% or more, including 97% or more identical to the sequence set forth in SEQ ID NO:108. In certain embodiments, the *candida*-specific primers include a primer containing a nucleotide sequence 85% or more, e.g., 90% or more, 95% or more, 98% or more, 99% or more, and up to 100% identical to the sequence set forth in SEQ ID NOs:1 or 2. In certain embodiments, the *candida*-specific primers are 85% or more, e.g., 90% or more, 95% or more, 98% or more, 99% or more, and up to 100% identical to the sequence set forth in SEQ ID NOs:1 or 2.

Dermatophyte

In some instances, the secondary clade member is a dermatophyte. The dermatophyte secondary clade may include a plurality of primary clade members. In some instances, the plurality of primary clade members that belong to dermatophytes include, without limitation, the genera/species *Trichophyton rubrum, T. mentagrophytes, Epidermophyton*, and *Microsporum*. Thus, in certain embodiments, dermatophyte-specific primers include primers that are designed to amplify target sequences within the genome of a dermatophyte to produce nucleic acid products that distinguish a dermatophyte from a non-dermatophyte (e.g., *candida*, or other non-dermatophyte saprophyte). As the dermatophyte-specific primers are designed to be specific to dermatophytes, the dermatophyte-specific primers, when used to perform PCR on a sample, may not provide information that distinguishes the presence or absence of a first primary clade member that belongs to dermatophytes from a second primary clade member that belongs to dermatophytes. Thus, the dermatophyte-specific primers may not provide information that is sufficient to identify individual species of dermatophytes, when the primers are used to determine that a dermatophyte is present in the sample. In some embodiments, the dermatophyte-specific primers may not provide information that is sufficient to identify a genus, e.g., a *Trichophyton, Epidermophyton*, and *Microsporum*, or species within dermatophytes, when the primers are used to determine that a dermatophyte is present in the sample.

In certain embodiments, dermatophyte-specific primers are designed to amplify a nucleic acid product when the primers are used to perform PCR with template nucleic acids obtained from a dermatophyte present in a sample, and designed not to amplify a nucleic acid product when a dermatophyte is not present in the sample assayed. In certain embodiments, dermatophyte-specific primers are designed to amplify a nucleic acid product when the primers are used to perform PCR with template nucleic acids in a sample containing a dermatophyte, and designed not to amplify a nucleic acid product in a sample containing a non-dermatophyte but not a dermatophyte. Thus, dermatophyte-specific primers that specifically amplify a nucleic acid product in dermatophytes may be designed to amplify homologous nucleotide sequences that have a high percentage of sequence identity among dermatophytes, but have lower percentage of sequence identity in non-dermatophytes (e.g., *candida* and saprophytes). In certain embodiments, the dermatophyte-specific primers are designed to amplify in a sample containing a first dermatophyte a target nucleotide sequence that is 70% or more, e.g., 80% or more, 85% or more, 90% or more, including 95% or more, and that may be 100% or less, e.g., 95% or less, 90% or less, 85% or less, including 80% or less identical to a homologous nucleotide sequence in one or more other dermatophytes. In some cases, the dermatophyte-specific primers may be designed to amplify in a sample containing a first dermatophyte a target nucleotide sequence that is 70% to 100%, e.g., 80% to 100%, including 85% to 100% identical to a homologous nucleotide sequence in one or more other dermatophytes.

In some embodiments, dermatophyte-specific primers are configured to amplify a nucleic acid product when nucleic acids containing the target nucleotide sequence from the dermatophyte as well as non-fungal nucleic acids are present in the sample, and not to amplify a nucleic acid product when the nucleic acids from the dermatophyte is absent from the sample and non-fungal nucleic acids are present in the sample. The non-fungal nucleic acids may include human genomic DNA and/or bacterial DNA. In certain embodiments, the dermatophyte-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In some cases, dermatophyte-specific primers are designed to amplify a first nucleic acid product when the dermatophyte-specific primers are used to perform PCR with template nucleic acids in a sample containing a dermatophyte, and non-dermatophyte-specific primers are designed to amplify a second nucleic acid product when the non-dermatophyte-specific primers are used to perform PCR with template nucleic acids in a sample containing the non-dermatophyte targeted by the non-dermatophyte-specific primers, where the first and second nucleic acid products are distinguishable.

Dermatophyte secondary clade-specific primers may be designed to be used in the present method in a single reaction mixture that includes any convenient number of secondary clade-specific primers. In certain embodiments, a pair (e.g., forward and reverse primer pair) of dermatophyte-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair being configured to amplify a different secondary clade-specific nucleotide sequence. In certain embodiments, a pair (e.g., forward and reverse primer pair) of dermatophyte-specific primers is designed to be used in a single reaction mixture that includes 1 to 10 pairs, e.g. 1 to 8 pairs, 1 to 6 pairs, 1 to 5 pairs, including 1 to 4 pairs of secondary clade-specific primers, each pair being configured to amplify a different secondary clade-specific nucleotide sequence. In certain embodiments, the pair of dermatophyte-specific primers is designed to be used in a single reaction mixture that includes a pair of *candida*- and/or one or more pairs of saprophyte secondary clade-specific primers.

The dermatophyte-specific primers may be designed to target any suitable nucleotide sequence that has a high percentage of sequence identity among dermatophytes and is divergent in non-dermatophytes. In certain embodiments, the dermatophyte-specific primers are configured to amplify a dermatophyte-specific nucleotide sequence within a nuclear-encoded ribosomal RNA gene. In certain embodiments, the dermatophyte-specific primers are configured to amplify a dermatophyte-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the dermatophyte-specific primers are configured to amplify a dermatophyte-specific nucleotide sequence encoding an 18S ribosomal RNA, or a portion thereof, and/or an internal transcribed spacer, or a portion thereof, adjacent the nucleotide sequence encoding the 18S ribosomal RNA.

In certain embodiments, the dermatophyte-specific primers are configured to amplify a nucleotide sequence that includes a sequence 70% or more, e.g., 80% or more, 90% or more, 95% or more, including 97% or more identical to the sequence set forth in SEQ ID NO:109, or to a contiguous nucleotide sequence that includes nucleotides 1 to 116 and nucleotides 194 to 231 of SEQ ID NO:109. In certain embodiments, the dermatophyte-specific primers are configured to amplify a nucleotide sequence 70% or more, e.g., 80% or more, 90% or more, 95% or more, including 97% or more identical to the sequence set forth in SEQ ID NO:109, or to a contiguous nucleotide sequence that includes nucleotides 1 to 116 and nucleotides 194 to 231 of SEQ ID NO:109. In certain embodiments, the dermatophyte-specific primers include a primer containing a nucleotide sequence 85% or more, e.g., 90% or more, 95% or more, 98% or more, including 99% or more identical to the sequence set forth in SEQ ID NOs:3 or 4. In certain embodiments, the dermatophyte-specific primers are 85% or more, e.g., 90% or more, 95% or more, 98% or more, including 99% or more identical to the sequence set forth in SEQ ID NOs:3 or 4.

Saprophyte

In some instances, the secondary clade member is a saprophyte (e.g., a non-dermatophyte, non-*candida* onychomycotic fungus). The saprophyte secondary clade may include a plurality of primary clade members. In some instances, the plurality of primary clade members that belong to saprophytes include, without limitation, the genera *Aspergillus, Penicillium, Paecilomyces, Fusarium, Acremonium, Scopulariopsis, Chaetomium, Curvularia, Alternaria, Mucor, Scytalidium* and *Rhizopus*. Thus, in certain embodiments, saprophyte-specific primers include primers that are designed to amplify target sequences within the genome of a saprophyte to produce nucleic acid products that distinguish a saprophyte from a non-saprophyte (e.g., *candida*, or dermatophyte). As the saprophyte-specific primers are designed to be specific to saprophytes, the saprophyte-specific primers, when used to perform PCR on a sample, may not provide information that is sufficient to identify a saprophyte genus or species, when the primers are used to determine that a saprophyte is present in the sample.

In certain embodiments, saprophyte-specific primers are designed to amplify a nucleic acid product when the primers are used to perform PCR with template nucleic acids obtained from a saprophyte present in a sample, and designed not to amplify a nucleic acid product when a saprophyte is not present in the sample assayed. In certain embodiments, saprophyte-specific primers are designed to amplify a nucleic acid product when the primers are used to perform PCR with template nucleic acids in a sample containing a saprophyte, and designed not to amplify a nucleic acid product in a sample containing a non-saprophyte but not a saprophyte. Thus, saprophyte-specific primers that specifically amplify a nucleic acid product in saprophytes may be designed to amplify homologous nucleotide sequences that have a high percentage of sequence identity among saprophytes, but have lower percentage of sequence identity in non-saprophytes (e.g., *candida* and dermatophytes). In certain embodiments, the saprophyte-specific primers are designed to amplify in a sample containing a first saprophyte a target nucleotide sequence that is 70% or more, e.g., 80% or more, 85% or more, 90% or more, including 95% or more, and that may be 100% or less, e.g., 95% or less, 90% or less, 85% or less, including 80% or less identical to a homologous nucleotide sequence in one or more other saprophytes. In some cases, the saprophyte-specific primers may be designed to amplify in a sample containing a first saprophyte a target nucleotide sequence that is 70% to 100%, e.g., 80% to 100%, including 85% to 100% identical to a homologous nucleotide sequence in one or more other saprophytes.

In some embodiments, saprophyte-specific primers are configured to amplify a nucleic acid product when nucleic acids containing the target nucleotide sequence from the saprophyte as well as non-fungal nucleic acids are present in the sample, and not to amplify a nucleic acid product when the nucleic acids from the saprophyte is absent from the sample and non-fungal nucleic acids are present in the sample. The non-fungal nucleic acids may include human genomic DNA and/or bacterial DNA. In certain embodiments, the saprophyte-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, saprophyte-specific primers are designed to amplify a first nucleic acid product when the saprophyte-specific primers are used to perform PCR with template nucleic acids in a sample containing a first subset of saprophytes, and are designed to amplify a second nucleic acid product when the primers are used to perform PCR with template nucleic acids in a sample containing a second subset of saprophytes that is different from the first subset of saprophytes, where the first and second nucleic acid products are distinguishable. In some cases, saprophyte-specific primers are designed to amplify a first nucleic acid product when the saprophyte-specific primers are used to perform PCR with template nucleic acids in a sample containing a saprophyte, and non-saprophyte-specific primers are designed to amplify a second nucleic acid product when the non-saprophyte-specific primers are used to perform PCR with template nucleic acids in a sample containing the non-saprophyte targeted by the non-saprophyte-specific primers, where the first and second nucleic acid products are distinguishable.

In some cases, the first and second nucleic acid products are distinguishable by having distinct expected melting temperature (Tm) range(s), as determined by a melt analysis. In some embodiments, the saprophyte-specific primers may be configured to amplify a first and second nucleic acid products, corresponding to a first and second subset of saprophytes, respectively, that have different expected Tm ranges and/or number of Tm ranges from each other. In some embodiments, the saprophyte-specific primers are configured to amplify a first nucleic acid product that has a different expected Tm range than the Tm range of a second nucleic acid product. The expected Tm range of the first nucleic acid product and the expected Tm range of the second nucleic acid product may be different by 0.5° C. or more, e.g., 1° C. or more, 2° C. or more, 3° C. or more, 4° C. or more, 5° C. or more, 6° C. or more, 8° C. or more, 10°

C. or more including 15° C. or more, and may be different by 20° C. or less, e.g., 15° C. or less, 12° C. or less, 10° C. or less, 9° C. or less, 8° C. or less, 7° C. or less, 6° C. or less, including 5° C. or less, as measured between the medians of the respective ranges. In some cases, the expected Tm range of the first nucleic acid product and the expected Tm range of the second nucleic acid product may be different by 0.5 to 20° C., e.g., 1 to 15° C., 1 to 10° C., including 2 to 10° C., as measured between the medians of the respective ranges.

Saprophyte secondary clade-specific primers may be designed to be used in the present method in a single reaction mixture that includes any convenient number of secondary clade-specific primers. In certain embodiments, a pair (e.g., forward and reverse primer pair) of saprophyte-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair being configured to amplify a different secondary clade-specific nucleotide sequence. In certain embodiments, a pair (e.g., forward and reverse primer pair) of saprophyte-specific primers is designed to be used in a single reaction mixture that includes 1 to 10 pairs, e.g. 1 to 8 pairs, 1 to 6 pairs, 1 to 5 pairs, including 1 to 4 pairs of secondary clade-specific primers, each pair being configured to amplify a different secondary clade-specific nucleotide sequence. In certain embodiments, the pair (e.g., forward and reverse primer pair) of saprophyte-specific primers is designed to be used in a single reaction mixture that includes a pair of *candida*- and/or one or more pairs of dermatophyte secondary clade-specific primers. In some embodiments, one or more pairs, e.g., two or more, 3 or more, 4 or more, including 5 or more saprophyte secondary clade-specific primers are configured to be used in a single reaction mixture in the present method, where each pair of saprophyte secondary clade-specific primers in the reaction mixture is configured to amplify a secondary clade-specific nucleotide sequence for different saprophyte secondary clade members. In some embodiments, 1 to 8 pairs, e.g., 1 to 6 pairs, 1 to 5 pairs, 1 to 4 pairs, 2 to 5 pairs, including 2 to 4 pairs of saprophyte secondary clade-specific primers are configured to be used in a single reaction mixture in the present method, where each pair of saprophyte secondary clade-specific primers in the reaction mixture is configured to amplify a secondary clade-specific nucleotide sequence for different saprophyte secondary clade members.

The saprophyte-specific primers may be designed to target any suitable nucleotide sequence that has a high percentage of sequence identity among saprophytes and is divergent in non-saprophytes. In certain embodiments, the saprophyte-specific primers are configured to amplify a saprophyte-specific nucleotide sequence within a nuclear-encoded ribosomal RNA gene. In certain embodiments, the saprophyte-specific primers are configured to amplify a saprophyte-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the saprophyte-specific primers are configured to amplify a saprophyte-specific nucleotide sequence encoding an 18S ribosomal RNA, or a portion thereof, and/or an internal transcribed spacer, or a portion thereof, adjacent the nucleotide sequence encoding the 18S ribosomal RNA.

In certain embodiments, the saprophyte-specific primers are configured to amplify a nucleotide sequence that includes a sequence 70% or more, e.g., 80% or more, 90% or more, 95% or more, including 97% or more identical to a sequence set forth in SEQ ID NOs: 110, 111, 112, 113 or 246. In certain embodiments, the saprophyte-specific primers are configured to amplify a nucleotide sequence 70% or more, e.g., 80% or more, 90% or more, 95% or more, including 97% or more identical to a sequence set forth in SEQ ID NOs: 110, 111, 112, 113 or 246. In certain embodiments, the saprophyte-specific primers include one or more pairs of primers, each pair containing a primer that includes a nucleotide sequence 85% or more, e.g., 90% or more, 95% or more, 98% or more, including 99% or more identical to a sequence of the pair of sequences set forth in SEQ ID NOs:5 and 6; SEQ ID NOs:7 and 8; SEQ ID NOs:9 and 10; SEQ ID NOs:11 and 12; or SEQ ID NOs:244 and 245. In certain embodiments, the saprophyte-specific primers include one or more pairs of primers, each pair containing a primer that includes a nucleotide sequence 85% or more, e.g., 90% or more, 95% or more, 98% or more, including 99% or more identical to each sequence of the pair of sequences set forth in SEQ ID NOs:5 and 6; SEQ ID NOs:7 and 8; SEQ ID NOs:9 and 10; SEQ ID NOs:11 and 12; or SEQ ID NOs:244 and 245. In certain embodiments, the saprophyte-specific primers include one or more pairs of primers, each pair containing a primer 85% or more, e.g., 90% or more, 95% or more, 98% or more, including 99% or more identical to each sequence of the pair of sequences set forth in SEQ ID NOs:5 and 6; SEQ ID NOs:7 and 8; SEQ ID NOs:9 and 10; SEQ ID NOs:11 and 12; or SEQ ID NOs:244 and 245.

Primer Design and Use in Assays

The dermatophyte-, *candida*-, and saprophyte-specific primers may be configured to generate PCR amplification products that are distinguishable from each other when any two or more of a dermatophyte, a *candida*, and a saprophyte are present in the sample. In certain embodiments dermatophyte-specific primers are configured to amplify a dermatophyte-specific nucleic acid product and *candida*-specific primers are configured to amplify a *candida*-specific nucleic acid product, where the dermatophyte-specific nucleic acid product and *candida*-specific nucleic acid product are distinguishable. In some cases, the dermatophyte- and *candida*-specific nucleic acid products are distinguishable by having distinct expected melting temperature (Tm) range(s), as determined by a melt analysis. Thus in some cases, the dermatophyte-specific primers may be configured to amplify a dermatophyte-specific nucleic acid product having different expected Tm ranges and/or expected number of Tm ranges compared to the expected Tm ranges and/or expected number of Tm ranges of a nucleic acid product amplified by *candida*-specific primers configured to amplify a *candida*-specific nucleic acid product. The expected Tm range of the *candida*-specific nucleic acid product and the expected Tm range of the dermatophyte-specific nucleic acid product may be different by 0.5° C. or more, e.g., 1° C. or more, 2° C. or more, 3° C. or more, 4° C. or more, 5° C. or more, 6° C. or more, 8° C. or more, including 10° C. or more, and may be different by 15° C. or less, 12° C. or less, 10° C. or less, 9° C. or less, 8° C. or less, 7° C. or less, 6° C. or less, including 5° C. or less, as measured between the medians of the respective ranges. In some cases, the expected Tm range of the *candida*-specific nucleic acid product and the expected Tm range of the dermatophyte-specific nucleic acid product may be different by 0.5 to 15° C., e.g., 1 to 12° C., 2 to 10° C., including 2 to 8° C., as measured between the medians of the respective ranges.

In certain embodiments *candida*-specific primers are configured to amplify a *candida*-specific nucleic acid product and saprophyte-specific primers are configured to amplify a saprophyte-specific nucleic acid product, where the *candida*-specific nucleic acid product and saprophyte-specific nucleic acid product are distinguishable. In some cases, the *candida*- and saprophyte-specific nucleic acid products are distinguishable by having distinct expected Tm range(s), as determined by a melt analysis. Thus in some cases, the *candida*-specific primers may be configured to amplify a *candida*-specific nucleic acid product having different expected Tm ranges and/or expected number of Tm ranges compared to the expected Tm ranges and/or expected number of Tm ranges of a nucleic acid product amplified by saprophyte-specific primers configured to amplify a saprophyte-specific nucleic acid product. The expected Tm range of the saprophyte-specific nucleic acid product and the expected Tm range of the *candida*-specific nucleic acid product may be different by 0.5° C. or more, e.g., 1° C. or more, 2° C. or more, 3° C. or more, 4° C. or more, 5° C. or more, 6° C. or more, 8° C. or more, including 10° C. or more, and may be different by 15° C. or less, 12° C. or less, 10° C. or less, 9° C. or less, 8° C. or less, 7° C. or less, 6° C. or less, including 5° C. or less, as measured between the medians of the respective ranges. In some cases, the expected Tm range of the saprophyte-specific nucleic acid product and the expected Tm range of the *candida*-specific nucleic acid product may be different by 0.5 to 15° C., e.g., 1 to 12° C., 2 to 10° C., including 2 to 8° C., as measured between the medians of the respective ranges.

In certain embodiments dermatophyte-specific primers are configured to amplify a dermatophyte-specific nucleic acid product and saprophyte-specific primers are configured to amplify a saprophyte-specific nucleic acid product, where the dermatophyte-specific nucleic acid product and saprophyte-specific nucleic acid product are distinguishable. In some cases, the dermatophyte- and saprophyte-specific nucleic acid products are distinguishable by having distinct expected Tm range(s). Thus in some cases, the dermatophyte-specific primers may be configured to amplify a dermatophyte-specific nucleic acid product having different expected Tm ranges and/or expected number of Tm ranges compared to the expected Tm ranges and/or expected number of Tm ranges of a nucleic acid product amplified by saprophyte-specific primers configured to amplify a saprophyte-specific nucleic acid product. The expected Tm range of the saprophyte-specific nucleic acid product and the expected Tm range of the dermatophyte-specific nucleic acid product may be different by 0.5° C. or more, e.g., 1° C. or more, 2° C. or more, 3° C. or more, 4° C. or more, 5° C. or more, 6° C. or more, 8° C. or more, including 10° C. or more, and may be different by 15° C. or less, 12° C. or less, 10° C. or less, 9° C. or less, 8° C. or less, 7° C. or less, 6° C. or less, including 5° C. or less, as measured between the medians of the respective ranges. In some cases, the expected Tm range of the saprophyte-specific nucleic acid product and the expected Tm range of the dermatophyte-specific nucleic acid product may be different by 0.5 to 15° C., e.g., 1 to 12° C., 2 to 10° C., including 2 to 8° C., as measured between the medians of the respective ranges.

A primer of the present disclosure may generally be 10 to 50 nucleotides (nt) long, e.g., 12 to 40 nt long, 15 to 30 nt long, including 15 to 25 nt long.

Primary Clade-Specific Primers

Aspects of the present disclosure include primary clade-specific primers that are designed to amplify target sequences within the genomes of primary clade members to produce nucleic acid products that distinguish one primary clade member from another primary clade member.

In certain embodiments, primary clade-specific primers are designed to amplify a nucleic acid product when the primers are used to perform PCR with template nucleic acids obtained from an organism that belongs to a primary clade member present in a sample, and designed not to amplify a nucleic acid product when the primary clade member is not present in the sample assayed. In certain embodiments, primary clade-specific primers are designed to amplify a nucleic acid product when the primers are used to perform PCR with template nucleic acids in a sample containing a target primary clade member, and designed not to amplify a nucleic acid product in a sample containing a non-target primary clade member but not the target primary clade member.

In some embodiments, a first PCR reaction performed using a first primary clade-specific primers in the presence of a first primary clade member in a sample may a have an expected Ct range different from the expected Ct range of a second PCR reaction performed using a second primary clade-specific primers in the presence of a second primary clade member in the sample. The Ct range of the first PCR reaction and the Ct range of the second PCR reaction may be different by 1 cycle or more, e.g., 2 cycles or more, 2.5 cycles or more, 3 cycles or more, 4 cycles or more, 5 cycles or more, 6 cycles or more, 8 cycles or more, including 10 cycles or more, and may be different by 12 cycles or less, 11 cycles or less, 10 cycles or less, 9 cycles or less, 8 cycles or less, 7 cycles or less, 6 cycles or less, including 5 cycles or less, as measured between the medians of the respective ranges. In some cases, the Ct range of the first nucleic acid product and the Ct range of the second nucleic acid product may be different by 1 to 12 cycles, e.g., 2 to 10 cycles, 2 to 9 cycles, including 3 to 8 cycles, as measured between the medians of the respective ranges.

In some cases, primary-clade specific primers are configured such that when the primers are used to perform a real-time PCR on a sample containing template nucleic acid from a primary clade member targeted by the primers, a Ct value and/or one or more Tm values may be obtained, where the Ct value and/or Tm values may provide for detecting the presence of the secondary clade member in the sample and distinguishing the primary clade member from other primary clade members that are not targeted by the primers. In certain embodiments, primary clade-specific primers are configured such that a combination of the Ct values and the Tm values provides for detecting the presence of a primary clade member among other primary clade members. In certain embodiments, primary clade-specific primers are configured such that a combination of the number of Tm ranges and the value of the Tm ranges provides for determining the presence of a primary clade member among other primary clade members. In certain embodiments, primary clade-specific primers are configured such that a combination of the Ct values, the number of Tm ranges and the value of the Tm ranges provides for detecting the presence of a primary clade member among other primary clade members.

Primary clade-specific primers may be designed to be used in the present method in a single reaction mixture that includes any convenient number of primary clade-specific primers. In certain embodiments, a pair of primary clade-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair in the reaction mixture being configured to amplify a different primary clade-specific nucleotide sequence. In certain embodiments, a pair of primary clade-specific primers is designed to be used in a single reaction mixture that includes 1 to 10 pairs, e.g. 1 to 5 pairs, including 1 to 4 pairs of primary clade-specific primers, each pair in the reaction mixture being configured to amplify a different primary clade-specific nucleotide sequence.

The primary clade-specific primers may be designed to target any suitable nucleotide sequence that has a high percentage of sequence identity among organisms that belong to a primary clade member and may be divergent in organisms that do not belong to the primary clade member. In certain embodiments, the primary clade-specific primers are configured to amplify a primary clade-specific nucleotide sequence within a nuclear-encoded ribosomal RNA gene. In certain embodiments, the primary clade-specific primers are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs; and/or a mitochondrial nucleotide sequence, including a nicotinamide adenine dinucleotide (NADH) dehydrogenase subunit gene or a putative reverse transcriptase gene, or portions thereof.

The primary clade member may be any suitable species and/or higher phylogenetic group of organisms that can be defined by one or more feature(s) of nucleic acids containing a nucleotide sequence associated with organisms that belong to the species or group, where the primary clade member belongs to a secondary clade member determined to be present using secondary clade-specific primers, as described herein.

Detection of Primary Clade Member within the Secondary Clade of *Candida*

In some instances, the primary clade member belongs to the secondary *candida* clade member, and may include, without limitation, the species *C. albicans, C. parapsilosis, C. glabrata, C. tropicalis, C. krusei, C. guilliermondii, C. haemulonii, C. lusitaiae* and *Malassezia pachydermatis*. Thus, in certain embodiments, primary clade-specific primers for the secondary *candida* clade member include primers that are designed to amplify target sequences within the genome of a *candida* fungus to produce nucleic acid products that distinguish one *candida* species from another *candida* species. In some embodiments, primary clade-specific primers for the secondary *candida* clade member include, without limitation, *C. albicans*-specific primers, *C. parapsilosis*-specific primers, *C. glabrata*-specific primers, *C. tropicalis*-specific primers, *C. krusei*-specific primers, *C. guilliermondii*-specific primers and *M. pachydermatis*-specific primers.

In certain embodiments, primary clade-specific primers for a secondary *candida* clade member, e.g., *C. albicans*-specific primers, *C. parapsilosis*-specific primers, etc., are designed to amplify a nucleic acid product when the primers are used to perform PCR with template nucleic acids obtained from an organism belonging to the primary clade member, e.g., *C. albicans, C. parapsilosis*, etc., that is present in a sample, and designed not to amplify a nucleic acid product when the primary clade member, e.g., *C. albicans, C. parapsilosis*, etc., is not present in the sample assayed. In certain embodiments, primary clade-specific primers for a secondary *candida* clade member are designed to amplify a nucleic acid product when the primers are used to perform PCR with template nucleic acids in a sample containing a primary clade member and designed not to amplify a nucleic acid product in a sample containing a non-primary clade member, e.g., non-*C. albicans*, non-*C. parapsilosis*, etc., but not containing the primary clade member. Thus, primary clade-specific primers for a secondary *candida* clade that specifically amplify a nucleic acid product in a primary clade member may be designed to amplify a nucleotide sequence that has low sequence identity in non-primary clade members.

In some embodiments, one or more primary clade-specific primers for a secondary *candida* clade member, e.g., *C. albicans*-specific primers, *C. parapsilosis*-specific primers, etc., are configured to amplify a nucleic acid product when nucleic acids containing the target nucleotide sequence from the primary clade member, e.g., *C. albicans, C. parapsilosis*, etc., as well as non-fungal nucleic acids are present in the sample, and not to amplify a nucleic acid product when the nucleic acids from the primary clade member is absent from the sample and non-fungal nucleic acids are present in the sample. The non-fungal nucleic acids may include human genomic DNA and/or bacterial DNA. In certain embodiments, the primary clade-specific primers for a secondary *candida* clade member have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, a first primary clade-specific primers for a secondary *candida* clade member, e.g., *C. albicans*-specific primers, are designed to amplify a first nucleic acid product when the first primary clade-specific primers are used to perform PCR with template nucleic acids in a sample containing a first primary clade member, e.g., *C. albicans*, and a second primary clade-specific primers for a secondary *candida* clade member, e.g., *C. parapsilosis*-specific primers, are designed to amplify a second nucleic acid product when the primers are used to perform PCR with template nucleic acids in a sample containing a second primary clade member, e.g., *C. parapsilosis*, where the first and second nucleic acid products are distinguishable. In some cases, the first and second nucleic acid products are distinguishable by having distinct melting temperature (Tm) range(s), as determined by performing a melt analysis, described below, and/or by having distinct rates of amplification, as determined by a Ct range.

In certain embodiments, primary clade-specific primers for a secondary *candida* clade member are designed to amplify a first nucleic acid product when the first primary clade-specific primers are used to perform PCR with template nucleic acids in a sample containing a first primary clade member, and are designed to amplify a second nucleic acid product when the primers are used to perform PCR with template nucleic acids in a sample containing a second primary clade member, where the first and second nucleic acid products are distinguishable. In some cases, the first and second nucleic acid products are distinguishable by having distinct melting temperature (Tm) range(s), as determined by performing a melt analysis, described below.

The primary clade-specific primers for a secondary *candida* clade member, e.g., *C. albicans*-specific primers, *C. parapsilosis*-specific primers, etc., may be designed to target any suitable nucleotide sequence. In certain embodiments, the primary clade-specific primers for a secondary *candida* clade member are configured to amplify a primary clade-specific nucleotide sequence within a nuclear-encoded ribosomal RNA gene. In certain embodiments, the primary clade-specific primers for a secondary *candida* clade member are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs.

In certain embodiments, the primary clade-specific primers for a secondary *candida* clade member are designed to amplify a primary clade-specific nucleotide sequence encoding a mitochondrial NADH dehydrogenase subunit, or a portion thereof, or a mitochondrial putative reverse transcriptase gene, or a portion thereof.

In certain embodiments, *C. albicans*-specific primers are designed to amplify a nucleotide sequence that includes a sequence 90% or more, e.g., 95% or more, 98% or more, including 99% or more identical to the sequence set forth in SEQ ID NO:114. In certain embodiments, *C. parapsilosis*-specific primers are designed to amplify a nucleotide sequence that includes a sequence 90% or more, e.g., 95% or more, 98% or more, including 99% or more identical to the sequence set forth in SEQ ID NO:115.

Detection of Primary Clade Member within the Secondary Clade of Dermatophyte

In some instances, the primary clade member belongs to the secondary dermatophyte clade member, and may include, without limitation, the genera/species *Trichophyton rubrum, T. mentagrophytes, Epidermophyton*, and *Microsporum*. Thus, in certain embodiments, primary clade-specific primers for the secondary dermatophyte clade member include primers that are designed to amplify target sequences within the genome of a dermatophyte to produce nucleic acid products that distinguish one dermatophyte genus/species from another dermatophyte genus/species. In some embodiments, primary clade-specific primers for the secondary dermatophyte clade member include, without limitation, *Trichophyton*-specific primers, *Epidermophyton*-specific primers and *Microsporum*-specific primers.

In certain embodiments, primary clade-specific primers for a secondary dermatophyte clade, e.g., *Trichophyton*-specific primers, *Epidermophyton*-specific primers and *Microsporum*-specific primers, etc., are designed to amplify a nucleic acid product when the primers are used to perform PCR with template nucleic acids obtained from an organism belonging to the primary clade member, e.g., *Trichophyton, Epidermophyton* and *Microsporum*, etc., that is present in a sample, and designed not to amplify a nucleic acid product when the primary clade member is not present in the sample assayed. In certain embodiments, primary clade-specific primers for a secondary dermatophyte clade member are designed to amplify a nucleic acid product when the primers are used to perform PCR with template nucleic acids in a sample containing a primary clade member and designed not to amplify a nucleic acid product in a sample containing a non-primary clade member, e.g., non-*Trichophyton*, non-*Epidermophyton*, non-*Microsporum*, etc., but not containing the primary clade member. Thus, primary clade-specific primers for a secondary dermatophyte clade member that specifically amplify a nucleic acid product in a primary clade member may be designed to amplify a nucleotide sequence that has low sequence identity in non-primary clade members.

In some embodiments, one or more primary clade-specific primers for a secondary dermatophyte clade member, e.g., *Trichophyton*-specific primers, *Epidermophyton*-specific primers and *Microsporum*-specific primers, etc., are configured to amplify a nucleic acid product when nucleic acids containing the target nucleotide sequence from the primary clade member, *Trichophyton, Epidermophyton* and *Microsporum*, etc., as well as non-fungal nucleic acids are present in the sample, and not to amplify a nucleic acid product when the nucleic acids from the primary clade member is absent from the sample and non-fungal nucleic acids are present in the sample. The non-fungal nucleic acids may include human genomic DNA and/or bacterial DNA. In certain embodiments, the primary clade-specific primers for a secondary dermatophyte clade member have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, a first primary clade-specific primers for a secondary dermatophyte clade member, e.g., *Epidermophyton*-specific primers, are designed to amplify a first nucleic acid product when the first primary clade-specific primers are used to perform PCR with template nucleic acids in a sample containing a first primary clade member, e.g., *Epidermophyton*, and a second primary clade-specific primers for a secondary dermatophyte clade member, e.g., *Microsporum*-specific primers, are designed to amplify a second nucleic acid product when the primers are used to perform PCR with template nucleic acids in a sample containing a second primary clade member, e.g., *Microsporum*, where the first and second nucleic acid products are distinguishable. In some cases, the first and second nucleic acid products are distinguishable by having distinct melting temperature (Tm) range(s), as determined by performing a melt analysis, described below, and/or by having distinct rates of amplification, as determined by a Ct range.

In certain embodiments, primary clade-specific primers for a secondary dermatophyte clade member, e.g., *Trichophyton*-specific primers, are designed to amplify a first nucleic acid product when the first primary clade-specific primers are used to perform PCR with template nucleic acids in a sample containing a first primary clade member, e.g., *T. mentagrophytes*, and are designed to amplify a second nucleic acid product when the primers are used to perform PCR with template nucleic acids in a sample containing a second primary clade member, e.g., *T. rubrum*, where the first and second nucleic acid products are distinguishable. In some cases, the first and second nucleic acid products are distinguishable by having distinct melting temperature (Tm) range(s), as determined by performing a melt analysis, described below.

The primary clade-specific primers for a secondary dermatophyte clade member, e.g., *Trichophyton*-specific primers, *Epidermophyton*-specific primers and *Microsporum*-specific primers, etc., may be designed to target any suitable nucleotide sequence. In certain embodiments, the primary clade-specific primers for a secondary dermatophyte clade member are configured to amplify a primary clade-specific nucleotide sequence within a nuclear-encoded ribosomal RNA gene. In certain embodiments, the primary clade-specific primers for a secondary dermatophyte clade member are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the primary clade-specific primers for a secondary dermatophyte clade member are designed to amplify a primary clade-specific nucleotide sequence encoding an 18S ribosomal RNA, or a portion thereof, a 5.8S ribosomal RNA, or portion thereof, and/or an internal transcribed spacer (ITS), or a portion thereof, adjacent the nucleotide sequence encoding the 18S ribosomal RNA or the 5.8S ribosomal RNA. In certain embodiments, the primary clade-specific primers for a secondary dermatophyte clade member are designed to amplify a primary clade-specific nucleotide sequence encoding ITS1 or ITS2.

In certain embodiments, *Trichophyton*-specific primers are designed to amplify a nucleotide sequence that includes a sequence 90% or more, e.g., 95% or more, 98% or more, including 99% or more identical to the sequence set forth in SEQ ID NOs:116 or 117. In certain embodiments, *Epidermophyton*-specific primers are designed to amplify a nucleotide sequence that includes a sequence 90% or more, e.g., 95% or more, 98% or more, including 99% or more identical to the sequence set forth in SEQ ID NO:118. In certain embodiments, *Microsporum*-specific primers are designed to amplify a nucleotide sequence that includes a sequence 90% or more, e.g., 95% or more, 98% or more, including 99% or more identical to the sequence set forth in SEQ ID NO:119.

Detection of Primary Clade Member within the Secondary Clade of Saprophyte

In certain embodiments, primary clade-specific primers for a secondary saprophyte clade are designed to amplify a nucleic acid product when the primers are used to perform PCR with template nucleic acids obtained from an organism belonging to the primary clade member, e.g., *Aspergillus, Penicillium, Paecilomyces, Fusarium, Acremonium, Scopulariopsis, Chaetomium, Curvularia, Alternaria, Mucor, Scytalidium* and *Rhizopus*, etc., that is present in a sample, and designed not to amplify a nucleic acid product when the primary clade member is not present in the sample assayed. In certain embodiments, primary clade-specific primers for a secondary saprophyte clade member are designed to amplify a nucleic acid product when the primers are used to perform PCR with template nucleic acids in a sample containing a primary clade member and designed not to amplify a nucleic acid product in a sample containing a non-primary clade member, e.g., non-*Aspergillus*, non-*Penicillium*, non-*Paecilomyces*, non-*Fusarium*, non-*Acremonium*, non-*Scopulariopsis*, non-*Chaetomium*, non-*Curvularia*, non-*Alternaria*, non-*Mucor*, non-*Scytalidium* or non-*Rhizopus*, etc., but not containing the primary clade member. Thus, primary clade-specific primers for a secondary saprophyte clade member that specifically amplify a nucleic acid product in a primary clade member may be designed to amplify a nucleotide sequence that has low sequence identity in non-primary clade members.

In some embodiments, one or more primary clade-specific primers for a secondary saprophyte clade member are configured to amplify a nucleic acid product when nucleic acids containing the target nucleotide sequence from the primary clade member, e.g., *Aspergillus, Penicillium, Paecilomyces, Fusarium, Acremonium, Scopulariopsis, Chaetomium, Curvularia, Alternaria, Mucor, Scytalidium* and *Rhizopus*, etc., as well as non-fungal nucleic acids are present in the sample, and not to amplify a nucleic acid product when the nucleic acids from the primary clade member is absent from the sample and non-fungal nucleic acids are present in the sample. The non-fungal nucleic acids may include human genomic DNA and/or bacterial DNA. In certain embodiments, the primary clade-specific primers for a secondary saprophyte clade member have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, a first primary clade-specific primers for a secondary saprophyte clade member are designed to amplify a first nucleic acid product when the first primary clade-specific primers are used to perform PCR with template nucleic acids in a sample containing a first primary clade member and a second primary clade-specific primers for a secondary saprophyte clade member are designed to amplify a second nucleic acid product when the primers are used to perform PCR with template nucleic acids in a sample containing a second primary clade member, where the first and second nucleic acid products are distinguishable. In some cases, the first and second nucleic acid products are distinguishable by having distinct melting temperature (Tm) range(s), as determined by, e.g., performing a melt analysis, and/or by having distinct rates of amplification, as determined by a Ct range.

In certain embodiments, primary clade-specific primers for a secondary saprophyte clade member are designed to amplify a first nucleic acid product when the first primary clade-specific primers are used to perform PCR with template nucleic acids in a sample containing a first primary clade member, and are designed to amplify a second nucleic acid product when the primers are used to perform PCR with template nucleic acids in a sample containing a second primary clade member, where the first and second nucleic acid products are distinguishable. In some cases, the first and second nucleic acid products are distinguishable by having distinct melting temperature (Tm) range(s), as determined by performing a melt analysis, described below.

The primary clade-specific primers for a secondary saprophyte clade member may be designed to target any suitable nucleotide sequence. In certain embodiments, the primary clade-specific primers for a secondary saprophyte clade member are configured to amplify a primary clade-specific nucleotide sequence within a nuclear-encoded ribosomal RNA gene. In certain embodiments, the primary clade-specific primers for a secondary saprophyte clade member are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the primary clade-specific primers for a secondary saprophyte clade member are designed to amplify a primary clade-specific nucleotide sequence encoding an encoding an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the primary clade-specific primers for a secondary saprophyte clade member are designed to amplify a primary clade-specific nucleotide sequence encoding ITS1 or ITS2.

In certain embodiments, *Acremonium*-specific primers are designed to amplify a nucleotide sequence that includes a sequence 90% or more, e.g., 95% or more, 98% or more, including 99% or more identical to the sequence set forth in SEQ ID NOs:236. In certain embodiments, *Acremonium*- specific primers are designed to amplify a nucleotide sequence 90% or more, e.g., 95% or more, 98% or more, including 99% or more identical to the sequence set forth in SEQ ID NOs:236.

In certain embodiments, *Alternaria*-specific primers are designed to amplify a nucleotide sequence that includes a sequence 90% or more, e.g., 95% or more, 98% or more, including 99% or more identical to the sequence set forth in SEQ ID NOs:237. In certain embodiments, *Alternaria*-specific primers are designed to amplify a nucleotide sequence 90% or more, e.g., 95% or more, 98% or more, including 99% or more identical to the sequence set forth in SEQ ID NOs:237.

In certain embodiments, *Curvularia*-specific primers are designed to amplify a nucleotide sequence that includes a sequence 90% or more, e.g., 95% or more, 98% or more, including 99% or more identical to the sequence set forth in SEQ ID NOs:238. In certain embodiments, *Curvularia*-specific primers are designed to amplify a nucleotide sequence 90% or more, e.g., 95% or more, 98% or more, including 99% or more identical to the sequence set forth in SEQ ID NOs:238.

In certain embodiments, *Scytalidium*-specific primers are designed to amplify a nucleotide sequence that includes a sequence 90% or more, e.g., 95% or more, 98% or more, including 99% or more identical to the sequence set forth in SEQ ID NOs:239. In certain embodiments, *Scytalidium*-specific primers are designed to amplify a nucleotide sequence 90% or more, e.g., 95% or more, 98% or more, including 99% or more identical to the sequence set forth in SEQ ID NOs:239.

In certain embodiments, *Aspergillus*-specific primers are designed to amplify a nucleotide sequence that includes a sequence 90% or more, e.g., 95% or more, 98% or more, including 99% or more identical to the sequence set forth in SEQ ID NOs:240. In certain embodiments, *Aspergillus*-specific primers are designed to amplify a nucleotide sequence 90% or more, e.g., 95% or more, 98% or more, including 99% or more identical to the sequence set forth in SEQ ID NOs:240.

In certain embodiments, *Fusarium*-specific primers are designed to amplify a nucleotide sequence that includes a sequence 90% or more, e.g., 95% or more, 98% or more, including 99% or more identical to the sequence set forth in SEQ ID NO:241 or 242. In certain embodiments, *Fusarium*-specific primers are designed to amplify a nucleotide sequence 90% or more, e.g., 95% or more, 98% or more, including 99% or more identical to the sequence set forth in SEQ ID NO:241 or 242.

In certain embodiments, *Scopulariopsis*-specific primers are designed to amplify a nucleotide sequence that includes a sequence 90% or more, e.g., 95% or more, 98% or more, including 99% or more identical to the sequence set forth in SEQ ID NO:243. In certain embodiments, *Scopulariopsis*-specific primers are designed to amplify a nucleotide sequence 90% or more, e.g., 95% or more, 98% or more, including 99% or more identical to the sequence set forth in SEQ ID NO:243.

Compositions Containing Clade-Specific Primers

Also provided herein is a composition that includes clade-specific primers, e.g., primary clade-specific primers or secondary clade-specific primers, which compositions may find use generating, or may be a part of, a reaction mixture for carrying out a PCR reaction, e.g., a real-time PCR reaction, as described herein. The composition may include at least one primer pair (e.g., a forward and reverse primer pair) for amplifying a target nucleotide sequence specific for a primary clade member or a secondary clade member, as described above. In some embodiments, the composition includes two or more pairs, e.g., three or more pairs, 4 or more pairs, 5 or more pairs, including 6 or more pairs of primers, and in some cases may include 10 or fewer pairs, e.g., 9 or fewer pairs, 8 or fewer pairs, 7 or fewer pairs, including 6 or fewer pairs of primers, each primer pair configured to amplify a target nucleotide sequence specific for a primary clade member or a secondary clade member. In certain embodiments, the composition includes 2 pairs to 10 pairs, e.g., 2 pairs to 8 pairs, 2 pairs to 7 pairs, 2 pairs to 6 pairs, including 2 pairs to 5 pairs of primers, each primer pair configured to amplify a target nucleotide sequence specific for a primary clade member or a secondary clade member.

The combination of primers present in the composition may be any suitable combination of primers, e.g., combination of primer pairs, for amplifying a target nucleotide sequence specific for a primary clade member or a secondary clade member, where the amplified products specific for the different clade members are distinguishable from each other, e.g., based on the Ct of the amplification reaction and/or Tm of the amplified products, as described herein. In some embodiments, the composition includes a *candida* secondary clade-specific primer pair and a dermatophyte secondary clade-specific primer pair, as described above, where amplification products of nucleotide sequences targeted by the *candida* secondary clade-specific primer pair and those targeted by the dermatophyte secondary clade-specific primer pair are distinguishable from each other, e.g., based on the Ct of the amplification reaction and/or Tm of the amplified products.

In certain embodiments, the composition includes a two or more pairs, e.g., three or more pairs, 4 or more pairs, 5 or more pairs, including 6 or more pairs of primers, and in some cases may include 10 or fewer pairs, e.g., 9 or fewer pairs, 8 or fewer pairs, 7 or fewer pairs, including 6 or fewer pairs of saprophyte secondary clade-specific primers, as described above, where amplification products of nucleotide sequences targeted by the primer pairs specific to different sets of saprophyte secondary clade members are distinguishable from each other by real-time PCR, e.g., based on the Ct of the amplification reaction and/or Tm of the amplified products.

The present composition may include any other suitable components for storing, transporting and/or carrying out a PCR reaction with the clade-specific primers. The composition may contain a suitable medium, e.g., an aqueous medium. A suitable aqueous medium includes, without limitation, water, a buffer solution, etc. The buffer may be any suitable buffer for storage of primers and/or for carrying out a PCR reaction. The buffer may have any suitable pH, such as, without limitation, a pH of from 6.0 to 9.0, e.g., from 6.5 to 8.9, from 7.0 to 8.7, from 7.5 to 8.6, including from 8.0 to 8.5. In some embodiments, the buffer is a Tris (tris(hydroxymethyl)aminomethane) buffer. In certain embodiments, the aqueous medium includes a chelator, such as a divalent cation chelator (e.g., ethylenediaminetetraacetic acid (EDTA)). In some embodiments, the aqueous medium includes a chelator (e.g., EDTA) and a buffer (e.g., Tris).

The present composition may be substantially free of enzymes and compounds that degrade nucleic acids, such as nucleases. In some embodiments, the composition is substantially sterile.

In some embodiments, the composition includes, without limitation, a nucleic acid template, primers, one or more polymerases, nucleotides, etc., suitable for performing a PCR reaction to amplify a nucleotide sequence targeted by the clade-specific primers (i.e., targeted by the clade-specific primer pairs). The polymerase may be any suitable polymerase, including, without limitation, a thermostable DNA polymerase, such as Taq polymerase, and variants thereof (e.g., commercially available variants of thermostable DNA polymerases). In some embodiments, the composition includes a nucleic acid intercalating dye, such as a fluorescent intercalating dye. The fluorescent intercalating dye may be any suitable DNA intercalating dye for use in real-time PCR, including, without limitation, SYBR® Green, SYTO® dyes, YO-PRO-1, LC Green, etc.

In some embodiments, the composition includes a hybridization probe configured to specifically anneal to a nucleic acid that contains a nucleotide sequence that is amplified by the clade-specific primers. The hybridization probe may be a fluorescent hybridization probe that changes its fluorescence properties based on whether the probe is hybridized to a target nucleic acid (e.g., by positioning a fluorescent dye attached to the probe at a sufficient distance to a fluorescent DNA intercalating dye to induce Frster resonance energy transfer (FRET) between the attached dye and the intercalating dye). Thus, in some embodiments, the clade-specific hybridization probe includes a fluorescent functional group (e.g., fluorescent dye) covalently attached to the probe nucleic acid. The excitation and emission wavelengths of the attached fluorescent dye and the intercalating dye may be suitably configured to promote a measurable, distance-dependent interaction between the attached dye and the intercalating dye. In certain embodiments, the clade-specific hybridization probe includes a 3' blocking group, e.g., biotin, that prevents use of the probe by a polymerase as a primer for polymerization.

Methods

Methods of Detecting an Onychomycotic Fungus

The number of primary clade members in the secondary clade member to which the onychomycotic fungus detected by the present methods belongs may be any suitable number that may be independently distinguished using the present methods, and may depend on, e.g., the sequence diversity of the target sequences amplified the primary clade-specific primers, the specificity of the primary clade-specific primers, the desired sensitivity and/or specificity of detection, complexity of the sample, etc. In some embodiments, the present method includes a secondary clade member includes one or more, e.g., two or more, three or more, 4 or more, 5 or more, including 7 or more primary clade members, and in some embodiments, includes 10 or less, e.g., 9 or less, 8 or less, 7 or less, including 5 or less primary clade members. In some embodiments, a secondary clade member includes 1 to 10, e.g., 2 to 9, 2 to 8, including 2 to 7 primary clade members.

In general, at least one of the plurality of secondary clade member includes two or more, e.g., 3 or more, 4 or more, 5 or more, 6 or more, 7 or more, 8 or more, and up to 10 primary clade members. In some embodiments, at least one of the plurality of secondary clade member includes 2 to 10, e.g., 2 to 9, 2 to 8, including 2 to 7 primary clade members. In some embodiments, each of the plurality of secondary clade members includes two or more, e.g., 3 or more, 4 or more, 5 or more, 6 or more, 7 or more, 8 or more, and up to 10 primary clade members. In some embodiments, each of the plurality of secondary clade members includes 2 to 10, e.g., 2 to 9, 2 to 8, including 2 to 7 primary clade members.

In certain embodiments, the dermatophyte secondary clade member includes 2 to 6, such as 2 to 5, or 2 to 4 primary clade members. In certain embodiments, the *candida* secondary clade member includes 2 to 4, such as 2 to 3, or 2 primary clade members. In certain embodiments, the saprophyte secondary clade member includes 2 to 10, such as 2 to 9, 2 to 8, or 2 to 7 primary clade members.

The screening steps, 210, 230, and 310, 330, of the present method may be carried out in a single reaction mixture, or a plurality of reaction mixtures, as appropriate. An implementation of the present method may include using a first portion of a sample as a template for a PCR reaction to screen for a secondary clade member 210, 230, and using a second portion of the sample for which the presence of the secondary clade member is detected to screen for a primary clade member 310, 330 that belongs to the secondary clade member. In certain embodiments, the present method of detecting an onychomycotic fungus in a sample includes performing the screening step 210, 310 in a first reaction mixture containing a first set of secondary clade-specific primers and a second reaction mixture containing a second set of secondary clade-specific primers, where the first and second sets of secondary clade-specific primers are specific for different secondary clade members. The first and second reaction mixtures may each contain at least a portion of the sample that is being tested for the presence or absence of the onychomycotic fungus, and a first and second PCRs (e.g., real-time PCRs), respectively, may be carried out.

In some embodiments, the first set of secondary clade-specific primers is specific for a first set of secondary clade members, which set of secondary clade members includes one or more of dermatophytes, *candida*, and saprophytes, and the second set of secondary clade-specific primers is specific for a second set of secondary clade members, which set of secondary clade members includes one or more of dermatophyte, *candida*, and saprophytes, where the first and second sets are different sets. "Different," as used in reference to different sets of secondary clade members, is meant to indicate that the sets are at least non-overlapping. In some embodiments, the first set of secondary clade-specific primers is specific for a first set of secondary clade members, which set of secondary clade members includes dermatophytes and *candida*, and the second set of secondary clade-specific primers is specific for a second set of secondary clade members, which set of secondary clade members includes saprophytes. In certain embodiments, a set of secondary clade members that includes saprophytes includes two or more, e.g., 3 or more, 4 or more, including 5 or more, and includes 8 or fewer, e.g., 6 or fewer, 5 or fewer, including 4 or fewer saprophyte secondary clade members, where the saprophyte secondary clade members among the set are distinct from each other. In certain embodiments, a set of secondary clade members that includes saprophytes includes 2 to 8, e.g., 2 to 6, 2 to 5, including 2 to 4 saprophyte secondary clade members, where the saprophyte secondary clade members among the set are distinct from each other.

The screening 230, 330 using primary-clade specific primers, to determine which of the primary clade members of the secondary clade member identified in the earlier screening 210, 310 may be present in the sample, may be performed in one or more (e.g., 2 or more, three or more, four or more, etc.) reaction mixtures. In some cases, a single reaction mixture that includes primary-clade specific primers that distinguish between two or more, e.g., three or more, 4 or more, 5 or more, and in some cases, 10 or fewer, 8 or fewer, 7 or fewer, including 6 or fewer different primary clade members is used, where each primary clade member may be targeted by a specific pair of primary-clade specific primers. In certain embodiments, a single reaction mixture that includes primary-clade specific primers that distinguish between 2 to 10, e.g., 2 to 8, 2 to 6, 2 to 5, including 2 to 4 different primary clade members is used, where each primary clade member may be targeted by a specific pair of primary-clade specific primers.

The various cutoff Ct values, reference Ct ranges, reference ΔCt ranges, and reference Tm or ΔTm ranges used in the present method may be obtained by any suitable method. In certain embodiments, the reference values and ranges are empirically determined using positive and negative control samples and reactions. In a positive control, a known organismal and/or synthetic source of nucleic acids may be used at defined quantities in a sample to run a real-time PCR reaction using known clade-specific primers, as described herein. The Ct and Tm values obtained using the positive control sample may contribute to defining the reference Ct ranges and reference Tm ranges. A plurality of positive control reactions may provide a range of Ct and Tm values, which may in turn define the reference Ct ranges and the reference Tm ranges. A positive control sample may be obtained from a sufficiently defined culture of a known organism, such as a culture of a known species of fungus, a culture known to contain at least a known species of fungus, or a synthetic nucleic acid source (e.g., gBlock® DNA). A negative control may involve a real-time PCR reaction run using known clade-specific primers, either without any nucleic acid template, or without the specific target nucleic acid template for the clade-specific primers in the sample. A Ct value obtained from the negative control reaction may be used to define a cutoff Ct value, as used herein. The reference ΔCt range may be obtained by running two real-time PCRs, one with a first secondary clade-specific primers and the other with a second secondary clade-specific primers, as described herein, and using samples having a known organismal source of nucleic acids for each reaction.

The cutoff Ct values ($Ct_{cutoff1}$, $Ct_{cutoff2}$ in the screening step 210, 310, 420, and the cutoff Ct values for screening 230, 330 for the primary clade member) may vary depending on, e.g., the sensitivity of the real-time PCR, which in turn may depend on e.g., the clade-specific primers, the nucleotide sequence amplified by the primers, the amount of template nucleic acid in the sample, the double-stranded DNA dye used to detect the amplification products, the real-time PCR system used, etc. The cutoff Ct value for a secondary clade-specific real-time PCR may be 24 or higher, e.g., 25 or higher, including 26 or higher, or 28 or higher, and may be 32 or lower, e.g., 30 or lower, 29 or lower, including 28 or lower. In some embodiments, the cutoff Ct value for a secondary clade-specific real-time PCR may be in the range of 24 to 32, e.g., 24 to 30, 25 to 30, 25 to 29, including 25 to 28, or 28 to 30.

In some embodiments, the cutoff Ct value for a secondary *candida* clade-specific real-time PCR may be 24 or higher, e.g., 25 or higher, including 26 or higher, or 28 or higher, and may be 32 or lower, e.g., 30 or lower, 29 or lower, including 28 or lower. In some embodiments, the cutoff Ct value for a secondary *candida* clade-specific real-time PCR may be in the range of 24 to 32, e.g., 24 to 30, 25 to 30, 25 to 29, including 25 to 28, or 28 to 30. In some embodiments, the cutoff Ct value for a secondary dermatophyte clade-specific real-time PCR may be 24 or higher, e.g., 25 or higher, including 26 or higher, or 28 or higher, and may be 32 or lower, e.g., 30 or lower, 29 or lower, including 28 or lower. In some embodiments, the cutoff Ct value for a secondary dermatophyte clade-specific real-time PCR may be in the range of 24 to 32, e.g., 24 to 30, 25 to 30, including 25 to 28, or 28 to 30. In some embodiments, the cutoff Ct value for a secondary saprophyte clade-specific real-time PCR may be 24 or higher, e.g., 25 or higher, including 26 or higher, or 28 or higher, and may be 32 or lower, e.g., 30 or lower, 29 or lower, including 28 or lower. In some embodiments, the Ct value for a secondary saprophyte clade-specific real-time PCR may be in the range of 24 to 32, e.g., 24 to 30, 25 to 30, 25 to 29, including 25 to 28, or 28 to 30.

The cutoff Ct value for a primary clade-specific real-time PCR may be 28 or higher, e.g., 30 or higher, including 31 or higher, and may be 38 or lower, e.g., 36 or lower, including 35 or lower. In some embodiments, the Ct value for a primary clade-specific real-time PCR may be in the range of 28 to 38, e.g., 28 to 35, 30 to 36, including 31 to 35. In some embodiments, the cutoff Ct value for a primary clade-specific real-time PCR for determining the presence or absence of a primary clade member of a *candida* secondary clade may be 30 or higher, e.g., 31 or higher, including 32 or higher, and may be 38 or lower, e.g., 36 or lower, including 35 or lower. In some embodiments, the cutoff Ct value for a primary clade-specific real-time PCR for determining the presence or absence of a primary clade member of a *candida* secondary clade may be in the range of 30 to 38, e.g., 30 to 35, 31 to 36, including 32 to 35.

In some embodiments, the cutoff Ct value for a primary clade-specific real-time PCR for determining the presence or absence of a primary clade member of a dermatophyte secondary clade may be 28 or higher, e.g., 30 or higher, including 31 or higher, and may be 36 or lower, e.g., 35 or lower, including 34 or lower. In some embodiments, the cutoff Ct value for a primary clade-specific real-time PCR for determining the presence or absence of a primary clade member of a dermatophyte secondary clade may be in the range of 28 to 36, e.g., 30 to 35, 30 to 34, including 31 to 34. In some embodiments, the cutoff Ct value for a primary clade-specific real-time PCR for determining the presence or absence of a *Trichophyton* may be 30 or higher, e.g., 31 or higher, including 32 or higher, and may be 36 or lower, e.g., 35 or lower, including 34 or lower. In some embodiments, the cutoff Ct value for a primary clade-specific real-time PCR for determining the presence or absence of a *Trichophyton* may be in the range of 30 to 36, e.g., 30 to 34, 31 to 35, including 32 to 34. In some embodiments, the cutoff Ct value for a primary clade-specific real-time PCR for determining the presence or absence of an *Epidermophyton* may be 28 or higher, e.g., 30 or higher, including 31 or higher, and may be 34 or lower, e.g., 33 or lower, including 32 or lower. In some embodiments, the cutoff Ct value for a primary clade-specific real-time PCR for determining the presence or absence of an *Epidermophyton* may be in the range of 28 to 34, e.g., 30 to 33, 30 to 32, including 31 to 32. In some embodiments, the cutoff Ct value for a primary clade-specific real-time PCR for determining the presence or absence of a *Microsporum* may be 30 or higher, e.g., 31 or higher, including 32 or higher, and may be 36 or lower, e.g., 35 or lower, including 34 or lower. In some embodiments, the cutoff Ct value for a primary clade-specific real-time PCR for determining the presence or absence of a *Microsporum* may be in the range of 30 to 36, e.g., 30 to 34, 31 to 35, including 32 to 34.

In some embodiments, the cutoff Ct value for a primary clade-specific real-time PCR for determining the presence or absence of a primary clade member of a saprophyte secondary clade may be 28 or higher, e.g., 30 or higher, including 31 or higher, and may be 36 or lower, e.g., 35 or lower, including 34 or lower. In some embodiments, the cutoff Ct value for a primary clade-specific real-time PCR for determining the presence or absence of a primary clade member of a saprophyte secondary clade may be in the range of 28 to 36, e.g., 30 to 34, 30 to 35, including 31 to 34.

The reference ΔCt range ($\Delta Ct_{range}$ in the screening step 210, 310, 440) may vary, and may be defined by a lower range limit and an upper range limit, where the lower range limit may be −15 or more, e.g., −12 or more, −10 or more, −8 or more, including −6 or more, −4 or more, and may be 0 or less, e.g., −1 or less, −2 or less, including −3 or less, and the upper limit may be 15 or less, e.g., 12 or less, 10 or less, 8 or less, 6 or less, 4 or less, and may be 0 or more, e.g., 1 or more, 2 or more, including 3 or more. In some embodiments, $\Delta Ct_{range}$ may be about −10 to about 10, e.g. about −8 to about 8, about −7 to about 7, about −6 to about 6, about −5 to about 5, about −4 to about 4, including about −3 to about 3.

The reference Ct range for screening 230, 330 for the primary clade member using primary-clade specific primers may vary, and may be defined by a lower range limit and an upper range limit, where the lower range limit may be in the range of 17 to 27, e.g., 18 to 27, including 19 to 27, and the upper range limit may be in the range of 21 to 35, e.g., 21 to 33, including 21 to 31. In some embodiments, the reference Ct range for determining the presence or absence of a primary clade member of a *candida* secondary clade using *C. albicans*-specific primers may be defined by a lower range limit and an upper range limit, where the lower range limit may be in the range of 19 to 26, e.g., 20 to 25, including 21 to 24, and the upper range limit may be in the range of 22 to 30, e.g., 23 to 28, including 24 to 27. In some embodiments, the reference Ct range for determining the presence or absence of a primary clade member of a *candida* secondary clade using *C. parapsilosis*-specific primers may be defined by a lower range limit and an upper range limit, where the lower range limit may be in the range of 19 to 26, e.g., 20 to 25, including 21 to 24, and the upper range limit may be in the range of 22 to 30, e.g., 23 to 28, including 24 to 27.

In some embodiments, the reference Ct range for determining the presence or absence of a primary clade member of a dermatophyte secondary clade using *T. mentagrophytes*-specific primers may be defined by a lower range limit and an upper range limit, where the lower range limit may be in the range of 20 to 29, e.g., 22 to 28, including 24 to 27, and the upper range limit may be in the range of 26 to 35, e.g., 27 to 33, including 24 to 31. In some embodiments, the reference Ct range for determining the presence or absence of a primary clade member of a dermatophyte secondary clade using *T. rubrum*-specific primers may be defined by a lower range limit and an upper range limit, where the lower range limit may be in the range of 18 to 23, e.g., 19 to 22, including 20 to 21, and the upper range limit may be in the range of 19 to 26, e.g., 20 to 25, including 21 to 24. In some embodiments, the reference Ct range for determining the presence or absence of a primary clade member of a dermatophyte secondary clade using *Epidermophyton*-specific primers may be defined by a lower range limit and an upper range limit, where the lower range limit may be in the range of 23 to 30, e.g., 24 to 29, including 25 to 28, and the upper range limit may be in the range of 26 to 35, e.g., 27 to 33, including 28 to 32. In some embodiments, the reference Ct range for determining the presence or absence of a primary clade member of a dermatophyte secondary clade using *Microsporum*-specific primers may be defined by a lower range limit and an upper range limit, where the lower range limit may be in the range of 18 to 26, e.g., 19 to 25, including 20 to 24, and the upper range limit may be in the range of 22 to 29, e.g., 23 to 28, including 24 to 27.

The Tm value obtained during analysis of reaction product nucleic acids (e.g., amplification product) may be the Tm value of any suitable hybridization product that includes the reaction product and whose Tm value can be used in the present methods to determine the presence of a primary clade member that belongs to a secondary clade member, as described herein. In some embodiments, the Tm value is the melting temperature of the amplification product, which may generally include the forward and reverse strands of a nucleic acid having the nucleotide sequence targeted by the clade-specific primers.

In some embodiments, the Tm value is the melting temperature of a hybridization between a) one or more of the forward and reverse strands of the amplification products; and b) a clade-specific hybridization probe. In some cases, clade-specific hybridization probes includes fluorescent hybridization specific probes that bind specifically to either strand of the amplification products as described in Schabereiter-Gurtner et al. ((2007) Journal of Clinical Microbiology, March 2007, p. 906-914. Vol. 45, No. 3.) and Hanami et al. ((2013) PLoS ONE 8(8): e70942. Doi:10.1371/journal.pone.0070942). The hybridization specific probes can be designed to have different melt temperatures using probe length and/or sequence to influence the Tm of the probe. The approach may be specific in that a single mis-match can influence the Tm of the probe and allow differentiation as described in Luo et al. ((2011) Journal of Clinical Microbiology, September 2011, p. 3132-3138. Vol. 49, No. 9). An approach that uses Tm determination with hybridization probes may increase design flexibility.

The reference Tm ranges for determining 210, 310 the presence or absence of a secondary clade member in a sample, and for determining 230, 330 the presence or absence of a primary clade member in the sample for which the secondary clade member to which the primary clade member belongs is determined to be present in the sample, may vary depending on, e.g., the clade-specific primers, the nucleotide sequence amplified by the primers, the amount of template nucleic acid in the sample, the double-stranded DNA dye used to detect the amplification products, the real-time PCR system used, the melt analysis method, etc. The reference Tm range for amplification products of a secondary clade-specific real-time PCR may be defined by an upper range limit and a lower range limit, where the lower range limit may be in the range of 70° C. to 87° C., e.g., 72° C. to 85° C., including 74° C. to 83° C., and the upper range limit may be in the range of 72° C. to 90° C., e.g., 74° C. to 88° C., including 75° C. to 86° C.

In some embodiments, the reference Tm range for amplification products of a secondary *candida* clade-specific real-time PCR may be defined by an upper range limit and a lower range limit, where the lower range limit may be in the range of 70° C. to 79° C., e.g., 72° C. to 78° C., including 74° C. to 77° C., and the upper range limit may be in the range of 75° C. to 85° C., e.g., 76° C. to 82° C., including 77° C. to 80° C.

In some embodiments, the reference Tm range for amplification products of a secondary dermatophyte clade-specific real-time PCR may be defined by an upper range limit and a lower range limit, where the lower range limit may be in the range of 75° C. to 85° C., e.g., 77° C. to 83° C., 76° C. to 81° C., 77° C. to 80° C., 80° C. to 84° C., including 81° C. to 83° C., and the upper range limit may be in the range of 78° C. to 90° C., e.g., 80° C. to 86° C., 79° C. to 83° C., 80° C. to 82° C., 81° C. to 86° C., including 83° C. to 85° C.

In some embodiments, the reference Tm range for amplification products of a secondary saprophyte clade-specific real-time PCR may be defined by an upper range limit and a lower range limit, where the lower range limit may be in the range of 75° C. to 82° C., e.g., 76° C. to 81° C., including 78° C. to 80° C., and the upper range limit may be in the range of 78° C. to 86° C., e.g., 79° C. to 84° C., including 80° C. to 82° C.

The reference Tm range for amplification products of a primary clade-specific real-time PCR may be defined by an upper range limit and a lower range limit, where the lower range limit may be in the range of 63° C. to 89° C., e.g., 66° C. to 88° C., including 68° C. to 87° C., and the upper range limit may be in the range of 65° C. to 92° C., e.g., 68° C. to 90° C., including 70° C. to 88° C.

In some embodiments, the reference Tm range for amplification products of a primary clade-specific real-time PCR for determining the presence or absence of a primary clade member of a *candida* secondary clade using *C. albicans*-specific primers may be defined by an upper range limit and a lower range limit, where the lower range limit may be in the range of 68° C. to 75° C., e.g., 70° C. to 74° C., including 71° C. to 73° C., and the upper range limit may be in the range of 71° C. to 78° C., e.g., 72° C. to 76° C., including 73° C. to 75° C. In some embodiments, the reference Tm range for amplification products of a primary clade-specific real-time PCR for determining the presence or absence of a primary clade member of a *candida* secondary clade using *C. parapsilosis*-specific primers may be defined by an upper range limit and a lower range limit, where the lower range limit may be in the range of 65° C. to 72.5° C., e.g., 67° C. to 71.5° C., including 68° C. to 70.5° C., and the upper range limit may be in the range of 68.5° C. to 75° C., e.g., 69.5° C. to 73° C., including 70.5° C. to 71° C.

In some embodiments, the reference Tm range for amplification products of a primary clade-specific real-time PCR for determining the presence or absence of a primary clade member of a dermatophyte secondary clade using *T. mentagrophytes*-specific primers may be defined by an upper range limit and a lower range limit, where the lower range limit may be in the range of 73° C. to 86° C., e.g., 75° C. to 84° C., 74° C. to 80° C., 75° C. to 77° C., 80° C. to 85° C. including 82° C. to 84° C., and the upper range limit may be in the range of 72° C. to 88° C., e.g., 76° C. to 85° C., 74° C. to 81° C., 77° C. to 79° C., 81° C. to 87° C. including 84° C. to 86° C. In some embodiments, the reference Tm range for amplification products of a primary clade-specific real-time PCR for determining the presence or absence of a primary clade member of a dermatophyte secondary clade using *T. rubrum*-specific primers may be defined by an upper range limit and a lower range limit, where the lower range limit may be in the range of 74° C. to 89° C., e.g., 76° C. to 87° C., 75° C. to 79° C., 76° C. to 77.5° C., 84° C. to 89° C. including 85° C. to 87° C., and the upper range limit may be in the range of 75° C. to 90° C., e.g., 77° C. to 88° C., 76° C. to 81° C., 77.5° C. to 79° C., 85° C. to 90° C. including 87° C. to 88° C. In some embodiments, the reference Tm range for amplification products of a primary clade-specific real-time PCR for determining the presence or absence of a primary clade member of a dermatophyte secondary clade using *Epidermophyton*-specific primers may be defined by an upper range limit and a lower range limit, where the lower range limit may be in the range of 77° C. to 85° C., e.g., 79° C. to 83° C., including 80° C. to 82° C., and the upper range limit may be in the range of 79° C. to 86° C., e.g., 80° C. to 84° C., including 81° C. to 83° C. In some embodiments, the reference Tm range for amplification products of a primary clade-specific real-time PCR for determining the presence or absence of a primary clade member of a dermatophyte secondary clade using *Microsporum*-specific primers may be defined by an upper range limit and a lower range limit, where the lower range limit may be in the range of 63° C. to 88° C., e.g., 67° C. to 85° C., 65° C. to 71° C., 67° C. to 69.5° C., 80° C. to 86° C., including 82° C. to 84.5° C., and the upper range limit may be in the range of 65° C. to 90° C., e.g., 68° C. to 87° C., 68° C. to 73° C., 69.5° C. to 71° C., 81° C. to 88° C., including 84.5° C. to 87° C.

In some embodiments, the reference Tm range for amplification products of a primary clade-specific real-time PCR for determining the presence or absence of a primary clade member of a saprophyte secondary clade using *Acremonium*-specific primers may be defined by an upper range limit and a lower range limit, where the lower range limit may be in the range of 79° C. to 85° C., e.g., 80° C. to 84° C. including 82° C. to 83° C., and the upper range limit may be in the range of 81° C. to 87° C., e.g., 82° C. to 85° C. including 83° C. to 84° C. In some embodiments, the reference Tm range for amplification products of a primary clade-specific real-time PCR for determining the presence or absence of a primary clade member of a saprophyte secondary clade using *Alternaria*-specific primers may be defined by an upper range limit and a lower range limit, where the lower range limit may be in the range of 75° C. to 78° C., e.g., 76° C. to 77° C. including 75° C. to 76° C., and the upper range limit may be in the range of 74° C. to 79° C., e.g., 75° C. to 78° C. including 76° C. to 77° C. In some embodiments, the reference Tm range for amplification products of a primary clade-specific real-time PCR for determining the presence or absence of a primary clade member of a saprophyte secondary clade using *Scytandium*-specific primers may be defined by an upper range limit and a lower range limit, where the lower range limit may be in the range of 82° C. to 87° C., e.g., 83° C. to 86° C. including 84° C. to 85° C., and the upper range limit may be in the range of 85° C. to 88° C., e.g., 86° C. to 87° C. including 85° C. to 86° C. In some embodiments, the reference Tm range for amplification products of a primary clade-specific real-time PCR for determining the presence or absence of a primary clade member of a saprophyte secondary clade using *Curvularia*-specific primers may be defined by an upper range limit and a lower range limit, where the lower range limit may be in the range of 76° C. to 79° C., e.g., 77° C. to 80° C. including 78° C. to 79.5° C., and the upper range limit may be in the range of 78° C. to 83° C., e.g., 79° C. to 82° C. including 80° C. to 81° C. In some embodiments, the reference Tm range for amplification products of a primary clade-specific real-time PCR for determining the presence or absence of a primary clade member of a saprophyte secondary clade using *Aspergillus*-specific primers may be defined by an upper range limit and a lower range limit, where the lower range limit may be in the range of 77° C. to 80° C., e.g., 78° C. to 81° C. including 79° C. to 80° C., and the upper range limit may be in the range of 78° C. to 83° C., e.g., 79° C. to 82° C. including 80° C. to 81° C. In some embodiments, the reference Tm range for amplification products of a primary clade-specific real-time PCR for determining the presence or absence of a primary clade member of a saprophyte secondary clade using *Fusarium*-specific primers may be defined by an upper range limit and a lower range limit, where the lower range limit may be in the range of 69° C. to 75° C., e.g., 70° C. to 74° C. including 71° C. to 73° C., and the upper range limit may be in the range of 72° C. to 76° C., e.g., 73° C. to 75° C. including 73.5° C. to 74.5° C. In some embodiments, the reference Tm range for amplification products of a primary clade-specific real-time PCR for determining the presence or absence of a primary clade member of a saprophyte secondary clade using *Scopulariopsis*-specific primers may be defined by an upper range limit and a lower range limit, where the lower range limit may be in the range of 80° C. to 86° C., e.g., 81° C. to 85° C. including 82° C. to 84° C., and the upper range limit may be in the range of 83° C. to 87° C., e.g., 84° C. to 86° C. including 84.5° C. to 85.5° C.

Further aspects of the present disclosure include performing control reactions to enable proper interpretation of results of the PCR on samples. Control reactions may include a positive control, negative control, extraction/inhibition control and a reagent blank control. In some embodiments, a positive control, as described above, is run in parallel to the sample to determine whether the reaction conditions are sufficient to generate a positive result when the sample contains an onychomycotic fungus of interest. In some embodiments, a negative control, as described above, is run in parallel to the sample to confirm that positive results are not obtained, e.g., due to contamination of the sample and/or reagent during handling. The Ct and/or Tm values obtained for the positive and/or negative control reactions may be compared to the reference Ct range, reference Tm values and/or reference Tm ranges for the clade-specific primer used in the control reactions to determine whether the obtained Ct and/or Tm values for the reaction are within the respective expected ranges.

In some embodiments, a control is performed to confirm proper PCR amplification from samples that are subjected to cell lysis and nucleic acid extraction processes, as described below (Extraction/Inhibition control; EC/IC). In certain embodiments, EC/IC includes adding an amount of a known nucleic acid to a sample for which the presence or absence of an onychomycotic fungus is to be determined before the sample is processed to lyse cells and extract nucleic acids from the cells, preparing the sample to lyse cells and release cellular nucleic acids, and performing real-time PCR on the sample using primers that amplifies a nucleotide sequence contained in the known nucleic acid to detect the presence of the known nucleic acid. The known nucleic acid may be any suitable nucleic acid, and may be, e.g., a *Saccharomyces pombe*, citrate synthase gene.

In some embodiments, the present method includes performing a reagent blank control (RB). The RB control may include adding an amount of known nucleic acid to a sample that does not contain any other source of nucleic acids, and processing the sample in parallel to a sample for which the presence or absence of an onychomycotic fungus is to be determined, and performing real-time PCR on the sample using primers that amplifies a nucleotide sequence contained in the known nucleic acid to detect the presence of the known nucleic acid. In some embodiments, the RB sample may be used as a negative control by performing a real-time PCR on the RB sample using clade-specific primers.

The PCR reactions employed in the present disclosure may be performed using any convenient common PCR reagents, other than the template and primers, and protocols. A PCR reaction mixture may contain any suitable ingredient for performing a PCR reaction, including, a nucleic acid template, primers, one or more polymerases, nucleotides, a buffer, etc. The PCR reaction may be a real-time PCR reaction. The real-time PCR may be carried out using any convenient reagent and equipment for performing real-time PCR to obtain Ct and Tm values of a reaction. In certain embodiments, the real-time PCR reaction mixture contains, in addition to components of a PCR reaction mixture, a double-stranded DNA (dsDNA) intercalating dye. Suitable dsDNA dyes include, but are not limited to, SYBR® Green, SYTO®9, LCGReen®, Chromofy™ and EvaGreen®.

Any suitable real-time PCR system may be used to run the PCR reaction and to obtain Ct and/or Tm values. The Tm value may be obtained by any suitable melt analysis method. In some embodiments, the melt analysis is a high resolution melt analysis (HRM) method, as described in, e.g., Mandviwala et al., 2010. J. Mol. Diagn. 12:91, which is incorporated herein by reference.

The PCR cycle parameters may be any suitable set of cycle parameters for amplifying the nucleotide sequences targeted by the clade-specific primers, when the sample contains nucleic acids that include the target nucleotide sequences in detectable amounts. In some embodiments, the cycle parameters include a denaturing temperature in the range of 90 to 100° C., a denaturing time in the range of 10 to 45 seconds; an annealing temperature that may vary with the primers used in the reaction, and may be in the range of 50 to 75° C., and an annealing time of 10 to 45 seconds; and an extension temperature in the range of 60 to 75° C., and an extension time in the range of 30 to 120 seconds. The PCR cycle may include detection of amplification products in the reaction mixture by, e.g., detecting the level of fluorescence in the reaction mixture at the end of a cycle. The number of cycles may range from 18 to 45 cycles, such as 20 to 40 cycles. In certain embodiments, the number of cycles is from 30 cycles to 45 cycles, e.g., from 33 cycles to 38 cycles, including from 35 cycles to 37 cycles. To obtain a melting temperature of amplification products, the PCR protocol may include a melt curve analysis step after the PCR cycles are completed.

The template nucleic acid used in the real-time PCR of the present method may be DNA, e.g., genomic DNA, mitochondrial DNA, or may be RNA, e.g., mRNA. In certain embodiments, if the template nucleic acid is derived from mRNA, the method includes extracting RNA from the sample and subjecting the extracted RNA to a reverse transcriptase to generate a cDNA library, which may then be used as a template for the real-time PCR. Any suitable method may be used to generate a cDNA library.

In some embodiments, the present method further includes generating a report indicating the presence or absence of one or more onychomycotic fungi in a sample subjected to the screening steps, as described herein. In some embodiments, the report contains a list of secondary clade members tested, and indicates the presence or absence of the tested secondary clade members in the sample. In some embodiments, the report includes a list of primary clade members tested, and indicates the presence or absence of the tested primary clade members in the sample. As shown in FIG. 39, the report may indicate the presence or absence of a *candida*, dermatophyte, or a saprophyte in the sample, and may further indicate the presence or absence of a species that belongs to the *candida* secondary clade member for which the presence or absence was tested. As shown in FIG. 57, the report may indicate the presence or absence of a *Candida*, dermatophyte, or a saprophyte in the sample, and may further indicate the presence or absence of the dermatophyte species or genera for which the presence or absence was tested. As shown in FIGS. 84A-84C, the report may indicate the presence of a saprophyte and absence of a *Candida*, dermatophyte, in the sample, and may further indicate the presence or absence of a specific saprophyte primary clade member.

The report may be provided in any suitable form, including, but not limited to, a report on a physical piece of paper, a report in digital form accessible by a user interface on a computer system (e.g., a web page, or an e-mail), an entry in a database of a patient's medical record, and/or a data file on a non-transient computer readable data-storage medium (e.g., a flash drive, hard drive, compact disc (CD), etc.).

Samples

The sample may be any suitable tissue in which the presence of an onychomycotic fungus is to be detected. In certain embodiments, the sample includes keratinous tissue, such as nail, skin, hair, etc. A nail sample may include a toenail, a fingernail, or portions thereof. In some embodiments, the sample includes bodily fluids, such as sweat, mucus, tears, saliva, etc.

In some embodiments, the sample includes nail clippings from one or more, e.g., 2 or more, 3 or more, 4 or more, 5 or more, including 8 or more fingernails and/or toenails, and includes nail clippings from 20 or less, e.g., 15 or less, 10 or less, 5 or less, including 3 or less fingernails. In some embodiments, the sample includes nail clippings from 1 to 20, e.g., 1 to 15, 1 to 10, 1 to 5, including 1 to 3 fingernails and/or toenails.

In some embodiments, the sample includes 0.1 mg or more, including 0.5 mg or more, 1 mg or more, 2 mg or more, 5 mg or more, 10 mg or more, 20 mg or more, 50 mg or more and includes 200 mg or less, including 150 mg or less, 100 mg or less, 80 mg or less, 50 mg or less, 20 mg or less, 10 mg or less, 5 mg or less, including 1 mg or less of nail clippings from one or more fingernails and/or toenails. In some embodiments, the sample includes nail clippings from one or more fingernails and/or toenails in the range of 0.1 to 200 mg, e.g., 0.5 to 100 mg, 0.5 to 20 mg, 0.5 to 10 mg, including 1 to 5 mg.

In some embodiments, the sample includes nucleic acids, e.g., DNA, at a concentration of 0.01 ng/μL or more, e.g., 0.05 ng/μL or more, 0.1 ng/μL or more, 1.0 ng/μL or more, 5.0 ng/μL or more, 10 ng/μL or more, including 50 ng/μL or more, and includes nucleic acids, e.g., DNA, at a concentration of 1,000 ng/μL or less, e.g., 500 ng/μL or less, 100 ng/μL or less, 50 ng/μL or less, 20 ng/μL or less, 10 ng/μL or less, 0.1 ng/μL or less, including 0.01 ng/μL or less. In some embodiments, the sample includes nucleic acids, e.g., DNA, at a concentration in the range of 0.01 ng/μL to 1,000 ng/μL, e.g., 0.01 ng/μL to 100 ng/μL, 0.1 ng/μL to 50 ng/μL, including 1 ng/μL to 20 ng/μL.

The sample may be labeled with an identifying label prior to analysis. In some embodiments, the identifying label may be a barcode label, or a radio-frequency identification (RFID) tag. The identifying label may encode information including the source of the sample (e.g., patient, clinic, hospital), the analysis performed (e.g., PCR, culture, histopathology), etc.

The sample may be prepared to lyse cells and release nucleic acids within cells into a solution using any suitable method, as described below. In some embodiments, the sample contains a suitable buffer for lysing cells, for stabilizing nucleic acids in the sample and/or for carrying out PCRs.

Method of Preparing a Sample

In certain embodiments, the present method includes preparing a sample, e.g., a nail sample, for screening by the method described herein. Preparing the sample may include treating the sample with mechanical, thermal, chemical and/or enzymatic methods of lysing cells and cellular compartments (e.g., plasma membrane, cell wall, nucleus, mitochondria, etc.) in the sample to release nucleic acids, e.g., DNA and/or RNA, into the bulk of the sample.

Any suitable method of mechanically lysing cells may be used. In some embodiments, mechanically lysing the cells includes, e.g., homogenizing, grinding, ultrasonicating or freezing the sample. In some embodiments, cells in the sample may be physically lysed by subjecting the sample to a blender, bead or ultrasonic homogenization, grinding by a mortar and pestle, French press, etc. Beads for homogenizing the sample may be, but are not limited to garnet, glass, ceramic, or steel beads. In some embodiments, the diameter of the beads is in the range of 0.05 mm to 5 mm, e.g., 0.1 mm to 4 mm, including 0.1 mm to 3 mm. The sample may be subjected to pulses of mechanical treatment, such as one or more, e.g., two or more, 3 or more, four or more pulses, and 8 or less, 6 or less, including 4 or less pulses. The pulse of a mechanical treatment may have a duration in the range of 10 to 60 seconds, e.g., 15 to 50 seconds, including 20 to 45 seconds.

Any suitable method of chemically lysing cells may be used. In some embodiments, chemical lysis methods include alkaline lysis, detergent lysis (e.g., sodium dodecyl sulfate (SDS)), solvent lysis (e.g., chloroform), etc. In one embodiment, chemically lysing cells involves use of a chaotropic agent, e.g., a chaotropic salt. Non-limiting examples of chaotropic agents include guanidinium isothiocyanate, guanidinium chloride, urea, thiourea, lithium perchlorate, lithium acetate, sodium iodide, phenol and others.

Any suitable method of enzymatically lysing cells may be used. In some embodiments, enzymatic lysis methods include treatment of the sample with protease, lipase, glycoside hydrolases, etc. In some embodiments, cells in the sample may be enzymatically lysed by subjecting the sample to proteinase K, trypsin, subtilisin, lyticase, lysozyme, collagenase, cellulase, glucanase, chitinase, pectinase, or amylase, etc.

Any suitable method of thermally lysing cells may be used. In some embodiments, the sample is subjected to a temperature of 50° C. or more, e.g., 60° C. or more, 70° C. or more, 80° C. or more, 90° C. or more, or 95° C. or more, and is subjected to a temperature of 100° C. or less, e.g., 98° C. or less, including 95° C. or less, to lyse the cells in the sample. In some embodiments, the sample is subjected to a temperature in the range of 50° C. to 100° C., e.g., 60° C. to 100° C., 70° C. to 100° C., 80° C. to 100° C., including 90° C. to 98° C., to lyse the cells in the sample. In some embodiments, the sample is subjected to heat for 5 to 60 minutes, e.g., 10 to 30 minutes, to lyse the cells. In certain embodiments, the sample is subjected to heat in the presence of a lysis buffer containing, e.g., enzymatic and/or chemical lysing agents.

In some embodiments, the preparing step includes subjecting a sample sequentially to two or more of mechanical, thermal, chemical and/or enzymatic methods of lysing cells, as described above. The order in which the sample is subjected to the methods of lysing cells may be any suitable order. In some embodiments, the sample is prepared by subjecting the sample to mechanical, enzymatic and thermal methods of lysing cells. In certain embodiments, the sample is prepared by subjecting the sample first to mechanical lysis, then to enzymatic lysis, and then to thermal lysis.

The preparing step may also include purifying the released nucleic acids after lysing the cells. The nucleic acids may be purified using any suitable method, including ethanol precipitation, and solid phase extraction by binding the nucleic acids to a spin column or a magnetic substrate, followed by elution. In some embodiments, nucleic acids released from lysed cells are used in the assay without purification.

Methods of Analyzing Ct and Tm Values

Any suitable portion of the present method of detecting an onychomycotic fungus in a sample using clade-specific primers may be performed by manual review of Ct and/or Tm values and/or melt curves (e.g., by a practitioner, such as a clinical laboratory personnel, a physician, a pharmacist, a nurse, etc.), or on a suitable computer system, or a combination thereof. In some embodiments, a method of analyzing Ct and/or Tm values obtained from a real-time PCR using the present clade-specific primers may be performed by manual review of Ct and/or Tm values and/or melt curves (e.g., by a practitioner, such as a clinical laboratory personnel, a physician, a pharmacist, a nurse, etc.), or on a suitable computer system, or a combination thereof.

The computer system may include a processor, a memory, input and output devices, a data storage unit, a networking interface, etc., as described below. The memory, which may be a non-transitory, computer-readable storage medium, may include various applications that are executed by the processor, including an operating system, and software applications. The software applications may include instructions that when executed cause the computer system to perform the method of analyzing Ct and/or Tm values obtained from a real-time PCR using the present clade-specific primers, as described herein.

Computer-Implemented Methods, Systems and Devices

The methods of the present disclosure can be computer-implemented, such that method steps (e.g., screening, determining, analyzing, calculating, and/or the like) are automated in whole or in part. Accordingly, the present disclosure provides methods, computer systems, devices and the like in connection with computer-implemented methods of detecting an onychomycotic fungus in a sample.

For example, the method steps, including obtaining Ct values and Tm values for a real-time PCR using clade-specific primers, analyzing the Ct values and Tm values, comparing Ct values and Tm values to cutoff and/or reference values and/or ranges, calculating $\Delta Ct_{2-1}$ and/or $\Delta Tm$, generating a report, and the like, can be completely or partially performed by a computer program product. Values obtained can be stored electronically, e.g., in a database, and can be subjected to an algorithm executed by a programmed computer. A database may store cutoff and/or reference values and/or ranges that are specific for a clade-specific primer and have a database structure that allows retrieval of the cutoff and/or reference values and/or ranges based on an identifying label for the clade-specific primer.

For example, the methods of the present disclosure can involve inputting Ct and Tm values (e.g., Ct and Tm values obtained for a sample, identifying label for the clade-specific primers used to obtain the Ct and Tm values, expected Ct and Tm values and/or ranges (e.g., $Ct_{cutoff}$, $\Delta Ct_{range}$, reference Tm, $\Delta Tm$ and Ct ranges) for clade-specific primers, etc.) into a computer programmed to execute an algorithm to perform the comparing and calculating step(s) described herein, and generate a report as described herein, e.g., by displaying or printing a report, e.g., a report indicating the presence or absence of a *candida*, a dermatophyte, and saprophyte, to an output device at a location local or remote to the computer.

The present disclosure thus provides a computer program product including a computer readable storage medium having a computer program stored on it. In certain aspects, the storage medium is non-transitory (e.g., a storage medium that is not a transitory wave or signal). The program can, when read by a computer, execute relevant calculations based on values obtained from analysis of one or more samples from an individual. The computer program product has stored therein a computer program for performing the calculation(s) and comparison(s).

The present disclosure provides systems for executing the program described above, which system generally includes: a) a central computing environment; b) an input device, operatively connected to the computing environment, to receive data, wherein the data can include, for example, Ct and/or Tm values or other information obtained from an assay using a sample from a subject, as described above; c) an output device, connected to the computing environment, to provide information to a user (e.g., medical personnel); and d) an algorithm executed by the central computing environment (e.g., a processor), where the algorithm is executed based on the data received by the input device, and wherein the algorithm analyzes the input data to determine the presence or absence of an onychomycotic fungal infection in the sample.

Computer Systems

Figure 90:
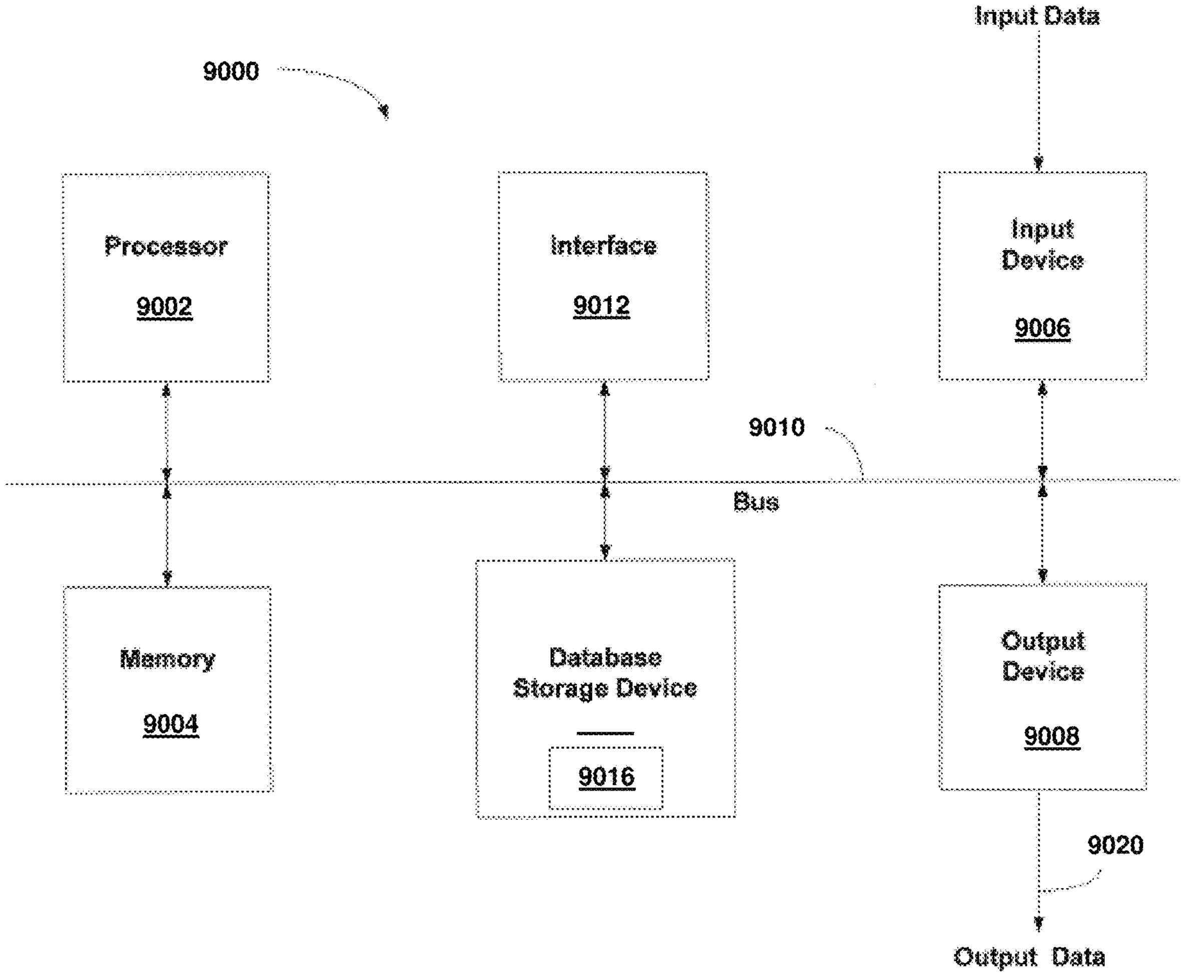
FIG. 90 shows a schematic diagram of a computer system, according to embodiments of the present disclosure.

A generalized example of a computerized embodiment in which programs to facilitate execution of the methods of the present disclosure can be implemented is depicted in FIG. 90, which illustrates a processing system 9000 which generally comprises at least one processor 9002, or processing unit or plurality of processors, memory 9004, at least one input device 9006 and at least one output device 9008, coupled together via a bus or group of buses 9010. In certain embodiments, input device 9006 and output device 9008 can be the same device. An interface 9012 can also be provided for coupling the processing system 9000 to one or more peripheral devices, for example interface 9012 can be a PCI card or PC card. At least one storage device 9014 which houses at least one database 9016 can also be provided.

The memory 9004 can be any form of memory device, for example, volatile or non-volatile memory, solid state storage devices, magnetic devices, etc. In certain aspects, the memory includes a non-transitory storage medium (e.g., a storage medium that is not a transitory wave or signal). The processor 9002 can comprise more than one distinct processing device, for example to handle different functions within the processing system 9000. Input device 9006 receives input data 9018 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 9018 can come from different sources, for example keyboard instructions in conjunction with data received via a network.

Output device 9008 produces or generates output data 9020 and can comprise, for example, a display device or monitor in which case output data 9020 is visual, a printer in which case output data 9020 is printed, a port for example a USB port, a peripheral component adaptor, a data transmitter or antenna such as a modem or wireless network adaptor, etc. Output data 9020 can be distinct and derived from different output devices, for example a visual display on a monitor in conjunction with data transmitted to a network. A user can view data output, or an interpretation of the data output, on, for example, a monitor or using a printer. The storage device 9014 can be any form of data or information storage means, for example, volatile or non-volatile memory, solid state storage devices, magnetic devices, etc.

In use, the processing system 9000 may be adapted to allow data or information to be stored in and/or retrieved from, via wired or wireless communication means, at least one database 9016. The interface 9012 may allow wired and/or wireless communication between the processing unit 9002 and peripheral components that may serve a specialized purpose. In general, the processor 9002 can receive instructions as input data 9018 via input device 9006 and can display processed results or other output to a user by utilizing output device 9008. More than one input device 9006 and/or output device 9008 can be provided. The processing system 9000 may be any suitable form of terminal, server, specialized hardware, or the like.

The processing system 9000 may be a part of a networked communications system. Processing system 9000 can connect to a network, for example the Internet or a WAN. Input data 9018 and output data 9020 can be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 9000 illustrated in FIG. 90 may operate in a networked environment using logical connections to one or more remote computers. The remote computer may be a personal computer, a server, a router, a network PC, a peer device, or other common network node, and typically includes many or all of the elements described above.

FIG. 90 is intended to provide a brief, general description of an illustrative and/or suitable example of a computing environment in which embodiments of the methods disclosed herein may be implemented. FIG. 90 is an example of a suitable environment and is not intended to suggest any limitation as to the structure, scope of use, or functionality of an embodiment of the present invention.

Figure 89:
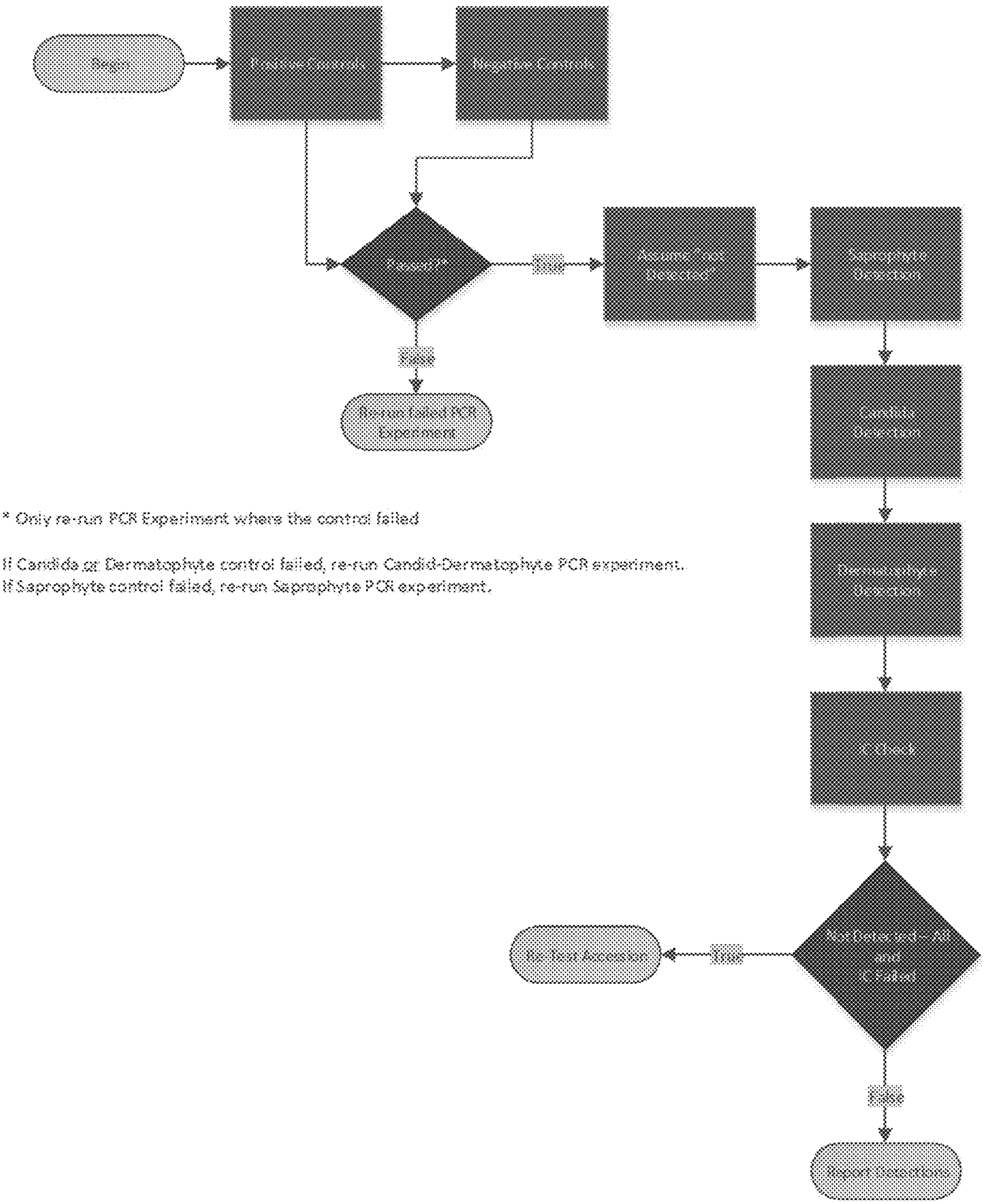
FIG. 89 shows a flow chart representing embodiments of the present disclosure.

Certain embodiments may be described with reference to acts and symbolic representations of operations (e.g., such as the flow diagrams shown in FIGS. 4 and 89) that are performed by one or more computing devices, such as the computing system environment 9000 of FIG. 90. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types.

Computer Program Products

The present disclosure provides computer program products that, when executed on a programmable computer such as that described above with reference to FIG. 90, can carry out the methods of the present disclosure. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" (e.g., "computer-readable medium") refers to any computer program product, apparatus and/or device (e.g., magnetic discs, optical disks, memory, etc.) used to provide machine instructions and/or data to a programmable processor, including a machine-readable medium that receives machine instructions as a machine-readable signal. According to certain embodiments, the machine-readable medium is non-transitory (e.g., a machine readable medium that is not a transitory wave or signal).

It will be apparent from this description that aspects of the present invention may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium (e.g., a non-transitory computer-readable medium) including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

Use of Assay to Facilitate Diagnosis and Selection of Therapy

The methods of the present disclosure find use in detecting an onychomycotic fungus in a sample to determine the presence of and/or the type of fungus at a site of infection, e.g., a nail infection, or a cutaneous region surrounding a nail. Determining the presence of a fungus, and, if present, identifying the type of fungus (e.g., *candida*, dermatophyte, or saprophyte; and/or *Candida* species or dermatophyte species) at the site suspected of a fungal infection can facilitate a medical professional in selection and/or administration of an antifungal medication that is more likely to provide a clinical benefit to the patient.

Thus, the present method finds use in diagnosing a nail infection in a patient, e.g., a human patient, suffering from a nail infection. The methods of the present disclosure thus may include obtaining a sample, e.g., a nail or other cutaneous sample associated with the nail, determining the presence or absence of an onychomycotic fungus in the sample and, if present, the type of fungus, using an assay method as described herein, generating a report that indicates the presence or absence of one or more onychomycotic fungi in the patient sample and, optionally, if present, identifying the likely type of fungus present in the infection, and, optionally, indicating suggested therapy(ies) for treatment of the infection based on the assay results.

The methods of the present disclosure can include selecting a therapy, e.g., an antifungal medication, based on the results of the assay. In some embodiments, the methods of the present disclosure can include administering a therapy, e.g., an antifungal medication, based on the results of the assay. Where the methods include selection and/or administration of an antifungal therapy, the therapy is selected according to the primary and/or secondary clade member detected. For example, where a *candida* infection is detected, then the therapy selected is one most likely effective against *candida*; where a primary member of a *candida* secondary clade is detected, then the therapy selected can be one most likely effective against that primary clade member. Where a dermatophyte infection is detected, then the therapy selected is one most likely effective against a dermatophyte; where a primary member of a dermatophyte secondary clade is detected, then the therapy selected can be one most likely effective against that primary clade member. Where a saprophyte infection is detected, then the therapy selected is one most likely effective against a saprophyte.

In some embodiments, the therapy includes administering a pharmaceutical compound. A pharmaceutical compound or drug suitable for treating onychomycosis may be administered using any suitable method. The pharmaceutical compound may be administered topically or systemically. In some embodiments, the pharmaceutical compound is administered orally or topically. An orally administered pharmaceutical compound for treating onychomycosis may include, without limitation, itraconazole, fluconazole, and/or terbinafine. A topically administered pharmaceutical compound for treating onychomycosis may include, without limitation, tavaborole, efinaconazole or ciclopirox. The pharmaceutical compound may be administered in any suitable dosage form, e.g., as a tablet, liquid, cream, emulsion, etc. and may be administered in conjunction with any suitable pharmaceutically acceptable carrier.

The therapy may also include providing a first pharmaceutical compound as a first line treatment of onychomycosis, and providing a second pharmaceutical compound as a second line treatment, and so on, depending on the outcome of each successive lines of treatment. Thus, in some embodiments, where a therapy is selected according to the primary and/or secondary clade member detected, the first and second lines of treatment may be selected according to the primary and/or secondary clade member detected. In some embodiments, where a therapy is selected according to the primary and/or secondary clade member detected, the first, second and third lines of treatment may be selected according to the primary and/or secondary clade member detected.

In some embodiments, where a *candida* is detected in a sample, the therapy may include administering a first line pharmaceutical compound that is itraconazole, a second line pharmaceutical compound that is fluconazole and/or a third line pharmaceutical compound that is terbinafine.

In some embodiments, where a dermatophyte is detected in a sample, the therapy may include administering a first line pharmaceutical compound that is terbinafine, a second line pharmaceutical compound that is fluconazole and/or a third line pharmaceutical compound that is itraconazole. In some embodiments, where a dermatophyte is detected in a sample, the therapy may include administering tavaborole or efinaconazole. In some embodiments, where *Trichophyton mentagrophytes* is detected in the sample, the therapy may include administering tavaborole or efinaconazole. In some embodiments, where *Trichophyton rubrum* is detected in the sample, the therapy may include administering tavaborole, efinaconazole or ciclopirox.

In some embodiments, where a saprophyte is detected in a sample, the therapy may include administering a first line pharmaceutical compound that is itraconazole, a second line pharmaceutical compound that is terbinafine and/or a third line pharmaceutical compound that is fluconazole. In some embodiments, where an *Acremonium* spp. is detected in the sample, the first line pharmaceutical compound may be terbinafine.

Where the assay results indicate the absence of a fungal infection, then the therapy selected can be one that does not involve an antifungal medication, thereby avoiding administration of such drugs where such is not likely to provide a clinical benefit In some embodiments, the present method of detecting an onychomycotic fungus in a sample may be performed in conjunction with more conventional methods of diagnosing an infection, such as microscopy, histology and fungal culture methods. In some embodiments, microscopic visualization of fungal elements in a nail sample may include using potassium hydroxide (KOH) to clarify a thin section of a nail sample from a patient.

The present method of detecting onychomycotic fungus in a sample can facilitate sensitive detection of an onychomycotic infection, as well as identification of the nature of the infecting organism. In some embodiments, the screening step using secondary clade-specific primers detects the presence of an organism that belongs to a secondary clade member (e.g., a dermatophyte secondary clade member or a saprophyte secondary clade member) at a DNA copy number of the secondary clade member of 1 or more, e.g., 2 or more, 4 or more, 10 or more, 50 or more, 100 or more, 200 or more, 500 or more, 1,000 or more, 1,500 or more, 2,000 or more, including 2,500 or more, and detects the presence of the secondary clade member at a DNA copy number of the secondary clade member of 15,000 or less, e.g., 12,000 or less, 5,000 or less, 2,500 or less, 2,000 or less, 1,000 or less, 500 or less, 200 or less, including 100 or less, in a reaction mixture. In some embodiments, the screening step using secondary clade-specific primers detects the presence of an organism that belongs to a secondary clade member at a DNA copy number of the secondary clade member in the range of 1 to 15,000, including 2 to 12,000, 4 to 5,000, 1,000 to 15,000, 1,500 to 10,000, including 1,500 to 5,000, in a reaction mixture.

In some embodiments, the screening step using primary clade-specific primers detects the presence of an organism that belongs to a primary clade member (e.g., a dermatophyte primary clade member or a saprophyte primary clade member) at a DNA copy number of the primary clade member of 5 or more, e.g., 10 or more, 20 or more, 50 or more, 100 or more, 150 or more, 300 or more, 500 or more, 1,000 or more, 2,000 or more, including 5,000 or more, and detects the presence of the primary clade member at a DNA copy number of the primary clade member of 10,000 or less, e.g., 7,000 or less, 5,000 or less, 2,500 or less, 1,000 or less, 500 or less, 200 or less, including 100 or less, in a reaction mixture. In some embodiments, the screening step using primary clade-specific primers detects the presence of an organism that belongs to a primary clade member at a DNA copy number of the primary clade member in the range of 5 to 10,000, e.g., 5 to 5,000, 5 to 1,000, 5 to 200, 100 to 10,000, 150 to 7,000, 150 to 2,000, including 150 to 500, in a reaction mixture.

The limit of detection for detecting the presence of an organism that belongs to a secondary clade member in a sample by the present methods may in certain cases be 0.0001 ng or more, e.g., 0.0002 ng or more, 0.0004 ng or more, 0.001 ng or more, 0.002 ng or more, 0.004 ng or more, 0.01 ng or more, 0.02 ng or more, 0.04 ng or more, including 0.1 ng or more, and may in certain cases be 10 ng or less, e.g., 5 ng or less, 1 ng or less, 0.4 ng or less, 0.2 ng or less, 0.1 ng or less, 0.04 ng or less, 0.02 ng or less, including 0.01 ng or less, of DNA per reaction (e.g., PCR reaction). In certain embodiments, the limit of detection for detecting the presence of an organism that belongs to a secondary clade member in a sample by the present methods may be 0.0001 ng to 10 ng, e.g., 0.0002 ng to 5 ng, 0.0004 ng to 5 ng, 0.0004 ng to 1 ng, including 0.0004 ng to 0.1 ng of DNA in a reaction mixture.

The limit of detection for detecting the presence of an organism that belongs to a primary clade member in a sample by the present method may in certain cases be 0.0001 ng or more, e.g., 0.0002 ng or more, 0.0004 ng or more, 0.001 ng or more, 0.002 ng or more, 0.004 ng or more, 0.01 ng or more, 0.02 ng or more, 0.04 ng or more, including 0.1 ng or more, and may in certain cases be 10 ng or less, e.g., 5 ng or less, 1 ng or less, 0.4 ng or less, 0.2 ng or less, 0.1 ng or less, 0.04 ng or less, 0.02 ng or less, including 0.01 ng or less, of DNA per reaction (e.g., PCR reaction). In certain embodiments, the limit of detection for detecting the presence of an organism that belongs to a primary clade member in a sample by the present methods may be 0.0001 ng to 10 ng, e.g., 0.0002 ng to 5 ng, 0.0004 ng to 5 ng, 0.0004 ng to 1 ng, including 0.0004 ng to 0.1 ng of DNA in a reaction mixture.

The limit of detection for detecting the presence of an organism that belongs to a secondary clade member (e.g., a *candida* secondary clade member) in a sample by the present methods may in certain cases be 100 colony forming units (CFU) or more, e.g., 200 CFU or more, 500 CFU or more, including 1,000 CFU or more, and may in certain cases be 10,000 CFU or less, e.g., 5,000 CFU or less, 4,000 CFU or less, including 3,500 or less, of the secondary clade member per reaction (e.g., PCR reaction). In certain embodiments, the limit of detection for detecting the presence of an organism that belongs to a secondary clade member in a sample by the present methods may be 100 CFU to 10,000 CFU, e.g., 200 CFU to 5,000 CFU, 500 CFU to 5,000 CFU, including 1,000 CFU to 4,000 CFU of the secondary clade member in a reaction mixture.

The limit of detection for detecting the presence of an organism that belongs to a primary clade member (e.g., a *candida* primary clade member) in a sample by the present method may in certain cases be 100 CFU or more, e.g., 200 CFU or more, 500 CFU or more, including 1,000 CFU or more, and may in certain cases be 10,000 CFU or less, e.g., 5,000 CFU or less, 4,000 CFU or less, including 3,500 or less, of the primary clade member per reaction (e.g., PCR reaction). In certain embodiments, the limit of detection for detecting a primary clade member in a sample by the present methods may be 100 CFU to 10,000 CFU, e.g., 200 CFU to 5,000 CFU, 500 CFU to 5,000 CFU, including 1,000 CFU to 4,000 CFU of the primary clade member in a reaction mixture.

The present method of detecting onychomycotic fungus in a sample provides a reproducible method of detecting and/or identifying an onychomycotic infection. The method may be reproducible by producing substantially the same results when the method is repeated on different portions of the same sample multiple times, repeated on different samples containing the same target nucleotide sequence, and/or when the method is repeated by a different practitioner and/or different instrument using portions of the same sample. In some instances, the coefficient of variation of the Ct and/or Tm values obtained in the present method across repetitions is 15% or less, e.g., 10% or less, 8% or less, 5% or less, including 3% or less. The assay may be reproducible when the assay is repeated 10 times or more, e.g., 12 times or more, 15 times or more, 18 times or more, 25 times or more, 30 times or more, including 50 times or more, and may be repeated 75 times or less, e.g., 65 times or less, 50 times or less, 40 times or less, 30 times or less, 25 times or less, 22 times or less, including 20 times or less. In some embodiments, the assay results are reproducible when the assay is repeated from 10 to 75 times, e.g., from 10 to 65 times, from 10 to 50 times, from 10 to 25 times, from 12 to 22 times, including 15 to 22 times.

The present method of detecting onychomycotic fungus in a sample is an accurate detection method. Accuracy of detection can be measured by the concordance between the result of the present PCR method with the result of sequencing nucleic acids in the sample to determine the presence and the type of onychomycotic fungus in a sample. In certain embodiments, the present PCR detection method has concordance with sequencing of 90% or more, e.g., 93% or more, including 95% or more.

In certain embodiments, the present method of detecting an onychomycotic fungus in a sample is a high-throughput method. In some embodiments, the method is a multiplexed method to determine the presence or absence of multiple onychomycotic fungi or multiple secondary clade members that contain onychomycotic fungi, as described above, in a single reaction mixture. In some embodiments, the present method determines the presence or absence of two or more, e.g., 3 or more, 4 or more, including 5 or more, and up to 6 secondary clade members in a single reaction mixture, by using a suitable number and combination of different secondary-clade specific primers, as described above, in the reaction mixture. In some embodiments, the present method determines the presence or absence of two or more, e.g., 3 or more, 4 or more, including 5 or more, and up to 6 primary clade members in a single reaction mixture, by using a suitable number and combination of different primary-clade specific primers, as described above, in the reaction mixture.

The present method of detecting an onychomycotic fungus in a sample can provide a more rapid detection method than conventional methods. For example, the turn-around time (e.g., the time between a sample is submitted for analysis and receiving the results of the analysis, e.g., receiving a report) of the present method for determining the presence or absence of an onychomycotic fungus in a sample can be 10 days or less, e.g., 7 days of less, 5 days or less, including 3 days or less, and may be 1 day or more, e.g., 2 days or more, including 3 days or more. In some embodiments, the turn-around time of the present method for determining the presence or absence of an onychomycotic fungus in a sample is in the range of 1 to 10 days, e.g., 1 to 7 days, 2 to 5 days, including 2 to 3 days.

Kits

Also provided herein is a kit that finds use in performing embodiments of the method of the present disclosure. The kit may include one or more primary clade-specific primer pairs specific for onychomycotic fungi, as described above, and a first and second sets of secondary clade-specific primer pairs, where the first set of secondary clade-specific primers is designed to determine the presence of one or more secondary clade members belonging to a first set of one or more secondary clade members, and the second set of secondary clade-specific primers are designed to determine the presence of one or more secondary clade members belonging to a second set of one or more secondary clade members, as described herein, and where the first and second sets of one or more secondary clade members are different sets. The secondary clade members may include a dermatophyte, a *candida*, and a saprophyte.

The kit may contain additional components that find use in preparing the sample before performing the screening PCR reactions. In some embodiments, the kit contains a homogenization element (e.g., homogenization beads, a homogenizer, etc.), homogenization buffer and/or a lysis buffer.

The kit may also contain instructions for practicing the present method. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Fungal Detection in Human Nails by Real Time PCR

I. Target Gene and Primer Sequences

Target organisms were identified by a literature search for onychomycosis etiology, and nail cultures. To assess the culture data, >17,000 consecutively accessioned culture-positive cases were reviewed. Gene sequences for target organisms were identified using the National Center for Biotechnology Information (NCBI) database and Basic Local Alignment Search Tool (BLAST®) "nucleotide blast" (nt/nr) query.

The 18S rRNA gene was used for PCR detection of fungi and yeast. Regions of the 18S rRNA gene are highly conserved among target organisms, thus allowing for amplification of multiple organisms with each primer pair. A database of rRNA consensus sequences for target organisms was constructed using Geneious® software, version 7.1.6 (Biomatters Ltd.).

Target regions for primer sequences were identified by identifying highly homologous regions among similar targets that were dissimilar to non-targeted species. Four primer pairs were used for detection of all targeted saprophytes. The four primer pairs are referred to as Saprophytes (a), Saprophytes (b), Saprophytes (c), and Saprophytes (d). Primer sequences are shown in Table 1.

TABLE 1

| Target | Forward primer | Reverse primer |
|---|---|---|
| Candida | GTC TGG GAA ATC TTG TGA AAC TCC (SEQ ID NO: 1) | GCC ATT CAA TCG GTA GTA GCG A (SEQ ID No: 2) |
| Dermatophyte | GGA GGT TGG AAA CGA CCG (SEQ ID NO: 3) | GCC CGC CGA GGC AAC C (SEQ ID NO: 4) |
| Saprophyte | GGG GCT CTT TTG GGT CTC (SEQ ID NO: 5) | GTC CAG CCG GAC CAG TAC T (SEQ ID NO: 6) |
| | AGA GGT GGG CAA CTA CCA CT (SEQ ID NO: 7) | CGC TGG TTC ACC AAC GGA G (SEQ ID NO: 8) |
| | TGG CAA CGA CCA CCT CAA G (SEQ ID NO: 9) | CCA GCC CGC CTT CAT ATT TGT (SEQ ID NO: 10) |
| | ACT CAC CAG GTC CAG ACA TAG (SEQ ID NO: 11) | GCA CCA CCA CCC ATA GAA TCT (SEQ ID NO: 12) |
| | GAA GGA TCA TTA CCG AGT TGA TTC G (SEQ ID NO: 244) | TCA GAC GGC AAC GTT CAC TG (SEQ ID NO: 245) |

Figure 5:
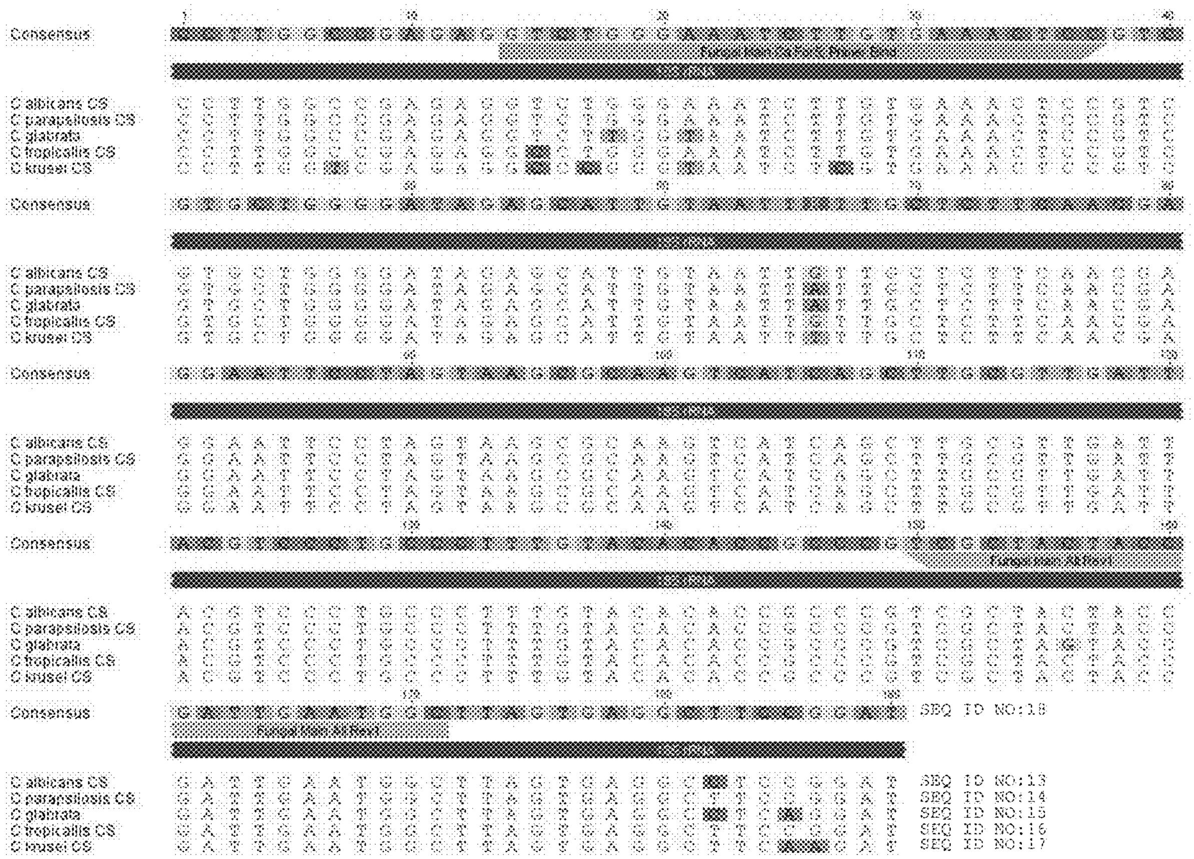
FIG. 5 shows alignments to genomic regions of primers designed to amplify *candida*-specific target sequences, according to embodiments of the present disclosure.

*Candida* primer alignment and target sequences are shown in FIG. 5. Alignment of genomic regions for the following organisms are shown: *C. albicans* (SEQ ID NO:13); *C. parapsilosis* (SEQ ID NO:14); *C. glabrata* (SEQ ID NO:15); *C. tropicalis* (SEQ ID NO:16); and *C. krusei* (SEQ ID NO:17). The consensus sequence is shown (SEQ ID NO:18).

Figure 6:
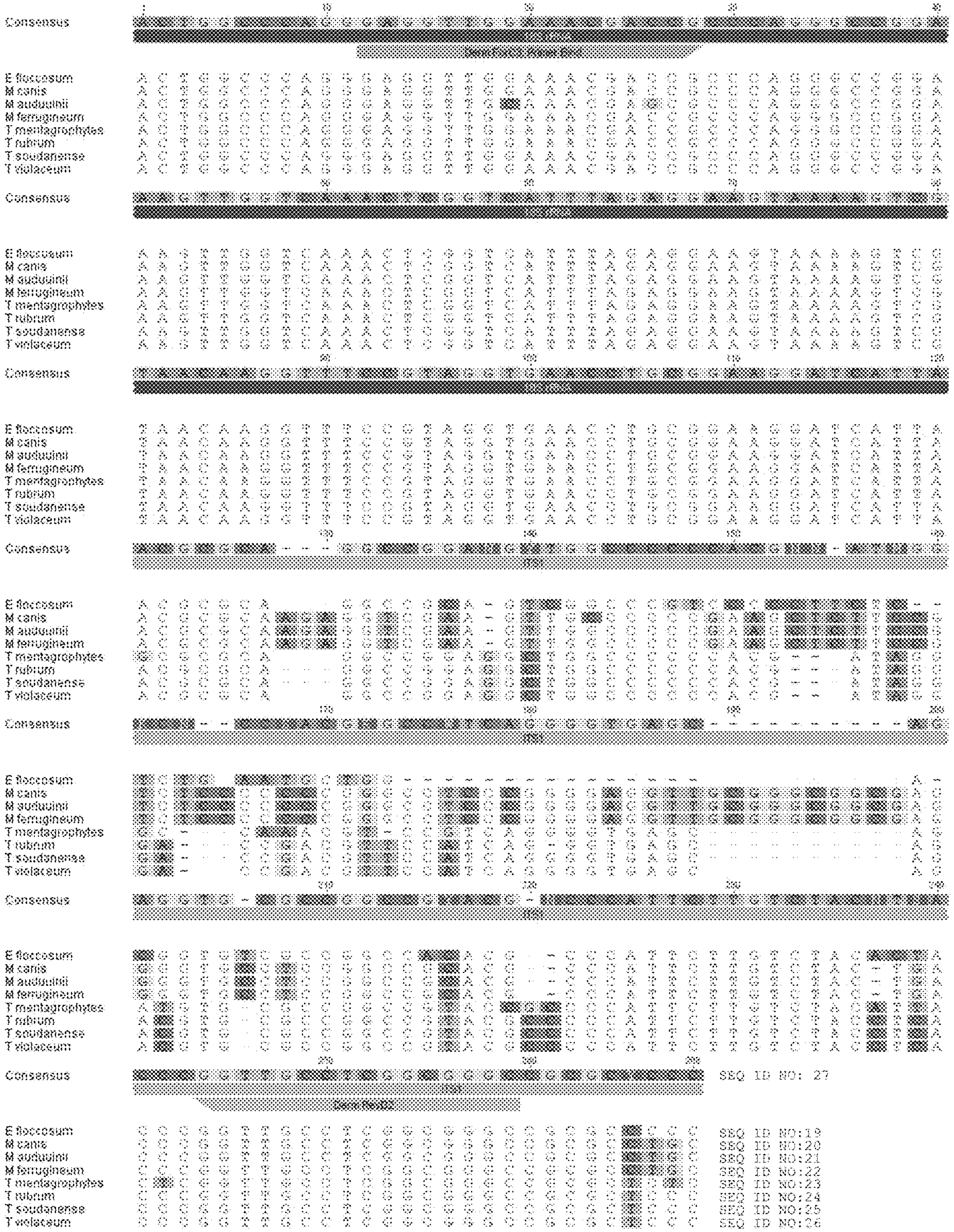
FIG. 6 shows alignments to genomic regions of primers designed to amplify dermatophyte-specific target sequences, according to embodiments of the present disclosure.

Dermatophyte primer alignment and target sequences are shown in FIG. 6. Alignment of genomic regions for the following organisms are shown: *Epidermophyton floccosum* (SEQ ID NO:19); *Microsporum canis* (SEQ ID NO:20); *M. audouinii* (SEQ ID NO:21); *M. ferrugineum* (SEQ ID NO:22); *Trichophyton mentagrophytes* (SEQ ID NO:23); *T. rubrum* (SEQ ID NO:24); *T. soudanense* (SEQ ID NO:25); and *T. violaceum* (SEQ ID NO:26). The consensus sequence is shown (SEQ ID NO:27).

Figure 7:
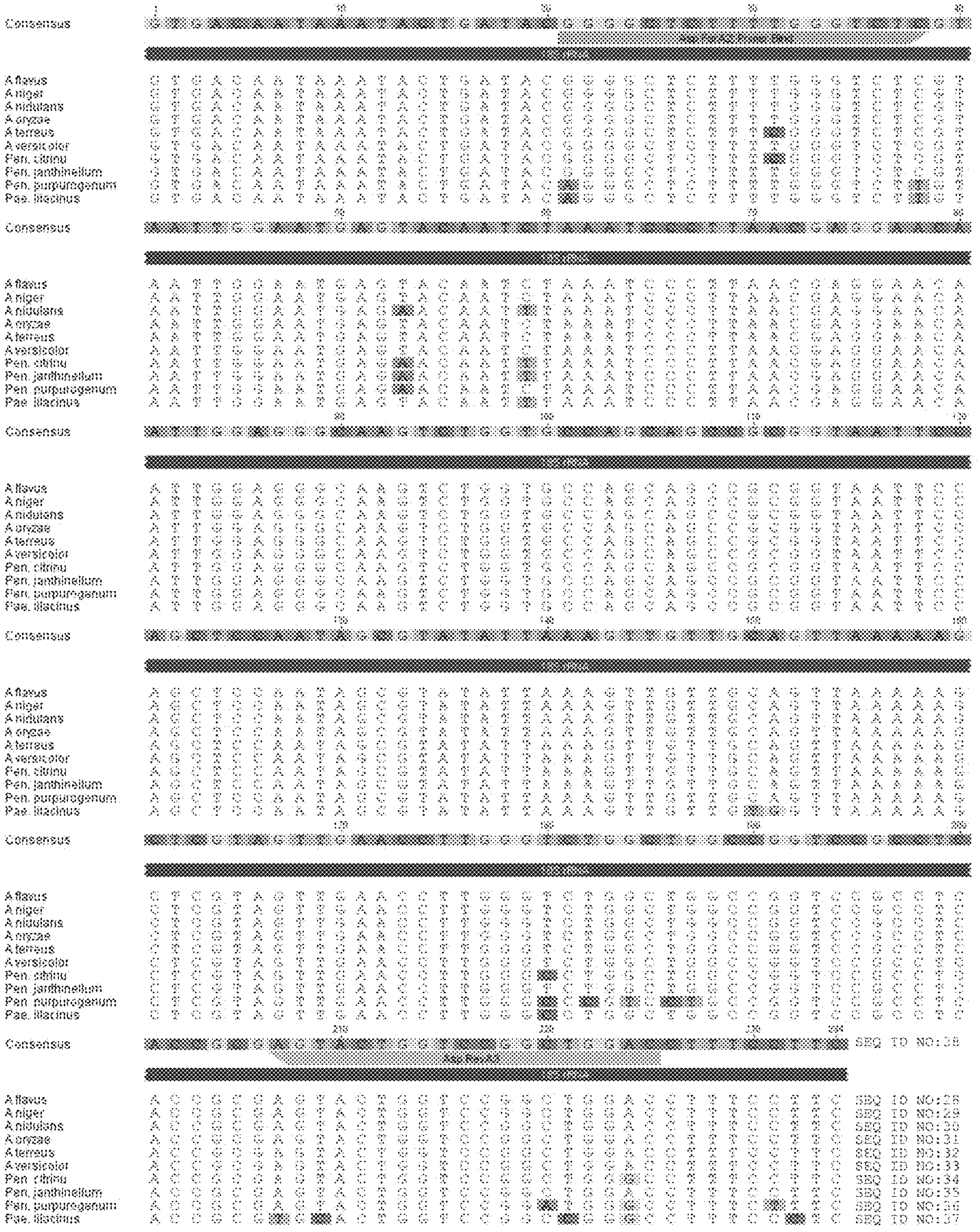
FIG. 7 shows alignments to genomic regions of primers designed to amplify saprophyte-specific target sequences, according to embodiments of the present disclosure.

Saprophytes (a) primer alignment and target sequences are shown in FIG. 7 Alignment of genomic regions for the following organisms are shown: *Aspergillus flavus* (SEQ ID NO:28); *A. niger* (SEQ ID NO:29); *A. nidulans* (SEQ ID NO:30); *A. terreus* (SEQ ID NO:31); *A. oryzae* (SEQ ID NO:32); *A. versicolor* (SEQ ID NO:33); *Penicillium citrinum* (SEQ ID NO:34); *Pen. janthinellum* (SEQ ID NO:35); *Pen. purpurogenum* (SEQ ID NO:36); and *Paecilomyces lilacinus* (SEQ ID NO:37). The consensus sequence is shown (SEQ ID NO:38).

Figure 8:
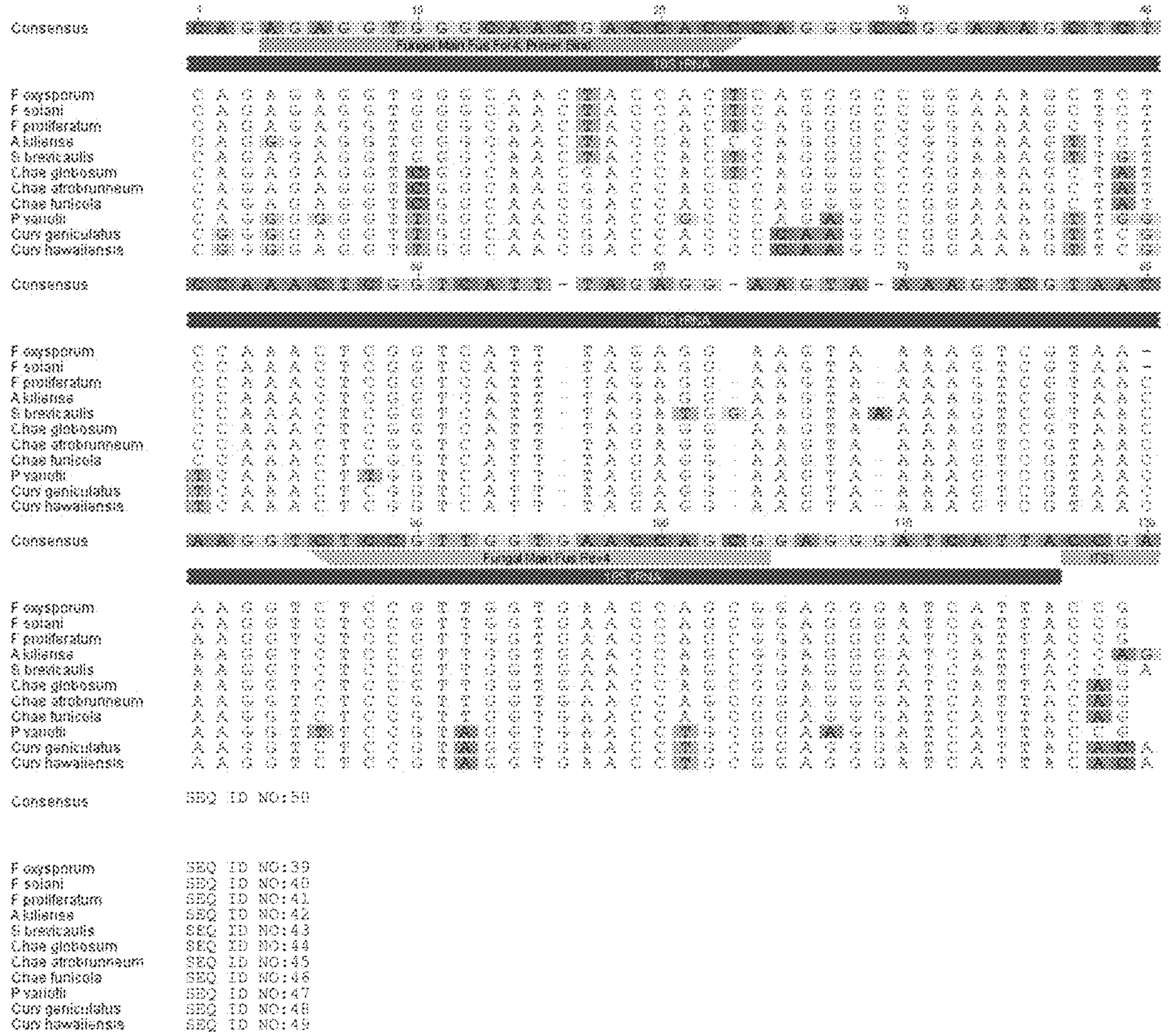
FIG. 8 shows alignments to genomic regions of saprophyte-specific primers designed to amplify target sequences, according to embodiments of the present disclosure.

Saprophytes (b) primer alignment and target sequences are shown in FIG. 8. Alignment of genomic regions for the following organisms are shown: *Fusarium oxysporum* (SEQ ID NO:39); *F. solani* (SEQ ID NO:40); *F. proliferatum* (SEQ ID NO:41); *Acremonium kiliense* (SEQ ID NO:42); *Scopulariopsis brevicaulis* (SEQ ID NO:43); *Chaetomium globosum* (SEQ ID NO:44); *Chae. atrobrunneum* (SEQ ID NO:45); *Chae. funicola* (SEQ ID NO:46); *Pae. variotti* (SEQ ID NO:47); *Curvularia geniculatus* (SEQ ID NO:48); and *Curv. hawaiiensis* (SEQ ID NO:49). The consensus sequence is shown (SEQ ID NO:50).

Figure 9:
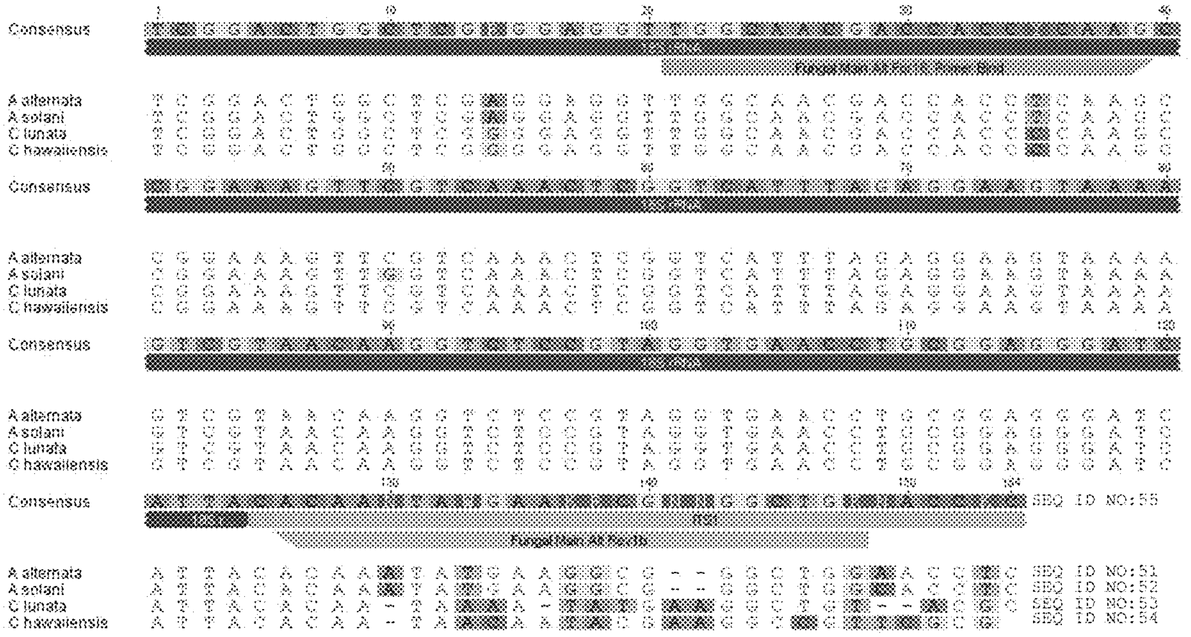
FIG. 9 shows alignments to genomic regions of saprophyte-specific primers designed to amplify target sequences, according to embodiments of the present disclosure.

Saprophytes (c) primer alignment and target sequences are shown in FIG. 9. Alignment of genomic regions for the following organisms are shown: *Alternaria alternata* (SEQ ID NO:51); *Alt. solani* (SEQ ID NO:52); *Cur. lunata* (SEQ ID NO:53); and *Cur. hawaiiensis* (SEQ ID NO:54). The consensus sequence is shown (SEQ ID NO:55).

Figure 10A:
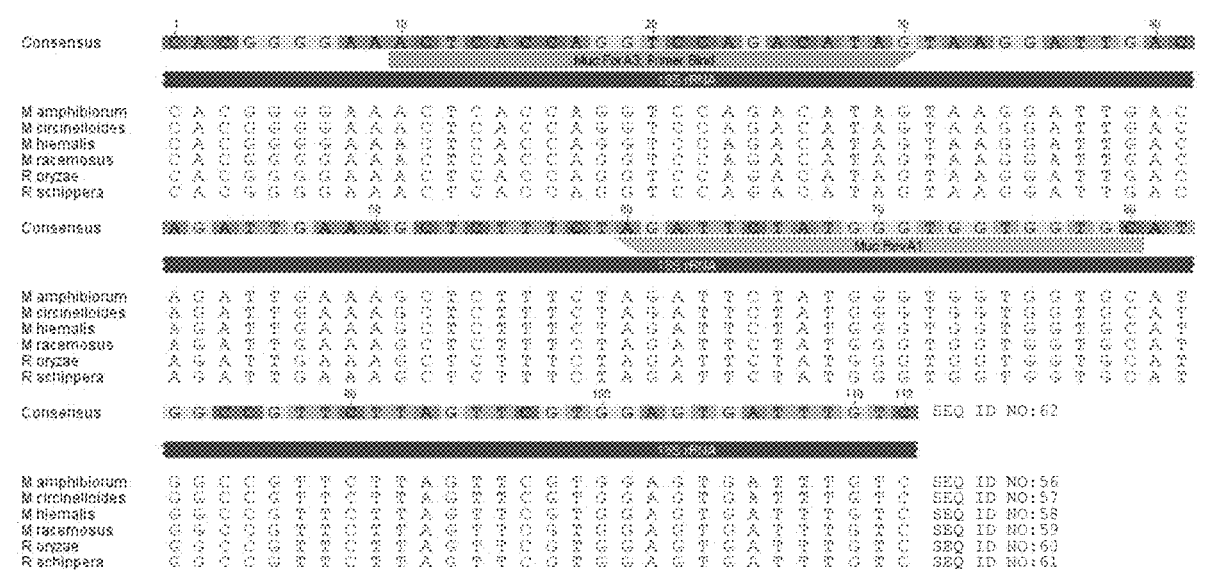
FIGS. 10A and 10B are a collection of images showing alignments to genomic regions of saprophyte-specific primers designed to amplify target sequences, according to embodiments of the present disclosure.

Saprophytes (d) primer alignment and target sequences are shown in FIG. 10A. Alignment of genomic regions for the following organisms are shown: *Mucor amphibiorum* (SEQ ID NO:56); *M. circinelloides* (SEQ ID NO:57); *M. hiemalis* (SEQ ID N058); *M. racemosus* (SEQ ID NO:59); *Rhizopus oryzae* (SEQ ID NO:60); and *R. schippera* (SEQ ID NO:61). The consensus sequence is shown (SEQ ID NO:62).

Figure 10B:
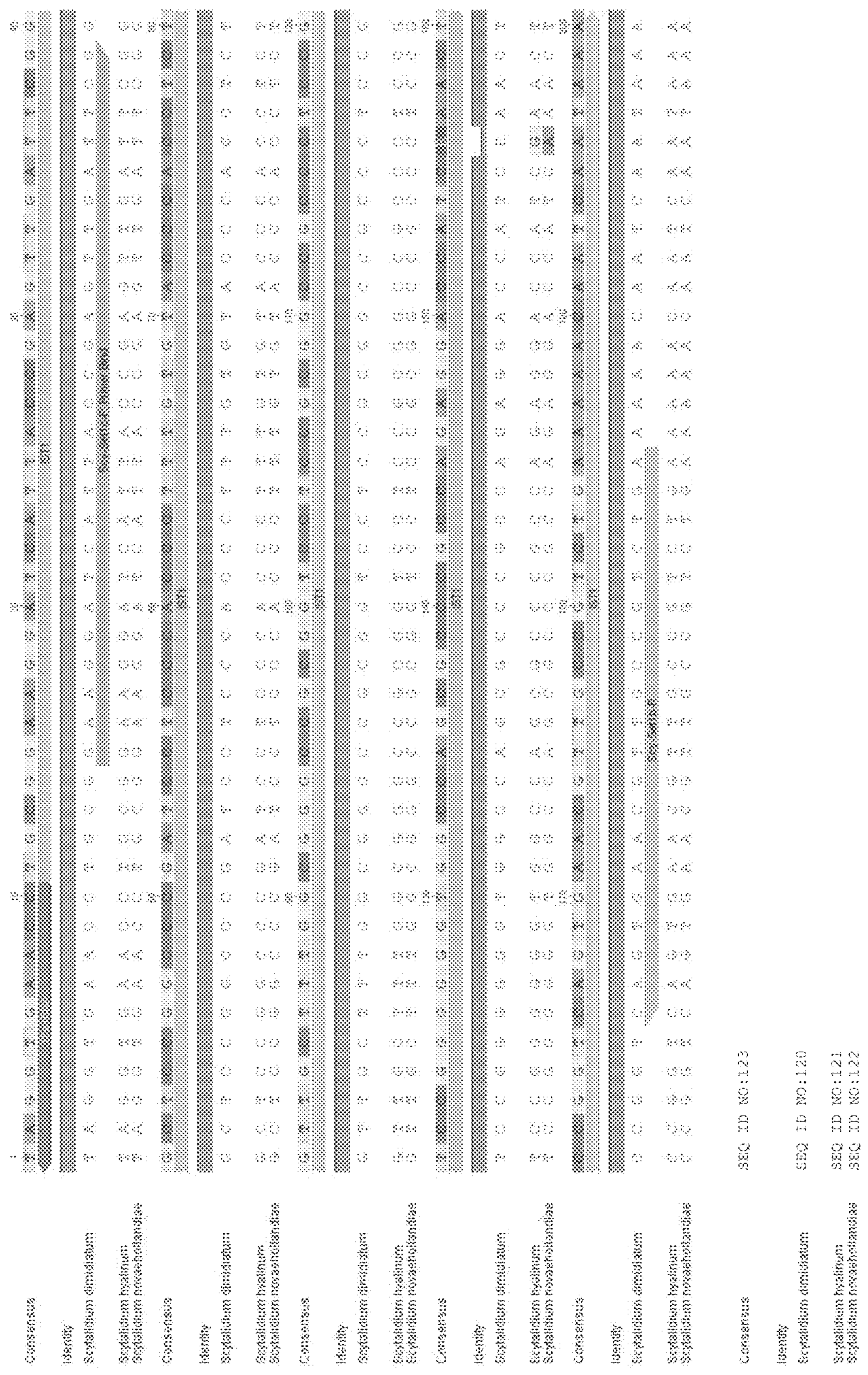

Saprophytes (e) primer alignment and target sequences are shown in FIG. 10B. Alignment of genomic regions for the following organisms are shown: *Scytalidium dimidiatum* (SEQ ID NO:120); *S. hyalinum* (SEQ ID NO:121); and *S. novaehollandiae* (SEQ ID NO:122). The consensus sequence is shown (SEQ ID NO:123).

II. Procedures

Specimen Collection.

Dry nail clippings were collected and transported using a sealed bag or other sterile container with a tightly fitting cap. Specimens were transported for receipt within four days of collection.

Specimen Grossing.

The gross description for all specimens was recorded, to include the source, number of fragments, size and shape of submitted specimens.

Following gross analysis, a portion of each submitted specimen was processed for histological analysis and a second portion processed for culture. Residual specimens were stored at 4-8° C. and subsequently used for PCR analysis.

Descriptions of Controls.

Extraction Control/Inhibition Control (EC/IC): EC/IC was used as a Positive Lysis control. gBlock® of *Saccharomyces pombe* citrate synthase gene added to all samples prior to cell lysis and detected by in a separate PCR reaction.

Reagent Blank (RB): RB was used as a Negative Lysis/Extraction Control. RBs were processed with each extraction batch and included in PCR analysis. Each RB includes EC/IC template DNA and were used to monitor for potential contamination introduced during the extraction process, and assessed for EC/IC detection.

Negative Nail (NN): NN was used as a Negative Control. NNs were processed and included in PCR analysis. Each NN included a fragment of clinically normal nail collected in-house and EC/IC template DNA and were used to monitor for interference introduced by nail matrix. NNs were only analyzed during validation and were not included during routine clinical sample processing.

PCR Positive Control (CTL): DNA extracted and purified from *Candida*, a dermatophyte and a saprophyte culture (ATCC) was included for each run. In addition, DNA was extracted and purified from cultures of seven different saprophytes, Sap1, Sap2, Sap3, Sap4, Sap5, Sap6, and Sap7 CTL. Two were included on each run as positive controls-Sap1CTL and a rotation of the remaining six CTLs were included on a weekly basis.

No template control (NTC): The NTC was used as a Reagent Contamination Control. NTC was included for each PCR Master Mix preparation, where molecular grade water is included with no nucleic acid template. NTC samples were used to monitor for PCR artifacts (such as primer dimers) and potential contamination.

DNA Extraction and Purification.

Nails were physically disrupted using ceramic bead homogenization. EC/IC was added and samples were treated with detergent-based lysis buffer and digested with Proteinase K. Samples were then heat-treated at a temperature above 90° C. DNA was purified from the lysate and concentrated using Plant DNeasy™ 96 kit (QIAGEN), or Mag-Bind® Plant DS DNA Kit (Omega Bio-tek), prior to PCR analysis.

Polymerase Chain Reaction (PCR).

Real-Time detection was utilized with fluorescent intercalating dye (SYBR® Green) to detect the presence of target organisms. Primers were designed to specifically amplify DNA from 3 categories of fungal organisms: *Candida*, dermatophytes and saprophytes.

Three separate PCR reactions were performed for each assay: Reaction 1 detects *Candida* and dermatophytes using two primer pairs; Reaction 2 detects saprophytes of interest using five primer pairs; Reaction 3 detects the EC/IC.

Results Interpretation.

The assay was designed such that the melting temperature (Tm) of the resulting PCR product is used to distinguish the organism category. Life Technologies' 7500 Software v2.0.6 or v2.3 was used for data acquisition. Both the 7500 Software v2.0.6 or v2.3 and High Resolution Melting (HRM) Software V3.0.1, together with custom data analysis software engine assessed the validity of the assay controls, the EC/IC for each sample, and generated results for each sample.

The interpretive algorithm (FIG. 89) considered the relative Ct values for the *Candida*/Dermatophyte and the Saprophyte PCR reactions to determine which reactions might be positive, then evaluated the Tm value(s) as determined by HRM analysis for only the reaction(s) considered positive by the relative Ct value assessment. Ct values above 30 for

*Candida* and Dermatophytes, and above 28 for Saprophytes were considered ‘Not Determined’, as Tm values for samples with a high Ct are non-specific and therefore no statistics were calculated when the Ct was above 30 (*Candida* and Dermatophyte) or above 28 (Saprophyte).

For *Candida* and dermatophyte detection, the saprophyte PCR reaction data points (Ct and Tm) were used by the data analysis algorithm to exclude cross reactivity and contamination. For saprophyte detection, the *Candida*/dermatophyte PCR reaction data points (Ct and Tm) were used by data analysis algorithm to exclude cross reactivity and contamination.

Samples negative for all targets were evaluated for successful EC/IC performance before a “Not Detected” interpretation was rendered.

III. Validation

Validation Summary.

Specificity.

The PCR assay only detected the intended targets without cross reactivity with other non-specific targets. DNA from 39 cultures was each tested for all three organism categories. The detected organism for each analysis is indicated.

For the *Candida* analysis, the following organisms were tested and gave a positive result: *C. albicans, C. glabrata, C. guilliermondii, C. kruseii, C. lusitaniae, C. orthopsilosis/parapsiolosis, C. tropicalis, Malassezia pachydermatis*. Dermatophytes and Saprophytes were not detected with *Candida*.

For the dermatophyte analysis, the following organisms were tested and gave a positive result: *T. mentatrophytes, T. rubrum, T. tonsurans, T. violaceum, Epidermophyton, M. canis, M. gypseum*. *Candida* and Saprophytes were not detected with dermatophytes.

For the saprophyte analysis, the following organisms were tested and gave a positive result: *Acremonium, Alternaria, Aspergillus, Chaetomium, Cuvularia, Fusarium, Mucor, Paecilomyces, Penicillium, Scopulariopsis, Scytalidium*. *Candida* and Dermatophytes were not detected with saprophytes.

No cross reactivity or interference was detected in the presence of *Pseudomonas aeruginosa, Proteus mirabilus, Staphylococcus aureus, Serratia marcescens, Streptococcus pyogenes*. No cross reactivity or interference was detected with human genome DNA.

Sensitivity.

19 organisms were tested using at least six concentrations of DNA. Sensitivity varied among the species tested and ranged from 4-54,054 copies.

Interday Reproducibility.

Interday reproducibility was evaluated using the performance of 10 (EC/IC) or 15 controls (*Candida*, Dermatophyte, Saprophyte) runs over at least 31 days. All coefficient of variation (CV) % values for interday reproducibility were less than 5%.

Interday reproducibility was also evaluated using the performance of 60 saprophyte (Sap1) control runs and 41 saprophyte (Sap7) controls runs over at least 99 days. All % CV values for interday reproducibility were less than 5%.

Intraday Repeatability.

Six specimens were prepared from primary clinical samples, each in triplicate (54 total results; 6 samples×3 replicates×3 targets (Can, Derm, Sap). 100% of triplicates samples gave identical results for all targets.

For saprophyte detection, eleven specimens and one negative nail DNA sample were prepared from cultured organism DNA and disease free nails respectively. Each were run in six replicates (204 total results). The saprophyte detection was 99.5% repeatable.

Run-to-Run Variability.

Inter-operator and inter-instrument testing demonstrated minimal variability in Ct (CV %<5) and Tm (CV %<1%) values with 100% accuracy in Control results.

Validation:

425 specimens were tested by PCR, with corresponding histopathology and culture results used for data correlation of each specimen. Correlation results for *Candida*, dermatophytes and saprophytes were calculated independently. Sample results with discordant identification (PCR vs. culture) were resolved by Sanger Sequence analysis of the DNA isolate used for the fungal PCR test.

163 of 232 (70.3%) of samples with discordant results (PCR vs. culture) were analyzed by Sanger Sequencing to further evaluate accuracy of the PCR assay. Total concordance values of the PCR assay with histopathology was 76.3%.

Total concordance values of the *Candida* PCR assay with *Candida* cultures was 94.6%. Total concordance values of the *Candida* PCR assay with *Candida* sequencing was 98.5%.

Total concordance values of the dermatophyte PCR assay with dermatophyte cultures was 65.2%. Total concordance values of the dermatophyte PCR assay with dermatophyte sequencing was 95.5%.

Total concordance values of the saprophyte PCR assay with saprophyte cultures was 78.6%. Total concordance values of the saprophyte PCR assay with saprophyte sequencing was 96.5%.

2839 further saprophyte specimens were tested by PCR. Histopathology and sequencing results indicate that saprophytes detected at a Ct>28 cycles contain few saprophytes of interest.

Specificity

Primer Cross Reactivity.

Design: DNA isolated from 39 individual fungal or yeast cultures were each tested using the fungal PCR method. The identities of in-house cultures were confirmed by DNA sequencing.

Results are shown in Tables 2.1 and 2.2 in FIGS. 11A-11B and Table 3 in FIG. 12.

Nine organisms (nine strains representing eight species), were identified as *Candida* positive. Neither dermatophytes nor saprophytes were detected with *Candida* primers (Tables 2.1 and 2.2, FIGS. 11A-11B).

Seven organisms (8 strains) were identified as dermatophytes. Neither *Candida* nor saprophytes were detected with dermatophytes primers (Tables 2.1 and 2.2, in FIGS. 11A-11B).

14 genera of saprophytes, including three strains of *Aspergillus* and *Fusarium*, were tested. Eleven of the 14 genera were detected as a saprophyte (Tables 2.1 and 2.2, in FIGS. 11A-11B), while three (Table 3 in FIG. 12) were not detected as saprophyte, *Candida* or dermatophyte. Neither *Candida* nor dermatophytes were detected with saprophytes primers.

These data demonstrated that the PCR conditions and application of the interpretive algorithm correctly identified 39 individual preparations of cultured fungi or yeast (Tables 2.1 and 2.2, in FIGS. 11A-11B). Cross reactivity to non-targeted organisms was not observed.

Additional saprophyte species are known to be present in nail specimens. The assay was designed to detect >78% of culture-positive saprophytes and >90% total yeast/fungal infections in submitted specimens, based on the frequency of each organism detected by culture within the laboratory. The remaining <10% of positivity by culture included organisms recognized as contaminants.

Negative Controls

Design: Reagent Blank (RB and No Template Control (NTC) results were monitored throughout the study to assess their intended performance.

Results for RB are shown in Table 4 in FIG. 13. No amplification was observed before cycle 30 (Saprophyte PCR) or cycle 28 (*Candida*/Dermatophyte PCR). No replicate had a Ct and Tm profile matching any fungal/yeast organisms of interest. All EC/IC templates were detected by PCR.

Results for No Template Control are shown in Table 5 in FIG. 14. No amplification was observed before cycle 30 (Saprophyte PCR) or cycle 35 (*Candida*/Dermatophyte PCR). No replicate had a Ct and Tm profile matching any fungal/yeast organisms of interest.

Results from the negative controls show that no contamination resulted from the extraction process, as indicated by negative results in the RB samples; the extraction process did not contribute to assay interference, as indicated by detection of the EC/IC template DNA in the RB samples; the PCR set-up process did not contribute to assay contamination, as indicated by negative results in the NTC samples; and that no PCR artifacts were observed, as indicated by negative results in the NTC samples.

Bacterial Interference

Design: Commercially available genomic DNA of bacteria commonly found in nail samples was tested with the fungal PCR method to test for cross reactivity of the fungal PCR assay with bacterial contaminants which may be present in nail specimens. Replicates of the same bacterial DNA was mixed with DNA from known fungal or yeast organisms, to assess the effect of bacterial DNA on fungal DNA identification.

The following five bacterial organisms were tested in triplicate for each of two concentrations: *P aeruginosa* (ATCC Cat #90270-5, lot 58304262), at 1750 pg; *P mirabilus* (ATCC Cat #12453D, lot 3573174), at 200 pg; *S aureus* (ATCC Cat #BAA-17170-5, lot 61274435), at 670 pg; *S marcences* (ATCC Cat #27137D-5, lot 59679187), at 730 pg; *S pyogenese* (ATCC Cat #BAA1063D-5, lot 57907321), at 200 pg. Genomic equivalent was calculated based on genome sizes and DNA concentration tested.

Results are shown in Tables 6.1 and 6.2, in FIG. 15A. In Bacteria only-Fungal PCR negative samples, no amplification was observed before cycle 33. For each organism no replicates had a Ct and Tm profile matching any fungal/yeast organisms of interest.

In Fungal DNA+Bacteria DNA samples, *C. parapsilosis* was detected at 0.01 ng/reaction (Rxn); *T rubrum* was detected at 0.1 ng/Rxn; *Aspergillus* was detected at 0.1 ng/Rxn, *Fusarium* was detected at 0.1 ng/Rxn and *Scytalidium* was detected at 0.1 ng/Rxn.

These results indicated that the five common pathogenic bacteria do not interfere with the assay at the indicated DNA quantity/genomic equivalents.

Human Genomic DNA Interference

Design: Because human genomic DNA (gDNA) is likely to be purified from the nail specimen concurrently with fungal DNA, pure human gDNA was tested in quadruplicate against the *Candida*/Dermatophyte and Saprophyte primer cocktails.

Stock DNA (Roche, Cat #1169112001, lot 14897020; 200 ng/μL) was diluted to five concentrations; 2, 1, 0.5, 0.25 and 0.125 ng/μL. Each concentration was tested one time with no interference seen. Two concentrations (0.25 and 0.05 ng/μL) were repeated in quadruplicate. 2 μL DNA was added per PCR reaction.

DNA concentrations were determined using a NanoDrop® for >400 extracted nail samples, with a range of <0.1 to <100 ng/μL. 62.6% of samples had a DNA concentration <6.0 ng/pt. The precise mix of human:fungal DNA cannot be determined for any sample. A tested range of 0.125-2 ng/μL human genomic DNA is representative of the sample set.

Results are shown in Tables 7.1 and 7.2, in FIG. 15B. In the Human DNA-only samples, no amplification was observed before cycle 32. For each sample, no replicates had a Ct and Tm profile matching any fungal/yeast organisms of interest.

In the Fungal DNA+human DNA samples, *C. parapsilosis* was detected at 0.01 ng/Rxn; *T rubrum* was detected at 0.1 ng/Rxn; *Aspergillus* was detected at 0.1 ng/Rxn, *Fusarium* was detected at 0.1 ng/Rxn and *Scytalidium* was detected at 0.1 ng/Rxn.

These results indicated that human DNA does not interfere with the assay at the indicated DNA quantities.

Sensitivity

Design:

DNA was isolated from 40 individual fungal or yeast in-house cultures were each tested using the fungal PCR method. The identity of in-house cultures were confirmed by DNA sequencing.

The sensitivity for this assay was expressed as ng of purified DNA per PCR reaction. The Copy #was calculated for each organism by dividing the limit of detection (LOD) in ng by the diploid C value (zbi(dot)ee/fungal-genomicsize/) and rounded to two significant figures.

Dilutions: Purified DNA concentrations were standardized to 20 ng/μL. Serial dilutions were performed and tested by PCR. Concentration replicates were inter-run and from more than one culture, when available. For Saprophytes, DNA was diluted with pooled extract from DNA purification of Negative Nails.

For *Candida*, LoD study was done by extracting DNA from *C. albicans* and *C. parapsilosis* cells of known density. Cultures of varying density based on the McFarland units were generated for both *C. albicans* and *C. parapsilosis* and used to make solutions of known numbers of cells in TE buffer. DNA was extracted from cells in 5-10 replicates per level. See also Example 2.

Results are shown in Tables 8.1 and 8.2, in FIGS. 16A-16B, for Dermatophytes and Saprophytes, and in Tables 8.1 and 8.3, in FIGS. 16A and 16C, for *Candida*. LODs (Limit of Detection) was determined as the lowest DNA or CFU quantity giving 100% positivity for the indicated organism (highlighted for each organism). At least ten replicates were tested to confirm the LOD for each organism.

Inter-Assay Reproducibility

Design:

For each run, four or five controls from commercial suppliers were used; one EC/IC, one *Candida*, one dermatophyte and one or two saprophytes. PCR was performed in 16 runs over 29 days and again in 62 runs over 99 days. For the EC/IC control, gBlock®/synthetic DNA (IDT DNA) was used. For the *Candida*, dermatophyte, and saprophyte controls, DNA extracted and purified from cultured organisms (ATCC) was used. The acceptance range for Ct and Tm values was set to CV %<5.0.

Results for the Extraction Control/Inhibition Control (EC/IC) are shown in Table 9 (FIG. 17). EC/IC results are shown for 11 runs on nine days. The acceptance criteria was Ct: 24.0-33.5; and Tm1: 74.5-77.0° C. (there was no Tm2).

Results were: a) Ct value range: 25.2-29.7; b) Tm1 value range: 75.1-76.2° C.; c) 12/12 demonstrated results consistent with EC/IC.

Results for the *Candida* Control using *Candida parapsilosis* (ATCC #22019D-5) DNA are shown in Table 10 in FIG. 18. *Candida* CTL results are shown for 15 runs on 11 days. The acceptance criteria were as follows: C/D Ct<26; and C/D Tm1 76.3-78.75° C. (there was no Tm2); and negative for dermatophytes and saprophytes. Results were: a) Ct value range: 22.0-25.1; b) Tm1 value range: 76.4-78.7° C.; c) 15/15 demonstrated results consistent with *Candida parapsilosis*.

Results for the dermatophyte Control using *Trichophyton mentagrophytes* (ATCC #9533D-2) DNA are shown in Table 11 in FIG. 19. Dermatophyte CTL results are shown for 15 runs on 11 days. The acceptance criteria were as follows: C/D Ct<26; C/D Tm1 82.0-85.5° C.; C/D Tm2 78.8-81.5° C.; and negative for *Candida* and saprophytes. Results were: a) Ct value range: 22.3-25.7; b) Tm1 value range: 82.4-84.3° C.; c) 15/15 demonstrated results consistent with *Trichophyton mentagrophytes*.

Results for two saprophyte Controls (Sap1 CTL using *Aspergillus flavus*(ATCC #204304D-2) DNA and Sap7 CTL using *Scytalidium* (In-House culture) DNA) are shown in Tables 12.1 and 12.2, respectively, in FIG. 20. Sap1 CTL results (Table 12.1) are shown for 60 runs over 99 days. Sap7 CTL results (Table 12.2) are shown for 41 runs over 99 days. Acceptance criteria were as follows: Sap Ct<26; Sap1 CTL Tm1 79.0-81.0° C., Sap7 CTL 83.0-86.0° C.; and negative for *Candida* and dermatophytes. Results for Sap1 CTL were: a) Ct value range: 18.7-22.9; b) Tm1 value range: 79.4-81.1° C.; c) 60/60 demonstrated results consistent with *Aspergillus flavus*. Results for Sap7 CTL were: a) Ct value range: 18.7-22.9; b) Tm1 value range: 79.4-81.1° C.; c) 60/60 demonstrated results consistent with *Scytalidium*.

The inter-assay reproducibility as seen from EC/IC, and all three positive controls were within the range of CV %<5.0 for both the Ct and Tm values.

Intra-Assay Repeatability

Design:

Six clinical nail samples were tested, each prepared in triplicate (Positive for either *Aspergillus, Paecilomyces* or *T. rubrum*). Thirty seven negative nail samples were tested, spiked with one of two different sources of either *C. albicans* (CaA or CaB) or *C. parapsilosis* (CpA or CpB) DNA prior to extraction, each prepared in quadruplicate, or with *Acremonium, Alternaria, Aspergillus, Curvularia, Fusarium, Mucor, Paecilomyces, Penicillium Rhizopus, Scopulariopsis* or *Scytalidium* DNA, each prepared as six replicates at three levels.

Results are show in Tables 13.1 and 13.2, in FIGS. 21A-21C.

*Candida* detection was 100% repeatable. 16/16 reactions with *Candida*-positive samples (*C. albicans/C. parapsilosis*) gave positive results when assayed for *Candida*. 216/216 reactions with *Candida*-negative samples gave negative results when assayed for *Candida* (these samples were *T. rubrum* or Saprophyte positive).

Dermatophyte detection was 100% repeatable. 9/9 reactions with dermatophyte-positive samples (*T. rubrum*) gave positive results when assayed for dermatophytes. 223 reactions with dermatophyte-negative samples gave negative results when assayed for dermatophytes (these samples were *Candida* or Saprophyte positive).

Saprophyte detection was 99.5% repeatable. 206/207 reactions with saprophyte-positive samples gave positive results when assayed for saprophytes. 25/25 reactions with saprophyte-negative samples gave negative results when assayed for saprophytes (these samples were *Candida* or Dermatophyte positive).

Inter- and Intra-Assay Variability Summary

Runs included in the validation study are summarized in Tables 14.1 and 14.2, in FIG. 22. Tested parameters and QC status is shown for each run.

Variability in extraction was tested for DNA purified from samples in 17 batches over 48 days, and by four different analysts and again in 51 batches over 120 days, and by 5 different analysts (Table 14.1 in FIG. 22).

Variability in PCR was tested in 15 batches over 22 days, by two different analysts and again in 63 batches over 68 days, and by 2 different analysts (Table 14.2 in FIG. 22).

Variability between instruments was tested on two different instruments: *Candida*/Dermatophyte X7 on instrument #1; 8X on instrument #2; Saprophyte X6 on instrument #1; X9 on instrument #2; EC/IC X3 on instrument #1; X5 on instrument #2.

As summarized on Table 9 in FIG. 17, Table 10 in FIG. 18, Table 11 in FIG. 19 and Tables 12.1 and 12.2, in FIG. 20, all CTL samples performed equivalently, regardless of operator or instrument.

Validation

Design-Histology and Culture as Reference Values.

Case reports were reviewed for histology and culture results and 409 samples were selected, where culture-positive results indicated the presence of either *Candida*, a dermatophyte or saprophytes. Histology results were considered positive if positive by Periodic Acid Shift (PAS) or Gomori methenamine silver (GMS), and negative if negative by PAS and GMS.

Culture positive criteria for *Candida*: positive for *C. albicans, C. glabrata, C. guilliermondii, C. kruseii, C. lusitaniae, C. orthopsilosis, C. parapsilosis, C. tropicalis, M pachydermatis.*

Culture positive criteria for Dermatophyte: *T. rubrum, T. mentagrophytes/interdigitale, T. tonsurans, T. violaceum, Epidermophyton, M. canis, M. gypseum.*

Culture positive criteria for Saprophyte: *Acremonium, Alternaria, Aspergillus, Chaetomium, Curvularia, Fusarium, Mucor, Paecilomyces, Penicillium, Scopulariopsis, Scytalidium.*

Processing steps for grossing nail specimens may yield a low-level sampling error, occurring when multiple nail fragments are submitted as one specimen. A large nail may have multiple small fragments submitted, with infection present on a portion of the nail and not in all fragments.

Separate nail fragments were used for histology and for culture; residual fragments were saved for PCR validation. A percentage of the discordant results may be due to this "random sampling."

DNA from the extract used in the PCR validation was submitted for Sanger Sequencing for discordant results and for 31 samples with PCR results equivalent to culture results as a quality measure (See full description below).

DNA Sequencing as Reference Values.

Following PCR with the Fungal Screening panel, extracted DNA for select samples was then subjected to another PCR reaction using primers targeting consensus regions for the fungal rRNA gene. The primers flanked regions of dissimilarity among the fungal species of interest such that the amplicon when subjected to Sanger Sequencing was used for identification. Sequence results were obtained for 193 samples. PCR, culture and sequencing results are shown. Samples positive by PCR for more than one reaction (Can+/Derm+ or Can+/Sap+ or Derm+/Sap+) were excluded.

Histology Concordance. Histology Concordance results are shown in Tables 15.1, 15.2 and 15.3 in FIGS. 23A-23B.

For Culture vs. Histology, 44.4% of Histology positive samples were negative by culture and 83.5% of Histology negative samples were negative by culture (Table 15.2 in FIG. 23B).

For Histology vs. PCR, histology results were stratified by staining intensity. 19.3% of PCR positive samples were negative or Rare+ by Histology and 81.5% of PCR negative samples were negative or Rare+ by Histology (Table 15.3 in FIG. 23B).

Validation: 409 specimens were analyzed for histopathology and culture results (Table 15.2 in FIG. 23B). 2768 additional samples were tested by PCR and Histology, with graded histological results (Table 15.3 in FIG. 23B).

The increased detection rate by PCR, when compared to culture, of Histology+ samples suggested increased sensitivity with the PCR assay when compared to culture. Additional testing was performed to confirm the presence and identity of organisms in these samples (See "Sequencing Concordance" and Table 20 in FIG. 26).

No significant difference was observed in *Candida* detection between either culture or PCR vs. Histology (Table 15.1 in FIG. 23A).

For Histology+ samples, the detection rate of dermatophytes was 2.5 fold (185 vs. 67) higher with PCR than with culture (Table 15.1 in FIG. 23A). The dermatophyte detection rate of Histology− samples was greater with PCR than with culture.

For Histology+ samples, the detection rate of saprophytes was 2.3 fold (86 vs. 40) lower with PCR than with culture (Table 15.1 in FIG. 23A). The saprophyte detection rate of Histology− samples was equivalent with PCR and culture.

For *Candida* detection, Histology+ and Histology−, PCR and culture results were similar.

For Dermatophyte detection, the increased detection rate by PCR, when compared to culture, of Histology+ samples suggested increased sensitivity with the PCR assay when compared to culture. Additional testing was performed to confirm the presence and identity of organisms in these samples (See "Sequencing Concordance" and Table 21 in FIG. 26).

For Saprophyte detection, additional testing was performed (See "Sequencing Concordance" and Table 21 in FIG. 26).

Culture Concordance.

Summary of Culture vs. PCR results, showing the concordance with culture, are shown in Table 16 in FIG. 24. Culture vs. PCR for *Candida*, dermatophytes and saprophytes individually are shown in Tables 17, 18 and 19 in FIG. 25.

Validation:

425 specimens were tested by PCR, with corresponding histopathology and culture results used for data correlation of each specimen. Correlation results for *Candida*, dermatophytes and saprophytes were calculated independently and shown in Table 21 in FIG. 26 and in Tables 22, 23 and 24 in FIG. 27. Sample results with discordant identification (PCR vs. culture) were resolved by Sanger Sequence analysis of the DNA isolate used for the fungal PCR test.

Total concordance values of the *Candida* PCR assay with *Candida* cultures was 94.6%. Total concordance values of the *Candida* PCR assay with *Candida* sequencing was 98.5%.

Total concordance values of the dermatophyte PCR assay with Dermatophyte cultures was 65.2%. Total concordance values of the Dermatophyte PCR assay with dermatophyte sequencing was 95.5%.

Total concordance values of the saprophyte PCR assay with saprophyte cultures was 78.6%. Total concordance values of the saprophyte PCR assay with saprophyte sequencing was 96.5%.

These data suggested that both the dermatophyte specificity and saprophyte specificity were improved with this PCR method. Additional testing was performed for dermatophytes and saprophytes (See "Sequencing Concordance" and Table 21 in FIG. 26).

Sequencing Concordance.

Sequencing methodology used is summarized in "DNA Sequencing Analysis Methodology", below. A summary of Sequencing vs. PCR results are shown in Tables 20 and 21 in FIG. 26. Sequencing vs. PCR for *Candida*, dermatophytes and saprophytes individually are shown in Tables 22, 23, and 24 in FIG. 27.

Of 30 concordant samples (Culture vs. PCR) analyzed, PCR results were confirmed by sequencing for 29 (96.7%) (Table 20 in FIG. 26). Of 163 discordant samples (Culture vs. PCR) analyzed, PCR results were confirmed by sequencing for 154 (94.5%) (Table 21 in FIG. 26).

For *Candida* detection, 4 of 5 (80.0%) of PCR positive samples tested by sequencing were confirmed *Candida* positive. For Dermatophyte detection, 127 of 129 (98.5%) of PCR positive samples tested by sequencing were confirmed dermatophyte positive. For Saprophyte detection, 13 of 13 (100%) of PCR positive samples tested by sequencing were confirmed saprophyte positive. For Negative detection, 10 of 16 (62.5%) of PCR negative samples tested by sequencing were confirmed negative for all target organisms.

Of 33 samples negative by PCR, 7 (21.2%) were positive by sequencing. This is likely due to primer design and the cycle used number for sequencing PCR.

Resolution of the PCR/culture discordant sample with sequencing showed 153 of 163 to be sequencing positive (93.9%) demonstrating that the PCR method developed for testing for the presence of fungi and yeast in human nails gives accurate results.

PCR versus sequencing concordance was 99% for *Candida* (Table 22 in FIG. 27), 95.9% for Dermatophytes (Table 23 in FIG. 27) and 98.5% for Saprophytes (Table 24 in FIG. 27).

DNA Sequencing Analysis Methodology

Gene sequences for target organisms were identified using the BLAST® nr/nt query. A database of rRNA consensus sequences for target organisms was constructed using Geneious® software, version 7.1.6. DNA sequence analysis was performed on all control material and select clinical specimens.

Forward and reverse sequencing primers were designed in the 18S rRNA gene to generate amplicons ~485 bp in length. Primers bound to consensus regions of the fungal 18S rRNA gene, with mismatches to human and bacterial gDNA.

PCR amplification was performed using GeneAmp® Fast PCR Master Mix (2×) (Life Technologies, Cat #435918) with a 14 μL reaction volume, primer concentration of 0.6 pM. Amplification was performed on the 7500 Fast Real-Time PCR System (Life Technologies) under the following conditions: initial hold at 95° C. for 10 seconds; followed by 40 cycles of 94° C. for 1 second, and 64° C. for 30 seconds; and a final extension at 72° C. for 10 seconds. Amplification was confirmed by gel electrophoresis analysis with the FlashGel™ system, 1.2% agarose (Lonza, Cat #570851).

Amplicon purification was performed either using the FlashGel™ Recovery Gel system (Lonza, Cat #570851) or QIAquick® 96 PCR Purification Kit (Qiagen, Cat #28181) and purified into Molecular Grade Water. Sequencing of purified amplicons was performed by the Georgia Genomics Facility (University of Georgia, Athens, Ga.). Cycle sequencing using the sample primers as for amplicon generation, provided to GGF at a concentration of 3.3 μM under lab-standard conditions using BigDye® version 3.1 on the ABI 3730XL platform.

Due to sample handling automation, all samples prepared on a 96 well plate were subjected to sequence analysis, regardless of agarose gel results.

Raw data was processed using the ABI 3730XL software and chromatograms (.ab) files were retrieved for sequence analysis.

Analysis of Sequence Data.

Forward and reverse chromatogram files were imported into Geneious 7.1.6 software. The de novo assembly function was used to align For and Rev sequences for each sample and the chromatogram quality was assessed. The resulting consensus sequence was exported for each sample and analyzed using the BLAST®) nr/nt query.

For all positive control samples, the top three reference sequences by BLAST® query to which control samples aligned were recorded (organism and accession number). To further confirm results, sequences were aligned with the in-house reference sequence database using Geneious® 7.1.6.

For all clinical samples, the top three reference sequences by BLAST® query to which a clinical sample aligned were recorded (organism and accession number). To further confirm results, sequences were aligned with the Geneious® 7.1.6 reference database.

For *Candida* detection, an alignment of six consensus reference sequences and three positive controls was performed. When the genera of the top 3 matches were in agreement, the organism identity was assigned by genera. When the genera of the top 3 matches were not in agreement, the sequence was aligned using the Geneious® 7.1.6 reference database and the organism identity was assigned by genera.

For saprophyte detection, an alignment of consensus reference sequences for 64 species (17 genera) and sequences of 12 positive saprophyte controls was performed. When the genera of the top 3 matches were in agreement, the organism identity was assigned by genera. When the genera of the top 3 matches were not in agreement, the sequence was aligned using the Geneious® 7.1.6 reference database and the organism identity was assigned by genera.

For dermatophyte detection, an alignment of consensus reference sequences and positive controls was performed for four dermatophytes (*T. rubrum, T. mentagrophytes, E. floccosum, M. auduuinii*). The sequence homology for the dermatophytes was very high within the region analyzed by these sequencing primers. All clinical samples identified as dermatophytes were aligned with the Geneious® 7.1.6 Dermatophyte reference database. From this alignment, the identity of clinical samples was made when 100% alignment was observed with reference and control sequences. These were identified as either *T. rubrum, T mentagrophytes, Epidermophyton* or *Microsporum*. Samples not showing 100% alignment to any of these four sequences were called as "dermatophytes."

Example 2

*Candida* Identification in Human Nail by Real Time PCR

The "*Candida* Identification by PCR" assay described below was performed after the presence or absence of a *Candida* in a sample was determined using the "Fungal Detection by PCR" assay (Example 1).

I. Target Gene and Primer Sequences

Target *Candida* organisms were identified by a literature search for onychomycosis etiology, and nail cultures. To assess the culture data, >17,000 consecutively accessioned culture-positive cases were reviewed. Gene sequences for target organisms were identified using the National Center for Biotechnology Information (NCBI) database and Basic Local Alignment Search Tool (BLAST®) "nucleotide blast" (nt/nr) query.

Yeast mitochondrial sequences were used for *C. albicans* and *C. parapsilosis* identification. Regions within the NADH dehydrogenase subunit gene for *C. albicans* and putative reverse transcriptase gene for *C. parapsilosis* were identified by assessing unique regions of *C. albicans* and *C. parapsilosis* that were dissimilar to non-targeted organisms. A BLAST® nt/nr search was performed for all four selected primer sequences, with not more than 50% homology identified to any other organism.

*Candida* species primer sequences are shown in Table 25.

TABLE 25

| Target | Forward primer | Reverse primer |
|---|---|---|
| *Candida albicans* | ATC GTA GCT GAG CGT AAG ACA TTA GGT TAT (SEQ ID NO: 63) | ATA GTA ACT CCG GGT GCG AAA GGT ATA A (SEQ ID No: 64) |
| *Candida parapsilosis* | TCT GAA GGT TGT ACG AAA TGG GGA AAA A (SEQ ID NO: 65) | CAG AAG ACC CTA GTA TCG CTG AAC CAA TTT (SEQ ID NO: 66) |

Figure 28:
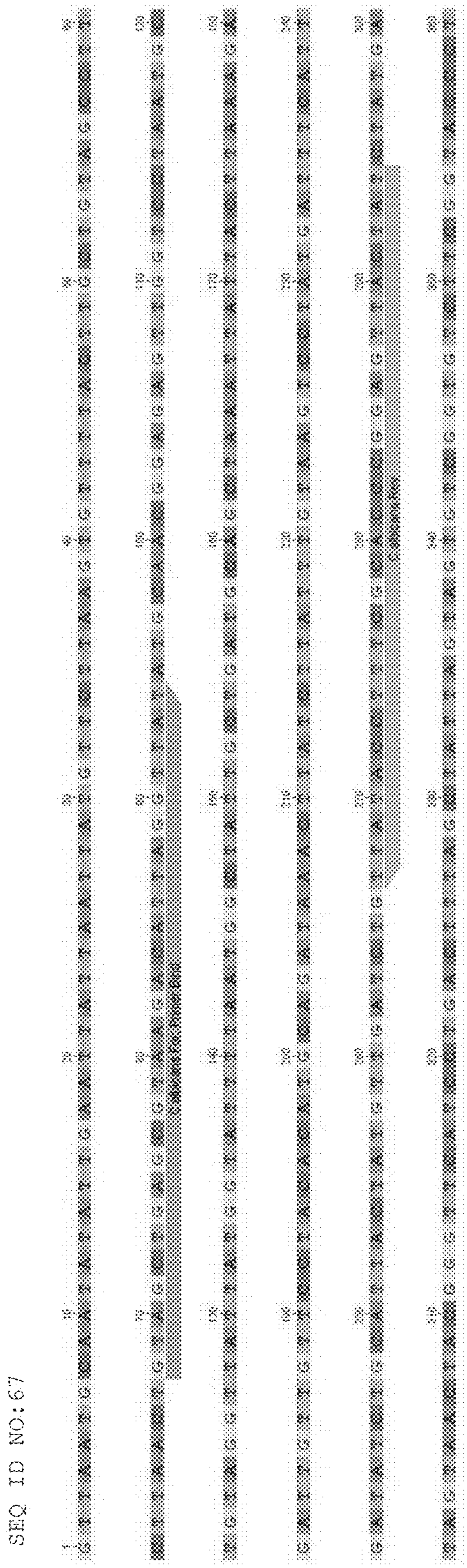
FIG. 28 shows alignments to genomic regions of primers designed to amplify a *Candida albicans*-specific target sequence, according to embodiments of the present disclosure.

*Candida albicans* primer alignment and target sequences are shown in FIG. 28. Genomic region including the target sequence for *Candida albicans* is shown (SEQ ID NO:67).

Figure 29:
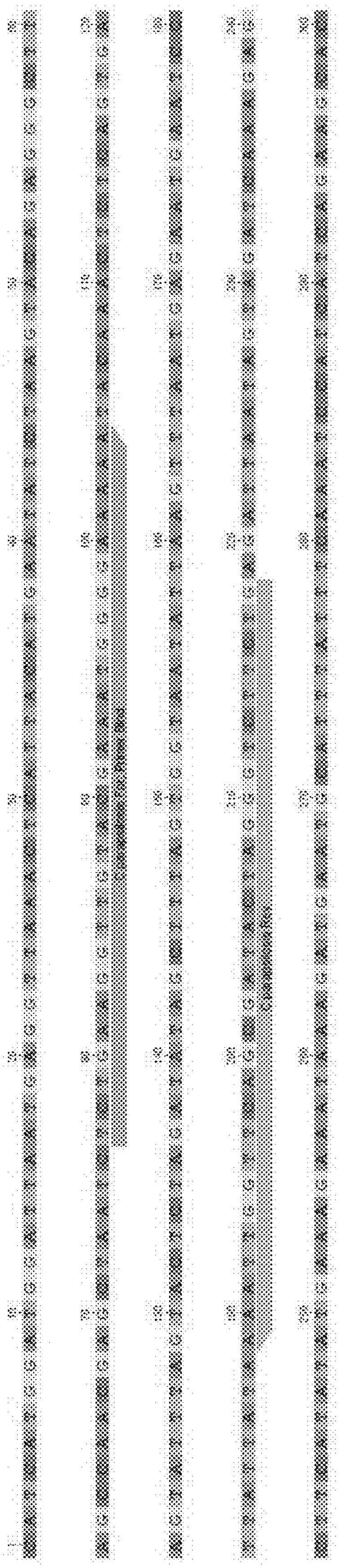
FIG. 29 shows alignments to genomic regions of primers designed to amplify a *Candida parapsilosis*-specific target sequence, according to embodiments of the present disclosure.

*Candida parapsilosis* primer alignment and target sequences are shown in FIG. 29. Genomic region including the target sequence for *Candida parapsilosis* is shown (SEQ ID NO:68).

II. Procedures

Specimen Collection, Specimen Grossing, and DNA Extraction and Purification were performed as described for the "Fungal Detection by PCR" (Example 1). DNA from the preparation used in screening for *Candida*, dermatophyte or saprophyte was used for *Candida* species identification.

Descriptions of Controls.

Extraction Control/Inhibition Control (EC/IC): EC/IC was used as a Lysis control. A gBlock® of *S. pombe* citrate synthase gene was added to all samples prior to cell lysis and detected in a separate PCR reaction. As the analysis of inhibition was performed as part of the "Fungal Detection by PCR" (Example 1), and the absence of inhibition was confirmed, this analysis was not repeated for the "*Candida* Identification by PCR" Assay.

Reagent Blank (RB): RB was used as a Negative Control. RBs were processed with each extraction batch and included in PCR analysis. Each RB includes EC/IC template DNA and were used to monitor for potential contamination introduced during the extraction process, and assessed for EC/IC detection.

PCR Positive Control (CTL): DNA extracted and purified from *C. parapsilosis* (ATCC) or *C. albicans* (In-House) was included for each run as positive controls.

No template control (NTC): The NTC was used as a Reagent Contamination Control. NTC was included for each PCR Master Mix preparation, where molecular grade water is included with no nucleic acid template. NTC samples were used to monitor for PCR artifacts (such as primer dimers) and potential contamination.

Polymerase Chain Reaction (PCR).

Real-Time detection was utilized with fluorescent intercalating dye (SYBR® Green) to detect the presence of target organisms. *C. albicans* and *C. parapsilosis* were each amplified with a unique set of primers.

Results Interpretation.

The assay was designed such that the melting temperature (Tm) of the resulting PCR product was used to distinguish the organisms. Life Technologies' 7500 Software v2.3 or v2.0.6 was used for data acquisition. The 7500 Software v2.3 or v2.0.6, together with custom data analysis software engine assessed the validity of the assay controls and generated results for each sample.

The interpretive algorithm considered the Ct value, then evaluated the Tm value(s) for those reaction(s) considered positive by the Ct value assessment. Ct values above 33 were considered "Not Detected", as Tm values for samples with a high Ct were non-specific and therefore no statistics was calculated when the Ct was above the stated threshold value. Tm1 was utilized for identification.

All samples analyzed were previously tested as *Candida*-positive by "Fungal Detection by PCR" (Example 1), therefore no further PCR inhibition testing was performed.

III. Validation

Validation Summary.

Specificity:

The PCR assay only detected the intended targets without cross reactivity with other non-specific targets. DNA from 39 cultures was each analyzed.

The following organisms were tested and gave negative results: *C. dubliniensis, C. glabrata, C. guilliermondii, C. haemulonii, C. kruseii, C. lusitaniae, C. troplicalis, M. pachydermatis; Acremonium, Alternaria, Aspergillus, Cuvularia, Fusarium, Mucor, Paecilomyces, Penicillium; Epidermophyton, Microsporum, T. mentagrophytes, T. rubrum.*

The following species were tested and identified: *C. albicans, C. parapsilosis.*

No cross reactivity or interference was detected in the presence of *P. aeruginosa, P. mirabilus, S. aureus, S. marcescens, S. pyogenes*. No cross reactivity or interference detected with human genomic DNA.

Sensitivity:

Genomic DNA from *C. albicans* and *C. parapsilosis* were each tested using at least six concentrations of DNA. Sensitivity varied among the species tested. *C. albicans* was detected at 3571 CFU; *C. parapsilosis* was detected at 3571 CFU.

Interday Reproducibility:

Interday reproducibility was evaluated using the performance of positive PCR controls run over 58 days. All CV % values for measured PCR parameters (Ct and Tms) were less than 5%.

Intraday Repeatability:

Eight specimens were prepared, each in triplicate or quadruplicate, by the addition of target DNA (5.0 or 2.0 ng DNA) to normal nails prior to lysis and DNA extraction. 100% of sample sets gave identical results, demonstrating intraday repeatability.

Run-to-Run Variability:

Inter-operator and inter-instrument testing demonstrated minimal variability in Ct and Tm (CV %<5%) values with 100% accuracy for Positive Control sample results.

Validation:

244 specimens were tested with the "*Candida* Identification by PCR" Assay. *Candida* detection using the "Fungal Detection by PCR" (Example 1) and species identification by Sanger Sequence analysis were used for results correlation for each specimen. The Concordance frequency of *C. albicans* detection or *C. parapsilosis* detection with Fungal (*Candida*) Detection by PCR (Example 1) was 98.0%. The Concordance frequency of *C. albicans* detection with sequencing was 100%; Concordance frequency of *C. parapsilosis* detection with sequencing was 98.5%.

Specificity

Primer Cross Reactivity

Fungal/Yeast Cross Reactivity Design: DNA isolated from 39 individual fungal or yeast cultures were each tested using the "*Candida* Identification by PCR" Assay. The identities of cultures were confirmed by DNA sequencing.

Fungal/Yeast Cross Reactivity Results are shown in Table 26 in FIG. 30. Both *C. albicans* and *C. parapsilosis* were tested and identified correctly, while the following were not detected: Eight *Candida* yeast species (14 strains) other than *C. albicans* and *C. parapsilosis*; nine Saprophytes genera (14 strains); and four Dermatophytes organisms (six strains).

These data demonstrate that the primer design, PCR conditions and application of the interpretive algorithm correctly identified the two *Candida* targets. Cross reactivity of these primers was not observed with dermatophytes and saprophytes.

Negative Controls

Negative Control Design: Reagent Blank (RB) and No Template Control (NTC) results were monitored throughout the study to assess their intended performance.

Reagent Blank Results are shown in Table 27 in FIG. 31. No amplification was observed before assay threshold Ct value of 34. No replicate had a Ct and Tm profile matching either *Candida* species detected by this assay (see "Inter-assay Reproducibility" for Tm ranges).

No Template Control Results are shown in Table 28 in FIG. 31. No amplification was observed before assay threshold Ct value of 34. No replicate had a Ct and Tm profile matching either *Candida* species detected by this assay (see "Inter-assay reproducibility" for Tm ranges).

Results from the negative controls show that no contamination resulted from the extraction process, as indicated by negative results in the RB samples; the PCR set-up process did not contribute to assay contamination, as indicated by negative results in the NTC samples; and no PCR artifacts were observed, as indicated by negative results in the NTC samples.

Bacterial Cross Reactivity and Interference

Bacterial Cross Reactivity and Interference Design: To test for cross reactivity, bacterial DNA from species commonly found in nails were tested by the "*Candida* Identification by PCR" Assay (Example 1). To assess the effect of bacterial DNA interference on *Candida* identification, bacterial DNA was mixed with *Candida* DNA and tested with the "*Candida* Identification by PCR" Assay. Five bacterial organisms, tested in duplicate or triplicate at two levels: *P. aeruginosa* (ATCC Cat #90270-5, lot 58304262), at $1.3\times10^4$ and $1.3\times10^5$ copies; *P. mirabilus* (ATCC Cat #12453D, lot 3573174), at $2.3\times10^3$ and $2.3\times10^4$ copies; *S. aureus* (ATCC Cat #BAA-17170-5, lot 61274435), at $1.1\times10^4$ and $1.1\times10^5$ copies; *S. marcences* (ATCC Cat #27137D-5, lot 59679187), at $6.4\times10^3$ and $6.4\times10^5$ copies; *S. pyogenese* (ATCC Cat #BAA1063D-5, lot 57907321), at $4.9\times10^3$ and $4.9\times10^4$ copies. Copy numbers were calculated using genome sizes and DNA concentration.

Bacterial Cross Reactivity and Interference Results are shown in Table 29 in FIG. 32. In Bacterial DNA only samples, no cross-reactivity with *Candida* primers was observed; no amplification was observed before assay threshold Ct value of 34; and no replicates had a Ct and Tm profile matching either *Candida* organism identified by the assay (see "Inter-assay Reproducibility" for Tm ranges).

In *Candida* DNA+Bacterial DNA samples, no interference by bacterial DNA was observed for *Candida* targets. *C. albicans* was detected at 0.1 ng/Rxn; and *C. parapsilosis* was detected at 0.1 ng/Rxn.

These results indicated that the five common pathogenic bacteria do not cross react or interfere with the assay at the indicated bacterial copy numbers.

Human Genomic DNA Cross Reactivity and Interference

Human Genomic DNA Cross Reactivity and Interference Design: Human genomic DNA (hgDNA) is likely to be purified from the nail specimen concurrently with *Candida* DNA. Pure hgDNA was tested in triplicate with the "*Candida* Identification by PCR" Assay to assess interference and cross reactivity with the assay.

Stock DNA (Roche, Cat #1169112001, lot 14897020; 200 ng/μL) was diluted to three concentrations; 2, 1, and 0.5 ng/μL (corresponding to ~320, ~160 and ~80 copies respectively). Each concentration was tested in quadruplicate. 2 μL DNA was added per PCR reaction.

DNA concentrations were determined using a NanoDrop® for >400 extracted nail samples, with a range of <0.1 to <100 ng/μL. 62.6% of samples had a DNA concentration <6.0 ng/μL. The precise mix of human: *Candida* DNA was not determined for any sample. A tested range of 0.5-2 ng/μL human genomic DNA (hgDNA) was representative of the sample set.

Copy numbers of hgDNA were calculated based on the human genome size and DNA concentration tested.

Human Genomic DNA Cross Reactivity and Interference Results are shown in Table 30 in FIG. 32.

In hgDNA samples, no cross-reactivity with *Candida* species primers was observed. No amplification was observed before assay threshold Ct value of 34. For each sample, no replicates had a Ct and Tm profile matching any *Candida* organisms of interest (see "Inter-assay Reproducibility" for Tm ranges).

In *Candida* DNA+human DNA samples, no interference by hgDNA was observed in the presence of *Candida* species targets. *C. albicans* was detected at 0.1 ng/Rxn; *C. parapsilosis* was detected at 0.1 ng/Rxn.

These results indicated that hgDNA did not cross react or interfere with the assay at the indicated copy numbers of hgDNA.

Sensitivity

Sensitivity Design: For *Candida* Cultures, DNA was isolated from two cultured isolates each for *C. albicans* and *C. parapsilosis*. LoD study was done by extracting DNA from *C. albicans* and *C. parapsilosis* cells of known density. Briefly, live cultures were grown on Potato Dextrose Agar (PDA) media, removed into 0.45% saline and mixed gently to generate homogeneous solutions. Serial dilutions were plated onto PDA plates to generate colony counts. The amount of cells in a solution density of 1 McFarland unit was determined. Cultures of varying density based on the McFarland units were generated for both *C. albicans* and *C. parapsilosis* and used to make solutions of known numbers of cells in TE buffer. DNA was extracted from cells in 5-10 replicates per level using the Qiagen DNEasy® 96 Plant Kit and the DNA was tested using both the Fungal Detection by PCR Assay and the "*Candida* Identification by PCR" Assay (Reflex). The identity of each culture was confirmed by DNA sequencing.

Quantification: The sensitivity for this assay was expressed as colony forming units per PCR reaction. The amount of cultured cells in a solution density of 1 McFarland unit was determined and dilutions were made prior to DNA purification.

Sensitivity was determined and reported as the limit of detection (LoD) in CFU per extraction and as ng DNA per extraction in Table 31.2 in FIG. 33. CFU was converted to ng DNA using known C values for *C. albicans* and *C. parapsilosis*. For Table 31.1 in FIG. 33, the sensitivity for this assay was expressed as ng of purified DNA per PCR reaction. Concentrations were standardized to 20 ng/μL and serial dilutions were performed and tested by PCR. The Copy #at the LOD was calculated for each organism by dividing the quantity (ng) by the diploid C value (www(dot)zbi(dot)ee/fungal-genomicsize/) and rounded to two significant figures.

Sensitivity Results are shown in Table 31.1 and Table 31.2, in FIG. 33. The limit of Detection (LOD) was determined as the lowest CFU quantity giving 100% positivity for the indicated organism. At least ten replicates were tested to confirm the LOD for each organism.

For the results shown in Table 31.2 in FIG. 33, sensitivity was determined to be at 3571 CFU (equivalent to 100 pg genomic DNA) for *C. albicans* and *C. parapsilosis*. Based upon the dilution factor of the extracted DNA into the PCR reaction, the detection sensitivity of the *Candida* Identification by PCR Assay is 0.003 ng per PCR reaction. The detection correlation between the "Fungal Detection by PCR" (Example 1) and the "*Candida* Identification by PCR" Assay was 98.0% (Table 36 in FIG. 38). The "Fungal Detection by PCR" (Example 1) was validated by comparing PCR results to those of culture and histology.

For the results shown in Table 31.1 in FIG. 33, sensitivity was determined to be at 540 copies for *C. albicans* and 150 copies for *C. parapsilosis*. The detection correlation between the "Fungal Detection by PCR" (Example 1) and the "*Candida* Identification by PCR" Assay was 98.0% (Table 36 in FIG. 38). The "Fungal Detection by PCR" (Example 1) was validated by comparing PCR results to those of culture and histology.

Inter-Assay Reproducibility

Inter-assay Reproducibility Design: For each run, one or two positive PCR controls were used. PCR was performed in 15 runs over 58 days to assess the inter-assay reproducibility. For the *C. albicans* and *C. parapsilosis* controls, DNA was extracted and purified from fungal culture. The acceptance range for Ct and Tm values was set to CV %<5.0.

Inter-assay Reproducibility Results for *Candida albicans* Control (Can2 CTL) are shown in Table 32 in FIG. 34. The acceptance criteria were Ct 22.2-25.6; and Tm1 72.0-74.0° C. The results were: a) Ct value range: 22.8-26.9* (*Ct values were higher for VAL01 and VAL02. The working stock prepared and used after on subsequent runs was a higher concentration of DNA. Statistics without VAL01 & VAL02: Mean: 23.2; StdDev: 0.35; CV %: 1.5%; Min: 22.8; Max: 24.0); b) Tm1 value range: 73.0-73.4° C.; c) 13/13 demonstrated the results consistent with *C. albicans*.

Inter-assay Reproducibility Results for *Candida parapsilosis* Control (Can2 CTL) are shown in Table 33 in FIG. 35. The acceptance criteria was Ct 22.0-25.6; and Tm1 69.0-71.4° C. Results were: a) Ct value range: 22.5-25.5; b) Tm1 value range: 69.9-70.8° C.; c) 15/15 demonstrated results consistent with *C. parapsilosis*.

The inter-assay reproducibility as seen with both positive controls was within the range of CV %<5.0 for both the Ct and Tm values.

Intra-Assay Repeatability

Intra-Assay Repeatability Design: 8 positive specimens were tested, either in triplicate or quadruplicate (28 specimens total). Eight negative nail specimens were spiked, with either *C. albicans* (C alb5.0, C alb 2.0, C alb1, Calb2) or *C. parapsilosis* (C para5.0, C para 2.0, C parap1, Cparap2) DNA prior to extraction, each prepared in triplicate or quadruplicate, as indicated.

Intra-Assay Repeatability Results are shown in Table 34 in FIG. 36.

*C. albicans* detection was 100% repeatable. 14/14 reactions with *C. albicans*-positive samples gave positive results when assayed for *C. albicans*.

*C. parapsilosis* detection was 100% repeatable. 14/14 reactions with *C. parapsilosis*-positive samples gave positive results when assayed for *C. parapsilosis*.

Inter- and Intra-Assay Variability Summary

Runs included in the validation study are summarized in Table 35 in FIG. 37.

Variability in extraction was tested for DNA purified from samples in 13 batches over 128 days and by four different analysts.

Variability in PCR was tested in 15 batches over 68 days, by three different analysts, and on two different instruments.

As summarized in Table 32 in FIG. 34 and Table 33 in FIG. 35, all CTL samples performed equivalently, regardless of operator or instrument.

Accuracy

Design for Accuracy Determination. *Candida* positive and negative specimens previously analyzed as part of "Fungal Detection by PCR (Example 1) validation were used to confirm the accuracy of the "*Candida* Identification by PCR" Assay. The "Fungal Detection by PCR" (Example 1) validation included assessment of histology and culture results. The identity of the organism present in each *Candida* positive specimen was determined by Sanger Sequence analysis.

Correlation with "Fungal Detection by PCR" (Example 1) is shown in Table 36 in FIG. 38. The results included 184 clinical specimens and 60 "positive" *Candida* specimens prepared by spiking a normal nail with either *C. albicans* (30) or *C. parapsilosis* (30) DNA prior to lysis and DNA extraction.

Detection of *C. albicans* and *C. parapsilosis* by Fungal Detection PCR (Example 1) and the *Candida* Identification PCR are similar, as indicated by concordance, sensitivity and specificity values above 97.0%.

Organism Identification Correlation

Design: "Positive" specimens were generated by spiking normal nails with DNA prior to sample lysis and extraction. Origin of sequence-positive specimens were: 30 "spiked" samples for *C. albicans*, and 8 clinical and 30 "spiked" samples for *C. parapsilosis*.

Only specimens positive for *Candida*, either by Sequencing or with the "Fungal Detection by PCR" (Example 1) were included in Identification Correlation study results. Values indicated as Sequencing-negative for a *Candida* species were the number of samples which were positive for the other *Candida* evaluated by this assay. Spiked samples were considered Sequencing positive, as the DNA spiked in prior to extraction had previously been sequenced. Sequencing was not repeated following spiking and extraction.

*Candida* Identification Correlation Results for *C. albicans* are shown in Table 37 in FIG. 38; and for *C. parapsilosis*, the results are shown in Table 38 in FIG. 38.

Results of the *Candida* Identification by PCR accuracy assessment demonstrated that the PCR method developed for identification of *C. albicans* and *C. parapsilosis* in human nails gave accurate results.

Example 3

Report Showing the Results of a Fungal Detection Assay (Example 1) and *Candida* Identification Assay (Example 2)

Results of an assay for screening and identification of an onychomycotic fungal infection in a sample, as described in Examples 1 and 2, can be provided in a report, indicating the presence or absence of *Candida*, dermatophyte, or saprophyte, and/or the presence or absence of *C. albicans* and *C. parapsilosis* in the sample. Examples of such a report are provided in FIG. 39.

Example 4

Dermatophyte Identification in Human Nail by Real Time PCR

The "Dermatophyte Identification by PCR" assay described below was performed after the presence or absence of a Dermatophyte in a sample was determined using the "Fungal Detection by PCR" assay (Example 1).

I. Target Gene and Primer Sequences

Target dermatophyte organisms were identified by a literature search for onychomycosis etiology, and nail cultures. To assess the culture data, >17,000 consecutively accessioned culture-positive cases were reviewed. Gene sequences for target organisms were identified using the National Center for Biotechnology Information (NCBI) database and Basic Local Alignment Search Tool (BLAST®) "nucleotide blast" (nt/nr) query.

A database of rRNA consensus sequences for target organisms was constructed using Geneious® software, version 7.1.6. Regions of within the ITS1 and ITS2 sequences of the 18S rRNA gene are highly varied among target dermatophytes and target regions for forward and reverse primer sequences were identified by assessing unique regions among the targeted organisms that were dissimilar to non-targeted organisms.

Dermatophyte genera primer sequences are shown in Table 39.

TABLE 39

| Target | Forward primer | Reverse primer |
|---|---|---|
| *Trichophyton* | ATC AGG GGT GAG CAG AYG T (SEQ ID NO: 69) | CGC TCA GAC TGA CAG CYC TT (SEQ ID No: 70) |
| *Epidermophyton* | CAT TGC GCC CTC TGG TAT TC (SEQ ID NO: 71) | CTC CAC CTT TCT CCT CTC CC (SEQ ID NO: 72) |

TABLE 39-continued

| Target | Forward primer | Reverse primer |
|---|---|---|
| *Microsporum* | TTG TCT ACT GAC CCG GTT (SEQ ID NO: 73) | GAA ACA AGA GTC CCC CTC AGG (SEQ ID NO: 74) |

Figure 40A:
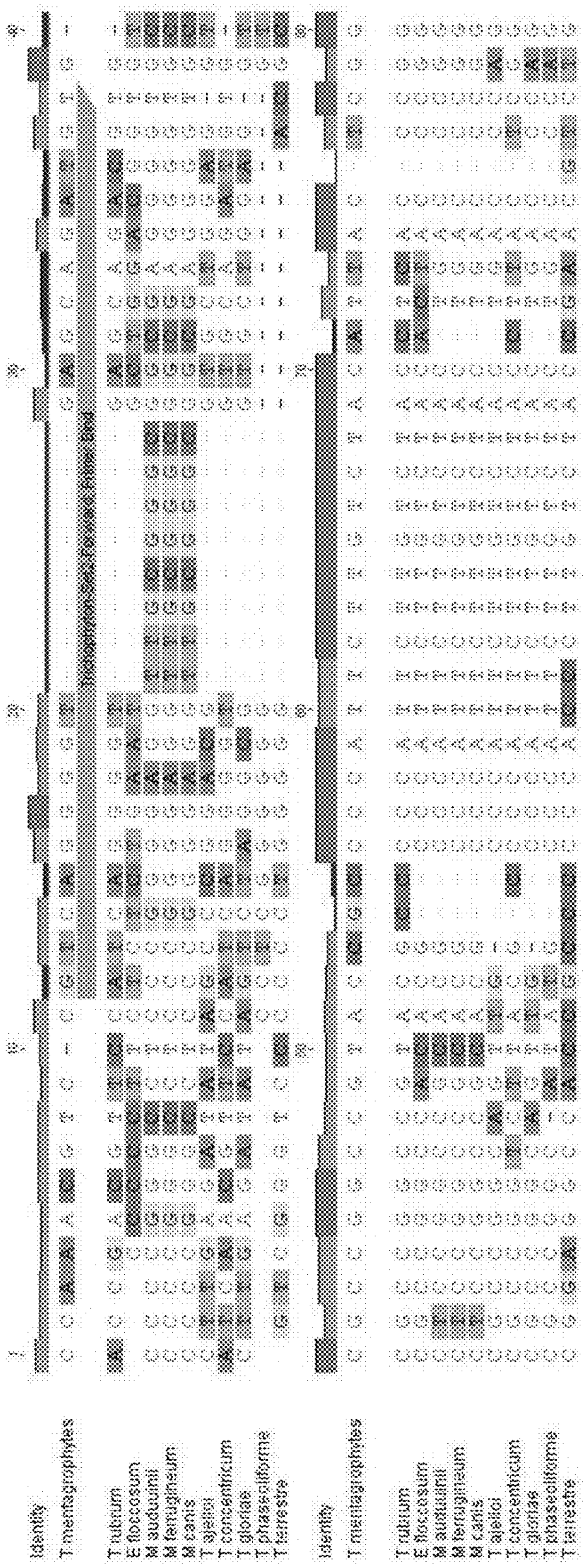
FIGS. 40A-40C show alignments to genomic regions of primers designed to amplify *Trichophyton mentagrophytes*- and *T. rubrum*-specific target sequences, according to embodiments of the present disclosure.
Figure 40B:
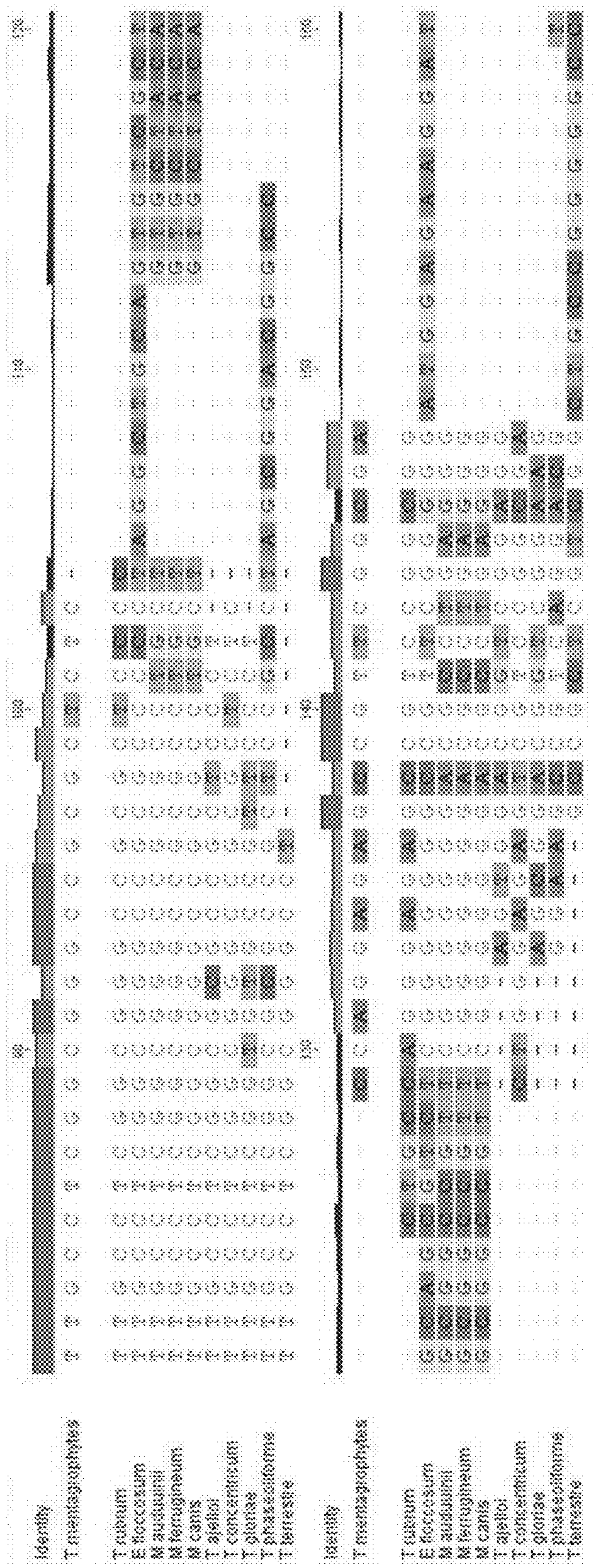
Figure 40C:
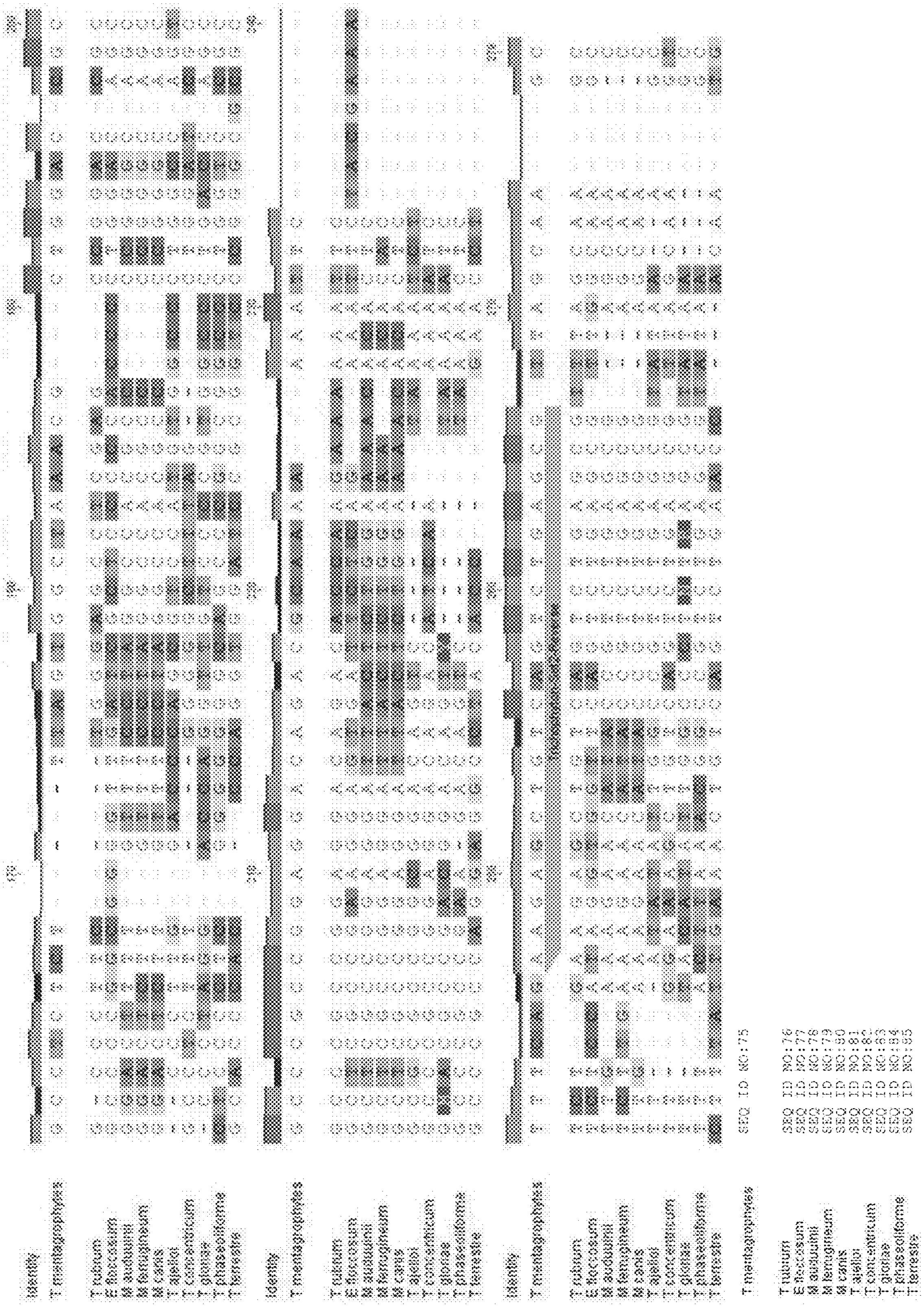

*Trichophyton* primer alignment, and target or non-target sequences are shown in FIGS. 40A-40C. Alignment of genomic regions for the following organisms are shown: *Trichophyton mentagrophytes* (SEQ ID NO:75); *T. rubrum* (SEQ ID NO:76), *E. floccosum* (SEQ ID NO:77); *M. audouinii* (SEQ ID NO:78); *M. ferrugineum* (SEQ ID NO:79); *M. canis* (SEQ ID NO:80); *T. ajelloi* (SEQ ID NO:81); *T concentricum* (SEQ ID NO:82); *T. gloriae* (SEQ ID NO:83); *T. phaseoliforme* (SEQ ID NO:84); and *T. terrestre* (SEQ ID NO:85).

Figure 41A:
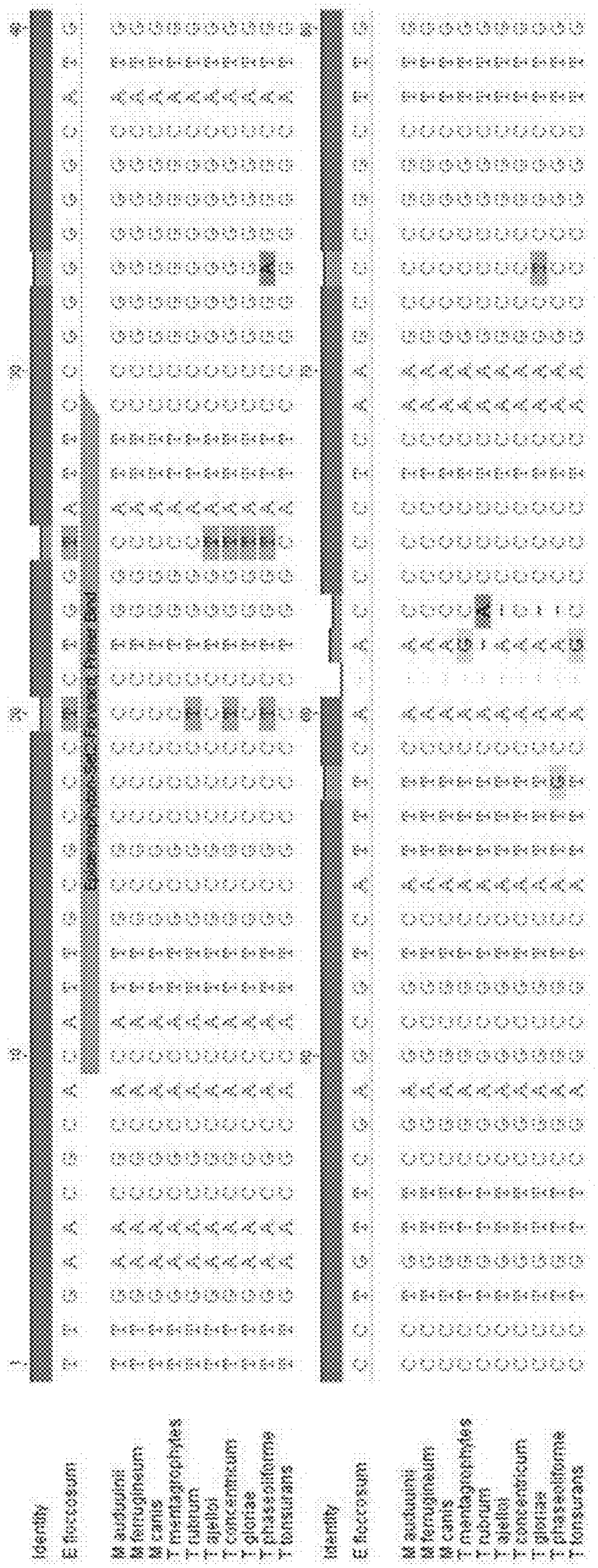
FIGS. 41A-41B show alignments to genomic regions of primers designed to amplify an *Epidermophyton*-specific target sequences, according to embodiments of the present disclosure.
Figure 41B:
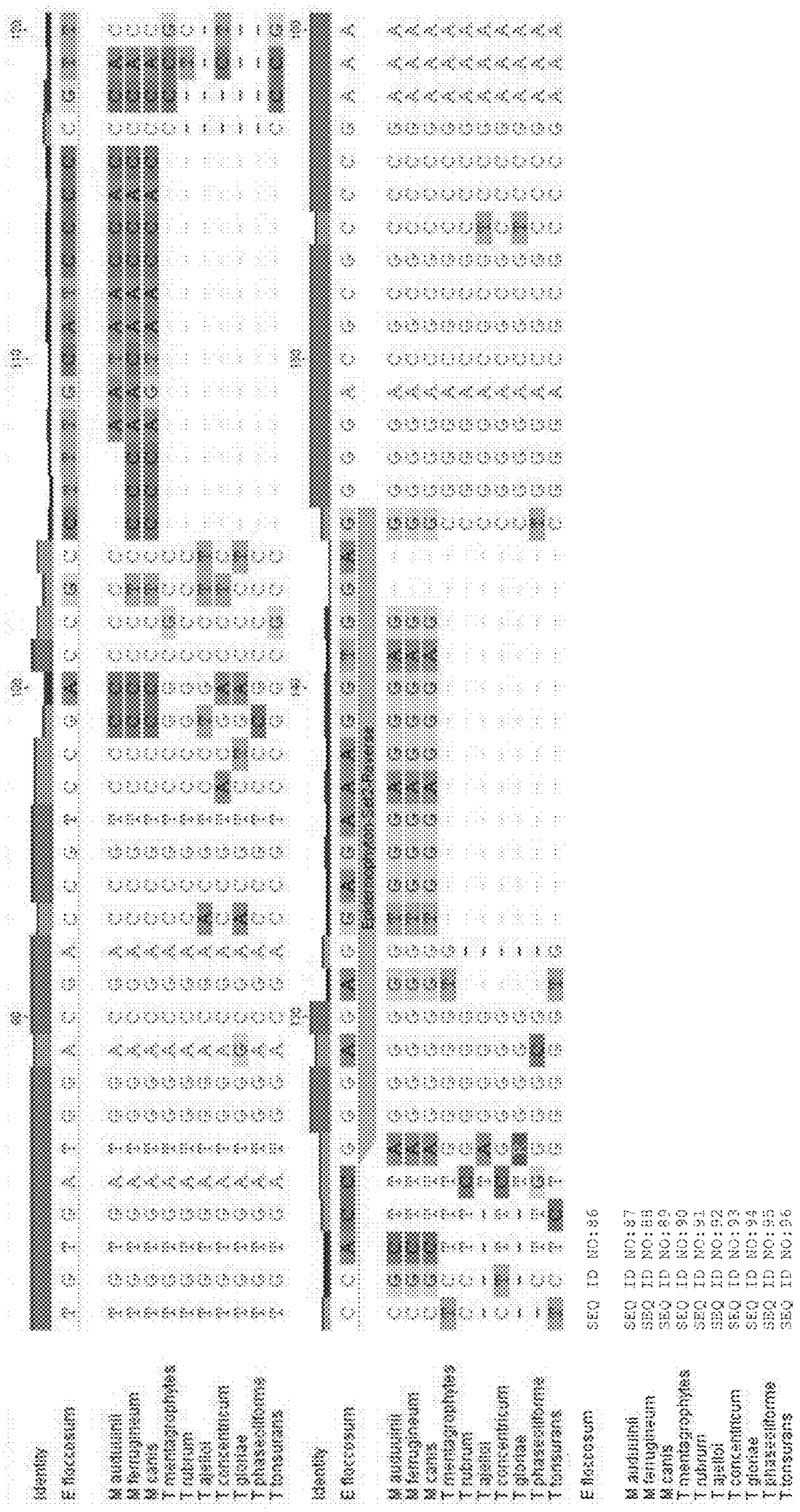

*Epidermophyton* primer alignment, and target or non-target sequences are shown in FIGS. 41A-41B. Alignment of genomic regions for the following organisms are shown: *E. floccosum* (SEQ ID NO:86); *M. audouinii* (SEQ ID NO:87); *M. ferrugineum* (SEQ ID NO:88); *M. canis* (SEQ ID NO:89); *T. mentagrophytes* (SEQ ID NO:90); *T rubrum* (SEQ ID NO:91); *T. ajelloi* (SEQ ID NO:92); *T concentricum* (SEQ ID NO:93); *T. gloriae* (SEQ ID NO:94); *T. phaseoliforme* (SEQ ID NO:95); and *T tonsurans* (SEQ ID NO:96).

Figure 42:
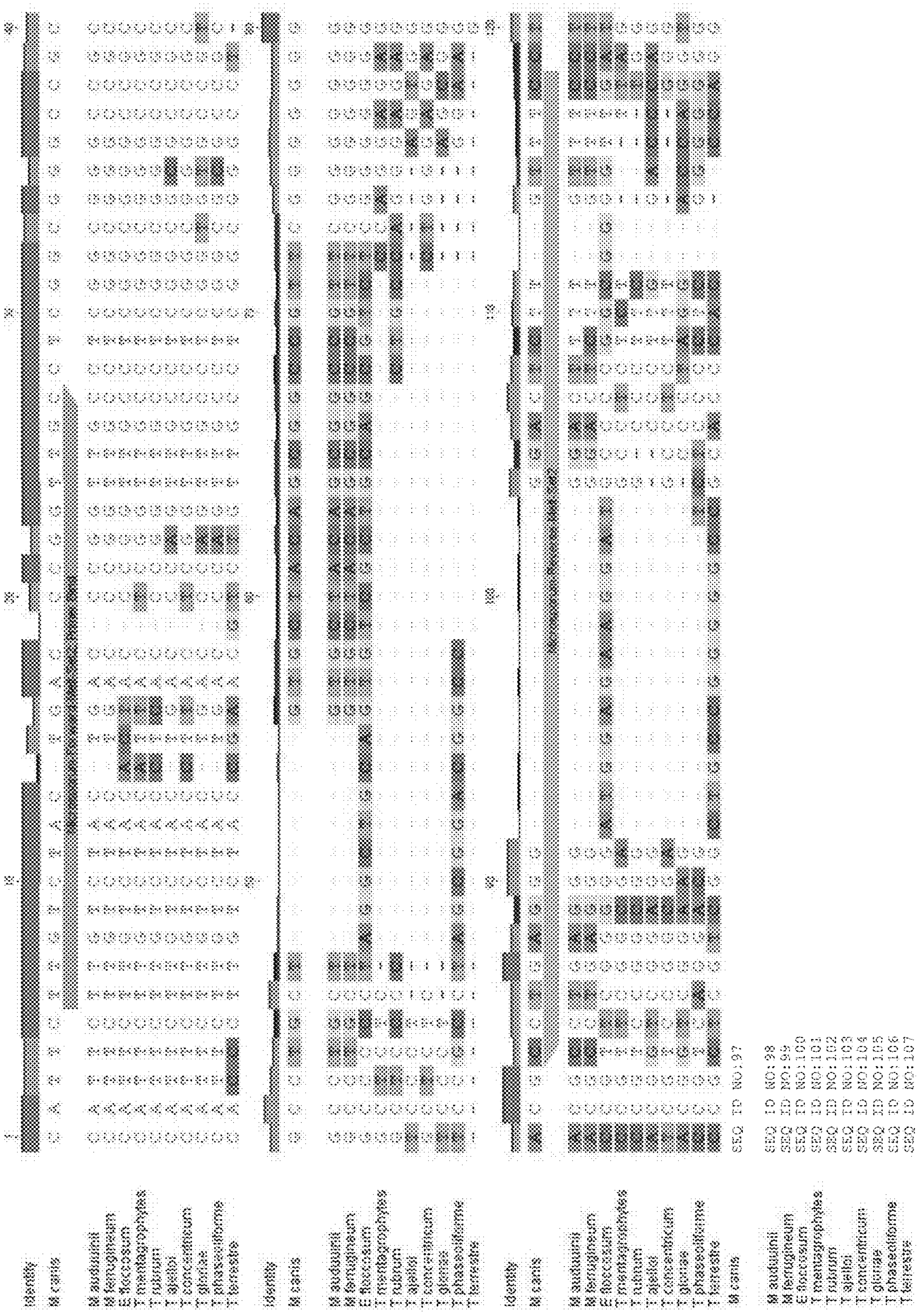
FIG. 42 shows alignments to genomic regions of primers designed to amplify *Microsporum*-specific target sequences, according to embodiments of the present disclosure.

*Microsporum* primer alignment, and target or non-target sequences are shown in FIG. 42. Alignment of genomic regions for the following organisms are shown: *M. canis* (SEQ ID NO:97); *M. audouinii* (SEQ ID NO:98); *M. ferrugineum* (SEQ ID NO:99); *E. floccosum* (SEQ ID NO:100); *T. mentagrophytes* (SEQ ID NO:101); *T. rubrum* (SEQ ID NO:102); *T. ajelloi* (SEQ ID NO:103); *T. concentricum* (SEQ ID NO:104); *T. gloriae* (SEQ ID NO:105); *T. phaseoliforme* (SEQ ID NO:106); and *T. terrestre* (SEQ ID NO:107).

II. Procedures

Specimen Collection, Specimen Grossing, and DNA Extraction and Purification were performed as described for the "Fungal Detection by PCR" (Example 1). DNA from the same preparation used in screening for dermatophytes was used for Dermatophyte genus or species identification.

Descriptions of Controls.

Extraction Control/Inhibition Control (EC/IC): EC/IC was used as a Lysis control. A gBlock® of *S. pombe* citrate synthase gene was added to all samples prior to cell lysis and detected in a separate PCR reaction. As the analysis of inhibition was performed as part of the "Fungal Detection by PCR" (Example 1), and the absence of inhibition was confirmed, this analysis was not repeated for the "Dermatophyte Identification by PCR" Assay.

Reagent Blank (RB): RB was used as a Negative Control. RBs were processed with each extraction batch and included in PCR analysis. Each RB includes EC/IC template DNA and were used to monitor for potential contamination introduced during the extraction process, and assessed for EC/IC detection.

PCR Positive Control (CTL): DNA extracted and purified from *T. mentagrophytes* (ATCC), *T. rubrum* (In-House) or *Microsporum* (In-House), or a gBlock® fragment of the *Epidermophyton* rRNA gene was included for each run as positive controls.

No template control (NTC): The NTC was used as a Reagent Contamination Control. NTC was included for each PCR Master Mix preparation, where molecular grade water is included with no nucleic acid template. NTC samples were used to monitor for PCR artifacts (such as primer dimers) and potential contamination.

Polymerase Chain Reaction (PCR).

Real-Time detection was utilized with fluorescent intercalating dye (SYBR® Green) to detect the presence of target organisms. Three primers pairs were designed to specifically amplify DNA from either *T. mentagrophytes* and *T. rubrum*, *E. floccosum* or *Microsporum* species.

Results Interpretation.

The assay was designed such that the melting temperature (Tm) of the resulting PCR product was used to distinguish the organisms. Life Technologies' 7500 Software v2.3 or v2.0.6 was used for data acquisition. The 7500 Software v2.3 or v2.0.6, together with custom data analysis software engine assessed the validity of the assay controls and generated results for each sample.

The interpretive algorithm considered the Ct value, then evaluated the Tm value(s) for those reaction(s) considered positive by the Ct value assessment. Ct values above 33 (*Trichophyton* and *Microsporum*) or 31.5 (*Epidermophyton*) were considered "Not Detected", as Tm values for samples with a high Ct were non-specific and therefore no statistics were calculated when the Ct was above the stated threshold value.

Tm1 and Tm2 were both utilized for identification.

All samples analyzed were previously tested as dermatophyte-positive by "Fungal Detection by PCR" (Example 1), therefore no further PCR inhibition testing was performed.

III. Validation

Validation Summary

Specificity:

The PCR assay only detected the intended targets without cross reactivity with other non-specific targets. DNA from 28 cultures was each analyzed. When cultured DNA was not available, (*T. verrucosum* and *T. violaceum*), synthetic DNA (gBlock) was used to test the target sequence region.

The following organisms were tested and gave negative results: *C. albicans, C. parapsilosis; Acremonium, Alternaria, Aspergillus, Cuvularia, Fusarium, Mucor, Paecilomyces, Penicillium.*

The following organisms were tested and identified: *T. mentatrophytes, T. rubrum, Epidermophyton, Microsporum.*

No cross reactivity or interference detected in the presence of *P. aeruginosa, P. mirabilus, S. aureus, S. marcescens, S. pyogenes*. No cross reactivity or interference detected with human genomic DNA.

Sensitivity: Genomic DNA (*T. mentagrophytes* and *T. rubrum*) or synthetic DNA (*Epidermophyton* and *Microsporum*) was tested using at least six concentrations of DNA. Sensitivity varied among the species tested. For the results shown in Table 45.1 in FIG. 48, the limit of detection by copy number per reaction was 280 copies for *T. mentagrophytes;* 280 copies for *T. rubrum;* 1900 copies for *Epidermophyton*; and 6500 copies for *Microsporum.*

Interday Reproducibility:

Interday reproducibility was evaluated using the performance of positive PCR controls run over 98 days. All CV % values for measured PCR parameters (Ct and Tms) were less than 5%.

Intraday Repeatability:

Five specimens were prepared from primary clinical samples, each in triplicate. Another nine specimens were prepared, each in triplicate, by the addition of target DNA (5.0 or 2.0 ng DNA) to normal nails prior to lysis and DNA extraction. 100% of triplicate samples gave identical results demonstrating intraday repeatability.

Run-to-Run Variability:

Inter-operator and inter-instrument testing demonstrated minimal variability in Ct and Tm (CV %<5%) values with 100% accuracy for Positive Control sample results.

Validation:

261 specimens were tested with the "Dermatophyte Identification by PCR" Assay. Dermatophyte detection using the "Fungal Detection by PCR" (Example 1) and identification of specific dermatophytes by Sanger Sequence analysis were used for assay accuracy determination. Concordance frequency of dermatophyte genus or species detection with Fungal (Dermatophyte) Detection by PCR (Example 1) was 98.5%. The Concordance frequency of sequencing with *T. mentagrophytes* detection was 99.4%; Concordance frequency of sequencing with *T. rubrum* detection was 99.4%; Concordance frequency of sequencing with *Epidermophyton* detection was 100%; and Concordance frequency of sequencing with *Microsporum* detection was 99.4%.

Specificity

Primer Cross Reactivity

Fungal/Yeast Cross Reactivity Design: DNA isolated from 37 individual fungal or yeast cultures were each tested using the "Dermatophyte Identification by PCR" Assay. The identities of cultures were confirmed by DNA sequencing.

Fungal/Yeast Cross Reactivity Results are shown in Table 40 in FIG. 43. Each of the four targeted dermatophytes were tested and identified correctly, while the following were not detected: two *Candida* species (5 strains); and eight Saprophytes genera (15 strains). Three other dermatophyte species, *T. verrucosm, T. tonsurans* and *T. violaceum* reacted weakly with *T. mentagrophytes* or *T. rubrum* primers.

These data demonstrate that the primer design, PCR conditions and application of the interpretive algorithm correctly identified the four target dermatophytes. Cross reactivity of these primers with *Candida* and saprophytic fungi was not observed.

Negative Controls

Negative Control Design: Reagent Blank (RB) and No Template Control (NTC) results were monitored throughout the study to assess their intended performance.

Reagent Blank (RB) Results are shown in Table 41 in FIG. 44. No amplification was observed before assay threshold Ct value of 31.5. No replicate had a Ct and Tm profile matching any dermatophyte of interest (see "Inter-assay Reproducibility" for Tm ranges).

No Template Control are shown in Table 42 in FIG. 45. No amplification was observed before assay threshold Ct value of 31.5. No replicate had a Ct and Tm profile matching any dermatophyte of interest (see "Inter-assay Reproducibility" for Tm ranges).

Results from the negative controls show that no contamination resulted from the extraction process, as indicated by negative results in the RB samples; the PCR set-up process did not contribute to assay contamination, as indicated by negative results in the NTC samples; and no PCR artifacts were observed, as indicated by negative results in the NTC samples.

Bacterial Cross Reactivity and Interference

Bacterial Cross Reactivity and Interference Design: To test for cross reactivity, bacterial DNA from species commonly found in nails were tested by the "Dermatophyte Identification by PCR" Assay (Example 1). To assess the effect of bacterial DNA interference on dermatophyte identification by PCR, bacterial DNA was mixed with dermatophyte DNA and tested with the "Dermatophyte Identification by PCR" Assay. Five bacterial organisms, tested in duplicate or triplicate at two concentrations. *P. aeruginosa* (ATCC Cat #90270-5, lot 58304262), at $1.3\times10^4$ and $1.3\times10^5$ copies; *P. mirabilus* (ATCC Cat #12453D, lot 3573174), at $2.3\times10^3$ and $2.3\times10^4$ copies; *S. aureus* (ATCC Cat #BAA-17170-5, lot 61274435), at $1.1\times10^4$ and $1.1\times10^5$ copies; *S. marcences* (ATCC Cat #27137D-5, lot 59679187), at $6.4\times10^3$ and $6.4\times10^4$ copies; *S. pyogenese* (ATCC Cat #BAA1063D-5, lot 57907321), at $4.9\times10^3$ and $4.9\times10^4$ copies. Copy numbers were calculated using genome sizes and DNA concentrations.

Bacterial Cross Reactivity and Interference Results are shown in Table 43 in FIG. 46. In Bacterial DNA only samples, no cross-reactivity with dermatophyte primers was observed; no amplification was observed before assay threshold Ct value of 31.5; and no replicates had a Ct and Tm profile matching a dermatophyte identified by the assay (see "Inter-assay Reproducibility" for Tm ranges).

In the Dermatophyte DNA+Bacterial DNA samples, no interference by bacterial DNA was observed for dermatophyte targets. *T. mentagrophytes* was detected at 0.1 ng/Rxn; *T. rubrum* was detected at 0.1 ng/Rxn; *Epidermophyton* was detected at 0.1 ng/Rxn; and *Microsporum* was detected at 0.008 ng/Rxn.

These results indicated that the five common pathogenic bacteria do not cross react or interfere with the assay at the indicated bacterial copy numbers.

Human Genomic DNA Cross Reactivity and Interference

Human Genomic DNA Cross Reactivity and Interference Design: Human genomic DNA (hgDNA) is likely to be purified from the nail specimen concurrently with dermatophyte DNA. Pure hgDNA was tested in triplicate with the "Dermatophyte Identification by PCR" Assay to assess interference and cross reactivity with the assay.

Stock DNA (Roche, Cat #1169112001, lot 14897020; 200 ng/μL) was diluted to three concentrations; 2, 1, and 0.5 ng/μL (corresponding to ~320, ~160 and ~80 copies respectively). Each concentration was tested in quadruplicate. 2 μL DNA was added per PCR reaction.

DNA concentrations were determined using a NanoDrop® for >400 extracted nail samples, with a range of <0.1 to <100 ng/μL. 62.6% of samples had a DNA concentration <6.0 ng/μL. The precise mix of human:dermatophyte DNA was not determined for any sample. A tested range of 0.5-2 ng/μL human genomic DNA was representative of the sample set.

Copy numbers of hgDNA were calculated based on the human genome size and DNA concentration tested.

Human Genomic DNA Cross Reactivity and Interference Results are shown in Table 44 in FIG. 47.

In hgDNA samples, no cross-reactivity with dermatophyte primers was observed. No amplification was observed before assay threshold Ct value of 34. For each organism no replicates had a Ct and Tm profile matching any dermatophyte organisms of interest (see "Inter-assay Reproducibility" for Tm ranges).

In Dermatophyte DNA+human DNA samples, no interference by hgDNA was observed in the presence of dermatophyte targets. *T. mentagrophytes* was detected at 0.1 ng/Rxn; *T. rubrum* was detected at 0.1 ng/Rxn; *Epidermophyton* was detected at 0.1 ng/Rxn; and *Microsporum* was detected at 0.008 ng/Rxn.

These results indicated that hgDNA did not cross react or interfere with the assay at the indicated copy numbers of hgDNA.

Sensitivity

Sensitivity Design: DNA was isolated from culture for *T. rubrum, T. interdigitale/mentagrophytes, Epidermophyton* and *Microsporum*. Each was tested using the "Dermatophyte Identification by PCR" Assay. The identity of each culture was confirmed by DNA sequencing.

Quantification: The sensitivity for this assay was expressed as ng of purified DNA per PCR reaction. Concentrations were standardized to 20 ng/μL and serial dilutions were performed using pooled extract from Negative Nail specimens and tested by PCR. The Copy #at the LOD was calculated for each organism by dividing the quantity (ng) by the diploid C value (www(dot)zbi(dot)ee/fungal-genomicsize/) and rounded to two significant figures.

The quantity of synthesized DNA solution (ng/μL), and the molecular weight were used to determine the final copy number in the stock concentration.

For Table 45.1 in FIG. 48, a synthetic 195-mer gBlock® fragment of the *Epidermophyton* rRNA gene was constructed. Serial dilutions of the gBlock were used for sensitivity testing. The quantity of synthesized DNA, as per the specifications sheet, and the molecular weight were used to determine the final copy number in the stock concentration.

For Table 45.1 in FIG. 48, a synthetic 1134-mer fragment of the *Microsporum* rRNA gene was amplified by PCR using primers which flank the *Microsporum* primers used in the "Dermatophyte Identification by PCR" Assay. Following purification, serial dilutions of the amplicon were used for sensitivity testing.

Sensitivity Results are shown in Table 45.1 in FIG. 48 and Table 45.2 in FIG. 49.

Limit of Detection (LOD) was determined as the lowest DNA quantity giving 100% positivity for the indicated organism. At least ten replicates were tested to confirm the LOD for each organism. The LOD study was done in a matrix using genomic DNA purified from each of the four target organisms. For the dilution matrix, DNA was extracted from clinically normal human nail specimens and screened for the presence of target organisms. Extracts were pooled from normal specimens confirmed negative for target organisms and the resulting pool was the matrix used to dilute genomic DNA for each target organism. Replicates of each level were tested, as indicated in Table 45.1 in FIG. 48 and Table 45.2 in FIG. 49.

For Table 45.1 in FIG. 48, the difference in units of DNA, ng for DNA from culture or fg for synthetic DNA, results from cultured DNA including the entire organism's genome and synthetic DNA representing only 195 or 1134 bases of DNA.

For the results shown in Table 45.1 in FIG. 48, sensitivity was determined to range from 280 to 6500 copies, depending upon the dermatophyte studied. The detection correlation between the "Fungal Detection by PCR" (Example 1) and the "Dermatophyte Identification by PCR" Assay is 98.0% (Table 52 in FIG. 56). The "Fungal Detection by PCR" (Example 1) was validated by comparing PCR results to those of culture and histology.

For the results shown in Table 45.2 in FIG. 49, sensitivity was determined to range from 0.001 ng to 0.01 ng (corresponding to from 21 to 167 copies), depending upon the dermatophyte studied. The detection correlation between the "Fungal Detection by PCR" (Example 1) and the "Dermatophyte Identification by PCR" Assay is 98.5% (Table 52 in FIG. 56). The "Fungal Detection by PCR" (Example 1) was validated by comparing PCR results to those of culture, histology and DNA sequencing.

Inter-Assay Reproducibility

Inter-assay Reproducibility Design: For each run, up to four positive PCR controls were used. PCR was performed in 21 runs over 98 days to assess the inter-assay reproducibility. *T. mentagrophytes* DNA was extracted and purified from culture; and *Epidermophyton* target was gBlock®/synthetic DNA.

Inter-assay Reproducibility Results for *Trichophyton mentagrophytes* Control are shown in Table 46 in FIG. 50. *Trichophyton mentagrophytes* (ATCC #9533D-2) was used as template. Acceptance criteria was Ct 25.4-29.5; Tm1 82.5-84.8° C.; Tm2 76.0-78.0° C. Results were: a) Ct value range: 26.2-30.1; b) Tm1 value range: 83.7-84.7° C.; c) Tm2 value range: 76.7-77.8° C.; d) 21/21 demonstrated results consistent with *T. mentagrophytes*.

Inter-assay Reproducibility Results for *T. rubrum* Control are shown in Table 47 in FIG. 51. Acceptance criteria was Ct 21.0-22.9; C/D Tm1 86.0-88.0° C.; Tm2 76.5-79.0° C. Results were: a) Ct value range: 19.6-22.6; b) Tm1 value range: 86.7-87.6° C.; c) Tm2 value range: 77.2-78.0° C.; d) 19/19 demonstrated results consistent with *T. rubrum*.

Inter-assay Reproducibility Results for *Epidermophyton* Control (Derm3 CTL) are shown in Table 48 in FIG. 52. Acceptance criteria was Ct 26.2-30.9; Tm1 80.0-82.5° C. Results were: a) Ct value range: 26.1-30.0; b) Tm1 value range: 81.6-82.4° C.; c) 18/18 demonstrated results consistent with *Epidermophyton*.

Inter-assay Reproducibility Results for *Microsporum* Control (Derm4 CTL) are shown in Table 49 in FIG. 53. Acceptance criteria Ct 22.1-25.0; Tm1 82.8-85.2° C.; Tm2 <76.0° C. or N/A* (*Tm1 for *Microsporum* overlaps with that of *T. mentagrophytes*. The absence of a Tm2 peak greater than 76.0° C. differentiated *T. mentagrophytes* from *Microsporum*.). Results were: a) Ct value range: 22.6-25.9; b) Tm1 value range: 84.1-85.1° C.; c) Tm2: 68.9-70.4° C. (N=11) or N/A (N=5); d) 16/16 demonstrated results consistent with *Microsporum*.

The inter-assay reproducibility as seen with all four positive controls was within the range of CV %<5.0 for both the Ct and Tm values.

Intra-Assay Repeatability

Intra-Assay Repeatability Design: 14 specimens were each tested in triplicate (42 specimens total): Five clinical nail samples were each prepared in triplicate (Four positive for either *T. mentagrophytes* or *T. rubrum* and one negative).

Nine negative nail specimens, spiked with one of three different sources of either *T. mentagrophytes* (Tr m2, Tr m2, Tr m3), *Epidermophyton* (Epi1, Epi2, Epi3) or *Microsporum* (Micr1, Micr2, Micr3) DNA prior to extraction, each prepared in triplicate.

Intra-Assay Repeatability Results are shown in Table 50 in FIG. 54.

Negative result detection was 100% repeatable (3/3 Not Detected).

*T. mentagrophytes* detection was 100% repeatable. 12/12 reactions with *T. mentagrophytes*-positive samples gave positive results when assayed for *T. mentagrophytes*.

*T. rubrum* detection was 100% repeatable. 9/9 reactions with *T. rubrum*-positive samples gave positive when assayed for *T. rubrum*.

*Epidermophyton* detection was 100% repeatable. 9/9 reactions with *Epidermophyton*-positive samples gave positive results when assayed for *Epidermophyton*.

*Microsporum* detection was 100% repeatable. 9/9 reactions with *Microsporum*-positive samples gave positive results when assayed for *Microsporum*.

Inter- and Intra-Assay Variability Summary

Runs included in the validation study are summarized in Table 51 in FIG. 55.

Variability in extraction was tested for DNA purified from samples in 17 batches over 156 days and by four different analysts.

Variability in PCR was tested in 21 batches over 90 days, by two different analysts and on two different instruments.

As summarized in Table 46 in FIG. 50, Table 47 in FIG. 51, Table 48 in FIG. 52, and Table 49 in FIG. 53, all CTL samples performed equivalently, regardless of operator or instrument.

Validation

Design for Accuracy Determination.

Dermatophyte positive and negative specimens previously analyzed as part of "Fungal Detection by PCR (Example 1) validation were used to confirm the accuracy of the "Dermatophyte Identification by PCR" Assay. The "Fungal Detection by PCR" (Example 1) validation included assessment of histology and culture results. The identity of the organism present in each dermatophyte-positive specimen was determined by Sanger Sequence analysis.

Correlation with "Fungal Detection by PCR" (Example 1) is shown in Table 52 in FIG. 56. The results included 177 clinical specimens and 23 "positive" *T. mentagrophytes* specimens prepared by spiking DNA with a normal nail prior to lysis and DNA extraction.

Detection of dermatophytes by the "Fungal Detection by PCR" (Example 1) and the "Dermatophyte Identification by PCR" are similar, as indicated by concordance, sensitivity and specificity values above 97.5%.

Dermatophyte genus/species identification correlation

Design: "Positive" specimens were generated by spiking DNA with normal nails prior to sample lysis and extraction. Origin of sequence-positive specimens were 5 clinical and 26 "spiked, samples for *T. mentagrophytes;* 73 clinical samples for *T. rubrum;* 2 clinical and 28 "spiked" samples for *Epidermophyton*; and 30 "spiked" samples for *Microsporum.*

Only specimens positive for a dermatophyte, either by Sequencing or with the "Fungal Detection by PCR" (Example 1) were included in Identification Correlation study results. Values indicated as Sequencing-negative for an organism were the number of samples which were positive for another dermatophyte. Spiked samples were considered Sequencing positive, as the DNA spiked in prior to extraction had previously been sequenced. Sequencing was not repeated following spiking and extraction.

Dermatophyte Identification Correlation Results for *T. mentagrophytes* are shown in Table 53 in FIG. 57; for *T. rubrum*, Table 54 in FIG. 57; for *Epidermophyton*, Table 55 in FIG. 57; and for *Microsporum*, Table 56 in FIG. 57.

Results of the Dermatophyte Identification by PCR accuracy assessment demonstrated that the PCR method developed for identification of dermatophytes in human nails gave accurate results.

Example 5

Report Showing the Results of a Fungal Detection Assay (Example 1) and Dermatophyte Identification Assay (Example 3)

Results of an assay for screening and identification of an onychomycotic fungal infection in a sample, as described in Examples 1 and 3, can be provided in a report, indicating the presence or absence of *Candida*, dermatophyte, or saprophyte, and/or the presence or absence of *T. mentagrophytes, T. rubrum*, an *Epidermophyton* species, and a *Microsporum* species in the sample. Examples of such a report are provided in FIG. 58.

Example 6

Saprophyte Identification in Human Nail by Real Time PCR

The "Sapratophyte Identification by PCR" assay described below was performed after the presence or absence of a Saprophyte in a sample was determined using the "Fungal Detection by PCR" assay (Example 1).

I. Target Gene Primer Sequences

Target Saprophyte organisms were identified by a literature search onychomycosis etiology, and nail cultures. To assess the culture data, >17,000 consecutively accessioned culture-positive cases were reviewed. Gene sequences for target organisms were identified using the National Center for Biotechnology Information (NCBI) database and Basic Local Alignment Search Tool (BLAST®) "nucleotide blast" (nt/nr) query.

A database of rRNA consensus sequences for target organisms was constructed using Geneious® software, version 7.1.6. Regions of within the ITS1 and ITS2 sequences of the 18S rRNA gene are highly varied among target saprophytes and target regions for forward and reverse primer sequences were identified by assessing unique regions among the targeted organisms that were dissimilar to non-targeted organisms.

Saprophyte genera primer sequences are shown in Table 57.

TABLE 57

| Target | Forward primer | Reverse primer |
|---|---|---|
| *Acremonium* | CGT CAT TTC AAC CCT CAG GAC C (SEQ ID NO: 222) | TGG GGG GTT TAA CGG CGT G (SEQ ID No: 223) |
| *Alternaria* | CCT CTC GGG GTT ACA GCC (SEQ ID NO: 224) | GTT ACT GAC GCT GAT TGC AAT TAC (SEQ ID NO: 225) |
| *Curvularia* | GCA ATC AGC GTC AGT ATA ACA AAT G (SEQ ID NO: 226) | GCT GAT TGC AAG CGC AAA AAT G (SEQ ID NO: 227) |
| *Scytalidium* | GAA GGA TCA TTA CCG AGT TGA TTC G (SEQ ID NO: 228) | TCA GAC GGC AAC GTT CAC TG (SEQ ID NO: 229) |
| *Aspergillus* | CGG AGG AAA AGA AAC CAA CC (SEQ ID NO: 230) | CGT TCC AGG GCA CTT AGA CA (SEQ ID NO: 231) |
| *Fusarium* | CGG CCA CGC CGT TAA AC (SEQ ID NO: 232) | GAT CCG AGG TCA ACA TTC AGA AG (SEQ ID NO: 233) |
| *Scopulariopsis* | GCG CGG CTA GCC CTA CG (SEQ ID NO: 234) | GGA CCG CCA CTA CAT TTC GG (SEQ ID NO: 235) |

*Acremonium* primer alignment, and target or non-target sequences are shown in FIG. 59. Alignment of genomic regions for the following organisms are shown: *Acremonium* kiliense (SEQ ID NO:124); *Aspergillus flavus* (SEQ ID NO:125); *Aspergillus terreus* (SEQ ID NO:126), *Alternaria*

*alternata* (SEQ ID NO:127); *Fusarium oxysporum* (SEQ ID NO:128); *Fusarium solani* (SEQ ID NO:129); *Scopulariopsis brevicaulis* (SEQ ID NO:130); *Scytalidium dimidiatum* (SEQ ID NO:131); *Curvularia lunata* (SEQ ID NO:132); *Chaetomium globosum* (SEQ ID NO:133); *Epicoccum purpurascens* (SEQ ID NO:134); *Paecilomyces lilacinus* (SEQ ID NO:135); *Paecilomyces variotii* (SEQ ID NO:136); and *Rhizopus oryzae* (SEQ ID NO:137).

*Alternaria* primer alignment, and target or non-target sequences are shown in FIG. 60. Alignment of genomic regions for the following organisms are shown: *Alternaria alternata* (SEQ ID NO:138); *Aspergillus flavus* (SEQ ID NO:139); *Aspergillus terreus* (SEQ ID NO:140), *Acremonium kiliense* (SEQ ID NO:141); *Fusarium oxysporum* (SEQ ID NO:142); *Fusarium solani* (SEQ ID NO:143); *Scopulariopsis brevicaulis* (SEQ ID NO:144); *Scytalidium dimidiatum* (SEQ ID NO:145); *Curvularia lunata* (SEQ ID NO:146); *Chaetomium globosum* (SEQ ID NO:147); *Epicoccum purpurascens* (SEQ ID NO:148); *Paecilomyces lilacinus* (SEQ ID NO:149); *Paecilomyces variotii* (SEQ ID NO:150); and *Rhizopus oryzae* (SEQ ID NO:151).

Figure 61A:
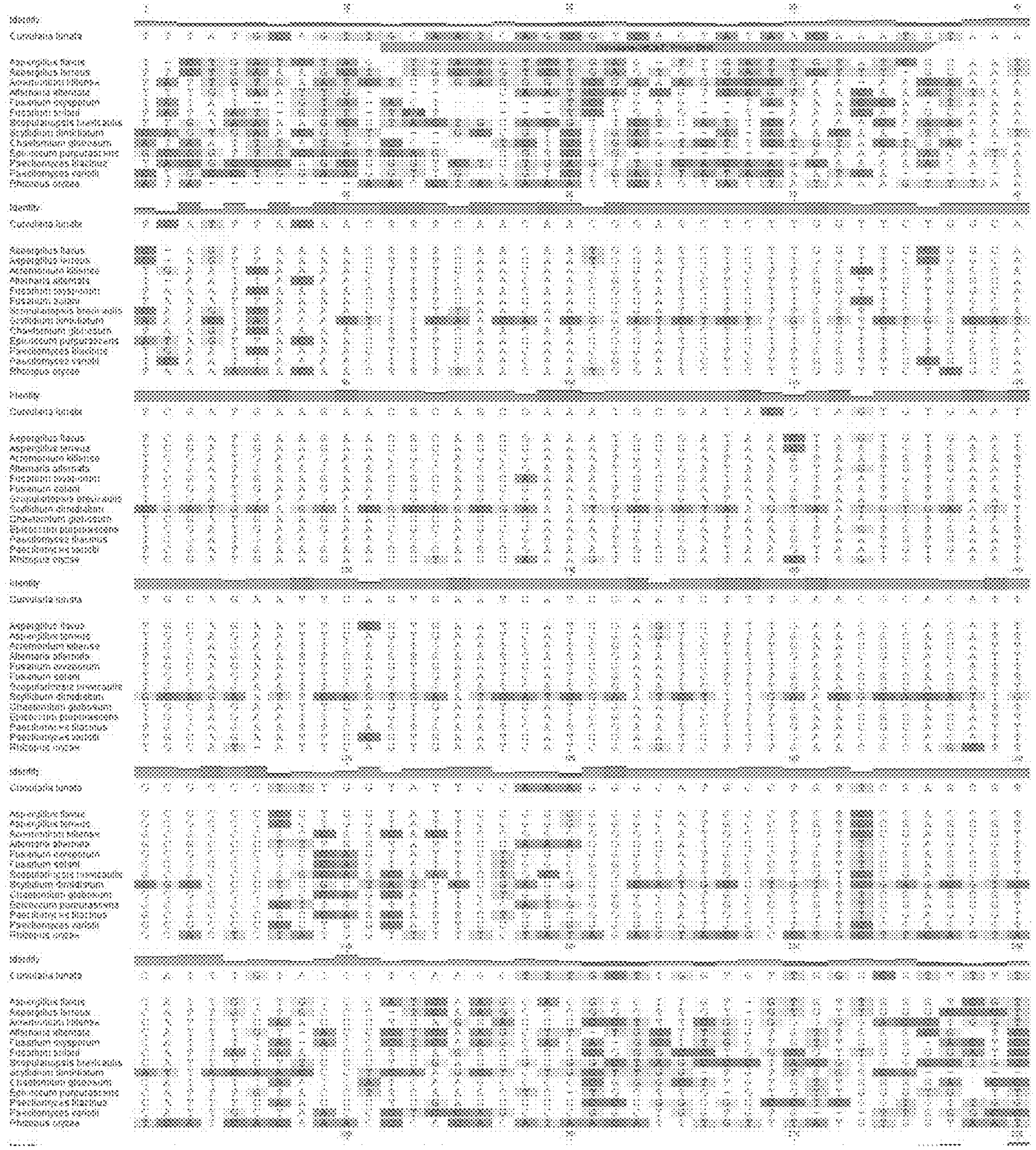

*Curvularia* primer alignment, and target or non-target sequences are shown in FIGS. 61A-61B. Alignment of genomic regions for the following organisms are shown: *Curvularia lunata* (SEQ ID NO:152); *Aspergillus flavus* (SEQ ID NO:153); *Aspergillus terreus* (SEQ ID NO:154), *Acremonium* kiliense (SEQ ID NO:155); *Alternaria alternata* (SEQ ID NO:156); *Fusarium oxysporum* (SEQ ID NO:157); *Fusarium solani* (SEQ ID NO:158); *Scopulariopsis brevicaulis* (SEQ ID NO:159); *Scytalidium dimidiatum* (SEQ ID NO:160); *Chaetomium globosum* (SEQ ID NO:161); *Epicoccum purpurascens* (SEQ ID NO:162); *Paecilomyces lilacinus* (SEQ ID NO:163); *Paecilomyces variotii* (SEQ ID NO:164); and *Rhizopus oryzae* (SEQ ID NO:165).

*Scytalidium* primer alignment, and target or non-target sequences are shown in FIG. 62. Alignment of genomic regions for the following organisms are shown: *Scytalidium dimidiatum* (SEQ ID NO:166); *Aspergillus flavus* (SEQ ID NO:167); *Aspergillus terreus* (SEQ ID NO:168), *Acremonium kiliense* (SEQ ID NO:169); *Alternaria alternata* (SEQ ID NO:170); *Fusarium oxysporum* (SEQ ID NO:171); *Fusarium solani* (SEQ ID NO:172); *Scopulariopsis brevicaulis* (SEQ ID NO:173); *Curvularia lunata* (SEQ ID NO:174); *Chaetomium globosum* (SEQ ID NO:175); *Epicoccum purpurascens* (SEQ ID NO:176); *Paecilomyces lilacinus* (SEQ ID NO:177); *Paecilomyces variotii* (SEQ ID NO:178); and *Rhizopus oryzae* (SEQ ID NO:179).

*Aspergillus* primer alignment, and target or non-target sequences are shown in FIG. 63. Alignment of genomic regions for the following organisms are shown: *Aspergillus flavus* (SEQ ID NO:180); *Aspergillus terreus* (SEQ ID NO:181), *Acremonium kiliense* (SEQ ID NO:182); *Alternaria alternata* (SEQ ID NO:183); *Fusarium oxysporum* (SEQ ID NO:184); *Fusarium solani* (SEQ ID NO:185); *Scopulariopsis brevicaulis* (SEQ ID NO:186); *Scytalidium dimidiatum* (SEQ ID NO:187); *Curvularia lunata* (SEQ ID NO:188); *Chaetomium globosum* (SEQ ID NO:189); *Epicoccum purpurascens* (SEQ ID NO:190); *Paecilomyces lilacinus* (SEQ ID NO:191); *Paecilomyces variotii* (SEQ ID NO:192); and *Rhizopus oryzae* (SEQ ID NO:193).

*Fusarium* primer alignment, and target or non-target sequences are shown in FIG. 64. Alignment of genomic regions for the following organisms are shown: *Fusarium oxysporum* (SEQ ID NO:194); *Fusarium solani* (SEQ ID NO:195); *Aspergillus flavus* (SEQ ID NO:196); *Aspergillus terreus* (SEQ ID NO:197), *Acremonium kiliense* (SEQ ID NO:198); *Alternaria alternata* (SEQ ID NO:199); *Scopulariopsis brevicaulis* (SEQ ID NO:200); *Scytalidium dimidiatum* (SEQ ID NO:201); *Curvularia lunata* (SEQ ID NO:202); *Chaetomium globosum* (SEQ ID NO:203); *Epicoccum purpurascens* (SEQ ID NO:204); *Paecilomyces lilacinus* (SEQ ID NO:205); *Paecilomyces variotii* (SEQ ID NO:206); and *Rhizopus oryzae* (SEQ ID NO:207).

*Scopulariopsis* primer alignment, and target or non-target sequences are shown in FIG. 65. Alignment of genomic regions for the following organisms are shown: *Scopulariopsis* brevicaulis (SEQ ID NO:208); *Aspergillus flavus* (SEQ ID NO:209); *Aspergillus terreus* (SEQ ID NO:210), *Acremonium kiliense* (SEQ ID NO:211); *Alternaria alternata* (SEQ ID NO:212); *Fusarium oxysporum* (SEQ ID NO:213); *Fusarium solani* (SEQ ID NO:214); *Scytalidium dimidiatum* (SEQ ID NO:215); *Curvularia lunata* (SEQ ID NO:216); *Chaetomium globosum* (SEQ ID NO:217); *Epicoccum purpurascens* (SEQ ID NO:218); *Paecilomyces lilacinus* (SEQ ID NO:219); *Paecilomyces variotii* (SEQ ID NO:220); and *Rhizopus oryzae* (SEQ ID NO:221).

II. Procedures

Specimen Collection, Specimen Grossing, and DNA Extraction and Purification were performed as described for the "Fungal Detection by PCR" (Example 1). DNA from the same preparation used in screening for saprophytes was used for Saprophyte genus or species identification.

Descriptions of Controls.

Extraction Control/Inhibition Control (EC/IC): EC/IC was used as a Lysis control. A gBlock® of *S. pombe* citrate synthase gene was added to all samples prior to cell lysis and detected in a separate PCR reaction. As the analysis of inhibition was performed as part of the "Fungal Detection by PCR" (Example 1), and the absence of inhibition was confirmed, this analysis was not repeated for the "Saprophyte Identification by PCR" Assay.

Reagent Blank (RB): RB was used as a Negative Control. RBs were processed with each extraction batch and included in PCR analysis. Each RB includes EC/IC template DNA and were used to monitor for potential contamination introduced during the extraction process, and assessed for EC/IC.

PCR Positive Control (CTL): DNA extracted and purified from *Aspergillus* (ATCC), *Acremonium* (In-House), *Alternaria* (In-House), *Fusarium* (In-House), *Scopulariopsis* (In-House) *Scytalidium* (In-House) or *Curvularia* (In-House), or a gBlock® fragment of the region of the rRNA gene corresponding to each specific primer set was included for each run as positive controls.

No template control (NTC): The NTC was used as a Reagent Contamination Control. NTC was included for each PCR Master Mix preparation, where molecular grade water is included with no nucleic acid template. NTC samples were used to monitor for PCR artifacts (such as primer dimers) and potential contamination.

Polymerase Chain Reaction (PCR).

Real-Time detection was utilized with fluorescent intercalating dye (SYBR® Green) to detect the presence of target organisms. Two primer cocktails were designed to specifically amplify DNA from targeted Saprophytes. Four saprophyte species (*Acremonium, Alternaria, Curvularia, Scytalidium*) were detected by the SapA cocktail and three saprophyte species (*Aspergillus, Fusarium, Scopulariopsis*) were detected by the SapB cocktail.

Results Interpretation.

The assay was designed such that the melting temperature (Tm) of the resulting PCR product was used to distinguish the organisms. Life Technologies' 7500 Software v2.3 was used for data acquisition. Both the 7500 Software v2.3, and High Resolution melting (FIRM) Software V2.0.1, together with custom data analysis software engine assessed the validity of the assay controls and generated results for each sample.

The interpretive algorithm considered the Ct value, then evaluated the Tm value(s) for those reaction(s) considered positive by the Ct value assessment. Ct values above threshold are considered "Not Detected." The Ct threshold ranges from 28.5-33 cycles, depending upon the species. Tm values for samples with a high Ct are non-specific and therefore no statistics are calculated when the Ct is above the stated threshold value.

Tm1 and Tm2 were both utilized for identification.

All samples analyzed were previously tested as saprophyte-positive by "Fungal Detection by PCR" (Example 1), therefore no further PCR inhibition testing was performed.

III. Validation

Specificity

Primer Cross Reactivity

Fungal/Yeast Cross Reactivity Design: DNA isolated from 36 individual fungal or yeast cultures were each tested using the "Saprophyte Identification by PCR" Assay. The identities of cultures were confirmed by DNA sequencing.

Fungal/Yeast Cross Reactivity Results are shown in Table 58 in FIG. 66. Each of the seven targeted saprophyte genera (11 strains) were tested and identified correctly, while the following were not detected: seven (9 strains); three Dermatophyte genera (8 strains) and 8 non-targeted saprophytes.

These data demonstrate that the primer design, PCR conditions and application of the interpretive algorithm correctly identified the four target dermatophytes. Cross reactivity of these primers with *Candida* and saprophytic fungi was not observed. Weak cross reactivity with other Dermatophytes was detected, however these species are rare in human onychomycosis.

Negative Controls

Negative Control Design: Reagent Blank (RB) and No Template Control (NTC) results were monitored throughout the study to assess their intended performance.

Reagent Blank Results are shown in Table 59 in FIG. 67. No amplification was observed before assay threshold Ct value of 28.5 (SapA) or 30 (SapB). No replicate had a Ct and Tm profile matching any saprophyte of interest (see "Inter-assay Reproducibility" for Tm ranges).

No Template Control are shown in Table 60 in FIG. 68. No amplification was observed before assay threshold Ct value of 28.5 (SapA) or 30 (SapB). No replicate had a Ct and Tm profile matching any saprophyte of interest (see "Inter-assay Reproducibility" for Tm ranges).

Results from the negative controls show that no contamination resulted from the extraction process, as indicated by negative results in the RB samples; the PCR set-up process did not contribute to assay contamination, as indicated by negative results in the NTC samples; and no PCR artifacts were observed, as indicated by negative results in the NTC samples.

Bacterial Cross Reactivity and Interference

Bacterial Cross Reactivity and Interference Design: To test for cross reactivity, bacterial DNA from species commonly found in nails were tested by the "Saprophyte Identification by PCR" Assay (Example 1). To assess the effect of bacterial DNA interference on saprophyte identification by PCR, bacterial DNA was mixed with saprophyte DNA and tested with the "Saprophyte Identification by PCR" Assay. Five bacterial organisms, tested in duplicate at two concentrations, 2 ng and 0.2 ng: *P. aeruginosa* (ATCC Cat #90270-5, lot 58304262); *P. mirabilus* (ATCC Cat #12453D, lot 3573174); *S. aureus* (ATCC Cat #BAA-17170-5, lot 61274435); *S. marcences* (ATCC Cat #27137D-5, lot 59679187); *S. pyogenese* (ATCC Cat #BAA1063D-5, lot 57907321).

Bacterial Cross Reactivity and Interference Results are shown in Table 61 in FIG. 69. In Bacterial DNA only samples, no cross-reactivity with saprophyte primers was observed, except for weak amplification of *S. marcences* with a *Scytalidium* melt profile; no amplification was observed before assay threshold Ct value of 28.5 (SapA) or 30 (SapB); and no replicates had a Ct and Tm profile matching a saprophyte identified by the assay (see "Inter-assay Reproducibility" for Tm ranges).

In the Saprophyte DNA+Bacterial DNA samples, minimal interference by bacterial DNA was observed for saprophyte targets. All seven targeted organisms were detected at 2.0 and 0.2 ng/Rxn.

These results indicated that the five common pathogenic bacteria do not cross react or interfere with the assay at the indicated bacterial copy numbers.

Human Genomic DNA Cross Reactivity and Interference

Human Genomic DNA Cross Reactivity and Interference Design: Human genomic DNA (hgDNA) is likely to be purified from the nail specimen concurrently with dermatophyte DNA. Pure hgDNA was tested at least seven times with the "Saprophyte Identification by PCR" Assay to assess interference and cross reactivity with the assay.

Stock DNA (Roche, Cat #1169112001, lot 14897020; 200 ng/μL) was diluted to two concentrations; 2, and 0.2 ng/μL. Each concentration was tested in at least seven times. 2 μL DNA was added per PCR reaction.

DNA concentrations were determined using a NanoDrop® for >400 extracted nail samples, with a range of <0.1 to <100 ng/μL. 62.6% of samples had a DNA concentration <6.0 ng/μL. The precise mix of human:saprophyte DNA was not determined for any sample. A tested range of 0.2-2 ng/μL human genomic DNA was representative of the sample set.

Copy numbers of hgDNA were calculated based on the human genome size and DNA concentration tested.

Human Genomic DNA Cross Reactivity and Interference Results are shown in Table 62 in FIG. 70.

In hgDNA samples, minimal cross-reactivity with saprophyte primers was observed. No amplification was observed before assay threshold Ct value of 28.5 (SapA) or 30 (SapB). For each organism no replicates had a Ct and Tm profile matching any saprophyte organisms of interest (see "Inter-assay Reproducibility" for Tm ranges).

In Saprophyte DNA+human DNA samples, minimal interference by hgDNA was observed in the presence of saprophyte targets. All seven targeted organisms were detected at 2.0 and 0.2 ng/Rxn.

These results indicated that hgDNA did not cross react or interfere with the assay at the indicated copy numbers of hgDNA.

Sensitivity

Sensitivity Design: DNA was isolated from culture for *Acremonium, Alternaria, Aspergillus, Curvularia, Fusarium, Scopulariopsis, Scytlaidium*. Each was tested using the "Saprophyte Identification by PCR" Assay. The identity of each culture was confirmed by DNA sequencing.

Quantification: The sensitivity for this assay was expressed as ng of purified DNA per PCR reaction. Concentrations were standardized to 20 ng/μL and serial dilutions were performed using pooled extract from Negative Nail specimens and tested by PCR. The Copy #at the LOD was calculated for each organism by dividing the quantity (ng) by the diploid C value (www(dot)zbi(dot)ee/fungal-genomicsize/) and rounded to two significant figures.

The quantity of synthesized DNA solution (ng/μL), and the molecular weight were used to determine the final copy number in the stock concentration.

Sensitivity Results are shown in Table 63 in FIG. 71.

Limit of Detection (LOD) was determined as the lowest DNA quantity giving 100% positivity for the indicated organism. At least ten replicates were tested to confirm the LOD for each organism.

For this assay, sensitivity was determined to range from 9 to 156 copies, depending upon the saprophyte studied. The detection correlation between the "Fungal Detection by PCR" (Example 1) and the "Saprophyte Identification by PCR" Assay is 89.8% (Table 73 in FIG. 81). The "Fungal Detection by PCR" (Example 1) was validated by comparing PCR results to those of culture and histology.

Inter-Assay Reproducibility

Inter-assay Reproducibility Design: For each run, seven positive PCR controls were used. PCR was performed in 94 runs over 103 days to assess the inter-assay reproducibility. 75 of 94 runs are shown. Ct values of both Saprophyte PCR reactions are shown. The Tm values are only shown for the Saprophyte PCR reaction that detected the indicated target (SapA: *Acremonium, Alternaria, Scytalidium, Curvularia* or SapB: *Aspergillus, Fusarium, Scopulariopsis*). All controls used DNA extracted and purified from culture.

Acceptance criteria was Ct and Tm values within 3 StdDev from the mean (shown for each organism) and CV %<5.0 for the detecting PCR reaction (SapA or SapB).

Inter-assay Reproducibility Results for *Acremonium* Control (Sap2R CTL) are shown in Table 64 in FIG. 72. *Acremonium* (In-House) was used as template. Acceptance criteria was SapA Ct 16.0-19.1; SapA Tm1 82.36-83.97. Results were: a) Ct value range:16.3-18.9; b) Tm1 value range: 82.54-83.79° C.; c) 75/75 demonstrated results consistent with *Acremonium.*

Inter-assay Reproducibility Results for *Alternaria* Control (Sap3R CTL) are shown in Table 65 in FIG. 73. Acceptance criteria was SapA Ct 17.9-19.7; SapA Tm1 75.44-76.88° C. Results were: a) Ct value range: 17.6-19.6; b) Tm1 value range: 75.46-76.61° C.; c) 75/75 demonstrated results consistent with *Alternaria.*

Inter-assay Reproducibility Results for *Scytalidium* Control (Sap7R CTL) are shown in Table 66 in FIG. 74. Acceptance criteria was SapA Ct 18.1-22.3; SapA Tm1 84.70-85.75° C. Results were: a) Ct value range: 18.8-21.6; b) Tm1 value range: 84.60-85.97° C.; c) 75/75 demonstrated results consistent with *Scytalidium.*

Inter-assay Reproducibility Results for *Curvularia* Control (Sap8R CTL) are shown in Table 67 in FIG. 75. in Acceptance criteria SapA Ct 17.2-21.0; SapA Tm1 78.79-80.59° C. Results were: a) Ct value range: 17.4-20.2; b) Tm1 value range: 78.99-80.46° C.; c) 75/75 demonstrated results consistent with *Curvularia.*

Inter-assay Reproducibility Results for *Aspergillus* Control (Sap1R CTL) are shown in Table 68 in FIG. 76. Acceptance criteria was SapB Ct 15.6-20.0; SapB Tm1 79.09-80.54° C. Results were: a) Ct value range: 16.8-20.6; b) Tm1 value range: 79.24-80.54° C.; c) 75/75 demonstrated results consistent with *Aspergillus.*

Inter-assay Reproducibility Results for *Fusarium* Control (Sap4R CTL) are shown in Table 69 in FIG. 77. Acceptance criteria was SapB Ct 19.7-26.6; SapB Tm1 72.17-74.50° C. Results were: a) Ct value range: 20.8-25.2; b) Tm1 value range: 72.33-74.08° C.; c) 75/75 demonstrated results consistent with *Fusarium.*

Inter-assay Reproducibility Results for *Scopulariopsis* Control (Sap6R CTL) are shown in Table 70 in FIG. 78. Acceptance criteria SapB Ct 18.2-21.0; SapB Tm1 83.31-85.43° C. Results were: a) Ct value range: 18.4-20.8; b) Tm1 value range: 83.41-85.02° C.; c) 75/75 demonstrated results consistent with *Scopulariopsis.*

The inter-assay reproducibility as seen with all seven positive controls was within the range of CV %<5.0 for both the Ct and Tm values.

Intra-Assay Repeatability 198 negative nail specimens, spiked with one of three different concentration sources of either *Acremonium, Alternaria, Aspergillus, Curvularia, Fusarium, Mucor, Paecilomyces, Penicillium, Rhizopus, Scopulariopsis*, or *Scytalidium* DNA prior to extraction, each prepared in triplicate and tested on each of two runs for a total of six replicates per level. As negative controls, three samples were prepared with negative nail specimens in the absence of saprophyte DNA.

Intra-Assay Repeatability Results are shown in Table 71 in FIG. 79.

Negative result detection was 100% repeatable (75/75 Not Detected).

*Acremonium* detection was 100% repeatable. 18/18 reactions with *Acremonium*-positive samples gave positive results when assayed for *Acremonium.*

*Alternaria* detection was 100% repeatable. 18/18 reactions with *Alternaria*-positive samples gave positive when assayed for *Alternaria.*

*Aspergillus* detection was 100% repeatable. 18/18 reactions with *Aspergillus*-positive samples gave positive results when assayed for *Aspergillus.*

*Curvularia* detection was 100% repeatable. 18/18 reactions with *Curvularia*-positive samples gave positive results when assayed for *Curvularia.*

*Fusarium* detection was 94.4% repeatable. 17/18 reactions with *Fusarium*-positive samples gave positive when assayed for *Fusarium.*

*Scopulariopsis* detection was 100% repeatable. 18/18 reactions with *Scopulariopsis*-positive samples gave positive results when assayed for *Scopulariopsis.*

*Scytalidium* detection was 100% repeatable. 18/18 reactions with *Scytalidium*-positive samples gave positive results when assayed for *Scytalidium.*

Inter- and Intra-Assay Variability Summary

Runs included in the validation study are summarized in Table 72 in FIG. 80.

Variability in extraction was tested for DNA purified from samples in 51 batches over 120 days and by two different analysts and on two different instruments.

Variability in PCR was tested in 103 batches over 103 days, by four different analysts and on six different instruments.

As summarized in Table 64 in FIG. 72, Table 65 in FIG. 73, Table 66 in FIG. 74, Table 67 in FIG. 75, Table 68 in FIG. 76, Table 69 in FIG. 77, and Table 70 in FIG. 78, all CTL samples performed equivalently, regardless of operator or instrument.

Accuracy

Design for Accuracy Determination.

Saprophyte positive and negative specimens previously analyzed as part of "Fungal Detection by PCR (Example 1) validation were used to confirm the accuracy of the "Saprophyte Identification by PCR" Assay. The "Fungal Detection by PCR" (Example 1) validation included assessment of histology results. The identity of the organism present in each saprophyte-positive specimen was determined by DNA Sequence analysis.

Correlation with "Fungal Detection by PCR" (Example 1) is shown in Table 73 in FIG. 81. The results included 1414 clinical specimens.

Previous In-House culture data (>17,000 consecutive culture accessions) suggested that 73.1% of samples containing a Saprophyte detectable with the "Fungal Detection by PCR" (Fungal Screen Assay, Example 1) contain a Saprophyte detectable with "Saprophyte Identification by PCR" ("Saprophyte Reflex Assay"). Therefore, the overall sensitivity of the Saprophyte Reflex Assay (when compared to Saprophyte detection with the Fungal Screen Assay) is estimated at 73±10%.

"Spiked" samples were prepared 1) to increase the total number of positive samples to >30 per organism for "Saprophyte Identification by PCR" ("Reflex Assay") vs. DNA Sequencing correlation studies (Table 74, in FIGS. 82A-82B to Table 81 in FIGS. 83) and 2) for the Inter-assay Intra-Assay Repeatability.

Samples that were not included in Table 73 in FIG. 81 include: a) Samples with a Fungal Detection Assay result of Saprophyte Detected, plus either *Candida* or Dermatophyte Detected, and with sequencing results corresponding to the *Candida* or Dermatophyte result, as sequencing results are unreliable for multiple targets; and b) "Spiked" sample results (100% of the 400 spiked samples gave the expected results for both the Fungal Screen and Saprophyte Reflex Assays).

Detection of saprophytes by the "Fungal Detection by PCR" (Example 1) and the "Saprophyte Identification by PCR" ("Reflex Assay") were similar, as indicated in Table 73 in FIG. 81 by concordance of 89.8%, sensitivity of 74.9% and specificity of 96.2%. Acceptance criteria was >86.0% concordance. The identification rate (positive for both "Fungal Detection by PCR" and "Saprophyte Identification by PCR") was 74.4%. It was concluded that 75% of saprophytes detected by "Fungal Detection by PCR" will be identified with "Saprophyte Identification by PCR".

Saprophyte genus/species identification correlation

Design: "Positive" specimens were generated by spiking DNA with normal nails prior to sample lysis and extraction. Origin of sequence-positive specimens were 145 clinical and 30 "spiked, samples for *Aspergillus;* 11 clinical and 38 "spiked" samples for *Acremonium;* 10 clinical and 42 "spiked" samples for *Alternaria;* 102 clinical and 34 "spiked" samples for *Fusarium;* 15 clinical and 39 "spiked" samples for *Scopulariopsis;* 15 clinical and 29 "spiked" samples for *Scytalidium*; and 1 clinical and 48 "spiked" samples for *Curvularia.*

Only specimens positive for a saprophyte, either by Sequencing or with the "Fungal Detection by PCR" (Example 1); positive for "Saprophyte Identification by PCR" for only one organism, and had conclusive sequencing results for a saprophyte were included in the Identification Correlation study results. Samples with dual infections of a saprophyte and either *Candida* or a Dermatophyte, where the sequence result confirmed a *Candida* or dermatophyte PCR result, were excluded. Values indicated as Sequencing-negative for an organism were the number of samples which were positive for another saprophyte within the same PCR reaction (SapA or SapB). Spiked samples were considered Sequencing positive, as the DNA spiked in prior to extraction had previously been sequenced. Sequencing was not repeated following spiking and extraction.

Table 81 in FIG. 83 summarizes the overall detection for the seven organisms targeted by the "Saprophyte Identification by PCR" ("Saprophyte Reflex Assay"). This sample set included those where a saprophyte was detected by the "Fungal Detection by PCR" ("Fungal Screening Assay"; Example 1), including 578 positive for any one of the seven organisms and 145 samples positive for a saprophyte NOT detected by the Fungal Reflex Assay. Results were confirmed by sequencing.

Saprophyte Identification Correlation Results are shown in FIGS. 82A-82B, in Table 74 for *Acremonium*; in Table 75 for *Alternaria*; in Table 76 for *Scytalidium*; in Table 77 *Curvularia*; in Table 78 for *Aspergillus*; in Table 79 for *Fusarium*; and in Table 80 for *Scopulariopsis.*

Results of the Saprophyte Identification by PCR accuracy assessment demonstrated that the PCR method developed for identification of saprophytes in human nails gave accurate results.

Example 7

Report Showing the Results of a Fungal Detection Assay (Example 1) and Saprophyte Identification Assay (Example 3)

Results of an assay for screening and identification of an onychomycotic fungal infection in a sample, as described in Examples 1 and 6, can be provided in a report, indicating the presence or absence of *Candida*, dermatophyte, or saprophyte, and/or the presence or absence of an *Acremonium* species, *Alternaria* species, *Aspergillus* species, *Curvularia* species, *Fusarium* species, *Scopulariopsis* species and a *Scytalidium* species in the sample. Examples of such a report are provided in FIGS. 84A-84C.

Example 8

Evaluation of Fungal Detection by Real-Time PCR Results Using Sequencing

DNA from 2,841 and 1,659 clinical samples were analyzed by the Fungal detection by real-time PCR (Example 1) by sequencing with respect to histopathology results. The results were divided into groups by a Ct cutoff value of <28 (458, 28% of total) and >28 (1201, 72% of total).

Figure 85:
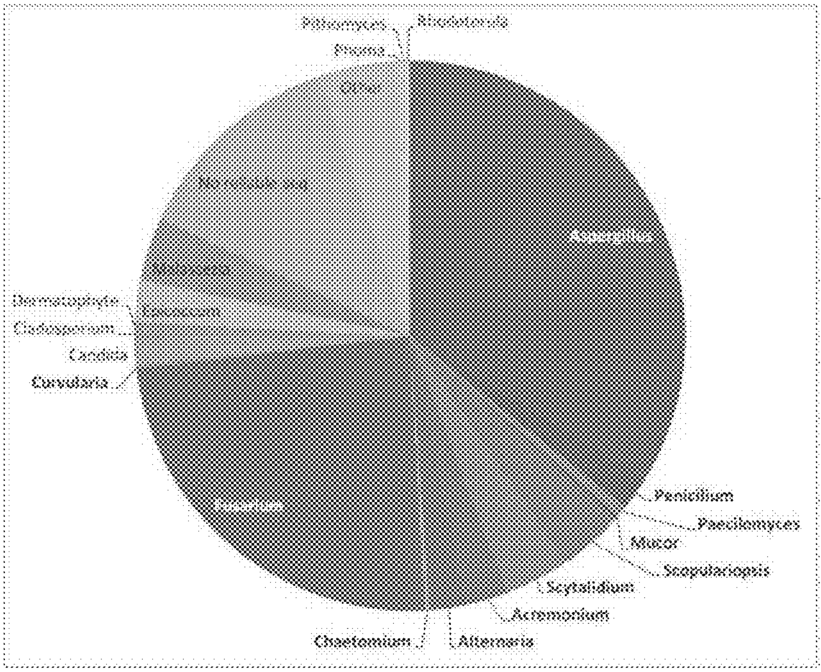
FIG. 85 is a collection of graphs and tables showing fungal organisms identified by sequencing nucleic acids in samples that had cycle threshold (Ct) values less than a cutoff value of 28 cycles when saprophyte secondary clade-specific primers were used during real time PCR, according to embodiments of the present disclosure.

FIG. 85 shows the sequencing result distribution for the samples with cutoff <28 cycles. Organisms targeted by the saprophyte panel are indicated in bold type on the graph. Seventy one percent of organisms from this group sequenced as saprophytes on the saprophyte screen panel, while 16.4% sequenced as organisms not targeted by the saprophyte screen panel.

Figure 86:
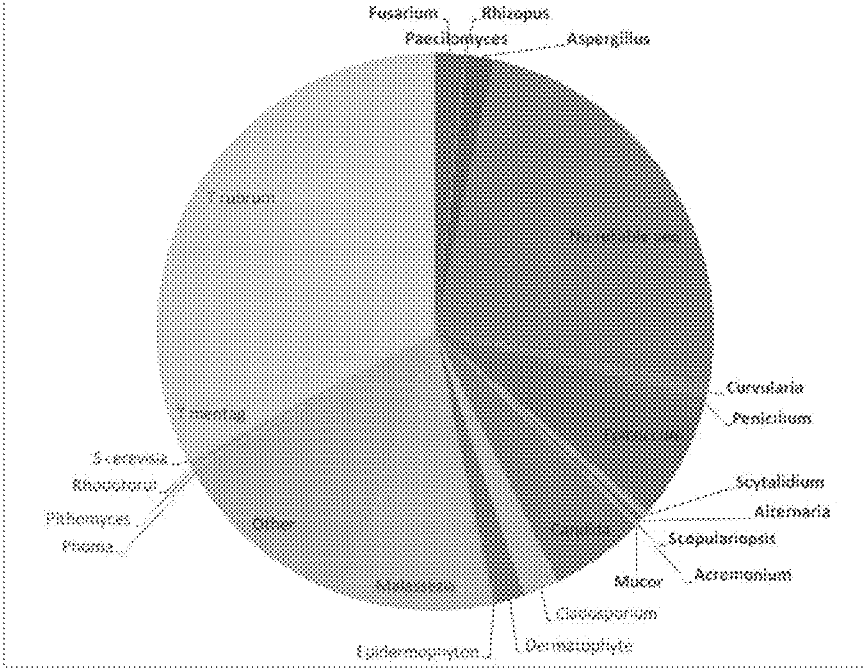
FIG. 86 is a collection of graphs and tables showing fungal organisms identified by sequencing nucleic acids in samples that had cycle threshold (Ct) values greater than a cutoff value of 28 cycles, when saprophyte secondary clade-specific primers were used during real time PCR, according to embodiments of the present disclosure.

FIG. 86 shows the sequencing result distribution for the samples with cutoff >28 cycles. Organisms targeted by the saprophyte panel are indicated in bold type on the graph. Only 5.9% of organisms from this group sequenced as saprophytes targeted by the saprophyte screen panel while 69.5% that sequenced were not targeted by the panel.

These results indicate a majority of the saprophytes germane to this assay are detected at a Ct of <28.

Notwithstanding the appended claims, aspects of the present disclosure may be defined by the following clauses.

1. A method of detecting an onychomycotic fungus in a sample, wherein the onychomycotic fungus belongs to a secondary clade member comprising one or more primary clade members, the method comprising:

i) screening a sample using a first and second sets of secondary clade-specific primers to determine whether a secondary clade member among a plurality of secondary clade members is present or absent in the sample, wherein the plurality of secondary clade members comprises:

(a) a dermatophyte;

(b) a *candida*; and (c) a saprophyte; and ii) after determining that the secondary clade member is present in the sample, screening the sample to determine whether an onychomycotic fungus is present or absent in the sample using primary clade-specific primers that are specific to a primary clade member that belongs to the secondary clade member.

2. The method of clause 1, wherein the screening step i) comprises:

performing a first polymerase chain reaction (PCR) using the first set of secondary clade-specific primers in a first reaction mixture; and performing a second PCR using the second set of secondary clade-specific primers in a second reaction mixture.

3. The method of clause 1 or 2, wherein the first and second sets of secondary clade-specific primers each comprise a primer pair that amplifies a secondary clade-specific nucleotide sequence within a nuclear-encoded ribosomal RNA (rRNA) gene.

4. The method of clause 3, wherein the secondary clade-specific nucleotide sequence encodes:

an 18S ribosomal RNA, or a portion thereof;

a 5.8S rRNA, or a portion thereof;

a 28S rRNA, or a portion thereof; or an internal transcribed spacer (ITS), or a portion thereof, adjacent the 18S, 5.8S or 28S rRNA in the nuclear-encoded rRNA gene.

5. The method of clause 4, wherein the secondary clade-specific nucleotide sequence encodes:

the 18S ribosomal RNA, or a portion thereof; or the ITS, or a portion thereof, adjacent the 18S rRNA.

6. The method of any one of clauses 1 to 5, wherein the first set of one or more secondary clade-specific primers comprises one or more primer pairs that amplify one or more nucleotide sequences 80% or more identical to a sequence selected from the group consisting of the sequences set forth in SEQ ID NOs:108 and 109, and wherein the second set of one or more secondary clade-specific primers comprises one or more primer pairs that amplify one or more nucleotide sequences 80% or more identical to a sequence selected from the group consisting of the sequences set forth in SEQ ID NOs: 110, 111, 112, 113 and 246.

7. The method of any one of clauses 1 to 6, wherein the screening step i) comprises:

i-1) performing a first real-time PCR using the first set of secondary clade-specific primers to obtain a first cycle threshold (Ct) value ($Ct_1$);

i-2) performing a second real-time PCR using the second set of secondary clade-specific primers to obtain a second Ct value ($Ct_2$); and i-3) analyzing the obtained first and second Ct values to determine whether a secondary clade member is present or absent.

8. The method of clause 7, wherein the first set of secondary clade-specific primers is specific for a first set of one or more secondary clade members, and the second set of one or more secondary clade-specific primers is specific for a second set of one or more secondary clade members, wherein the first and second sets of one or more secondary clade members are different sets, and wherein the analyzing step i-3) comprises determining that the sample comprises or does not comprise a secondary clade member that belongs to a set among the first and second sets of one or more secondary clade members, based on:

a comparison between $Ct_1$ and a first cutoff Ct value ($Ct_{cutoff2}$);

a comparison between $Ct_2$ and a second cutoff Ct value ($Ct_{cutoff2}$); and/or a difference between $Ct_1$ and $Ct_2$.

9. The method of clause 8, wherein the determining step comprises, when $Ct_1$ is below $Ct_{cutoff2}$ and $Ct_2$ is below $Ct_{cutoff2}$:

calculating $\Delta Ct_{2-1}=Ct_2-Ct_1$;

comparing $\Delta Ct_{2-1}$ with a reference Ct range ($\Delta Ct_{range}$) defining an upper limit and a lower limit; and determining that:

the first but not the second set of one or more secondary clade members is present, when $\Delta Ct_{2-1}$ is greater than the upper limit of $\Delta Ct_{range}$;

the second but not the first set of one or more secondary clade members is present, when $\Delta Ct_{2-1}$ is lower than the lower limit of $\Delta Ct_{range}$; and the first and the second sets of one or more secondary clade members are present, when $\Delta Ct_{2-1}$ is within $\Delta Ct_{range}$.

10. The method of clause 8, wherein the determining step comprises:

determining that:

the first but not the second set of one or more secondary clade members is present, when $Ct_1$ is below $Ct_{cutoff1}$ and $Ct_2$ is above $Ct_{cutoff2}$;

the second but not the first set of one or more secondary clade members is present, when $Ct_1$ is above $Ct_{cutoff1}$ and $Ct_2$ is below $Ct_{cutoff2}$; and the first and the second sets of one or more secondary clade members are absent, when $Ct_1$ is above $Ct_{cutoff1}$ and $Ct_2$ is above $Ct_{cutoff2}$.

11. The method of any of clauses 8 to 10, wherein the analyzing step i-3) further comprises:

obtaining one or more first melting temperature (Tm) values for a reaction product of the real-time PCR performed using the set of secondary clade-specific primers specific for the identified set of one or more secondary clade members; and after determining that the set of one or more secondary clade members to which the secondary clade member belongs is present in the sample, determining whether a secondary clade member is present or absent in the sample based on the obtained one or more first Tm values.

12. The method of clause 11, wherein determining whether a secondary clade member is present or absent in the sample based on the obtained one or more first Tm values comprises comparing the obtained one or more first Tm values with one or more reference Tm ranges specific for secondary clade members belonging to the identified set of one or more secondary clade members, wherein the secondary clade member is determined to be present in the sample when the one of more first Tm values is within the one or more reference Tm ranges specific for the secondary clade member.

13. The method of clause 11 or 12, wherein the analyzing step i-3) comprises:

obtaining two or more first Tm values for a reaction product of the real-time PCR performed using the set of secondary clade-specific primers specific for the identified set of one or more secondary clade members; and after determining that the set of one or more secondary clade members to which the secondary clade member belongs is present in the sample, determining whether a secondary clade member is present or absent in the sample based on a comparison between the difference between two of the two or more first Tm values (ΔTm) and a reference Tm difference range, wherein the secondary clade member is determined to be present in the sample when the ΔTm is within the reference Tm difference range.

14. The method of any one of clauses 11 to 13, wherein the obtaining one or more first Tm values comprises using high resolution melt analysis.

15. The method of clauses 11 to 14, wherein the obtaining one or more first Tm values comprises obtaining the Tm value of a hybridization between the reaction product and a clade-specific hybridization probe configured to hybridize to the reaction product.

16. The method of any one of clauses 1 to 15, wherein the plurality of secondary clade members comprises a plurality of saprophyte secondary clade members.

17. The method of clause 16, wherein the first set of one or more secondary clade members comprises a dermatophyte and a *candida*, and the second set of one or more secondary clade members comprises the plurality of saprophyte secondary clade members.

18. The method of any of clauses 1 to 17, wherein the primary clade-specific primers comprise one or more primer pairs configured to amplify a nucleotide sequence within a nuclear-encoded ribosomal RNA (rRNA) gene, or a mitochondrial nucleotide sequence.

19. The method of clause 18, wherein the primary clade-specific nucleotide sequence encodes:

an 18S ribosomal RNA, or a portion thereof;

a 28S ribosomal RNA, or a portion thereof;

a 5.8S ribosomal RNA or a portion there of; and/or an ITS, or a portion thereof, adjacent the 18S, 28S or 5.8S rRNA in the nuclear-encoded rRNA gene, and wherein the mitochondrial nucleotide sequence encodes a nicotinamide adenine dinucleotide (NADH) dehydrogenase subunit gene, or a portion thereof, or a putative reverse transcriptase gene, or a portion thereof.

20. The method of clause 19, wherein the primary clade-specific nucleotide sequence encodes:

the 18S ribosomal RNA, or a portion thereof; and/or the ITS, or a portion thereof, adjacent the 18S rRNA.

21. The method of any one of clauses 1 to 20, wherein the primary clade-specific primers comprise one or more primer pairs configured to amplify one or more nucleotide sequences 80% or more identical to a sequence selected from the group consisting of the sequences set forth in SEQ ID NOs:114, 115, 116, 117, 118, 119, 236, 237, 238, 239, 240, 241, and 242.

22. The method of any one of clauses 1 to 21, wherein the screening step ii) comprises performing one or more real-time PCR using the primary clade-specific primers.

23. The method of clause 22, wherein the screening step ii) further comprises obtaining:

one or more third Ct values; and one or more second Tm values; and analyzing the obtained third Ct and second Tm values to determine whether an onychomycotic fungus is present or absent in the sample.

24. The method of clause 23, wherein the onychomycotic fungus is determined to be present when the obtained one or more third Ct values fall within one or more reference Ct ranges specific for the onychomycotic fungus, and the obtained one or more second Tm values fall within one or more reference Tm ranges specific for the onychomycotic fungus.

25. The method of any one of clauses 1 to 24, wherein the sample is obtained from a human subject.

26. The method of any one of clauses 1 to 25, wherein the method further comprises preparing the sample before the screening step i).

27. The method of clause 26, wherein the preparing step comprises releasing nucleic acids from a cellular compartment in the sample by subjecting the sample to mechanical, chemical, thermal and/or enzymatic treatments.

28. A method comprising:

i) obtaining in a sample:

a first Ct value ($Ct_1$) from a first real-time PCR performed in a first reaction mixture using a first set of primers designed to amplify nucleic acid products comprising a first set of one or more nucleotide sequences; and a second Ct value ($Ct_2$) from a second real-time PCR performed in a second reaction mixture using a second set of primers designed to amplify nucleic acid products comprising a second set of one or more nucleotide sequences;

ii) determining whether a set of one or more nucleotide sequences to which a nucleic acid belongs is present or absent in the sample, based on:

a comparison between $Ct_1$ and a first cutoff Ct value ($Ct_{cutoff2}$);

a comparison between $Ct_2$ and a second cutoff Ct value ($Ct_{cutoff2}$); and/or a difference between $Ct_1$ and $Ct_2$, iii) obtaining one or more Tm values for a reaction product of the first and/or second real-time PCR performed using the set of primers designed to amplify nucleic acid products comprising the identified set of one or more nucleotide sequences; and iv) after determining that the set of one or more nucleotide sequences to which the nucleic acid belongs is present in the sample, determining whether the nucleic acid is present in the sample based on the obtained one or more Tm values.

29. The method of clause 28, wherein whether the set of one or more nucleotide sequences to which a nucleic acid belongs is present or absent in the sample is determined based on the obtained one or more Tm values comprises and one or more reference Tm ranges specific for nucleic acid products amplified by the set of primers designed to amplify nucleic acid products comprising the identified set of one or more nucleotide sequences, wherein the nucleic acid is determined to be present in the sample when the obtained one or more Tm values are within the one or more reference Tm ranges.

30. The method of clause 28 or 29, comprising:

iii) obtaining two or more Tm values for a reaction product of each of the first and/or second real-time PCR performed using the set of primers designed to amplify nucleic acid products comprising the identified set of one or more nucleotide sequences; and iv) after determining that the set of one or more nucleotide sequences to which the nucleic acid belongs is present in the sample, determining whether the nucleic acid is present in the sample based on a comparison between the difference between two of the two or more Tm values (ΔTm) and a reference Tm difference range, wherein the nucleic acid is determined to be present in the sample when the ΔTm is within the reference Tm difference range.

31. The method of any one of clauses 28 to 30, wherein the determining step ii) comprises, when $Ct_1$ is below $Ct_{cutoff1}$ and $Ct_2$ is below $Ct_{cutoff2}$:

calculating $\Delta Ct_{2-1}=Ct_2-Ct_1$;

comparing $\Delta Ct_{2-1}$ with a reference Ct range ($\Delta Ct_{range}$) defining an upper limit and a lower limit; and determining that:

the first but not the second set of one or more nucleotide sequences is present, when $\Delta Ct_{2-1}$ is greater than the upper limit of $\Delta Ct_{range}$, the second but not the first set of one or more nucleotide sequences is present, when $\Delta Ct_{2-1}$ is lower than the lower limit of $\Delta Ct_{range}$; and the first and the second sets of one or more nucleotide sequences are present, when $\Delta Ct_{2-1}$ is within $\Delta Ct_{range}$.

32. The method of clause 31, wherein the determining step ii) comprises:

determining that:

the first but not the second set of one or more nucleotide sequences is present, when $Ct_1$ is below $Ct_{cutoff1}$ and $Ct_2$ is above $Ct_{cutoff2}$;

the second but not the first set of one or more nucleotide sequences is present, when $Ct_1$ is above $Ct_{cutoff1}$ and $Ct_2$ is below $Ct_{cutoff2}$; and the first and second sets of one or more nucleotide sequences are absent, when $Ct_1$ is above $Ct_{cutoff1}$ and $Ct_2$ is above $Ct_{cutoff2}$.

33. A computer-implemented method of analyzing Ct and Tm values to determine whether a secondary clade member of an onychomycotic fungus is present or absent in a sample, the method comprising inputting, into a computer system configured to perform the method of any one of clauses 28 to 32:

a first Ct value ($Ct_1$) and one or more first Tm values from a first real-time PCR performed on a sample in a first reaction mixture using a first set of secondary-clade specific primers for a first secondary clade member; and a second Ct value ($Ct_2$) and one or more second Tm values from a second real-time PCR performed on the sample in a second reaction mixture using a second set of secondary-clade primers for a second secondary clade member, wherein the first and second secondary clade members are chosen from the group consisting of: dermatophytes, *candida*, and saprophytes, and combinations thereof, to generate a report, wherein the report indicates that a secondary clade member of an onychomycotic fungus is present or absent in the sample.

34. A computer system comprising:

a) a processor; and b) a memory operably coupled to the processor, wherein the memory includes instructions stored therein for analyzing Ct and Tm values to determine whether an onychomycotic fungus is present or absent in a sample, wherein the instructions, when executed by the processor, cause the processor to perform the method of any one of clauses 28 to 32.

35. A kit for identifying an onychomycotic fungus in a sample, wherein the onychomycotic fungus belongs to a secondary clade member comprising one or more primary clade members, the kit comprising:

primary clade-specific primers specific for one or more onychomycotic fungi; and a first and second sets of secondary clade-specific primers, wherein the first set of secondary clade-specific primers is designed to amplify a nucleotide sequence specific to one or more secondary clade members belonging to a first set of one or more secondary clade members, and wherein the second set of secondary clade-specific primers are designed to amplify a nucleotide sequence specific to one or more secondary clade members belonging to a second set of one or more secondary clade members, wherein the first and second sets of one or more secondary clade members are different sets, and wherein the first and second sets of secondary clade members collectively comprise:

(a) a dermatophyte;

(b) a *candida*; and (c) a saprophyte.

36. The kit of clause 35, wherein the first and second sets of secondary clade members comprise a plurality of saprophyte secondary clade members.

37. The kit of clause 35 or 36, wherein the first and second sets of secondary clade-specific primers comprise primers that are designed to amplify secondary clade-specific nucleotide sequences within a nuclear-encoded ribosomal RNA (rRNA) gene.

38. The kit of clause 37, wherein the secondary clade-specific nucleotide sequence encodes:

an 18S ribosomal RNA, or a portion thereof;

a 5.8S rRNA, or a portion thereof;

a 28S rRNA, or a portion thereof; and/or an internal transcribed spacer (ITS), or a portion thereof, adjacent the 18S, 5.8S or 28S rRNA in the nuclear-encoded rRNA gene.

39. The kit of clause 36, wherein the secondary clade-specific nucleotide sequence encodes:

an 18S ribosomal RNA, or a portion thereof; and/or an ITS, or a portion thereof, adjacent the 18S rRNA.

40. The kit of any one of clauses 35 to 39, wherein:

the first set of secondary clade-specific primers comprises primers that amplify one or more nucleotide sequences 80% or more identical to a sequence selected from the group consisting of the sequences set forth in SEQ ID NOs:108 and 109; and the second set of secondary clade-specific primers comprises primers that amplify one or more nucleotide sequences 80% or more identical to a sequence selected from the group consisting of the sequences set forth in SEQ ID NOs: 110, 111, 112, 113 or 246.

41. The kit of any one of clauses 35 to 40, wherein the primary clade-specific primers comprise one or more primer pairs configured to amplify a nucleotide sequence 80% or more identical to a sequence selected from the group consisting of the sequences set forth in SEQ ID NOs:114, 115, 116, 117, 118, 119, 236, 237, 238, 239, 240, 241, and 242.

42. The kit of any one of clauses 35 to 41, wherein the kit further comprises a homogenization and/or lysis buffer.

43. The kit of any one of clauses 35 to 42, wherein the kit further comprises a sample homogenization element configured to mechanically lyse the sample.

44. A composition comprising two or more pairs of primers, each pair of primers configured to amplify a target nucleotide sequence of an onychomycotic fungus that belongs to a secondary clade member comprising one or more primary clade members, wherein each primer pair is specific to a different secondary clade member, wherein the secondary clade member comprises:

(a) a dermatophyte;

(b) a *candida*; and (c) a saprophyte.

45. The composition of clause 44, further comprising a buffer.

46. The composition of clause 44 or 45, further comprising a thermostable DNA polymerase.

47. The composition of any one of clauses 44 to 46, wherein the secondary clade member comprises a plurality of saprophyte secondary clade members.

48. The composition of clause 47, wherein the composition comprises:

a dermatophyte secondary clade-specific primer pair and a *candida* secondary clade-specific primer pair; or primer pairs specific to two or more different saprophyte secondary clade members.

49. The composition of any one of clauses 44 to 48, wherein the target sequence comprises a nucleotide sequence within a nuclear-encoded ribosomal RNA (rRNA) gene.

50. The composition of clause 49, wherein the target sequence encodes:

an 18S ribosomal RNA, or a portion thereof;

a 5.8S rRNA, or a portion thereof;

a 28S rRNA, or a portion thereof; and/or an internal transcribed spacer (ITS), or a portion thereof, adjacent the the 18S, 5.8S or 28S rRNA in the nuclear-encoded rRNA gene.

51. The composition of clause 50, wherein the target sequence encodes:

an 18S ribosomal RNA, or a portion thereof; and/or an ITS, or a portion thereof, adjacent the 18S rRNA.

52. The composition of any one of clauses 44 to 51, wherein the target sequence is 80% or more identical to a nucleotide sequence selected from the group consisting of the sequences set forth in SEQ ID NOs:108-113 and 246.

53. The composition of any one of clauses 44 to 52, wherein the composition further comprises a fluorescent DNA intercalating dye.

54. A method of making real-time PCR primers for screening a sample, the method comprising:

i) identifying a target nucleotide sequence specific to a clade comprising a plurality of species and that comprises a nucleotide sequence conserved within the clade;

ii) generating a primer pair designed to amplify nucleic acid products comprising the target nucleotide sequence; and iii) performing a plurality of real-time PCRs using the generated primer pair in:

(a) a positive control sample comprising the target nucleotide sequence to obtain one or more ranges of one or more Tm values, thereby generating one or more reference Tm ranges; and (b) a negative control sample that does not comprise the target nucleotide sequence to obtain a range of Ct values, thereby generating a cutoff Ct value, wherein the one or more reference Tm ranges and the cutoff Ct value provide for a determination of the presence or absence in a sample of a species belonging to the clade when the generated primer pair is used to perform a real-time PCR in the sample.

55. The method of clause 54, wherein the method comprises adding a nucleotide sequence tag to one or more primers of the primer pair to generate a tagged primer pair when the target nucleotide sequence amplified by the primer pair without the sequence tag does not provide for a determination of the presence of a species belonging to the clade in the sample.

While embodiments of the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method of analyzing a sample, the method comprising:
   (i) extracting nucleic acid from a sample to obtain an initial nucleic acid sample;
   (ii) performing at least two polymerase chain reactions (PCRs) on the initial nucleic acid sample, wherein the reaction mixes for the at least two PCRs comprise:
      (a) a first set of PCR primers comprising one or more primer pairs, wherein the primer pair(s) from the first set detect(s) various onychomycotic fungi of the dermatophyte clade,
      (b) a second set of PCR primers comprising one or more primer pairs, wherein the primer pair(s) from the second set detect(s) various onychomycotic fungi of the *candida* clade, and
      (c) a third set of PCR primers comprising one or more primer pairs, wherein the primer pair(s) from the third set detect various onychomycotic fungi of the saprophyte clade;
      wherein: (i) each reaction mix comprises a different set of the PCR primers or (ii) one of the reaction mixes comprises two sets of the PCR primers and another reaction mix comprises one set of the PCR primers; and
   (iii) based on the results of step (iii), selecting one or more sets of primary clade specific PCR primer pairs from:
      (a) a fourth set of PCR primer pairs, wherein the different primer pairs in the fourth set specifically amplify nucleic acids from different onychomycotic fungi of the dermatophyte clade,
      (b) a fifth set of PCR primer pairs, wherein the different primer pairs in the fifth set specifically amplify nucleic acids from different onychomycotic fungi of the *candida* clade, and
      (c) a sixth set of PCR primer pairs, wherein the different primer pairs in the sixth set specifically amplify nucleic acids from different onychomycotic fungi of the saprophyte clade; and
   (iv) performing one or more subsequent PCRs on the initial nucleic acid sample, wherein the reaction mix for each of the subsequent PCRs comprises one or more primer pairs from the selected set(s) of primary clade specific PCR primer pairs;
   wherein the primary clade-specific primer pairs are configured to amplify a primary clade-specific nucleotide sequence encoding:
      an 18S ribosomal RNA, or a portion thereof;
      an internal transcribed spacer (ITS), or a portion thereof, adjacent the 18S, 28S or 5.8S rRNA within a nuclear-encoded rRNA gene; or
      a mitochondrial nucleotide sequence.

2. The method of claim 1, wherein a primer pair from the first set, the second set, and the third set of PCR primers amplifies a nucleotide sequence within a nuclear-encoded ribosomal RNA (rRNA) gene specific to the corresponding clade.

3. The method of claim 2, wherein the amplification products produced in step (ii) comprise an amplification product for each of the following clade-specific nuclear encoded rRNA:
   an 18S ribosomal RNA (rRNA), or a portion thereof;
   a 5.8S rRNA, or a portion thereof;
   a 28S rRNA, or a portion thereof;
   a portion of an internal transcribed spacer 1 (ITS1) adjacent the 18S rRNA;
   a portion of an internal transcribed spacer 2 (ITS2) adjacent the 5.8S rRNA; and
   a portion of an internal transcribed spacer 2 (ITS2) adjacent the 28S rRNA.

4. The method of claim 1, wherein the primer pairs selected in step (iii) are configured to amplify a primary clade-specific nucleotide sequence within a nuclear-encoded ribosomal RNA (rRNA) gene or a mitochondrial nucleotide sequence.

5. The method of claim 4, wherein the primary clade-specific nucleotide sequence encodes:
   an 18S ribosomal RNA, or a portion thereof;
   a 28S ribosomal RNA, or a portion thereof;
   a 5.8S ribosomal RNA or a portion there of; and/or
   an ITS, or a portion thereof, adjacent the 18S, 28S or 5.8S rRNA in the nuclear-encoded rRNA gene, and
   wherein the mitochondrial nucleotide sequence encodes:
   a nicotinamide adenine dinucleotide (NADH) dehydrogenase subunit gene, or a portion thereof, or
   a putative reverse transcriptase gene, or a portion thereof.

6. The method of claim 1, wherein performing the at least two subsequent PCRs comprise performing one or more real-time PCR using the selected set(s) of primary clade-specific PCR primer pairs.

7. The method of claim 1, wherein the sample is obtained from a human subject.

8. The method of claim 1, wherein the sample is a sample of nail.

9. The method of claim 8, wherein the nucleic acid is extracted from the nail using a mechanical, chemical, thermal and/or enzymatic treatment.

10. A method analyzing a sample, the method comprising:

(i) extracting nucleic acid from a sample to obtain an initial nucleic acid sample;

(ii) performing at least two polymerase chain reactions (PCRs) on the initial nucleic acid sample, wherein the reaction mixes for the at least two PCRs comprise:

(a) a first set of PCR primers comprising one or more primer pairs, wherein the primer pair(s) from the first set detect(s) various onychomycotic fungi of the dermatophyte clade, (b) a second set of PCR primers comprising one or more primer pairs, wherein the primer pair(s) from the second set detect(s) various onychomycotic fungi of the *candida* clade, and (c) a third set of PCR primers comprising one or more primer pairs, wherein the primer pair(s) from the third set detect various onychomycotic fungi of the saprophyte clade;

wherein: (i) each reaction mix comprises a different set of the PCR primers or (ii) one of the reaction mixes comprises two sets of the PCR primers and another reaction mix comprises one set of the PCR primers; and (iii) based on the results of step (iii), selecting one or more sets of primary clade specific PCR primer pairs from:

(a) a fourth set of PCR primer pairs, wherein the different primer pairs in the fourth set specifically amplify nucleic acids from different onychomycotic fungi of the dermatophyte clade, (b) a fifth set of PCR primer pairs, wherein the different primer pairs in the fifth set specifically amplify nucleic acids from different onychomycotic fungi of the *candida* clade, and (c) a sixth set of PCR primer pairs, wherein the different primer pairs in the sixth set specifically amplify nucleic acids from different onychomycotic fungi of the saprophyte clade; and (v) performing one or more subsequent PCRs on the initial nucleic acid sample, wherein the reaction mix for each of the subsequent PCRs comprises one or more primer pairs from the selected set(s) of primary clade specific PCR primer pairs.

* * * * *

SEQUENCE LISTING

```
<160> NUMBER OF SEQ ID NOS: 246

<210> SEQ ID NO 1
<211> LENGTH: 24
<212> TYPE: DNA
<213> ORGANISM: Artificial Sequence
<220> FEATURE:
<223> OTHER INFORMATION: Synthetic nucleic acid

<400> SEQUENCE: 1

gtctgggaaa tcttgtgaaa ctcc                                  24


<210> SEQ ID NO 2
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 2

gccattcaat cggtagtagc ga                                    22


<210> SEQ ID NO 3
<211> LENGTH: 18
<212> TYPE: DNA
<213> ORGANISM: Artificial Sequence
<220> FEATURE:
<223> OTHER INFORMATION: Synthetic nucleic acid
```

<400> SEQUENCE: 3
ggaggttgga aacgaccg 18

<210> SEQ ID NO 4
<211> LENGTH: 16
<212> TYPE: DNA
<213> ORGANISM: Artificial Sequence
<220> FEATURE:
<223> OTHER INFORMATION: Synthetic nucleic acid

<400> SEQUENCE: 4
gcccgccgag gcaacc 16

<210> SEQ ID NO 5
<211> LENGTH: 18
<212> TYPE: DNA
<213> ORGANISM: Artificial Sequence
<220> FEATURE:
<223> OTHER INFORMATION: Synthetic nucleic acid

<400> SEQUENCE: 5
ggggctcttt tgggtctc 18

<210> SEQ ID NO 6
<211> LENGTH: 19
<212> TYPE: DNA
<213> ORGANISM: Artificial Sequence
<220> FEATURE:
<223> OTHER INFORMATION: Synthetic nucleic acid

<400> SEQUENCE: 6
gtccagccgg accagtact 19

<210> SEQ ID NO 7
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 7
agaggtgggc aactaccact 20

<210> SEQ ID NO 8
<211> LENGTH: 19
<212> TYPE: DNA
<213> ORGANISM: Artificial Sequence
<220> FEATURE:
<223> OTHER INFORMATION: Synthetic nucleic acid

<400> SEQUENCE: 8
cgctggttca ccaacggag 19

<210> SEQ ID NO 9
<211> LENGTH: 19
<212> TYPE: DNA
<213> ORGANISM: Artificial Sequence
<220> FEATURE:
<223> OTHER INFORMATION: Synthetic nucleic acid

<400> SEQUENCE: 9
tggcaacgac cacctcaag 19

<210> SEQ ID NO 10

<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 10
ccagcccgcc ttcatatttg t 21

<210> SEQ ID NO 11
<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 11
actcaccagg tccagacata g 21

<210> SEQ ID NO 12
<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 12
gcaccaccac ccatagaatc t 21

<210> SEQ ID NO 13
<211> LENGTH: 189
<212> TYPE: DNA
<213> ORGANISM: Candida albicans

<400> SEQUENCE: 13
ccttggccga gaggtctggg aaatcttgtg aaactccgtc gtgctgggga tagagcattg 60
taattgttgc tcttcaacga ggaattccta gtaagcgcaa gtcatcagct tgcgttgatt 120
acgtccctgc cctttgtaca caccgcccgt cgctactacc gattgaatgg cttagtgagg 180
cctccggat 189

<210> SEQ ID NO 14
<211> LENGTH: 189
<212> TYPE: DNA
<213> ORGANISM: Candida parapsilosis

<400> SEQUENCE: 14
ccttggccga gaggtctggg aaatcttgtg aaactccgtc gtgctgggga tagagcattg 60
taattattgc tcttcaacga ggaattccta gtaagcgcaa gtcatcagct tgcgttgatt 120
acgtccctgc cctttgtaca caccgcccgt cgctactacc gattgaatgg cttagtgagg 180
cttccggat 189

<210> SEQ ID NO 15
<211> LENGTH: 189
<212> TYPE: DNA
<213> ORGANISM: Candida glabrata

<400> SEQUENCE: 15
ccttggccga gaggtcttgg taatcttgtg aaactccgtc gtgctgggga tagagcattg 60
taattattgc tcttcaacga ggaattccta gtaagcgcaa gtcatcagct tgcgttgatt 120
acgtccctgc cctttgtaca caccgcccgt cgctagtacc gattgaatgg cttagtgagg 180
cctcaggat 189

<210> SEQ ID NO 16
<211> LENGTH: 189
<212> TYPE: DNA
<213> ORGANISM: Candida tropicalis

<400> SEQUENCE: 16
ccttggccga gaggcctggg aaatcttgtg aaactccgtc gtgctgggga tagagcattg 60
taattgttgc tcttcaacga ggaattccta gtaagcgcaa gtcatcagct tgcgttgatt 120
acgtccctgc cctttgtaca caccgcccgt cgctactacc gattgaatgg cttagtgagg 180
cttccggat 189

<210> SEQ ID NO 17
<211> LENGTH: 189
<212> TYPE: DNA
<213> ORGANISM: Candida kruseii

<400> SEQUENCE: 17
ccttggtcga gaggcccggg taatctcgtg aaactccgtc gtgctgggga tagagcattg 60
taatttttgc tcttcaacga ggaattccta gtaagcgcaa gtcatcagct tgcgttgatt 120
acgtccctgc cctttgtaca caccgcccgt cgctactacc gattgaatgg cttagtgagg 180
cttcaagat 189

<210> SEQ ID NO 18
<211> LENGTH: 189
<212> TYPE: DNA
<213> ORGANISM: Artificial Sequence
<220> FEATURE:
<223> OTHER INFORMATION: Synthetic nucleic acid

<400> SEQUENCE: 18
ccttggccga gaggtctggg aaatcttgtg aaactccgtc gtgctgggga tagagcattg 60
taattrttgc tcttcaacga ggaattccta gtaagcgcaa gtcatcagct tgcgttgatt 120
acgtccctgc cctttgtaca caccgcccgt cgctactacc gattgaatgg cttagtgagg 180
cttccggat 189

<210> SEQ ID NO 19
<211> LENGTH: 233
<212> TYPE: DNA
<213> ORGANISM: Epidermophyton floccosum

<400> SEQUENCE: 19
actggcccag ggaggttgga aacgaccgcc cagggccgga aagttggtca aactcggtca 60
tttagaggaa gtaaaagtcg taacaaggtt tccgtaggtg aacctgcgga aggatcatta 120
acgcgcaggc cgcagtcggc ccgtccccct tctctctgaa tgctggacgg tgtcgccggc 180
cacacgccca ttcttgtcta cactacccgg ttgcctcggc gggccgcgcc ccc 233

<210> SEQ ID NO 20
<211> LENGTH: 264
<212> TYPE: DNA
<213> ORGANISM: Microsporum canis

<400> SEQUENCE: 20
actggcccag ggaggttgga aacgaccgcc cagggccgga aagttggtca aactcggtca 60

-continued

```
tttagaggaa gtaaaagtcg taacaaggtt tccgtaggtg aacctgcgga aggatcatta    120

acgcgcaaga ggtcgaagtt gccccccgaa gctcttccgt ctccccccg ggcctcccgg    180

ggaggttgcg ggcggcgagg ggtgcctccg gccgcacgcc cattcttgtc tactgacccg    240

gttgcctcgg cgggccgcgc ctgc                                           264


<210> SEQ ID NO 21
<211> LENGTH: 264
<212> TYPE: DNA
<213> ORGANISM: Microsporum auduuinii

<400> SEQUENCE: 21

actggcccag ggaggttgca aacgagcgcc cagggccgga aagttggtca aactcggtca     60

tttagaggaa gtaaaagtcg taacaaggtt tccgtaggtg aacctgcgga aggatcatta    120

acgcgcaaga ggtcgaagtt ggcccccgaa gctcttccgt ctccccccg ggcctcccgg    180

ggaggttgcg ggcggcgagg ggtgcctccg gccgcacgcc cattcttgtc tactgacccg    240

gttgcctcgg cgggccgcgc ctgc                                           264


<210> SEQ ID NO 22
<211> LENGTH: 264
<212> TYPE: DNA
<213> ORGANISM: Microsporum ferrugineum

<400> SEQUENCE: 22

actggcccag ggaggttgga aacgaccgcc cagggccgga aagttggtca aactcggtca     60

tttagaggaa gtaaaagtcg taacaaggtt tccgtaggtg aacctgcgga aggatcatta    120

acgcgcaaga ggtcgaagtt ggcccccgaa gctcttccgt ctccccccg ggcctcccgg    180

ggaggttgcg ggcggcgagg ggtgcctccg gccgcacgcc cattcttgtc tactgacccg    240

gttgcctcgg cgggccgcgc ctgc                                           264


<210> SEQ ID NO 23
<211> LENGTH: 247
<212> TYPE: DNA
<213> ORGANISM: Trichophyton mentagrophytes

<400> SEQUENCE: 23

actggcccag ggaggttgga aacgaccgcc cagggccgga aagttggtca aactcggtca     60

tttagaggaa gtaaaagtcg taacaaggtt tccgtaggtg aacctgcgga aggatcatta    120

gcgcgcaggc cggaggctgg ccccccacga tagggccaaa cgtccgtcag ggtgagcag    180

atgtgcgccg gccgtaccgc cccattcttg tctacattac tcggttgcct cggcgggccg    240

cgctctc                                                              247


<210> SEQ ID NO 24
<211> LENGTH: 247
<212> TYPE: DNA
<213> ORGANISM: Trichophyton rubrum

<400> SEQUENCE: 24

actggcccag ggaggttgga aacgaccgcc cagggccgga aagttggtca aactcggtca     60

tttagaggaa gtaaaagtcg taacaaggtt tccgtaggtg aacctgcgga aggatcatta    120

acgcgcaggc cggaggctgg ccccccacga tagggaccga cgttccatca gggtgagcag    180

acgtgcgccg gccgtacgcc cccattcttg tctacctcac ccggttgcct cggcgggccg    240

cgctccc                                                              247
```

<210> SEQ ID NO 25
<211> LENGTH: 248
<212> TYPE: DNA
<213> ORGANISM: Trichophyton soudanense

<400> SEQUENCE: 25
actggcccag ggaggttgga aacgaccgcc cagggccgga aagttggtca aactcggtca 60
tttagaggaa gtaaaagtcg taacaaggtt tccgtaggtg aacctgcgga aggatcatta 120
acgcgcaggc cggaggctgg ccccccacga tagggaccga cgttccatca ggggtgagca 180
gacgtgcgcc ggccgtacgc ccccattctt gtctacctca cccggttgcc tcggcgggcc 240
gcgctccc 248

<210> SEQ ID NO 26
<211> LENGTH: 248
<212> TYPE: DNA
<213> ORGANISM: Trichophyton violaceum

<400> SEQUENCE: 26
actggcccag ggaggttgga aacgaccgcc cagggccgga aagttggtca aactcggtca 60
tttagaggaa gtaaaagtcg taacaaggtt tccgtaggtg aacctgcgga aggatcatta 120
acgcgcaggc cggaggctgg ccccccacga tagggaccga cgttccatca ggggtgagca 180
gacgtgcgcc ggccgtacgc ccccattctt gtctacctca cccggttgcc tcggcgggcc 240
gcgctccc 248

<210> SEQ ID NO 27
<211> LENGTH: 250
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (150)..(151)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 27
actggcccag ggaggttgga aacgaccgcc cagggccgga aagttggtca aactcggtca 60
tttagaggaa gtaaaagtcg taacaaggtt tccgtaggtg aacctgcgga aggatcatta 120
acgcgcaggc cggangytgg ccccccacgn natmggkcnc csacgkgccw tcaggggtga 180
gcagaggtgc gccggccgya cgncccattc ttgtctacnt sacccggttg cctcggcggg 240 ccgcgcyccc 250

<210> SEQ ID NO 28

<211> LENGTH: 234
<212> TYPE: DNA
<213> ORGANISM: Aspergillus flavus

<400> SEQUENCE: 28
gtgacaataa atactgatac ggggctcttt tgggtctcgt aattggaatg agtacaatct 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 29
<211> LENGTH: 234
<212> TYPE: DNA
<213> ORGANISM: Aspergillus niger

<400> SEQUENCE: 29
gtgacaataa atactgatac ggggctcttt tgggtctcgt aattggaatg agtacaatct 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 30
<211> LENGTH: 234
<212> TYPE: DNA
<213> ORGANISM: Aspergillus nidulans

<400> SEQUENCE: 30
gtgacaataa atactgatac ggggctcttt tgggtctcgt aattggaatg agaacaattt 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 31
<211> LENGTH: 234
<212> TYPE: DNA
<213> ORGANISM: Aspergillus oryzae

<400> SEQUENCE: 31
gtgacaataa atactgatac ggggctcttt tgggtctcgt aattggaatg agtacaatct 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 32
<211> LENGTH: 234
<212> TYPE: DNA
<213> ORGANISM: Aspergillus terreus

<400> SEQUENCE: 32
gtgacaataa atactgatac ggggctcttt cgggtctcgt aattggaatg agtacaatct 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 33
<211> LENGTH: 234
<212> TYPE: DNA
<213> ORGANISM: Aspergillus versicolor

<400> SEQUENCE: 33
gtgacaataa atactgatac ggggctcttt tgggtctcgt aattggaatg agtacaatct 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 34
<211> LENGTH: 234
<212> TYPE: DNA
<213> ORGANISM: Penicillium citrinu

<400> SEQUENCE: 34
gtgacaataa atactgatac ggggctcttt cgggtctcgt aattggaatg agaacaattt 60
aaatccctta acgaggaaca attggagggc aagtctggtg ccagcagccg cggtaattcc 120
agctccaata gcgtatatta aagttgttgc agttaaaaag ctcgtagttg aaccttgggc 180
ctggctggcc ggtccgcctc accgcgagta ctggtccggc tgggcctttc cttc 234

<210> SEQ ID NO 35
<211> LENGTH: 234
<212> TYPE: DNA
<213> ORGANISM: Penicillium janthinellum

<400> SEQUENCE: 35
gtgacaataa atactgatac ggggctcttt tgggtctcgt aattggaatg agaacaattt 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 36
<211> LENGTH: 234
<212> TYPE: DNA
<213> ORGANISM: Penicillium purpurogenum

<400> SEQUENCE: 36
gtgacaataa atactgatac agggctcttt tgggtcttgt aattggaatg agaacaatct 60
aaatccctta acgaggaaca attggagggc aagtctggtg ccagcagccg cggtaattcc 120
agctccaata gcgtatatta aagttgttgc agttaaaaag ctcgtagttg aaccttgggc 180
ccgtcctgcc ggtccgcctc accgcgagta ctggtccgga tgggcctttc tttc 234

<210> SEQ ID NO 37
<211> LENGTH: 234
<212> TYPE: DNA
<213> ORGANISM: Paecilomyces lilacinus

<400> SEQUENCE: 37
gtgacaataa atactgatac agggctcttt tgggtcttgt aattggaatg agtacaattt 60
aaatccctta acgaggaaca attggagggc aagtctggtg ccagcagccg cggtaattcc 120
agctccaata gcgtatatta aagttgttgt ggttaaaaag ctcgtagttg aaccttgggc 180
ctggctggcc ggtccgcctc accgcgtgca ctggtccggc cgggcctttc cctc 234

-continued

<210> SEQ ID NO 38
<211> LENGTH: 234
<212> TYPE: DNA
<213> ORGANISM: Artificial Sequence
<220> FEATURE:
<223> OTHER INFORMATION: Synthetic nucleic acid

<400> SEQUENCE: 38
gtgacaataa atactgatac ggggctcttt tgggtctcgt aattggaatg agtacaatct 60
aaatccctta acgaggaaca attggagggc aagtctggtg ccagcagccg cggtaattcc 120
agctccaata gcgtatatta aagttgttgc agttaaaaag ctcgtagttg aaccttgggt 180
ctggctggcc ggtccgcctc accgcgagta ctggtccggc tggacctttc cttc 234

<210> SEQ ID NO 39
<211> LENGTH: 116
<212> TYPE: DNA
<213> ORGANISM: Fusarium oxysporum

<400> SEQUENCE: 39
cagagaggtg ggcaactacc actcagggcc ggaaagctct ccaaactcgg tcatttagag 60
gaagtaaaag tcgtaacaag gtctccgttg gtgaaccagc ggagggatca ttaccg 116

<210> SEQ ID NO 40
<211> LENGTH: 116
<212> TYPE: DNA
<213> ORGANISM: Fusarium solani

<400> SEQUENCE: 40
cagagaggtg ggcaactacc actcagggcc ggaaagctct ccaaactcgg tcatttagag 60
gaagtaaaag tcgtaacaag gtctccgttg gtgaaccagc ggagggatca ttaccg 116

<210> SEQ ID NO 41
<211> LENGTH: 116
<212> TYPE: DNA
<213> ORGANISM: Fusarium proliferatum

<400> SEQUENCE: 41
cagagaggtg ggcaactacc actcagggcc ggaaagctct ccaaactcgg tcatttagag 60
gaagtaaaag tcgtaacaag gtctccgttg gtgaaccagc ggagggatca ttaccg 116

<210> SEQ ID NO 42
<211> LENGTH: 117
<212> TYPE: DNA
<213> ORGANISM: Acremonium kiliense

<400> SEQUENCE: 42
cagggaggtg ggcaactacc acccagggcc ggaaagttct ccaaactcgg tcatttagag 60
gaagtaaaag tcgtaacaag gtctccgttg gtgaaccagc ggagggatca ttaccag 117

<210> SEQ ID NO 43
<211> LENGTH: 119
<212> TYPE: DNA
<213> ORGANISM: Scopulariopsis brevicaulis

<400> SEQUENCE: 43
cagagaggtg ggcaactacc actcagggcc ggaaagttgt ccaaactcgg tcatttagat 60
ggaagtaaaa agtcgtaaca aggtctccgt tggtgaacca gcggagggat cattaccga 119

<210> SEQ ID NO 44
<211> LENGTH: 116
<212> TYPE: DNA
<213> ORGANISM: Chaetomium globosum

<400> SEQUENCE: 44
cagagaggtc ggcaacgacc actcagggcc ggaaagctat ccaaactcgg tcatttagag 60
gaagtaaaag tcgtaacaag gtctccgttg gtgaaccagc ggagggatca ttacag 116

<210> SEQ ID NO 45
<211> LENGTH: 116
<212> TYPE: DNA
<213> ORGANISM: Chaetomium atrobrunneum

<400> SEQUENCE: 45
cagagaggtc ggcaacgacc acccagggcc ggaaagctat ccaaactcgg tcatttagag 60
gaagtaaaag tcgtaacaag gtctccgttg gtgaaccagc ggagggatca ttacag 116

<210> SEQ ID NO 46
<211> LENGTH: 116
<212> TYPE: DNA
<213> ORGANISM: Chaetomium funicola

<400> SEQUENCE: 46
cagagaggtc ggcaacgacc acccagggcc ggaaagctat ccaaactcgg tcatttagag 60
gaagtaaaag tcgtaacaag gtctccgttg gtgaaccagc ggagggatca ttacag 116

<210> SEQ ID NO 47
<211> LENGTH: 116
<212> TYPE: DNA
<213> ORGANISM: Paecilomyces variotii

<400> SEQUENCE: 47
caggggggtt ggcaacgacc gcccagagcc ggaaagttgg tcaaacttgg tcatttagag 60
gaagtaaaag tcgtaacaag gtttccgtag gtgaacctgc ggaaggatca ttaccg 116

<210> SEQ ID NO 48
<211> LENGTH: 117
<212> TYPE: DNA
<213> ORGANISM: Curvularia geniculatus

<400> SEQUENCE: 48
cggggaggtt ggcaacgacc accccaagcc ggaaagttcg tcaaactcgg tcatttagag 60
gaagtaaaag tcgtaacaag gtctccgtag gtgaacctgc ggagggatca ttacaca 117

<210> SEQ ID NO 49
<211> LENGTH: 117
<212> TYPE: DNA
<213> ORGANISM: Curvularia hawaiiensis

<400> SEQUENCE: 49
cggggaggtt ggcaacgacc accccaagcc ggaaagttcg tcaaactcgg tcatttagag 60
gaagtaaaag tcgtaacaag gtctccgtag gtgaacctgc ggagggatca ttacaca 117

<210> SEQ ID NO 50
<211> LENGTH: 117
<212> TYPE: DNA
<213> ORGANISM: Artificial Sequence
<220> FEATURE:
<223> OTHER INFORMATION: Synthetic nucleic acid

<400> SEQUENCE: 50
cagagaggtg ggcaacgacc acccagggcc ggaaagctct ccaaactcgg tcatttagag 60
gaagtaaaag tcgtaacaag gtctccgttg gtgaaccagc ggagggatca ttaccga 117

<210> SEQ ID NO 51
<211> LENGTH: 152
<212> TYPE: DNA
<213> ORGANISM: Alternaria alternata

<400> SEQUENCE: 51
tcggactggc tcgaggaggt tggcaacgac cacctcaagc cggaaagttc gtcaaactcg 60
gtcatttaga ggaagtaaaa gtcgtaacaa ggtctccgta ggtgaacctg cggagggatc 120
attacacaaa tatgaaggcg ggctggaacc tc 152

<210> SEQ ID NO 52
<211> LENGTH: 152
<212> TYPE: DNA
<213> ORGANISM: Alternaria solani

<400> SEQUENCE: 52
tcggactggc tcgaggaggt tggcaacgac cacctcaagc cggaaagttg gtcaaactcg 60
gtcatttaga ggaagtaaaa gtcgtaacaa ggtctccgta ggtgaacctg cggagggatc 120
attacacaaa tatgaaggcg ggctggcacc tc 152

<210> SEQ ID NO 53
<211> LENGTH: 150
<212> TYPE: DNA
<213> ORGANISM: Curvularia lunata

<400> SEQUENCE: 53
tcggactggc tcggggaggt tggcaacgac caccccaagc cggaaagttc gtcaaactcg 60
gtcatttaga ggaagtaaaa gtcgtaacaa ggtctccgta ggtgaacctg cggagggatc 120
attacacaat aaaatatgaa ggctgtacgc 150

<210> SEQ ID NO 54
<211> LENGTH: 152
<212> TYPE: DNA
<213> ORGANISM: Curvularia hawaiiensis

<400> SEQUENCE: 54
tcggactggc tcggggaggt tggcaacgac caccccaagc cggaaagttc gtcaaactcg 60
gtcatttaga ggaagtaaaa gtcgtaacaa ggtctccgta ggtgaacctg cggagggatc 120
attacacaat aacaatacga aggccgttcg cg 152

<210> SEQ ID NO 55
<211> LENGTH: 154
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (141)..(142)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t

<400> SEQUENCE: 55
tcggactggc tcgrggaggt tggcaacgac caccycaagc cggaaagttc gtcaaactcg 60
gtcatttaga ggaagtaaaa gtcgtaacaa ggtctccgta ggtgaacctg cggagggatc 120
attacacaan tawgaakrcg nnggctgkna cckc 154

<210> SEQ ID NO 56
<211> LENGTH: 112
<212> TYPE: DNA
<213> ORGANISM: Mucor amphibiorum

<400> SEQUENCE: 56
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 57
<211> LENGTH: 112
<212> TYPE: DNA
<213> ORGANISM: Mucor circinelloides

<400> SEQUENCE: 57
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 58
<211> LENGTH: 112
<212> TYPE: DNA
<213> ORGANISM: Mucor hiemalis

<400> SEQUENCE: 58
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 59
<211> LENGTH: 112
<212> TYPE: DNA
<213> ORGANISM: Mucor recemosus

<400> SEQUENCE: 59
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 60
<211> LENGTH: 112
<212> TYPE: DNA
<213> ORGANISM: Rhizopus oryzae

<400> SEQUENCE: 60
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 61
<211> LENGTH: 112
<212> TYPE: DNA
<213> ORGANISM: Rhizopus schippera

<400> SEQUENCE: 61
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 62
<211> LENGTH: 112
<212> TYPE: DNA
<213> ORGANISM: Artificial Sequence
<220> FEATURE:
<223> OTHER INFORMATION: Synthetic nucleic acid

<400> SEQUENCE: 62
cacggggaaa ctcaccaggt ccagacatag taaggattga cagattgaaa gctctttcta 60
gattctatgg gtggtggtgc atggccgttc ttagttcgtg gagtgatttg tc 112

<210> SEQ ID NO 63
<211> LENGTH: 30
<212> TYPE: DNA
<213> ORGANISM: Candida albicans

<400> SEQUENCE: 63
atcgtagctg agcgtaagac attaggttat 30

<210> SEQ ID NO 64
<211> LENGTH: 28
<212> TYPE: DNA
<213> ORGANISM: Candida albicans

<400> SEQUENCE: 64
atagtaactc cgggtgcgaa aggtataa 28

<210> SEQ ID NO 65
<211> LENGTH: 28
<212> TYPE: DNA
<213> ORGANISM: Candida parapsilosis

<400> SEQUENCE: 65
tctgaaggtt gtacgaaatg gggaaaaa 28

<210> SEQ ID NO 66
<211> LENGTH: 30
<212> TYPE: DNA
<213> ORGANISM: Candida parapsilosis

<400> SEQUENCE: 66
cagaagaccc tagtatcgct gaaccaattt 30

<210> SEQ ID NO 67
<211> LENGTH: 360
<212> TYPE: DNA
<213> ORGANISM: Candida albicans

<400> SEQUENCE: 67
gttaatgcaa tatattgaat tattaattat gttcttaagt gttttacttg ctgtagcctt 60
cttaactgta gctgagcgta agacattagg ttatatgcaa cggagagttg gtcctaatgc 120
tgtaggttat tatggtattt taatggctat tgctgatgca gctaaattat tacttaaaga 180
gattgttgtt cctacacatg cagataaact tatcttattt gtaagtccta tgatttcatt 240
gatatctgca ttactatgtt gatctgttat acctttcgca cccggagtta ctatctatga 300
tagtaactac gggttcatcc tgactttagc tattagtagt gtcggtgtct tcggtaccct 360

-continued

<210> SEQ ID NO 68
<211> LENGTH: 300
<212> TYPE: DNA
<213> ORGANISM: Candida parapsilosis

<400> SEQUENCE: 68
catcatggat ggattaatga ggttaaactc attacatgaa tatctaagta cagagggctt 60
agccaacgag ctaatctctg aaggttgtac gaaatgggga aaaatacaaa ctctcagtga 120
agtatttagt actctagata tagctttagt ggtaatatta agtttaatga gaatgaatcc 180
ttattataaa attggttcag cgatactagg gtcttctgag attaatagta gatcaaagag 240
cttcatatat gaaagaaata aagatgaatg catttatttc aaatccatca tcagaagcac 300

<210> SEQ ID NO 69
<211> LENGTH: 19
<212> TYPE: DNA
<213> ORGANISM: Artificial Sequence
<220> FEATURE:
<223> OTHER INFORMATION: Synthetic nucleic acid

<400> SEQUENCE: 69
atcaggggtg agcagaygt 19

<210> SEQ ID NO 70
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 70
cgctcagact gacagcyctt 20

<210> SEQ ID NO 71
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 71
cattgcgccc tctggtattc 20

<210> SEQ ID NO 72
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 72
ctccaccttt ctcctctccc 20

<210> SEQ ID NO 73
<211> LENGTH: 18
<212> TYPE: DNA
<213> ORGANISM: Artificial Sequence
<220> FEATURE:
<223> OTHER INFORMATION: Synthetic nucleic acid

<400> SEQUENCE: 73
ttgtctactg acccggtt 18

<210> SEQ ID NO 74

-continued

<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 74
gaaacaagag tccccctcag g 21

<210> SEQ ID NO 75
<211> LENGTH: 207
<212> TYPE: DNA
<213> ORGANISM: Trichophyton mentagrophytes

<400> SEQUENCE: 75
caaacgtccg tcaggggtga gcagatgtgc gccggccgta ccgccccatt cttgtctaca 60
ttactcggtt gcctcggcgg gccgcgctct cccaggagag ccgttcggcg agcctctctt 120
tagtggctaa acgctggacc gcgcccgccg gaggacagac gcaaaaaaat tctttcagaa 180
gagctgtcag tctgagcgtt agcaagc 207

<210> SEQ ID NO 76
<211> LENGTH: 214
<212> TYPE: DNA
<213> ORGANISM: Trichophyton rubrum

<400> SEQUENCE: 76
accgacgttc catcaggggt gagcagacgt gcgccggccg tacgcccccca ttcttgtcta 60 cctcacccgg ttgcctcggc gggccgcgct ccccctgcca gggagagccg tccggcgggc 120
ccttctggga gcctcgagcc ggaccgcgcc cgccggagga cagacaccaa gaaaaaattc 180
tctgaagagc tgtcagtctg agcgtttagc aagc 214

<210> SEQ ID NO 77
<211> LENGTH: 257
<212> TYPE: DNA
<213> ORGANISM: Epidermophyton floccosum

<400> SEQUENCE: 77 ccccttctc tctgaatgct ggacggtgtc gccggccaca cgcccattct tgtctacact 60
acccggttgc ctcggcgggc cgcgcccccct aggctgcagt gtcgctgcag cgtctcgggg 120
gggccgttcg ggggatggag aaggatgccc cggcggggtt gatcgctccc ccacccctgg 180
acagcgctcg ccgaaggagt gattctcaga aattctacga aatctccata ggtggttcag 240
tctgagcgtt ggcaagc 257

<210> SEQ ID NO 78
<211> LENGTH: 233
<212> TYPE: DNA
<213> ORGANISM: Microsporum auduuinii

<400> SEQUENCE: 78
ccccgggcct cccggggagg ttgcgggcgg cgaggggtgc ctccggccgc acgcccattc 60
ttgtctactg acccggttgc ctcggcgggc cgcgcctgct gtgctacagc ggccgttcgg 120
gggggacgcc tgagggggac ttttgtttcc taggccacgc cccgggcagc gctcgccgga 180
ggattactct ggaaaacaca ctcttgaaag aacataccgt ctgagcgagc aac 233

<210> SEQ ID NO 79
<211> LENGTH: 233

<212> TYPE: DNA
<213> ORGANISM: Microsporum ferrugineum

<400> SEQUENCE: 79
ccccgggcct cccggggagg ttgcgggcgg cgaggggtgc ctccggccgc acgcccattc 60
ttgtctactg acccggttgc ctcggcgggc cgcgcctgct gtgctacagc ggccgttcgg 120
gggggacgcc tgagggggac tcttgtttcc taggccacgc cccgggcagc gctcgccgga 180
ggattactct ggaaaacaca ctcttgaaag aacataccgt ctgagcgagc aac 233

<210> SEQ ID NO 80
<211> LENGTH: 233
<212> TYPE: DNA
<213> ORGANISM: Microsporum canis

<400> SEQUENCE: 80
ccccgggcct cccggggagg ttgcgggcgg cgaggggtgc ctccggccgc acgcccattc 60
ttgtctactg acccggttgc ctcggcgggc cgcgcctgct gtgctacagc ggccgttcgg 120
gggggacgcc tgagggggac tcttgtttcc taggccacgc cccgggcagc gctcgccgga 180
ggattactct ggaaaacaca ctcttgaaag aacataccgt ctgagcgagc aac 233

<210> SEQ ID NO 81
<211> LENGTH: 195
<212> TYPE: DNA
<213> ORGANISM: Trichophyton ajelloi

<400> SEQUENCE: 81
cttgagatat agcccggacg gtgctggagg tcgccggcag ttgcccattc ttgtctactg 60
acccagttgc ctcggcgcgc cgctccctag tggacggtcg gaggcccttg gacccagcgt 120
ccatgtggcc ctggccagtg cgcgccggcg gacagtctaa aatctttata tattggccgt 180
ctgagcgtat aaagc 195

<210> SEQ ID NO 82
<211> LENGTH: 201
<212> TYPE: DNA
<213> ORGANISM: Trichophyton concentricum

<400> SEQUENCE: 82
atcaacgttc catcaggggt gtgcagatgt gcgccggtct tacgccccat tcttgtctac 60
cttactcggt tgcctcggcg ggccgcgctc tcctgggaga gtcgtccggc gagcctcttt 120
gggggcttta gctggatcgc gcccgccgga ggacagacat caaaaaatct tggaaagctg 180
tcagtctgag cgttagcaag t 201

<210> SEQ ID NO 83
<211> LENGTH: 196
<212> TYPE: DNA
<213> ORGANISM: Trichophyton gloriae
<220> FEATURE:
<221> NAME/KEY: misc_feature
<222> LOCATION: (183)..(183)
<223> OTHER INFORMATION: n is a, c, g, or t

<400> SEQUENCE: 83
cttgagatat agtctaggcg gtgctggagg tcgccggcag ttgcccattc ttgtctactg 60
acccagttgc ctcggtgtgc cgttccctag cggacggtcg gaagccctag gaccaggttg 120
tccccgtggc cctgaccagc gmacgccgac ggacagtyta aaaatcttta catattggcc 180
ctntragcgt ataagc 196

<210> SEQ ID NO 84
<211> LENGTH: 192
<212> TYPE: DNA
<213> ORGANISM: Trichophyton phaseoliforme

<400> SEQUENCE: 84
cctcgggggg gtcgccggca tatgcccatt cttgtctact gacccagttg cctcggcgcg 60
ccgctccgcc tagcggacgg ccggaagccg tcaggacgtc tcccctcggg ggggcagccc 120
ggcggccctg gtccgcgccc gccgaagaca gtctaaaact ctttacttaa acggccgtct 180
gagcgtataa gc 192

<210> SEQ ID NO 85
<211> LENGTH: 198
<212> TYPE: DNA
<213> ORGANISM: Trichophyton terrestre

<400> SEQUENCE: 85
gtcgggtccc ccctgggggga cgccggaggc caccgccccc cacccttgtc taccgaacgt 60
ctgttgcctc ggcgggcctg ccgctcgtcg gctgccgggg gccgcaccca cccaggtgga 120
tccgcggtcc cgggcgcgcg cccgccagga ggcctacacc gaacctcttt attgaaactg 180
tcagtctgaa ccacaatg 198

<210> SEQ ID NO 86
<211> LENGTH: 159
<212> TYPE: DNA
<213> ORGANISM: Epidermophyton floccosum

<400> SEQUENCE: 86
ttgaacgcac attgcgccct ctggtattcc ggggggcatg cctgttcgag cgtcatttca 60
acccctcaag cccggcttgt gtgatggacg accgtccgac cgcctttgca tcccccgttc 120
caccgggaga ggagaaaggt ggaggggacg cgcccgaaa 159

<210> SEQ ID NO 87
<211> LENGTH: 154
<212> TYPE: DNA
<213> ORGANISM: Microsporum auduuinii

<400> SEQUENCE: 87
ttgaacgcac attgcgcccc ctggcattcc ggggggcatg cctgttcgag cgtcatttca 60
acccctcaag cccggcttgt gtgatggacg accgtccccc cccaataacc acccaccgct 120 tagggggggtg ggagggaggg ggacgcgccc gaaa 154

<210> SEQ ID NO 88
<211> LENGTH: 157
<212> TYPE: DNA
<213> ORGANISM: Microsporum ferrugineum

<400> SEQUENCE: 88
ttgaacgcac attgcgcccc ctggcattcc ggggggcatg cctgttcgag cgtcatttca 60
acccctcaag cccggcttgt gtgatggacg accgtccccc ctccccaaca accacccacc 120
gcttaggggg gtgggaggga gggggacgcg cccgaaa 157

<210> SEQ ID NO 89
<211> LENGTH: 157

-continued

<212> TYPE: DNA
<213> ORGANISM: Microsporum canis

<400> SEQUENCE: 89
ttgaacgcac attgcgcccc ctggcattcc ggggggcatg cctgttcgag cgtcatttca 60
acccctcaag cccggcttgt gtgatggacg accgtccccc ctccccagta accacccacc 120
gcttaggggg gtgggaggga gggggacgcg cccgaaa 157

<210> SEQ ID NO 90
<211> LENGTH: 135
<212> TYPE: DNA
<213> ORGANISM: Trichophyton mentagrophytes

<400> SEQUENCE: 90
ttgaacgcac attgcgcccc ctggcattcc ggggggcatg cctgttcgag cgtcatttca 60
gcccctcaag cccggcttgt gtgatggacg accgtccggc gcccccgtct ttgggggtgc 120
gggacgcgcc cgaaa 135

<210> SEQ ID NO 91
<211> LENGTH: 130
<212> TYPE: DNA
<213> ORGANISM: Trichophyton rubrum

<400> SEQUENCE: 91
ttgaacgcac attgcgccct ctggcattcc ggggggcatg cctgttcgag cgtcatttca 60
accctcaagc ccggcttgtg tgatggacga ccgtccggcc cctcccttcg gggcgggac 120 gcgcccgaaa 130

<210> SEQ ID NO 92
<211> LENGTH: 124
<212> TYPE: DNA
<213> ORGANISM: Trichophyton ajelloi

<400> SEQUENCE: 92
ttgaacgcac attgcgcccc ctggtattcc ggggggcatg cctgttcgag cgtcatttca 60
accctcaagc ccggcttgtg tgatggacga acgtcctgcc tttaggggcg ggacgcgtcc 120
gaaa 124

<210> SEQ ID NO 93
<211> LENGTH: 131
<212> TYPE: DNA
<213> ORGANISM: Trichophyton concentricum

<400> SEQUENCE: 93
ttgaacgcac attgcgccct ctggtattcc ggggggcatg cctgttcgag cgtcatttca 60
acccctcaag cccggcttgt gtgatggacg accgtacgac ctcctctttc gggggcggga 120
cgcgcccgaa a 131

<210> SEQ ID NO 94
<211> LENGTH: 124
<212> TYPE: DNA
<213> ORGANISM: Trichophyton gloriae

<400> SEQUENCE: 94
ttgaacgcac attgcgcccc ctggtattcc ggggggcatg cctgttcgag cgtcatttca 60
accctcaagc tcggcttgtg tgatgggcga acgtctgacc cttrggggcg ggacgcgtcc 120

-continued

```
gaaa                                                                 124


<210> SEQ ID NO 95
<211> LENGTH: 127
<212> TYPE: DNA
<213> ORGANISM: Trichophyton phaseoliforme

<400> SEQUENCE: 95

ttgaacgcac attgcgccct ctggtattcc ggagggcatg cctgttcgag cgtcattgca     60

accctcaagc ccggcttgtg tgatggacga ccgtcccgcc cccttggggc gtgggacgcg    120

cccgaaa                                                              127


<210> SEQ ID NO 96
<211> LENGTH: 135
<212> TYPE: DNA
<213> ORGANISM: Trychophyton tonsurans

<400> SEQUENCE: 96

ttgaacgcac attgcgcccc ctggcattcc ggggggcatg cctgttcgag cgtcatttca     60

gcccctcaag cccggcttgt gtgatggacg accgtccggc gcccccgtct ctgggggtgc    120

gggacgcgcc cgaaa                                                     135


<210> SEQ ID NO 97
<211> LENGTH: 96
<212> TYPE: DNA
<213> ORGANISM: Microsporum canis

<400> SEQUENCE: 97

cattcttgtc tactgacccg gttgcctcgg cgggccgcgc ctgctgtgct acagcggccg     60

ttcggggggg acgcctgagg gggactcttg tttcct                               96


<210> SEQ ID NO 98
<211> LENGTH: 96
<212> TYPE: DNA
<213> ORGANISM: Microsporum auduuinii

<400> SEQUENCE: 98

cattcttgtc tactgacccg gttgcctcgg cgggccgcgc ctgctgtgct acagcggccg     60

ttcggggggg acgcctgagg gggacttttg tttcct                               96


<210> SEQ ID NO 99
<211> LENGTH: 96
<212> TYPE: DNA
<213> ORGANISM: Microsporum ferrugineum

<400> SEQUENCE: 99

cattcttgtc tactgacccg gttgcctcgg cgggccgcgc ctgctgtgct acagcggccg     60

ttcggggggg acgcctgagg gggactcttg tttcct                               96


<210> SEQ ID NO 100
<211> LENGTH: 119
<212> TYPE: DNA
<213> ORGANISM: Epidermophyton floccosum

<400> SEQUENCE: 100

cattcttgtc tacactaccc ggttgcctcg gcgggccgcg ccccctaggc tgcagtgtcg     60

ctgcagcgtc tcgggggggc cgttcggggg atggagaagg atgccccggc ggggttgat     119
```

<210> SEQ ID NO 101
<211> LENGTH: 77
<212> TYPE: DNA
<213> ORGANISM: Trichophyton mentagrophytes

<400> SEQUENCE: 101
cattcttgtc tacattactc ggttgcctcg gcgggccgcg ctctcccagg agagccgttc 60
ggcgagcctc tctttag 77

<210> SEQ ID NO 102
<211> LENGTH: 80
<212> TYPE: DNA
<213> ORGANISM: Trichophyton rubrum

<400> SEQUENCE: 102
cattcttgtc tacctcaccc ggttgcctcg gcgggccgcg ctccccctgc cagggagagc 60
cgtccggcgg gcccttctgg 80

<210> SEQ ID NO 103
<211> LENGTH: 72
<212> TYPE: DNA
<213> ORGANISM: Trichophyton ajelloi

<400> SEQUENCE: 103
cattcttgtc tactgaccca gttgcctcgg cgcgccgctc cctagtggac ggtcggaggc 60
ccttggaccc ag 72

<210> SEQ ID NO 104
<211> LENGTH: 76
<212> TYPE: DNA
<213> ORGANISM: Trichophyton concentricum

<400> SEQUENCE: 104
cattcttgtc taccttactc ggttgcctcg gcgggccgcg ctctcctggg agagtcgtcc 60
ggcgagcctc tttggg 76

<210> SEQ ID NO 105
<211> LENGTH: 73
<212> TYPE: DNA
<213> ORGANISM: Trichophyton gloriae

<400> SEQUENCE: 105
cattcttgtc tactgaccca gttgcctcgg tgtgccgttc cctagcggac ggtcggaagc 60
cctaggacca ggt 73

<210> SEQ ID NO 106
<211> LENGTH: 88
<212> TYPE: DNA
<213> ORGANISM: Trichophyton phaseoliforme

<400> SEQUENCE: 106
cattcttgtc tactgaccca gttgcctcgg cgcgccgctc cgcctagcgg acggccggaa 60
gccgtcagga cgtctcccct cggggggg 88

<210> SEQ ID NO 107
<211> LENGTH: 76
<212> TYPE: DNA
<213> ORGANISM: Trichophyton terrestre

<400> SEQUENCE: 107 caccccttgtc taccgaacgt ctgttgcctc ggcgggcctg ccgctcgtcg gctgccgggg 60
gccgcaccca cccagg 76

<210> SEQ ID NO 108
<211> LENGTH: 158
<212> TYPE: DNA
<213> ORGANISM: Artificial Sequence
<220> FEATURE:
<223> OTHER INFORMATION: Synthetic nucleic acid

<400> SEQUENCE: 108
gtctgggaaa tcttgtgaaa ctccgtcgtg ctggggatag agcattgtaa ttrttgctct 60
tcaacgagga attcctagta agcgcaagtc atcagcttgc gttgattacg tccctgccct 120
ttgtacacac cgcccgtcgc tactaccgat tgaatggc 158

<210> SEQ ID NO 109
<211> LENGTH: 231
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (139)..(140)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t

<400> SEQUENCE: 109
gaggttggaa acgaccgccc agggccggaa agttggtcaa actcggtcat ttagaggaag 60
taaaagtcgt aacaaggttt ccgtaggtga acctgcggaa ggatcattaa cgcgcaggcc 120
ggangytggc cccccacgnn atcmggkcnc csacgkgccw tcaggggtga gcagaggtgc 180
gccggccgya cgncccattc ttgtctacnt sacccggttg cctcggcggg c 231

<210> SEQ ID NO 110
<211> LENGTH: 205
<212> TYPE: DNA
<213> ORGANISM: Artificial Sequence
<220> FEATURE:
<223> OTHER INFORMATION: Synthetic nucleic acid

<400> SEQUENCE: 110
ggggctcttt tgggtctcgt aattggaatg agtacaatct aaatccctta acgaggaaca 60
attggagggc aagtctggtg ccagcagccg cggtaattcc agctccaata gcgtatatta 120
aagttgttgc agttaaaaag ctcgtagttg aaccttgggt ctggctggcc ggtccgcctc 180
accgcgagta ctggtccggc tggac 205

<210> SEQ ID NO 111
<211> LENGTH: 98

<212> TYPE: DNA
<213> ORGANISM: Artificial Sequence
<220> FEATURE:
<223> OTHER INFORMATION: Synthetic nucleic acid

<400> SEQUENCE: 111
agaggtgggc aactaccact cagggccgga aagctctcca aactcggtca tttagaggaa    60
gtaaaagtcg taacaaggtc tccgttggtg aaccagcg    98

<210> SEQ ID NO 112
<211> LENGTH: 126
<212> TYPE: DNA
<213> ORGANISM: Artificial Sequence
<220> FEATURE:
<223> OTHER INFORMATION: Synthetic nucleic acid

<400> SEQUENCE: 112
tggcaacgac cacctcaagc cggaaagttc gtcaaactcg gtcatttaga ggaagtaaaa    60
gtcgtaacaa ggtctccgta ggtgaacctg cggagggatc attacacaaa tatgaaggcg    120
ggctgg    126

<210> SEQ ID NO 113
<211> LENGTH: 128
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t

<400> SEQUENCE: 113
tggcaacgac caccycaagc cggaaagttc gtcaaactcg gtcatttaga ggaagtaaaa    60
gtcgtaacaa ggtctccgta ggtgaacctg cggagggatc attacacaan tawgaakrcg    120 nnggctgk    128

<210> SEQ ID NO 114
<211> LENGTH: 227
<212> TYPE: DNA
<213> ORGANISM: Candida albicans

<400> SEQUENCE: 114
gtagctgagc gtaagacatt aggttatatg caacggagag ttggtcctaa tgctgtaggt    60
tattatggta ttttaatggc tattgctgat gcagctaaat tattacttaa agagattgtt    120
gttcctacac atgcagataa acttatctta tttgtaagtc ctatgatttc attgatatct    180
gcattactat gttgatctgt tatacctttc gcacccggag ttactat    227

<210> SEQ ID NO 115
<211> LENGTH: 142
<212> TYPE: DNA
<213> ORGANISM: Candida parapsilosis

<400> SEQUENCE: 115
tctgaaggtt gtacgaaatg gggaaaaata caaactctca gtgaagtatt tagtactcta    60
gatatagctt tagtggtaat attaagttta atgagaatga atccttatta taaaattggt    120
tcagcgatac tagggtcttc tg 142

<210> SEQ ID NO 116
<211> LENGTH: 189
<212> TYPE: DNA
<213> ORGANISM: Tricophyton mentagrophytes

<400> SEQUENCE: 116
gtcaggggtg agcagatgtg cgccggccgt accgccccat tcttgtctac attactcggt 60
tgcctcggcg ggccgcgctc tcccaggaga gccgttcggc gagcctctct ttagtggcta 120
aacgctggac cgcgcccgcc ggaggacaga cgcaaaaaaa ttctttcaga agagctgtca 180
gtctgagcg 189

<210> SEQ ID NO 117
<211> LENGTH: 194
<212> TYPE: DNA
<213> ORGANISM: Tricophyton rubrum

<400> SEQUENCE: 117
atcaggggtg agcagacgtg cgccggccgt acgcccccat tcttgtctac ctcacccggt 60
tgcctcggcg ggccgcgctc cccctgccag ggagagccgt ccggcgggcc ccttctggga 120
gcctcgagcc ggaccgcgcc cgccggagga cagacaccaa gaaaaaattc tctgaagagc 180
tgtcagtctg agcg 194

<210> SEQ ID NO 118
<211> LENGTH: 135
<212> TYPE: DNA
<213> ORGANISM: Artificial Sequence
<220> FEATURE:
<223> OTHER INFORMATION: Synthetic nucleic acid

<400> SEQUENCE: 118
cattgcgccc tctggtattc cggggggcat gcctgttcga gcgtcatttc aacccctcaa 60
gcccggcttg tgtgatggac gaccgtccga ccgcctttgc atccccgtt ccaccgggag 120 aggagaaagg tggag 135

<210> SEQ ID NO 119
<211> LENGTH: 90
<212> TYPE: DNA
<213> ORGANISM: Artificial Sequence
<220> FEATURE:
<223> OTHER INFORMATION: Synthetic nucleic acid

<400> SEQUENCE: 119
ttgtctactg acccggttgc ctcggcgggg ccgcgcctgc tgtgctacag cggccgttcg 60 gggggacgc ctgaggggga ctcttgtttc 90

<210> SEQ ID NO 120
<211> LENGTH: 200
<212> TYPE: DNA
<213> ORGANISM: Scytalidium dimidiatum
<220> FEATURE:
<221> NAME/KEY: misc_feature
<222> LOCATION: (60)..(60)
<223> OTHER INFORMATION: n is a, c, g, or t

<400> SEQUENCE: 120
taggtgaacc tgcggaagga tcattaccga gttgattcgg gctccggccc gatcctcccn 60
ccctttgtgt acccacctct gttgctttgg cgggccgcgg tcctccgcgg ccgccctccg 120
tccggggggt ggccagcgcc cgccagagga ccatcraact ccggtcagtg aacgttgccg 180
tctgaaaaac aatcaataaa 200

<210> SEQ ID NO 121
<211> LENGTH: 200
<212> TYPE: DNA
<213> ORGANISM: scytalidium hyalinum

<400> SEQUENCE: 121
taggtgaacc tgcggaagga tcattaccga gttgattcgg gctccggccc gatcctccca 60
ccctttgtgt acccacctct gttgctttgg cgggccgcgg tcctccgcgg ccgccctccg 120
tccggggggt ggccagcgcc cgccagagga ccatcgaact ccggtcagtg aacgttgccg 180
tctgaaaaac aatcaataaa 200

<210> SEQ ID NO 122
<211> LENGTH: 200
<212> TYPE: DNA
<213> ORGANISM: scytalidium novaehollandiae

<400> SEQUENCE: 122
taggtgaacc tgcggaagga tcattaccga gttgattcgg gctccggccc gatcctccca 60
ccctttgtgt acccacctct gttgctttgg cgggccgcgg tcctccgcgg ccgccctccg 120
tccggggggt ggccagcgcc cgccagagga ccatcaaact ccggtcagtg aacgttgccg 180
tctgaaaaac aatcaataaa 200

<210> SEQ ID NO 123
<211> LENGTH: 200
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (60)..(60)
<223> OTHER INFORMATION: n is a, c, g, or t

<400> SEQUENCE: 123
taggtgaacc tgcggaagga tcattaccga gttgattcgg gctccggccc gatcctcccn 60
ccctttgtgt acccacctct gttgctttgg cgggccgcgg tcctccgcgg ccgccctccg 120
tccggggggt ggccagcgcc cgccagagga ccatcraact ccggtcagtg aacgttgccg 180
tctgaaaaac aatcaataaa 200

<210> SEQ ID NO 124
<211> LENGTH: 170
<212> TYPE: DNA
<213> ORGANISM: Acremonium kiliense

<400> SEQUENCE: 124
gagcgtcatt tcaaccctca ggaccccctt tcgggggga cctggtgctg gggatcagcg 60
gcctccgggc ccctgtcccc caaattgagt ggcggtcgcg ccgcagcctc ccctgcgtag 120
tagcacacct cgcaccggag agcggctcgg ccacgccgtg aaaccccaa 170

<210> SEQ ID NO 125
<211> LENGTH: 175
<212> TYPE: DNA
<213> ORGANISM: Aspergillus flavus

<400> SEQUENCE: 125
gagcgtcatt gctgcccatc aagcacggct tgtgtgttgg gtcgtcgtcc cctctccggg 60
ggggacgggc cccaaaggca gcggcggcac cgcgtccgat cctcgagcgt atggggcttt 120
gtcacccgct ctgtaggccc ggccggcgct tgccgaacgc aaatcaatct ttttc 175

<210> SEQ ID NO 126
<211> LENGTH: 175
<212> TYPE: DNA
<213> ORGANISM: Aspergillus terreus

<400> SEQUENCE: 126
gagcgtcatt gctgccctca agcccggctt gtgtgttggg ccctcgtccc ccggctcccg 60
ggggacgggc ccgaaaggca gcggcggcac cgcgtccggt cctcgagcgt atggggcttc 120
gtcttccgct ccgtaggccc ggccggcgcc cgccgacgca tttatttgca acttg 175

<210> SEQ ID NO 127
<211> LENGTH: 164
<212> TYPE: DNA
<213> ORGANISM: Alternaria alternata

<400> SEQUENCE: 127
gagcgtcatt tgtaccctca agctttgctt ggtgttgggc gtcttgtctc tagctttgct 60
ggagactcgc cttaaagtaa ttggcagccg gcctactggt ttcggagcgc agcacaagtc 120
gcactctcta tcagcaaagg tctagatcca ttaagccttt tttc 164

<210> SEQ ID NO 128
<211> LENGTH: 157
<212> TYPE: DNA
<213> ORGANISM: Fusarium oxysporum

<400> SEQUENCE: 128
gagcgtcatt tcaaccctca agcacagctt ggtgttggga ctcgcgttaa ttcgcgttcc 60
tcaaattgat tggcggtcac gtcgagcttc catagcgtag tagtaaaacc ctcgttactg 120
gtaatcgtcg cggccacgcc gttaaacccc aacttct 157

<210> SEQ ID NO 129
<211> LENGTH: 177
<212> TYPE: DNA
<213> ORGANISM: Fusarium solani

<400> SEQUENCE: 129
gagcgtcatt acaaccctca ggcccccggg cctggcgttg gggatcggcg gaagccccct 60
gtgggcacac gccgtccccc aaatacagtg gcggtcccgc cgcagcttcc attgcgtagt 120
agctaacacc tcgcaactgg agagcggcgc ggccahgccg taaaacaccc aacttct 177

<210> SEQ ID NO 130
<211> LENGTH: 195
<212> TYPE: DNA
<213> ORGANISM: Scopulariopsis brevicaulis

<400> SEQUENCE: 130
gagcgtcatt tcttccctcg agcgcggcta gccctacggg gcctgccgtc gcccggtgtt 60
ggggctctac gggtggggct cgtccccccc gcagtccccg aaatgtagtg gcggtccagc 120
cgcggcgccc cctgcgtagt agatcctaca tctcgcatcg ggtcccggcg aaggccagcc 180
gtcgaacctt ttatt 195

<210> SEQ ID NO 131
<211> LENGTH: 158
<212> TYPE: DNA
<213> ORGANISM: Scytalidium dimidiatum

<400> SEQUENCE: 131
agcgtcatta caaccctcaa gctctgcttg gtgttgggca ccgcccttcc gcgggcgcgc 60
ctcaaagacc tcggcggtgg cgtcttgcct cgagcgtagt agaaaacacc tcgctttgga 120
gcgcacggcg ccgcccgccg gacgaacctt ttgaactt 158

<210> SEQ ID NO 132
<211> LENGTH: 173
<212> TYPE: DNA
<213> ORGANISM: Curvularia lunata

<400> SEQUENCE: 132
gagcgtcatt tgtaccctca agctttgctt ggtgttgggc gttttttgtc tttggttgcc 60
aaagactcgc cttaaaagga ttggcagccg gcctactggt ttcgcagcgc agcacatttt 120
tgcgcttgca atcagcaaaa gaggacggca atccatcaag actccttctc acg 173

<210> SEQ ID NO 133
<211> LENGTH: 158
<212> TYPE: DNA
<213> ORGANISM: Chaetomium globosum

<400> SEQUENCE: 133
gagcgtcatt tcaaccatca agcccccggg cttgtgttgg ggacctgcgg ctgccgcagg 60
ccctgaaaag cagtggcggg ctcgctgtcg caccgagcgt agtagcatac atctcgctct 120
ggtcgcgccg cgggttccgg ccgttaaacc accttttt 158

<210> SEQ ID NO 134
<211> LENGTH: 154
<212> TYPE: DNA
<213> ORGANISM: Epicoccum purpurascens

<400> SEQUENCE: 134
gagcgtcatt tgtaccttca agctctgctt ggtgttgggt gtttgtctcg cctctgcgtg 60
tagactcgcc ttaaaacaat tggcagccgg cgtattgatt tcggagcgca gtacatctcg 120
cgctttgcac tcataacgac gacgtccaaa agta 154

<210> SEQ ID NO 135
<211> LENGTH: 167
<212> TYPE: DNA
<213> ORGANISM: Paecilomyces lilacinus

<400> SEQUENCE: 135
gagcgtcatt tcaaccctcg agcccccccg ggggcctcgg tgttggggga cggcacacca 60
gccgcccccg aaatgcagtg gcgaccccgc cgcagcctcc cctgcgtagt agcacacacc 120
tcgcaccgga gcgcggaggc ggtcacgccg taaaacgccc aactttc 167

<210> SEQ ID NO 136
<211> LENGTH: 174
<212> TYPE: DNA
<213> ORGANISM: Paecilomyces variotii
<220> FEATURE:
<221> NAME/KEY: misc_feature
<222> LOCATION: (159)..(159)

<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t

<400> SEQUENCE: 136
gagcgtcatt gctaaccctc cagcccggct ggtgtgttgg gccgccgtcc cccctccccg 60
ggggacgggc ccgaaaggca gcggcggcgt cgcgtccggt cctcgagcgt atggggctct 120
gtcacacgct tcagtagaac cggccggctt gctggccana cgaccntcac nggt 174

<210> SEQ ID NO 137
<211> LENGTH: 185
<212> TYPE: DNA
<213> ORGANISM: Rhizopus oryzae

<400> SEQUENCE: 137
cagtatcatc acaaacccac acataacatt tgtttatgtg gtaatgggtc gcatcgctgt 60
tttattacag tgagcaccta aaatgtgtgt gattttctgt ctggcttgct aggcaggaat 120
attacgctgg tctcaggatc tttttctttg gttcgcccag gaagtaaagt acaagagtat 180
aatcc 185

<210> SEQ ID NO 138
<211> LENGTH: 151
<212> TYPE: DNA
<213> ORGANISM: Alternaria alternata

<400> SEQUENCE: 138
aatatgaagg cgggctggaa cctctcgggg ttacagcctt gctgaattat tcacccttgt 60
cttttgcgta cttcttgttt ccttggtggg ttcgcccacc actaggacaa acataaacct 120
tttgtaattg caatcagcgt cagtaacaaa t 151

<210> SEQ ID NO 139
<211> LENGTH: 131
<212> TYPE: DNA
<213> ORGANISM: Aspergillus flavus

<400> SEQUENCE: 139
agtgtagggt tcctagcgag cccaacctcc cacccgtgtt tactgtacct tagttgcttc 60
ggcgggcccg ccattcatgg ccgccggggg ctctcagccc cgggcccgcg cccgccggag 120
acaccacgaa c 131

<210> SEQ ID NO 140
<211> LENGTH: 135
<212> TYPE: DNA
<213> ORGANISM: Aspergillus terreus

<400> SEQUENCE: 140
agtgcgggtc tttatggccc aacctcccac ccgtgactat tgtaccttgt tgcttcggcg 60
ggcccgccag cgttgctggc cgccgggggg cgactcgccc ccgggcccgt gcccgccgga 120
gaccccaaca tgaac 135

<210> SEQ ID NO 141
<211> LENGTH: 110

<212> TYPE: DNA
<213> ORGANISM: Acremonium kiliense

<400> SEQUENCE: 141
gagtgcccta ggctctccaa cccattgtga acatacctat cgttccctcg gcgggctcag 60
cgcgcggtgc ctccgggctc cgggcgtccg ccggggacaa ccaaactctg 110

<210> SEQ ID NO 142
<211> LENGTH: 106
<212> TYPE: DNA
<213> ORGANISM: Fusarium oxysporum

<400> SEQUENCE: 142
agtttacaac tcccaaaccc ctgtgaacat accacttgtt gcctcggcgg atcagcccgc 60
tcccggtaaa acgggacggc ccgccagagg acccctaaac tctgtt 106

<210> SEQ ID NO 143
<211> LENGTH: 108
<212> TYPE: DNA
<213> ORGANISM: Fusarium solani

<400> SEQUENCE: 143
agttatacaa ctcatcaacc ctgtgaacat acctaaaacg ttgcttcggc gggaacagac 60
ggccccgtaa caacgggccg cccccgccag aggaccccta actctgtt 108

<210> SEQ ID NO 144
<211> LENGTH: 136
<212> TYPE: DNA
<213> ORGANISM: Scopulariopsis brevicaulis

<400> SEQUENCE: 144
aagttactct tcaaaaccca ttgtgaacct tacctcttgc cgcgcgttgc ctcggcgggg 60
aggcggggtc tgggtcggcg cgcccctcac cgggccgccg tccccgtccc cgtccccgcc 120
ggccgcgcca aactct 136

<210> SEQ ID NO 145
<211> LENGTH: 142
<212> TYPE: DNA
<213> ORGANISM: Scytalidium dimidiatum
<220> FEATURE:
<221> NAME/KEY: misc_feature
<222> LOCATION: (39)..(39)
<223> OTHER INFORMATION: n is a, c, g, or t

<400> SEQUENCE: 145
cattaccgag ttgattcggg ctccggcccg atcctcccnc cctttgtgta cccacctctg 60
ttgctttggc gggccgcggt cctccgcggc cgccctccgt ccggggggtg gccagcgccc 120
ccagaggacc atcraactcc gg 142

<210> SEQ ID NO 146
<211> LENGTH: 140
<212> TYPE: DNA
<213> ORGANISM: Curvularia lunata

<400> SEQUENCE: 146
ataaaatatg aaggctgtac gcggctgtgc tctcgggcca gttttgcgga ggctgaatta 60
tttattaccc ttgtcttttg cgcacttgtt gtttcctggg cgggttcgcc cgccaccagg 120
accacatcat aaaccttttt 140

<210> SEQ ID NO 147
<211> LENGTH: 127
<212> TYPE: DNA
<213> ORGANISM: Chaetomium globosum

<400> SEQUENCE: 147
gagttgcaaa ctccctaacc attgtgaacg ttacctatac cgttgcttcg gcgggcggcc 60
ccggggttta ccccccgggc gcccctgggc cccaccgcgg gcgcccgccg gaggtcacca 120
aactctt 127

<210> SEQ ID NO 148
<211> LENGTH: 100
<212> TYPE: DNA
<213> ORGANISM: Epicoccum purpurascens

<400> SEQUENCE: 148
gagtttgtag acttcggtct gctacctctt acccatgtct tttgagtacc ttcgtttcct 60
cggcgggtcc gcccgccgat tggacaacat tcaaaccctt 100

<210> SEQ ID NO 149
<211> LENGTH: 123
<212> TYPE: DNA
<213> ORGANISM: Paecilomyces lilacinus

<400> SEQUENCE: 149
gagttataca actcccaaac ccactgtgaa ccttacctca gttgcctcgg cgggaacgcc 60
ccggccgcct gcccccgcgc cggcgccgga cccaggcgcc cgccgcaggg accccaaact 120
ctc 123

<210> SEQ ID NO 150
<211> LENGTH: 142
<212> TYPE: DNA
<213> ORGANISM: Paecilomyces variotii

<400> SEQUENCE: 150
gagtgagggt ccctcggggc ccaacctccc atccgtgttg tcctgacacc tgttgcttcg 60
gcgggcccgc cgtggttcac gccccggccg ccggggggtt cacgcccccg ggcccgcgcc 120
cgccgaagac ccctggaacg ct 142

<210> SEQ ID NO 151
<211> LENGTH: 152
<212> TYPE: DNA
<213> ORGANISM: Rhizopus oryzae

<400> SEQUENCE: 151
tgttaaagcg ccttacctct tagggtttcc tctggggtaa gtgattgctt ctacactgtg 60
aaaatttggc tgagagactc agactggtca tgggtagacc tatctggggt ttgatcgatg 120
ccactcctgg tttcaggagc acccttcata at 152

<210> SEQ ID NO 152
<211> LENGTH: 341
<212> TYPE: DNA
<213> ORGANISM: Curvularia lunata

<400> SEQUENCE: 152
tttatgcagt tgcaatcagc gtcagtataa caaatgtaaa tcatttacaa ctttcaacaa 60
cggatctctt ggttctggca tcgatgaaga acgcagcgaa atgcgatacg tagtgtgaat 120
tgcagaattc agtgaatcat cgaatctttg aacgcacatt gcgccctttg gtattccaaa 180
gggcatgcct gttcgagcgt catttgtacc ctcaagcttt gcttggtgtt gggcgttttt 240
tgtctttggt tgccaaagac tcgccttaaa aggattggca gccggcctac tggtttcgca 300
gcgcagcaca tttttgcgct tgcaatcagc aaaagaggac g 341

<210> SEQ ID NO 153
<211> LENGTH: 338
<212> TYPE: DNA
<213> ORGANISM: Aspergillus flavus

<400> SEQUENCE: 153
tctgatctag tgaagtctga gttgattgta tcgcaatcag ttaaaacttt caacaatgga 60
tctcttggtt ccggcatcga tgaagaacgc agcgaaatgc gataactagt gtgaattgca 120
gaattccgtg aatcatcgag tctttgaacg cacattgcgc cccctggtat tccggggggc 180
atgcctgtcc gagcgtcatt gctgcccatc aagcacggct tgtgtgttgg gtcgtcgtcc 240
cctctccggg ggggacgggc cccaaaggca gcggcggcac cgcgtccgat cctcgagcgt 300
atggggcttt gtcacccgct ctgtaggccc ggccggcg 338

<210> SEQ ID NO 154
<211> LENGTH: 339
<212> TYPE: DNA
<213> ORGANISM: Aspergillus terreus

<400> SEQUENCE: 154
ttctgaaagc ttgcagtctg agtgtgattc tttgcaatca gttaaaactt tcaacaatgg 60
atctcttggt tccggcatcg atgaagaacg cagcgaaatg cgataactaa tgtgaattgc 120
agaattcagt gaatcatcga gtctttgaac gcacattgcg cccccctggta ttccgggggg 180 catgcctgtc cgagcgtcat tgctgccctc aagcccggct tgtgtgttgg gccctcgtcc 240
cccggctccc gggggacggg cccgaaaggc agcggcggca ccgcgtccgg tcctcgagcg 300
tatggggctt cgtcttccgc tccgtaggcc cggccggcg 339

<210> SEQ ID NO 155
<211> LENGTH: 339
<212> TYPE: DNA
<213> ORGANISM: Acremonium kiliense

<400> SEQUENCE: 155
tattgtgaat ctctgagggg cgaaagcccg aaaacaaaat gaatcaaaac tttcaacaac 60
ggatctcttg gctctggcat cgatgaagaa cgcagcgaaa tgcgataagt aatgtgaatt 120
gcagaattca gtgaatcatc gaatctttga acgcacattg cgcccgccgg cactccggcg 180
ggcatgcctg tccgagcgtc atttcaaccc tcaggacccc ctttcggggg ggacctggtg 240
ctggggatca gcggcctccg ggcccctgtc ccccaaattg agtggcggtc gcgccgcagc 300
ctcccctgcg tagtagcaca cctcgcaccg gagagcggc 339

<210> SEQ ID NO 156
<211> LENGTH: 323
<212> TYPE: DNA
<213> ORGANISM: Alternaria alternata

<400> SEQUENCE: 156
tttgtaattg caatcagcgt cagtaacaaa ttaataatta caactttcaa caacggatct 60

-continued

```
cttggttctg gcatcgatga agaacgcagc gaaatgcgat aagtagtgtg aattgcagaa    120

ttcagtgaat catcgaatct ttgaacgcac attgcgccct ttggtattcc aaagggcatg    180

cctgttcgag cgtcatttgt accctcaagc tttgcttggt gttgggcgtc ttgtctctag    240

ctttgctgga gactcgcctt aaagtaattg gcagccggcc tactggtttc ggagcgcagc    300

acaagtcgca ctctctatca gca                                            323
```

<210> SEQ ID NO 157
<211> LENGTH: 313
<212> TYPE: DNA
<213> ORGANISM: Fusarium oxysporum

<400> SEQUENCE: 157

```
tatatgtaac ttctgagtaa aaccataaat aaatcaaaac tttcaacaac ggatctcttg     60

gttctggcat cgatgaagaa cgcagcaaaa tgcgataagt aatgtgaatt gcagaattca    120

gtgaatcatc gaatctttga acgcacattg cgcccgccag tattctggcg ggcatgcctg    180

ttcgagcgtc atttcaaccc tcaagcacag cttggtgttg ggactcgcgt taattcgcgt    240

tcctcaaatt gattggcggt cacgtcgagc ttccatagcg tagtagtaaa accctcgtta    300

ctggtaatcg tcg                                                       313
```

<210> SEQ ID NO 158
<211> LENGTH: 333
<212> TYPE: DNA
<213> ORGANISM: Fusarium solani
<220> FEATURE:
<221> NAME/KEY: misc_feature
<222> LOCATION: (11)..(11)
<223> OTHER INFORMATION: n is a, c, g, or t

<400> SEQUENCE: 158

```
tataatgttt nttctgagta aacaagcaaa taaattaaaa ctttcaacaa cggatctctt     60

ggctctggca tcgatgaaga acgcagcgaa atgcgataag taatgtgaat tgcagaattc    120

agtgaatcat cgaatctttg aacgcacatt gcgcccgcca gtattctggc gggcatgcct    180

gttcgagcgt cattacaacc ctcaggcccc cgggcctggc gttggggatc ggcggaagcc    240

ccctgtgggc acacgccgtc ccccaaatac agtggcggtc ccgccgcagc ttccattgcg    300

tagtagctaa cacctcgcaa ctggagagcg gcg                                 333
```

<210> SEQ ID NO 159
<211> LENGTH: 360
<212> TYPE: DNA
<213> ORGANISM: Scopulariopsis brevicaulis

<400> SEQUENCE: 159

```
ttgaaaaagc gtactgcacg ttctgattca aaacaaaaaa caagtcaaaa cttttaacaa     60

cggatctctt ggttctggca tcgatgaaga acgcagcgaa atgcgataag taatgtgaat    120

tgcagaattc agtgaatcat cgaatctttg aacgcacatt gcgcccggca gcaatctgcc    180

gggcatgcct gtccgagcgt catttcttcc ctcgagcgcg gctagcccta cggggcctgc    240

cgtcgcccgg tgttggggct ctacgggtgg ggctcgtccc ccccgcagtc cccgaaatgt    300

agtggcggtc cagccgcggc gccccctgcg tagtagatcc tacatctcgc atcgggtccc    360
```

<210> SEQ ID NO 160
<211> LENGTH: 316
<212> TYPE: DNA
<213> ORGANISM: Scytalidium dimidiatum

<400> SEQUENCE: 160
cagtgaacgt tgccgtctga aaaacaatca ataaactaaa actttcaaca acggatctct 60
tggttctggc atcgatgaag aacgcagcga aatgcgataa gtaatgtgaa ttgcagaatt 120
cagtgaatca tcgaatcttt gaacgcacat tgcgcccctc ggtattccga ggggcatgcc 180
tgttcgagcg tcattacaac cctcaagctc tgcttggtgt tgggcaccgc ccttccgcgg 240
gcgcgcctca aagacctcgg cggtggcgtc ttgcctcgag cgtagtagaa aacacctcgc 300
tttggagcgc acggcg 316

<210> SEQ ID NO 161
<211> LENGTH: 321
<212> TYPE: DNA
<213> ORGANISM: Chaetomium globosum

<400> SEQUENCE: 161
ataatttatg gcctctctga gtcttctgta ctgaataagt caaaactttc aacaacggat 60
ctcttggttc tggcatcgat gaagaacgca gcgaaatgcg ataagtaatg tgaattgcag 120
aattcagtga atcatcgaat ctttgaacgc acattgcgcc cgccagcatt ctggcgggca 180
tgcctgttcg agcgtcattt caaccatcaa gcccccgggc ttgtgttggg gacctgcggc 240
tgccgcaggc cctgaaaagc agtggcgggc tcgctgtcgc accgagcgta gtagcataca 300
tctcgctctg gtcgcgccgc g 321

<210> SEQ ID NO 162
<211> LENGTH: 313
<212> TYPE: DNA
<213> ORGANISM: Epicoccum purpurascens

<400> SEQUENCE: 162
gcagttgcaa tcagcgtctg aaaaaacata atagttacaa ctttcaacaa cggatctctt 60
ggttctggca tcgatgaaga acgcagcgaa atgcgataag tagtgtgaat tgcagaattc 120
agtgaatcat cgaatctttg aacgcacatt gcgccccttg gtattccatg ggcatgcct 180 gttcgagcgt catttgtacc ttcaagctct gcttggtgtt gggtgtttgt ctcgcctctg 240
cgtgtagact cgccttaaaa caattggcag ccggcgtatt gatttcggag cgcagtacat 300
ctcgcgcttt gca 313

<210> SEQ ID NO 163
<211> LENGTH: 334
<212> TYPE: DNA
<213> ORGANISM: Paecilomyces lilacinus

<400> SEQUENCE: 163
tacgcccagc gggtctctga gttgcacaag caaaaacaaa tgaatcaaaa ctttcaacaa 60
cggatctctt ggttctggca tcgatgaaga acgcagcgaa atgcgataag taatgtgaat 120
tgcagaattc agtgaatcat cgaatctttg aacgcacatt gcgcccgcca gcattctggc 180
gggcatgcct gttcgagcgt catttcaacc ctcgagcccc cccgggggcc tcggtgttgg 240
gggacggcac accagccgcc cccgaaatgc agtggcgacc ccgccgcagc ctcccctgcg 300
tagtagcaca cacctcgcac cggagcgcgg aggc 334

<210> SEQ ID NO 164
<211> LENGTH: 334
<212> TYPE: DNA

<213> ORGANISM: Paecilomyces variotii

<400> SEQUENCE: 164
ctgcctggaa ggttgcgtct gagtatacaa tcaatcaatt aaaactttca acaacggatc 60
tcttggttcc ggcatcgatg aagaacgcag cgaaatgcga taagtaatgt gaattgcaga 120
attccgtgaa tcatcgaatc tttgaacgca cattgcgccc cctggcattc cggggggcat 180
gcctgtccga gcgtcattgc taaccctcca gcccggctgg tgtgttgggc cgccgtcccc 240
cctccccggg ggacgggccc gaaaggcagc ggcggcgtcg cgtccggtcc tcgagcgtat 300
ggggctctgt cacacgcttc agtagaaccg gccg 334

<210> SEQ ID NO 165
<211> LENGTH: 350
<212> TYPE: DNA
<213> ORGANISM: Rhizopus oryzae

<400> SEQUENCE: 165
ataaacctag aaattcagta ttataaagtt taataaaaaa caacttttaa caatggatct 60
cttggttctc gcatcgatga agaacgtagc aaagtgcgat aactagtgtg aattgcatat 120
tcagtgaatc atcgagtctt tgaacgcagc ttgcactcta tggtttttct atagagtacg 180
cctgcttcag tatcatcaca aacccacaca taacatttgt ttatgtggta atgggtcgca 240
tcgctgtttt attacagtga gcacctaaaa tgtgtgtgat ttctgtctg gcttgctagg 300 caggaatatt acgctggtct caggatcttt ttctttggtt cgcccaggaa 350

<210> SEQ ID NO 166
<211> LENGTH: 196
<212> TYPE: DNA
<213> ORGANISM: Scytalidium dimidiatum
<220> FEATURE:
<221> NAME/KEY: misc_feature
<222> LOCATION: (59)..(59)
<223> OTHER INFORMATION: n is a, c, g, or t

<400> SEQUENCE: 166
taggtgaact gcggaaggat cattaccgag ttgattcggg ctccggcccg atcctcccnc 60
cctttgtgta cccacctctg ttgctttggc gggccgcggt cctccgcggc cgccctccgt 120
ccggggggtg gccagcgccc ccagaggacc atcraactcc ggtcagtgaa cgttgccgtc 180
tgaaaaacaa tcaata 196

<210> SEQ ID NO 167
<211> LENGTH: 179
<212> TYPE: DNA
<213> ORGANISM: Aspergillus flavus

<400> SEQUENCE: 167
gatcattacc gagtgtaggg ttcctagcga gcccaacctc ccacccgtgt ttactgtacc 60
ttagttgctt cggcgggccc gccattcatg gccgccgggg gctctcagcc ccgggcccgc 120
gcccgccgga gacaccacga actctgtctg atctagtgaa gtctgagttg attgtatcg 179

<210> SEQ ID NO 168
<211> LENGTH: 185
<212> TYPE: DNA
<213> ORGANISM: Aspergillus terreus

<400> SEQUENCE: 168
gatcattacc gagtgcgggt ctttatggcc caacctccca cccgtgacta ttgtaccttg 60

-continued

```
ttgcttcggc gggcccgcca gcgttgctgg ccgccggggg gcgactcgcc cccgggcccg    120

tgcccgccgg agaccccaac atgaaccctg ttctgaaagc ttgcagtctg agtgtgattc    180

tttgc                                                                185


<210> SEQ ID NO 169
<211> LENGTH: 161
<212> TYPE: DNA
<213> ORGANISM: Acremonium kiliense

<400> SEQUENCE: 169

gatcattacc agagtgccct aggctctcca acccattgtg aacataccta tcgttccctc     60

ggcgggctca gcgcgcggtg cctccgggct ccgggcgtcc gccggggaca accaaactct    120

gattttattg tgaatctctg aggggcgaaa gcccgaaaac a                        161


<210> SEQ ID NO 170
<211> LENGTH: 163
<212> TYPE: DNA
<213> ORGANISM: Alternaria alternata

<400> SEQUENCE: 170

gatcattaca caaatatgaa ggcgggctgg aacctctcgg ggttacagcc ttgctgaatt     60

attcaccctt gtcttttgcg tacttcttgt ttccttggtg ggttcgccca ccactaggac    120

aaacataaac cttttgtaat tgcaatcagc gtcagtaaca aat                      163


<210> SEQ ID NO 171
<211> LENGTH: 146
<212> TYPE: DNA
<213> ORGANISM: Fusarium oxysporum

<400> SEQUENCE: 171

gatcattacc gagtttacaa ctcccaaacc cctgtgaaca taccacttgt tgcctcggcg     60

gatcagcccg ctcccggtaa aacgggacgg cccgccagag gacccctaaa ctctgtttct    120

atatgtaact tctgagtaaa accata                                         146


<210> SEQ ID NO 172
<211> LENGTH: 148
<212> TYPE: DNA
<213> ORGANISM: Fusarium solani
<220> FEATURE:
<221> NAME/KEY: misc_feature
<222> LOCATION: (132)..(132)
<223> OTHER INFORMATION: n is a, c, g, or t

<400> SEQUENCE: 172

gatcattacc gagttatwca actcatcaac cctgtgaaca tacctaaaac gttgcttcgg     60

cgggaacaga cggccccgta acaacgggcc gcccccgcca gaggacccct aactctgttt    120

htataatgtt tnttctgagt aaacaagc                                       148


<210> SEQ ID NO 173
<211> LENGTH: 190
<212> TYPE: DNA
<213> ORGANISM: Scopulariopsis brevicaulis

<400> SEQUENCE: 173

gatcattacc gaagttactc ttcaaaaccc attgtgaacc ttacctcttg ccgcgcgttg     60

cctcggcggg gaggcggggt ctgggtcggc gcgcccctca ccgggccgcc gtccccgtcc    120
```

ccgtccccgc cggccgcgcc aaactctaaa tttgaaaaag cgtactgcac gttctgattc 180
aaaacaaaaa 190

<210> SEQ ID NO 174
<211> LENGTH: 184
<212> TYPE: DNA
<213> ORGANISM: Curvularia lunata

<400> SEQUENCE: 174
gatcattaca caataaaata tgaaggctgt acgcggctgt gctctcgggc cagttttgcg 60
gaggctgaat tatttattac ccttgtcttt tgcgcacttg ttgtttcctg ggcgggttcg 120
cccgccacca ggaccacatc ataaaccttt tttatgcagt tgcaatcagc gtcagtataa 180
caaa 184

<210> SEQ ID NO 175
<211> LENGTH: 166
<212> TYPE: DNA
<213> ORGANISM: Chaetomium globosum

<400> SEQUENCE: 175
ttaagagttg caaactccct aaccattgtg aacgttacct ataccgttgc ttcggcgggc 60
ggccccgggg tttacccccc gggcgcccct gggccccacc gcgggcgccc gccggaggtc 120
accaaactct tgataattta tggcctctct gagtcttctg tactga 166

<210> SEQ ID NO 176
<211> LENGTH: 137
<212> TYPE: DNA
<213> ORGANISM: Epicoccum purpurascens

<400> SEQUENCE: 176
gatcattacc tagagtttgt agacttcggt ctgctacctc ttacccatgt cttttgagta 60
ccttcgtttc ctcggcgggt ccgcccgccg attggacaac attcaaaccc tttgcagttg 120
caatcagcgt ctgaaaa 137

<210> SEQ ID NO 177
<211> LENGTH: 171
<212> TYPE: DNA
<213> ORGANISM: Paecilomyces lilacinus

<400> SEQUENCE: 177
gatcattacc gagttataca actcccaaac ccactgtgaa ccttacctca gttgcctcgg 60
cgggaacgcc ccggccgcct gcccccgcgc cggcgccgga cccaggcgcc cgccgcaggg 120
accccaaact ctcttgcatt acgcccagcg ggtctgagtt gcacaagcaa a 171

<210> SEQ ID NO 178
<211> LENGTH: 186
<212> TYPE: DNA
<213> ORGANISM: Paecilomyces variotii

<400> SEQUENCE: 178
gatcattacc gagtgagggt ccctcggggc ccaacctccc atccgtgttg tcctgacacc 60
tgttgcttcg gcgggcccgc cgtggttcac gccccggccg ccggggggtt cacgcccccg 120
ggcccgcgcc cgccgaagac ccctggaacg ctgcctggaa ggttgcgtct gagtatacaa 180
tcaatc 186

-continued

```
<210> SEQ ID NO 179
<211> LENGTH: 189
<212> TYPE: DNA
<213> ORGANISM: Rhizopus oryzae

<400> SEQUENCE: 179

atcattaatt atgttaaagc gccttacctc ttagggtttc ctctggggta agtgattgct      60

tctacactgt gaaaatttgg ctgagagact cagactggtc atgggtagac ctatctgggg    120

tttgatcgat gccactcctg gtttcaggag cacccttcat aataaaccta gaaattcagt    180

attataaag                                                            189

<210> SEQ ID NO 180
<211> LENGTH: 152
<212> TYPE: DNA
<213> ORGANISM: Aspergillus flavus

<400> SEQUENCE: 180

taagcggagg aaaagaaacc aaccgggatt gcctcagtaa cggcgagtga agcggcaaga     60

gctcaaattt gaaagctggc tccttcgggg tccgcattgt aatttgcaga ggatgcttcg   120

ggtgcggccc ctgtctaagt gccctggaac gg                                  152

<210> SEQ ID NO 181
<211> LENGTH: 152
<212> TYPE: DNA
<213> ORGANISM: Aspergillus terreus

<400> SEQUENCE: 181

taagcggagg aaaagaaacc aaccgggatt gcctcagtaa cggcgagtga agcggcaaga     60

gctcaaattt gaaagctggc tccttcgggg tccgcattgt aatttgcaga ggatgcttcg   120

ggtgcagccc ccgtctaagt gccctggaac gg                                  152

<210> SEQ ID NO 182
<211> LENGTH: 146
<212> TYPE: DNA
<213> ORGANISM: Acremonium kiliense

<400> SEQUENCE: 182

taagcggagg aaaagaaaca acagggattg ctcagtaacg gcgagtgaag cggcaacagc     60

tcaaatttga aatctggccg caaggtccga gttgtaattt gtagaggatg cttttggcga   120

ggtgccttcc gagttccctg gaacgg                                         146

<210> SEQ ID NO 183
<211> LENGTH: 152
<212> TYPE: DNA
<213> ORGANISM: Alternaria alternata

<400> SEQUENCE: 183

taagcggagg aaaagaaacc aacagggatt gccctagtaa cggcgagtga agcggcaaca     60

gctcaaattt gaaatctggc tcttttagag tccgagttgt aatttgcaga gggcgctttg   120

gctttggcag cggtccaagt tccttggaac ag                                  152

<210> SEQ ID NO 184
<211> LENGTH: 148
<212> TYPE: DNA
<213> ORGANISM: Fusarium oxysporum

<400> SEQUENCE: 184
```

-continued taagcggagg aaaagaaacc aacagggatt gccctagtaa cggcgagtga agcggcaaca 60
gctcaaattt gaaatctggc tctcgggccc gagttgtaat ttgtagagga tacttttgat 120
gcggtgcctt ccgagttccc tggaacgg 148

<210> SEQ ID NO 185
<211> LENGTH: 148
<212> TYPE: DNA
<213> ORGANISM: Fusarium solani

<400> SEQUENCE: 185
taagcggagg aaaagaaacc aacagggatt gcctcagtaa cggcgagtga agcggcaaca 60
gctcaaattt gaaatctggc tctcgggccc gagttgtaat ttgtagagga tgcttttggt 120
gaggtgcctt ccgagttccc tggaacgg 148

<210> SEQ ID NO 186
<211> LENGTH: 153
<212> TYPE: DNA
<213> ORGANISM: Scopulariopsis brevicaulis

<400> SEQUENCE: 186
taagcggagg aaaagaaacc aacagggatt gccttagtaa cggcgagtga agcggcaaca 60
gctcaaattt gaaatctggt ccccttttggg ggcccgagtt gtaatttgaa gaggatgctt 120
ttggcgaggc gccgtccgag ttccctggaa cgg 153

<210> SEQ ID NO 187
<211> LENGTH: 152
<212> TYPE: DNA
<213> ORGANISM: Scytalidium dimidiatum

<400> SEQUENCE: 187
aagcggagga aaagaaacca acagggattg cctcagtaac ggcgagtgaa gcggcaacag 60
ctcaaatttg aaagctggcc cccccggggg tccgcgttgt aatttgtaga ggatgattcg 120
gcgagggctc ccgcctaagt cccctggaac gg 152

<210> SEQ ID NO 188
<211> LENGTH: 152
<212> TYPE: DNA
<213> ORGANISM: Curvularia lunata

<400> SEQUENCE: 188
taagcggagg aaaagaaacc aacagggatt gccctagtaa cggcgagtga agcggcaaca 60
gctcaaattt gaaatctggc tctttcagag tccgagttgt aatttgcaga gggcgctttg 120
gctttggcag cggtccaagt tccttggaac ag 152

<210> SEQ ID NO 189
<211> LENGTH: 146
<212> TYPE: DNA
<213> ORGANISM: Chaetomium globosum

<400> SEQUENCE: 189
taagcggagg aaaagaaacc aacagggatt gccctagtaa cggcgagtga agcggcaaca 60
gctcaaattt gaaatctggc ttcggcccga gttgtaattt gcagaggaag ctttaggcgc 120
ggcaccttct gagtcccctg gaacgg 146

<210> SEQ ID NO 190
<211> LENGTH: 152

<212> TYPE: DNA
<213> ORGANISM: Epicoccum purpurascens

<400> SEQUENCE: 190
taagcggagg aaaagaaacc aacagggatt gccctagtaa cggcgagtga agcggcaaca 60
gctcaaattt gaaatctggc gtctttggcg tccgagttgt aatttgcaga gggcgctttg 120
gcattggcag cggtccaagt tccttggaac ag 152

<210> SEQ ID NO 191
<211> LENGTH: 149
<212> TYPE: DNA
<213> ORGANISM: Paecilomyces lilacinus

<400> SEQUENCE: 191
taagcggagg aaaagaaacc aacagggatt gccccagtaa cggcgagtga agcggcaaca 60
gctcaaattt gaaatctggc ccccagggcc cgagttgtaa tttgcagagg atgcttttgg 120
cgcggtgcct tccgagttcc ctggaacgg 149

<210> SEQ ID NO 192
<211> LENGTH: 152
<212> TYPE: DNA
<213> ORGANISM: Paecilomyces variotii

<400> SEQUENCE: 192
taagcggagg aaaagaaacc aacagggatt gccccagtaa cggcgagtga agcggcaaga 60
gctcaaattt gaaatctggc ccctccgggg tccgagttgt aatttgcaga ggatgcttcg 120
ggcgcggtcc ccgtctaagt accctggaac gg 152

<210> SEQ ID NO 193
<211> LENGTH: 130
<212> TYPE: DNA
<213> ORGANISM: Rhizopus oryzae

<400> SEQUENCE: 193
ttatttactt aatcttgact cgcctaaaaa attaaaaaaa aaaaattttt ttattacaac 60 ttttttttt tttttctcct ttttgtgtag ttaatactct attaaattta tttacttggt 120
attataacga 130

<210> SEQ ID NO 194
<211> LENGTH: 72
<212> TYPE: DNA
<213> ORGANISM: Fusarium oxysporum

<400> SEQUENCE: 194
ctggtaatcg tcgcggccac gccgttaaac cccaacttct gaatgttgac ctcggatcag 60
gtaggaatac cc 72

<210> SEQ ID NO 195
<211> LENGTH: 73
<212> TYPE: DNA
<213> ORGANISM: Fusarium solani

<400> SEQUENCE: 195
ctggagagcg gcgcggccac gccgtaaaac acccaacttc tgaatgttga cctcgaatca 60
ggtaggaata ccc 73

<210> SEQ ID NO 196

<211> LENGTH: 67
<212> TYPE: DNA
<213> ORGANISM: Aspergillus flavus

<400> SEQUENCE: 196
gcccggccgg cgcttgccga acgcaaatca atctttttcc aggttgacct cggatcaggt 60
agggata 67

<210> SEQ ID NO 197
<211> LENGTH: 75
<212> TYPE: DNA
<213> ORGANISM: Aspergillus terreus

<400> SEQUENCE: 197
gcccggccgg cgcccgccga cgcatttatt tgcaacttgt ttttttccag gttgacctcg 60
gatcaggtag ggata 75

<210> SEQ ID NO 198
<211> LENGTH: 67
<212> TYPE: DNA
<213> ORGANISM: Acremonium kiliense

<400> SEQUENCE: 198
cggagagcgg ctcggccacg ccgtgaaacc cccaattttt taaggttgac ctcggatcag 60
gtaggaa 67

<210> SEQ ID NO 199
<211> LENGTH: 61
<212> TYPE: DNA
<213> ORGANISM: Alternaria alternate

<400> SEQUENCE: 199
cagcaaaggt ctagcatcca ttaagccttt tttcaacttt tgacctcgga tcaggtaggg 60
a 61

<210> SEQ ID NO 200
<211> LENGTH: 65
<212> TYPE: DNA
<213> ORGANISM: Scopulariopsis brevicaulis

<400> SEQUENCE: 200
gggtcccggc gaaggccagc cgtcgaacct tttatttcat ggtttgacct cggatcaggt 60
agggt 65

<210> SEQ ID NO 201
<211> LENGTH: 72
<212> TYPE: DNA
<213> ORGANISM: Scytlidium dimidiatum

<400> SEQUENCE: 201
ggagcgcacg gcgccgcccg ccggacgaac cttttgaact ttctcaaggt tgacctcgga 60
tcaggtaggg at 72

<210> SEQ ID NO 202
<211> LENGTH: 60
<212> TYPE: DNA
<213> ORGANISM: Curvularia lunata

<400> SEQUENCE: 202
caaaagagga cggcaatcca tcaagactcc ttctcacgtt gacctcggat caggtaggga 60

<210> SEQ ID NO 203
<211> LENGTH: 60
<212> TYPE: DNA
<213> ORGANISM: Chaetomium globosum

<400> SEQUENCE: 203
cgcgggttcc ggccgttaaa ccaccttttt aacccaaggt tgacctcgga tcaggtagga 60

<210> SEQ ID NO 204
<211> LENGTH: 62
<212> TYPE: DNA
<213> ORGANISM: Chaetomium globosum

<400> SEQUENCE: 204
ctcataacga cgacgtccaa aagtacattt ttacactctt gacctcggat caggtaggga 60
ta 62

<210> SEQ ID NO 205
<211> LENGTH: 67
<212> TYPE: DNA
<213> ORGANISM: Paecilomyces lilacinus

<400> SEQUENCE: 205
ggagcgcgga ggcggtcacg ccgtaaaacg cccaactttc ttagagttga cctcggatca 60
ggtagga 67

<210> SEQ ID NO 206
<211> LENGTH: 80
<212> TYPE: DNA
<213> ORGANISM: Paecilomyces variotii
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 206
gtagaaccgg ccggcttgct ggccanacga ccntcacngg tcacctatat ttttctctta 60
ggttgacctc ggatcaggta 80

<210> SEQ ID NO 207
<211> LENGTH: 67
<212> TYPE: DNA
<213> ORGANISM: Rhizopus oryzae

<400> SEQUENCE: 207
gcccaggaag taaagtacaa gagtataatc cagcaacttt caaactatga tctgaagtca 60
ggtggga 67

<210> SEQ ID NO 208
<211> LENGTH: 118
<212> TYPE: DNA
<213> ORGANISM: Scopulariopsis brevicaulis

<400> SEQUENCE: 208
ccctcgagcg cggctagccc tacggggcct gccgtcgccc ggtgttgggg ctctacgggt 60
ggggctcgtc ccccccgcag tccccgaaat gtagtggcgg tccagccgcg gcgccccc 118

<210> SEQ ID NO 209
<211> LENGTH: 91
<212> TYPE: DNA
<213> ORGANISM: Aspergillus flavus

<400> SEQUENCE: 209
ccatcaagca cggcttgtgt gttgggtcgt cgtcccctct ccggggggga cgggccccaa 60
aggcagcggc ggcaccgcgt ccgatcctcg a 91

<210> SEQ ID NO 210
<211> LENGTH: 91
<212> TYPE: DNA
<213> ORGANISM: Aspergillus terreus

<400> SEQUENCE: 210
cctcaagccc ggcttgtgtg ttgggccctc gtcccccggc tcccggggga cgggcccgaa 60
aggcagcggc ggcaccgcgt ccggtcctcg a 91

<210> SEQ ID NO 211
<211> LENGTH: 100
<212> TYPE: DNA
<213> ORGANISM: Acremonium kiliense

<400> SEQUENCE: 211
ccctcaggac cccctttcgg gggggacctg gtgctgggga tcagcggcct ccgggcccct 60
gtcccccaaa ttgagtggcg gtcgcgccgc agcctcccct 100

<210> SEQ ID NO 212
<211> LENGTH: 92
<212> TYPE: DNA
<213> ORGANISM: Alternaria alternata

<400> SEQUENCE: 212
ccctcaagct ttgcttggtg ttgggcgtct tgtctctagc tttgctggag actcgcctta 60
aagtaattgg cagccggcct actggtttcg ga 92

<210> SEQ ID NO 213
<211> LENGTH: 43
<212> TYPE: DNA
<213> ORGANISM: Fusarium oxysporum

<400> SEQUENCE: 213
ccctcaagca cagcttggtg ttgggactcg cgttaattcg cgt 43

<210> SEQ ID NO 214
<211> LENGTH: 99
<212> TYPE: DNA
<213> ORGANISM: Fusarium solani

<400> SEQUENCE: 214
ccctcaggcc cccgggcctg gcgttgggga tcggcggaag ccccctgtgg gcacacgccg 60
tcccccaaat acagtggcgg tcccgccgca gcttccatt 99

<210> SEQ ID NO 215
<211> LENGTH: 80
<212> TYPE: DNA
<213> ORGANISM: Scytalidium dimidiatum

<400> SEQUENCE: 215
cctcaagctc tgcttggtgt tgggcaccgc ccttccgcgg gcgcgcctca aagacctcgg 60
cggtggcgtc ttgcctcgag 80

<210> SEQ ID NO 216
<211> LENGTH: 92
<212> TYPE: DNA
<213> ORGANISM: Curvularia lunata

<400> SEQUENCE: 216
ccctcaagct ttgcttggtg ttgggcgttt tttgtctttg gttgccaaag actcgcctta 60
aaaggattgg cagccggcct actggtttcg ca 92

<210> SEQ ID NO 217
<211> LENGTH: 82
<212> TYPE: DNA
<213> ORGANISM: Chaetomium globosum

<400> SEQUENCE: 217
ccatcaagcc cccgggcttg tgttggggac ctgcggctgc cgcaggccct gaaaagcagt 60
ggcgggctcg ctgtcgcacc ga 82

<210> SEQ ID NO 218
<211> LENGTH: 91
<212> TYPE: DNA
<213> ORGANISM: Epicoccum purpurascens

<400> SEQUENCE: 218
ccttcaagct ctgcttggtg ttgggtgttt gtctcgcctc tgcgtgtaga ctcgccttaa 60
aacaattggc agccggcgta ttgatttcgg a 91

<210> SEQ ID NO 219
<211> LENGTH: 90
<212> TYPE: DNA
<213> ORGANISM: Paecilomyces lilacinus

<400> SEQUENCE: 219
ccctcgagcc cccccggggg cctcggtgtt gggggacggc acaccagccg cccccgaaat 60
gcagtggcga ccccgccgca gcctcccctg 90

<210> SEQ ID NO 220
<211> LENGTH: 92
<212> TYPE: DNA
<213> ORGANISM: Paecilomyces variotii

<400> SEQUENCE: 220
ccctccagcc cggctggtgt gttgggccgc cgtcccccct ccccggggga cgggcccgaa 60
aggcagcggc ggcgtcgcgt ccggtcctcg ag 92

<210> SEQ ID NO 221
<211> LENGTH: 105
<212> TYPE: DNA
<213> ORGANISM: Rhizopus oryzae

<400> SEQUENCE: 221
cccacacata acatttgttt atgtggtaat gggtcgcatc gctgttttat tacagtgagc 60
acctaaaatg tgtgtgattt tctgtctggc ttgctaggca ggaat 105

<210> SEQ ID NO 222
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 222
cgtcatttca accctcagga cc 22

<210> SEQ ID NO 223
<211> LENGTH: 19
<212> TYPE: DNA
<213> ORGANISM: Artificial Sequence
<220> FEATURE:
<223> OTHER INFORMATION: Synthetic nucleic acid

<400> SEQUENCE: 223 tgggggggttt aacggcgtg 19

<210> SEQ ID NO 224
<211> LENGTH: 18
<212> TYPE: DNA
<213> ORGANISM: Artificial Sequence
<220> FEATURE:
<223> OTHER INFORMATION: Synthetic nucleic acid

<400> SEQUENCE: 224
cctctcgggg ttacagcc 18

<210> SEQ ID NO 225
<211> LENGTH: 24
<212> TYPE: DNA
<213> ORGANISM: Artificial Sequence
<220> FEATURE:
<223> OTHER INFORMATION: Synthetic nucleic acid

<400> SEQUENCE: 225
gttactgacg ctgattgcaa ttac 24

<210> SEQ ID NO 226
<211> LENGTH: 25
<212> TYPE: DNA
<213> ORGANISM: Artificial Sequence
<220> FEATURE:
<223> OTHER INFORMATION: Synthetic nucleic acid

<400> SEQUENCE: 226
gcaatcagcg tcagtataac aaatg 25

<210> SEQ ID NO 227
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 227
gctgattgca agcgcaaaaa tg 22

<210> SEQ ID NO 228
<211> LENGTH: 25
<212> TYPE: DNA
<213> ORGANISM: Artificial Sequence
<220> FEATURE:
<223> OTHER INFORMATION: Synthetic nucleic acid

<400> SEQUENCE: 228
gaaggatcat taccgagttg attcg 25

<210> SEQ ID NO 229
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 229
tcagacggca acgttcactg 20

<210> SEQ ID NO 230
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 230
cggaggaaaa gaaaccaacc 20

<210> SEQ ID NO 231
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 231
cgttccaggg cacttagaca 20

<210> SEQ ID NO 232
<211> LENGTH: 17
<212> TYPE: DNA
<213> ORGANISM: Artificial Sequence
<220> FEATURE:
<223> OTHER INFORMATION: Synthetic nucleic acid

<400> SEQUENCE: 232
cggccacgcc gttaaac 17

<210> SEQ ID NO 233
<211> LENGTH: 23
<212> TYPE: DNA
<213> ORGANISM: Artificial Sequence
<220> FEATURE:
<223> OTHER INFORMATION: Synthetic nucleic acid

<400> SEQUENCE: 233
gatccgaggt caacattcag aag 23

<210> SEQ ID NO 234
<211> LENGTH: 17
<212> TYPE: DNA
<213> ORGANISM: Artificial Sequence
<220> FEATURE:
<223> OTHER INFORMATION: Synthetic nucleic acid

<400> SEQUENCE: 234
gcgcggctag ccctacg 17

<210> SEQ ID NO 235

<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 235
ggaccgccac tacatttcgg 20

<210> SEQ ID NO 236
<211> LENGTH: 166
<212> TYPE: DNA
<213> ORGANISM: Artificial Sequence
<220> FEATURE:
<223> OTHER INFORMATION: Synthetic nucleic acid

<400> SEQUENCE: 236
cgtcatttca accctcagga ccccctttcg ggggggacct ggtgctgggg atcagcggcc 60
tccgggcccc tgtcccccaa attgagtggc ggtcgcgccg cagcctcccc tgcgtagtag 120
cacacctcgc accggagagc ggctcggcca cgccgtgaaa ccccca 166

<210> SEQ ID NO 237
<211> LENGTH: 127
<212> TYPE: DNA
<213> ORGANISM: Artificial Sequence
<220> FEATURE:
<223> OTHER INFORMATION: Synthetic nucleic acid

<400> SEQUENCE: 237
cctctcgggg ttacagcctt gctgaattat tcacccttgt cttttgcgta cttcttgttt 60
ccttggtggg ttcgcccacc actaggacaa acataaacct tttgtaattg caatcagcgt 120
cagtaac 127

<210> SEQ ID NO 238
<211> LENGTH: 319
<212> TYPE: DNA
<213> ORGANISM: Artificial Sequence
<220> FEATURE:
<223> OTHER INFORMATION: Synthetic nucleic acid

<400> SEQUENCE: 238
gcaatcagcg tcagtataac aaatgtaaat catttacaac tttcaacaac ggatctcttg 60
gttctggcat cgatgaagaa cgcagcgaaa tgcgatacgt agtgtgaatt gcagaattca 120
gtgaatcatc gaatctttga acgcacattg cgccctttgg tattccaaag ggcatgcctg 180
ttcgagcgtc atttgtaccc tcaagctttg cttggtgttg ggcgtttttt gtctttggtt 240
gccaaagact cgccttaaaa ggattggcag ccggcctact ggtttcgcag cgcagcacat 300
ttttgcgctt gcaatcagc 319

<210> SEQ ID NO 239
<211> LENGTH: 171
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (46)..(46)
<223> OTHER INFORMATION: n is a, c, g, or t

<400> SEQUENCE: 239
gaaggatcat taccgagttg attcgggctc cggcccgatc ctcccnccct ttgtgtaccc 60
acctctgttg ctttggcggg ccgcggtcct ccgcggccgc cctccgtccg gggggtggcc 120
agcgcccgcc agaggaccat craactccgg tcagtgaacg ttgccgtctg a 171

<210> SEQ ID NO 240
<211> LENGTH: 148
<212> TYPE: DNA
<213> ORGANISM: Aspergillus flavus

<400> SEQUENCE: 240
cggaggaaaa gaaaccaacc gggattgcct cagtaacggc gagtgaagcg gcaagagctc 60
aaatttgaaa gctggctcct tcggggtccg cattgtaatt tgcagaggat gcttcgggtg 120
cggcccctgt ctaagtgccc tggaacgg 148

<210> SEQ ID NO 241
<211> LENGTH: 45
<212> TYPE: DNA
<213> ORGANISM: Fusarium oxysporum

<400> SEQUENCE: 241
cggccacgcc gttaaacccc aacttctgaa tgttgacctc ggatc 45

<210> SEQ ID NO 242
<211> LENGTH: 46
<212> TYPE: DNA
<213> ORGANISM: Artificial Sequence
<220> FEATURE:
<223> OTHER INFORMATION: Synthetic nucleic acid

<400> SEQUENCE: 242
cggccahgcc gtaaaacacc caacttctga atgttgacct cgaatc 46

<210> SEQ ID NO 243
<211> LENGTH: 96
<212> TYPE: DNA
<213> ORGANISM: Artificial Sequence
<220> FEATURE:
<223> OTHER INFORMATION: Synthetic nucleic acid

<400> SEQUENCE: 243
gcgcggctag ccctacgggg cctgccgtcg cccggtgttg gggctctacg ggtggggctc 60
gtcccccccg cagtccccga aatgtagtgg cggtcc 96

<210> SEQ ID NO 244
<211> LENGTH: 25
<212> TYPE: DNA
<213> ORGANISM: Artificial Sequence
<220> FEATURE:
<223> OTHER INFORMATION: Synthetic nucleic acid

<400> SEQUENCE: 244
gaaggatcat taccgagttg attcg 25

<210> SEQ ID NO 245
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 245
tcagacggca acgttcactg 20

```
<210> SEQ ID NO 246
<211> LENGTH: 171
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (46)..(46)
<223> OTHER INFORMATION: n is a, c, g, or t

<400> SEQUENCE: 246

gaaggatcat taccgagttg attcgggctc cggcccgatc ctcccnccct ttgtgtaccc      60

acctctgttg ctttggcggg ccgcggtcct ccgcggccgc cctccgtccg gggggtggcc    120

agcgcccgcc agaggaccat craactccgg tcagtgaacg ttgccgtctg a             171
```